United States Patent
Fuchss et al.

(10) Patent No.: US 11,608,338 B2
(45) Date of Patent: *Mar. 21, 2023

(54) IMIDAZOLONYLQUINOLINES AND THE USE THEREOF AS ATM KINASE INHIBITORS

(71) Applicant: Merck Patent GmbH, Darmstadt (DE)

(72) Inventors: Thomas Fuchss, Bensheim-Auerbach (DE); Kai Schiemann, Seeheim-Jugenheim (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/204,619

(22) Filed: Mar. 17, 2021

(65) Prior Publication Data

US 2021/0198257 A1 Jul. 1, 2021

Related U.S. Application Data

(60) Division of application No. 16/910,438, filed on Jun. 24, 2020, now Pat. No. 10,975,075, which is a continuation of application No. 16/353,559, filed on Mar. 14, 2019, now Pat. No. 10,745,399, which is a division of application No. 15/563,680, filed as application No. PCT/EP2016/000542 on Mar. 31, 2016, now Pat. No. 10,457,677.

(30) Foreign Application Priority Data

Apr. 2, 2015 (EP) ..................................... 15000968

(51) Int. Cl.
| | | |
|---|---|---|
| C07D 471/04 | (2006.01) | |
| C07D 519/00 | (2006.01) | |
| A61P 35/00 | (2006.01) | |
| A61K 31/4375 | (2006.01) | |
| A61K 45/06 | (2006.01) | |

(52) U.S. Cl.
CPC ........ *C07D 471/04* (2013.01); *A61K 31/4375* (2013.01); *A61K 45/06* (2013.01); *A61P 35/00* (2018.01); *C07D 519/00* (2013.01)

(58) Field of Classification Search
CPC .............. A61K 31/4375; C07D 471/04; C07D 546/82; C07D 514/293
See application file for complete search history.

(56) References Cited

U.S. PATENT DOCUMENTS

| | | | |
|---|---|---|---|
| 7,998,972 | B2 | 8/2011 | Garcia-Echeverria et al. |
| 8,106,202 | B2 | 1/2012 | Sallares et al. |
| 8,431,592 | B2 | 4/2013 | Garcia-Echeverria et al. |
| 8,557,984 | B2 | 10/2013 | Bouillot |
| 8,778,927 | B2 | 7/2014 | Dorsch et al. |
| 9,365,579 | B2 | 6/2016 | Wishart et al. |
| 9,370,508 | B2 | 6/2016 | Garcia-Echeverria et al. |
| 9,598,408 | B2 | 3/2017 | Fuchss et al. |
| 9,879,003 | B2 | 1/2018 | Gray et al. |
| 2010/0311714 | A1 | 12/2010 | Furet et al. |
| 2012/0282252 | A1 | 11/2012 | Garcia-Echeverria |
| 2013/0245061 | A1 | 9/2013 | Cao et al. |
| 2015/0157645 | A1 | 6/2015 | Hirawat et al. |
| 2015/0210708 | A1 | 7/2015 | Wishart et al. |

FOREIGN PATENT DOCUMENTS

| | | |
|---|---|---|
| CN | 102372711 A | 3/2012 |
| CN | 102399218 A | 4/2012 |
| CN | 103012398 A | 4/2013 |
| WO | 03097641 A2 | 11/2003 |
| WO | 06100226 A1 | 9/2006 |
| WO | 06122806 A2 | 11/2006 |
| WO | 08103636 A1 | 8/2008 |
| WO | 09118324 A1 | 10/2009 |
| WO | 09152133 A1 | 12/2009 |
| WO | 10037715 A1 | 4/2010 |
| WO | 10139747 A1 | 12/2010 |
| WO | 2010139731 A1 | 12/2010 |
| WO | 2011054846 A1 | 5/2011 |
| WO | 2012028233 A1 | 3/2012 |
| WO | 12075253 A2 | 6/2012 |
| WO | 13154778 A1 | 10/2013 |
| WO | 13184621 A1 | 12/2013 |

OTHER PUBLICATIONS

International Search Report PCT/EP2016/000542 dated Jul. 5, 2016.

*Primary Examiner* — Susanna Moore
(74) *Attorney, Agent, or Firm* — Millen White Zelano and Branigan, PC; Csaba Henter

(57) ABSTRACT

Compounds of the formula (I), in which R1, R3, Het[1] and HET have the meanings given in claim 1, are ATM kinase inhibitors and can be employed, inter alia, for the treatment of cancer.

8 Claims, No Drawings

IMIDAZOLONYLQUINOLINES AND THE USE THEREOF AS ATM KINASE INHIBITORS

BACKGROUND OF THE INVENTION

The present invention relates to specific imidazolonylquinoline compounds and to the use thereof in the inhibition, regulation and/or modulation of signal transduction by kinases, in particular ATM kinase, furthermore to pharmaceutical compositions which comprise these compounds, and to the use of the compounds for the treatment of diseases which relate to ATM kinase, in particular cancer.

The serine/threonine protein kinase ATM (ataxia telangiectasia mutated kinase) belongs to the PIKK family of kinases having catalytic domains which are homologous with phosphoinositide-3 kinases (PI3 kinase, PI3K). These kinases are involved in a multiplicity of key cellular functions, such as cell growth, cell proliferation, migration, differentiation, survival and cell adhesion. In particular, these kinases react to DNA damage by activation of the cell cycle arrest and DNA repair programmes (DDR: DNA damage response). ATM is a product of the ATM gene and plays a key role in the repair of damage to the DNA double strand (DSB. double strand breaks) by homologous recombination and non-homologous end-to-end joining (NHEJ). Double-strand damage of this type is particularly cytotoxic.

One of the constant features of tumours in humans is their genomic instability, where the specific defects of the DNA repair mechanism in most types of cancer are unknown to date. This instability represents the therapeutic starting point for chemotherapy, which has been predominantly practised for some time. In addition, there are a few syndromes in which the basic genetic influencing factor can be attributed to mutation, accompanied by a loss of function, of a gene which modulates the reaction to damage to the DNA double strand. This includes ataxia telangiectasia, which is caused by a defective ATM gene. A common feature of all these syndromes is that they cause extreme radiation sensitivity (Lavin & Shiloh (1997) Annu. Rev. Immunol. 15: 177; Rotman & Shiloh (1998) Hum. Mol. Genet. 7: 1555, incorporated in their totality herein by way of reference). ATM-defective cells are correspondingly sensitive to agents and measures which cause damage to the DNA double strand, which makes ATM an attractive target for chemo- and radiosensitisation in cancer treatment.

Although the molecules caffeine and wortmannin which were initially investigated against this background exhibited radiosensitisation, attributed, inter alia, to inhibition of ATM, they are, however, too toxic in vivo for possible therapeutic use. Staring from the chemical structure of the PI3K inhibitor LY294002, KuDOS Pharmaceuticals developed the first potent and selective ATM inhibitor: KU-55933 (2-morpholino-6-(thianthren-1-yl)-4H-pyran-4-one). This facilitated sensitisation to ionising radiation and DNA double strand-damaging chemotherapeutic agents (Hickson, I., et al. (2004). Cancer Res 64, 9152-9159, incorporated in its totality herein by way of reference). However, KU-55933 proved to be unsuitable for in vivo use, presumably owing to its high lipophilicity. Based on KU-55933, KU-60019 (2-((2S,6R)-2,6-dimethylmorpholino)-N-(5-(6-morpholino-4-oxo-4H-pyran-2-yl)-9H-thioxanthen-2-yl)acetamide) and KU-559403 (2-(4-methylpiperazin-1-yl)-N-[5-(6-morpholino-4-oxopyran-2-yl)thioxanthen-2-yl]acetamide) were developed with slight modification of the basic structure, enabling solubility and potency to be improved. In the meantime, it has been reported, for example, that it has been possible to sensitise glioblastoma-initiating cells for irradiation safely and effectively by KU-60019, from which it was concluded that KU-60019 is able to function for radiation sensitisation of a whole series of brain tumours (Vecchio D. et al. (2015), Int. J. Cancer 136: 1445, incorporated in its totality herein by way of reference).

The provision of small molecules which effectively inhibit, regulate and/or modulate signal transduction by kinases, in particular ATM kinase, is desirable and an object of the present invention.

It is furthermore desirable that kinase inhibitors of this type are selective, i.e. have no or significantly lower activity against other kinases. Thus, off-target effects or associated toxicities can be reduced.

DESCRIPTION OF THE INVENTION

The object has surprisingly been achieved by compounds of the formula (I)

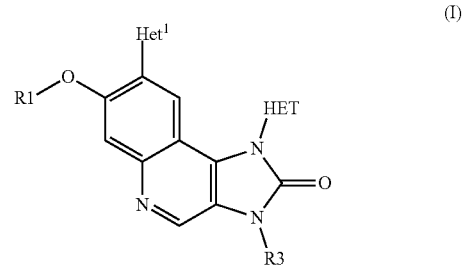

(I)

where
R1 denotes A,
R3 denotes A or H,
A in each case independently denotes unbranched or branched alkyl having 1, 2, 3, 4, 5, 6, 7, 8, 9 or 10 C atoms, where, independently of one another, 1, 2, 3, 4, 5, 6 or 7 H atoms may be replaced by Hal,
$Het^1$ denotes mono- or bicyclic heteroaryl having 2, 3, 4, 5, 6, 7, 8 or 9 C atoms and 1, 2, 3 or 4 N, O and/or S atoms, which may be unsubstituted or mono-, di- or trisubstituted, independently of one another, by Hal, A, CN, —$(CY_2)_p$—OY, —$(CY_2)_p$—NYY, —$(CY_2)_p$—COOY, —$(CY_2)_p$—CO—NYY, —$(CY_2)_p$—NY—COY, -$Het^2$ and/or —$SO_2$-$Het^2$,
$Het^2$ denotes a monocyclic saturated heterocycle having 2, 3, 4, 5, 6 or 7 C atoms and 1, 2, 3 or 4 N, O and/or S atoms, which may be unsubstituted or monosubstituted by A,
HET denotes a 5- or 6-membered aromatic heterocycle having 1, 2 or 3 N atoms and optionally an O atom or S atom, where this heterocycle is linked to the N atom of the skeleton via a ring C atom and where this heterocycle may be unsubstituted or substituted by one, two or three substituents, which are selected, independently of one another, from the group consisting of: Hal, A, $Het^2$, CN, —$(CY_2)_p$—OY, —$(CY_2)_p$—OZ, —$(CY_2)_p$—O-$Het^2$, —$(CY_2)_p$—O—$(CY_2)_t$-$Het^2$, —$(CY_2)_p$—O—$(CY_2)_t$—NYY, —$(CY_2)_p$—O—$(CY_2)_t$—OY, —$(CY_2)_p$—O—$(CY_2)_t$—POAA, —$(CY_2)_p$—NYY, —$(CY_2)_p$—COOY, —$(CY_2)_p$—CO—NYY, —$(CY_2)_p$—NY—COY, —$SO_2$-$Het^2$, CyA, —$(CY_2)_p$—O—$(CY_2)_t$—$SO_2$—Y, —$(CY_2)_p$—NY—$SO_2$—Y, and —$(CY_2)_p$—$SO_2$—Y, and where this heterocycle may be part of a bicyclic 11- or 12-membered aromatic heterocycle, where this bicyclic aromatic heterocycle may overall be unsubstituted or substituted by one, two, three or more substituents, which are selected, independently of one another, from the group consisting of: Hal, A, Het$^2$, —CN, —(CY$_2$)$_p$—OY, —(CY$_2$)$_p$—OZ, —(CY$_2$)$_p$—O-Het$^2$, —(CY$_2$)$_p$—O—(CY$_2$)$_t$-Het$^2$, —(CY$_2$)$_p$—O—(CY$_2$)$_t$—NYY, —(CY$_2$)$_p$—O—(CY$_2$)$_t$—OY, —(CY$_2$)$_p$—O—(CY$_2$)$_t$—POAA, —(CY$_2$)$_p$—NYY, —(CY$_2$)$_p$—COOY, —(CY$_2$)$_p$—CO—NYY, —(CY$_2$)$_p$—NY—COY, —SO$_2$-Het$^2$, CyA, —(CY$_2$)$_p$—O—(CY$_2$)$_t$—SO$_2$—Y, —(CY$_2$)$_p$NY—SO$_2$—Y, and —(CY$_2$)$_p$—SO$_2$—Y, Y denotes H or A, Z denotes unbranched or branched alkenyl having 2, 3, 4, 5, 6, 7, 8, 9 or 10 C atoms, where, independently of one another, 1, 2, 3, 4, 5, 6 or 7 H atoms may be replaced by Hal, CyA denotes cycloalkyl having 3, 4, 5, 6, 7 or 8 ring C atoms which is unsubstituted or mono- or polysubstituted, independently of one another, by Hal, A, CN, —(CY$_2$)$_p$—OY, —(CY$_2$)$_p$—NYY, —(CY$_2$)$_p$—COOY, —(CY$_2$)$_p$—CO—NYY and/or —(CY$_2$)$_p$—NY—COY, Hal denotes F, Cl, Br or I, and P denotes 0, 1, 2, 3, 4, 5 or 6 t denotes 1, 2, 3, 4, 5 or 6, and/or pharmaceutically usable derivative, salt, solvate, tautomer, stereoisomer thereof, including mixtures thereof in all ratios.

As stated in greater detail below, the compounds are to be understood in such a way that the atoms, such as, for example, H, C, N, in each case also include the heavier isotopes of these atoms. This applies, in particular, to H, where deuterium can advantageously be employed, as shown by the examples.

Compounds according to the invention have surprisingly proven to be potent inhibitors of ATM kinase. Even more surprising is the selectivity for other related kinases, such as, for example, mTOR (mammalian target of rapamycin) kinase, a further protein kinase from the PIK kinase family (also known as class IV PI3K).

In total contrast to the present invention, international patent application WO 2010/139731 discloses that the imidazolonylquinoline compounds described and claimed there are preferably inhibitors of class I PI3 kinases and/or mTOR kinase. Class I PI3 kinases are lipid kinases. Correspondingly, experimental data show IC$_{50}$ values for mTOR in the range down to less than 3 nM, i.e. very strong inhibition.

The compounds according to the invention again impressively confirm how structural differences that at first sight appear relatively small exert a crucial influence on the biological activity.

In addition, the compounds according to the invention are also distinguished by the absence of the frequently observed, undesired inhibition of cardiac ion channels, in particular of Kv1.11 hERG, blockage of which may result in life-threatening arrhythmia.

The compounds according to the invention thus open up completely new possibilities in cancer therapy, for example as monotherapy in the case of tumours having defective DNA double-strand repair ability or in combination with radio- or chemotherapy, in particular as radio- and chemosensitisers in the treatment of cancer, particularly preferably as radiosensitisers.

The compounds of the formula (I) can therefore be used for the inhibition of cancer and for the sensitisation of cancer cells to anti-cancer agents and/or ionising radiation. The invention also relates to the use of the compounds of the formula (I) in the treatment of cancer, tumours and/or metastases, in combination with radiotherapy and/or an anti-cancer agent, preferably radiotherapy.

Above and below, the radicals R1, R3, Y, A, Z, CyA, Het$^1$, Het$^2$, HET and Hal as well as p and t have the meanings indicated above in the case of the formula (I), unless expressly indicated otherwise. In the case of the multiple occurrence of individual residues within a compound or radical, the residues adopt, independently of one another, the meanings indicated, unless expressly indicated otherwise. For example, the residues YY in the radical —NYY, in which they may occur multiple times, are identical or different, but are preferably in each case selected, independently of one another, from the meanings indicated above and/or below (for example methyl and/or ethyl), unless expressly indicated otherwise. In the case of the multiple occurrence of Y, the radical may alternatively also be denoted by Y', Y", Y''' and Y''''. A corresponding situation applies to the other residues or number variables. Correspondingly, the formulation "cycloalkyl which is unsubstituted or mono- or polysubstituted, independently of one another, by Hal, A, . . . and/or —(CY$_2$)$_p$—NY—COY''" means that the cycloalkyl radical may be monosubstituted by one of the said substituents, or may have a plurality of substituents, which are selected, independently of one another, from the said substituents, in the case of cycloalkyl Hal, A, CN, —(CY$_2$)$_p$—OY, —(CY$_2$)$_p$—NYY, —(CY$_2$)$_p$—COOY, —(CY$_2$)$_p$—CO—NYY and/or —(CY$_2$)$_p$—NY—COY, i.e., for example, a cyclohexyl having the three substituents fluorine, chlorine and —CH$_2$—NH$_2$.

The terms used here for the definition of the compounds are generally based on the rules of the IUPAC organisation for chemical compounds and in particular organic compounds. The terms for the explanation of the above-mentioned compounds of the invention always have the following meanings, unless indicated otherwise in the description or claims.

The term "unsubstituted" means that a radical, a group or a residue carries no substituents. The term "substituted" means that a radical, a group or a residue carries one or more substituents. If only "substituted" is mentioned below with respect to a certain group or a certain radical whose substitution is defined specifically in connection with the above formula (I), it goes without saying that this substitution corresponds to that mentioned above, unless specifically indicated otherwise. It also goes without saying here in the sense of the invention that a radical can adopt all meanings mentioned previously in the description for the corresponding radical through reference to "the above-mentioned meaning" without specification thereof in greater detail.

"A" stands for an unbranched or branched alkyl having 1, 2, 3, 4, 5, 6, 7, 8, 9 or 10 C atoms, where, independently of one another, 1, 2, 3, 4, 5, 6 or 7 H atoms may be replaced by Hal. "A" is particularly preferably unbranched or branched alkyl having 1, 2, 3, 4, 5 or 6 C atoms, where, independently of one another, 1, 2, 3, 4 or 5 H atoms may be replaced by Hal, i.e. F, Cl, Br and/or I. It goes without saying that Hal in this connection can stand for various halogens F, Cl, Br, I, i.e., for example, 1 H may be replaced by F, another H may be replaced by Cl. Very particular preference is given to C$_{1-4}$-alkyl, where, independently of one another, 1, 2 or 3 H atoms may be replaced by Hal. A C$_{1-4}$-alkyl of this type is, for example, methyl, ethyl, propyl, isopropyl, butyl, isobutyl, sec-butyl, tert-butyl, fluoromethyl, difluoromethyl, trifluoromethyl, pentafluoroethyl, 1,1,1-trifluoroethyl or bromomethyl, most preferably methyl, ethyl, fluoromethyl, difluoromethyl or trifluoromethyl. It goes without saying that the respective meanings of "A" are independent of one another in the radicals of a formula according to the invention.

"Alkyl" herein denotes a saturated hydrocarbon radical, which is unbranched (linear) or branched and preferably has 1, 2, 3, 4, 5, 6, 7, 8, 9 or 10 C atoms, i.e. $C_{1-10}$-alkyl. Examples of alkyl radicals are methyl, ethyl, propyl, isopropyl, 1,1-, 1,2- or 2,2-dimethylpropyl, 1-ethylpropyl, 1-ethyl-1-methylpropyl, 1-ethyl-2-methylpropyl, 1,1,2- or 1,2,2-trimethylpropyl, butyl, isobutyl, sec-butyl, tert-butyl, 1-, 2- or 3-methylbutyl, 1,1-, 1,2-, 1,3-, 2,2-, 2,3- or 3,3-dimethylbutyl, 1- or 2-ethylbutyl, pentyl, isopentyl, neopentyl, tert-pentyl, 1-, 2-, 3- or 4-methylpentyl, hexyl.

"Z" herein denotes unbranched or branched alkenyl having 2, 3, 4, 5, 6, 7, 8, 9 or 10 C atoms, where, independently of one another, 1, 2, 3, 4, 5, 6 or 7 H atoms may be replaced by Hal. Alkenyls have at least one C—C double bond, may, in particular, also have two double bonds (dienes). Examples of suitable alkenyls are vinyl, allyl, propenyl —$CH_2CH=CH_2$; —$CH=CH—CH_3$; —$C(=CH_2)$—$CH_3$), 1-, 2- or 3-butenyl, isobutenyl, 2-methyl-1- or 2-butenyl, 3-methyl-1-butenyl, 1,3-butadienyl, 2-methyl-1,3-butadienyl, 2,3-dimethyl-1,3-butadienyl, 1-, 2-, 3- or 4-pentenyl and hexenyl, particularly preferably allyl.

The term "CyA" herein denotes cycloalkyl, in particular cyclic alkyl having 3, 4, 5 6, 7 or 8 ring C atoms, i.e. $C_{3-6}$-cycloalkyl which may be unsubstituted or mono- or polysubstituted, for example di- or trisubstituted, independently of one another, by Hal, A, CN, —$(CY_2)_p$—OY, —$(CY_2)_p$—NYY, —$(CY_2)_p$—COOY, —$(CY_2)_p$—CO—NYY and/or —$(CY_2)_p$—NY—COY. Examples of unsubstituted cycloalkyls are cyclopropyl, cyclobutyl, cyclopentyl, cyclohexyl, cycloheptyl and cyclooctyl. Unsubstituted cyycloalkyl groups are preferred herein, in particular cyclopropyl.

"Het$^1$" herein denotes a mono- or bicyclic aromatic heterocycle, i.e. hetaryl or heteroaryl, having 2, 3, 4, 5, 6, 7, 8 or 9 C atoms and 1, 2, 3 or 4 N, O and/or S atoms, i.e. at least one heteroatom, which may be unsubstituted or mono-, di- or trisubstituted, independently of one another, by Hal, A, CN, —$(CY_2)_p$—OY, —$(CY_2)_p$—NYY, —$(CY_2)_p$—COOY, —$(CY_2)_p$—CO—NYY, —$(CY_2)_p$—NY—COY, -Het$^2$ and/or —$SO_2$-Het$^2$ "Het$^1$" thus denotes a 5, 6, 7, 8, 9, 10, 11, 12, 13, 14 or 15, preferably 5-10-membered mono- or bicyclic aromatic hydrocarbon radical which includes at least 1, if appropriate also 2, 3, 4 or 5 heteroatoms, in particular nitrogen, oxygen and/or sulfur, where the heteroatoms may be identical different. The number of nitrogen atoms is preferably 0, 1, 2, 3 or 4, and the number of oxygen and sulfur atoms is, independently of one another, 0 or 1, where at least one heteroatom must be present. Heterocycles containing nitrogen atoms are preferred. "Het$^1$" can be selected, irrespective of further substitutions, from, for example: furyl, in particular 2- or 3-furyl, thienyl, in particular 2- or 3-thienyl, pyrrolyl, in particular 1-, 2- or 3-pyrrolyl, imidazolyl, in particular 1-, 2-, 4- or 5-imidazolyl, pyrazolyl, in particular 1-, 3-, 4- or 5-pyrazolyl, oxazolyl, in particular 2-, 4- or 5-oxazolyl, isoxazolyl, in particular 3-, 4- or 5-isoxazolyl, thiazolyl, in particular 2-, 4- or 5-thiazolyl, isothiazolyl, in particular 3-, 4- or 5-isothiazolyl, pyridyl, in particular 2-, 3- or 4-pyridyl, where pyridyl and pyridinyl are used synonymously herein, pyrimidinyl, in particular 2-, 4-, 5- or 6-pyrimidinyl, triazolyl, in particular 1,2,3-triazol-1-, -4- or -5-yl, 1,2,4-triazol-1-, -3- or 5-yl, triazinyl, tetrazolyl, in particular 1- or 5-tetrazolyl, oxadiazolyl, in particular 1,2,3-oxadiazol-4- or -5-yl, 1,2,4-oxadiazol-3- or -5-yl, thiadiazolyl, in particular 1,3,4-thiadiazol-2- or -5-yl, 1,2,4-thiadiazol-3- or -5-yl, 1,2,3-thiadiazol-4- or -5-yl, pyridazinyl, in particular 3- or 4-pyridazinyl, pyrazinyl, indolyl, in particular 1-, 2-, 3-, 4-, 5-, 6- or 7-indolyl, isoindolyl, in particular 4- or 5-isoindolyl, benzimidazolyl, in particular 1-, 2-, 4- or 5-benzimidazolyl, indazolyl, in particular 1-, 2-, 3-, 4-, 5-, 6- or 7-indazolyl, benzopyrazolyl, in particular 1-, 3-, 4-, 5-, 6- or 7-benzopyrazolyl, benzoxazolyl, in particular 2-, 4-, 5-, 6- or 7-benzoxazolyl, benzisoxazolyl, in particular 3-, 4-, 5-, 6-, or 7-benzisoxazolyl, benzothiazolyl, in particular 2-, 4-, 5-, 6- or 7-benzothiazolyl, benzisothiazolyl, in particular 2-, 4-, 5-, 6- or 7-benzisothiazolyl, 4-, 5-, 6- or 7-benz-2,1,3-oxadiazolyl, quinolyl, in particular 2-, 3-, 4-, 5-, 6-, 7- or 8-quinolyl, isoquinolyl, in particular 1-, 3-, 4-, 5-, 6-, 7- or 8-isoquinolyl, cinnolinyl, in particular 3-, 4-, 5-, 6-, 7- or 8-cinnolinyl, quinazolinyl, in particular 2-, 4-, 5-, 6-, 7- or 8-quinazolinyl, quinoxalinyl, in particular 5- or 6-quinoxalinyl, 2-, 3-, 5-, 6-, 7- or 8-2H-benzo[1,4]-oxazinyl, 1,3-benzodioxol-5-yl, 1,4-benzodioxan-6-yl, 2,1,3-benzothiadiazol-4- or -5-yl, 2,1,3-benzoxadiazol-5-yl, phthalazinyl, indolizinyl, and pteridinyl. The linking "-"Het$^1$ can take place via any ring member of the heteroaryl group, so long as it appears chemically appropriate, where bonding via a C atom is preferred. If only one of the two rings in a bicyclic aromatic heterocycle (annelated rings) contains one or more heteroatoms, the linking preferably takes place via the ring which contains the heteroatom(s). One ring contains no heteroatom if none of the atoms forming the ring is a heteroatom, including atoms which are to be assigned to both rings. Particularly preferred embodiments of Het1 are mentioned below.

"Het$^2$" herein is a monocyclic saturated heterocycle having 2, 3, 4, 5, 6 or 7 C atoms and 1, 2, 3 or 4 N, O and/or S atoms, which may be unsubstituted or monosubstituted by A. "Het$^2$" preferably denotes a monocyclic saturated heterocycle having 3, 4 or 5 C atoms and 1 or 2 N and/or O atoms. Examples of Het$^2$ are aziridinyl, oxiranyl, thiaranyl, azetidinyl, oxetanyl, dioxetanyl, thietanyl, pyrrolidinyl, tetrahydrofuranyl, dithiolanyl, oxazolidinyl, piperidinyl, tetrahydropyranyl, piperazinyl, dioxanyl, thiomorpholinyl, morpholinyl, oxepanyl, thiepanyl, and azepanyl. N-containing monocyclic saturated heterocycles are preferred, for example, azetidinyl, pyrrolidinyl, piperidinyl, piperazinyl and morpholinyl, where these may in accordance with the general definition be unsubstituted or monosubstituted by A. Unsubstituted azetidinyl, pyrrolidinyl, piperidinyl, piperazinyl and morpholinyl count amongst preferred embodiments, particularly preferably azetidinyl and piperazinyl. Furthermore, tetrahydropyranyl is also preferred. The linking "-"Het$^2$ in the group —$SO_2$-Het$^2$ typically takes place via a C atom. Otherwise, i.e., for example, as a substituent of HET, the linking can take place via any ring member of the heterocycle group, so long as it appears chemically appropriate, where here too bonding via a C atom is preferred.

For the purposes of the present invention, "HET" stands for a 5- or 6-membered aromatic heterocycle having 1, 2 or 3 N atoms and optionally an O atom or S atom, where this heterocycle is linked to the N atom of the skeleton via a ring C atom and where this heterocycle may be unsubstituted or substituted by one, two or three substituents, which are selected, independently of one another, from the group consisting of: Hal, A, Het$^2$, CN, —$(CY_2)_p$—OY, —$(CY_2)_p$—OZ, —$(CY_2)_p$—O-Het$^2$, —$(CY_2)_p$—O—$(CY_2)_t$-Het$^2$, —$(CY_2)_p$—O—$(CY_2)_t$—NYY, —$(CY_2)_p$—O—$(CY_2)_t$—OY, —$(CY_2)_p$—O—$(CY_2)_t$—POAA, —$(CY_2)_p$—NYY, —$(CY_2)_p$—COOY, —$(CY_2)_p$—CO—NYY, —$(CY_2)_p$—NY—COY, —$SO_2$-Het$^2$, CyA, —$(CY_2)_p$—O—$(CY_2)_t$—

SO$_2$—Y, —(CY$_2$)$_p$—NY—SO$_2$—Y, and —(CY$_2$)$_p$—SO$_2$—Y, and where this heterocycle may be part of a bicyclic 11- or 12-membered aromatic heterocycle, where this bicyclic aromatic heterocycle may overall be unsubstituted or substituted by one, two, three or more substituents, which are selected, independently of one another, from the group consisting of: Hal, A, Het$^2$, —CN, —(CY$_2$)$_p$—OY, —(CY$_2$)$_p$—OZ, —(CY$_2$)$_p$—O-Het$^2$, —(CY$_2$)$_p$—O—(CY$_2$)$_t$-Het$^2$, —(CY$_2$)$_p$—O—(CY$_2$)$_t$—NYY, —(CY$_2$)$_p$—O—(CY$_2$)$_t$—OY, —(CY$_2$)$_p$O—(CY$_2$)$_t$—POAA, —(CY$_2$)$_p$—NYY, —(CY$_2$)$_p$—COOY, —(CY$_2$)$_p$—CO—NYY, —(CY$_2$)$_p$—NY—COY, —SO$_2$—Het$^2$, CyA, —(CY$_2$)$_p$—O—(CY$_2$)$_t$—SO$_2$—Y, —(CY$_2$)$_p$—NY—SO$_2$—Y, and —(CY$_2$)$_p$—SO$_2$—Y. In other words, the second ring of the bicyclic aromatic heterocycle may also be correspondingly substituted. In a first embodiment, "HET" is thus a monocyclic 5- or 6-membered aromatic heterocycle, in a second embodiment is a bicyclic 11- or 12-membered aromatic heterocycle, where it should be understood that the linking to the imidazolonylquinoline skeleton takes place via the ring of the bicyclic heterocycle that corresponds to the monocyclic HET. Specifically, this means that, in the case of, for example, benzannelated systems, the linking takes place via the ring that contains the heteroatom(s), so long as the heteroatom(s) are to be assigned to only one ring (and are not involved in the linking to the second ring). In the bicyclic 11- or 12-membered aromatic heterocycle, both rings are aromatic. The fact that the bicyclic heterocycle may overall be substituted by one, two, three or more substituents is thus tantamount to these substituents being able to be positioned overall at any desired point of the heterocycle (i.e. as desired on any one of the ring parts).

The term "Hal", or also "halogen", "halogen atom", "halogen substituent", herein denotes one or more atoms of fluorine (F), bromine (Br), chlorine (Cl) or iodine (I). The terms "dihalogen", "trihalogen" and "perhalogen" relate to two, three or four substituents, where each substituent can be selected, independently of one another, from the group of F, Cl, Br or I. "Halogen" preferably means F, Cl or Br. F and Cl are particularly preferred, in particular if the halogens are substituents on an alkyl (haloalkyl) or alkoxy group (for example CF$_3$ and CF$_3$O).

"CN" can stand both for cyano and also for isocyano, where the meaning cyano (—CN) is preferred.

—POAA, —COOY, —CO—NYY, —COOY and —NY—COY are conventional notations for the following groups:

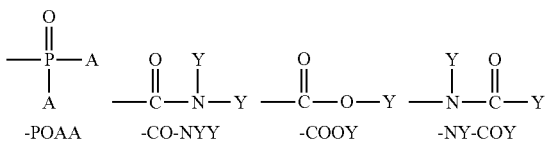

The index p preferably denotes 0, 1, 2 or 3, particularly preferably 0.

The index t preferably denotes 1, 2, 3 or 4, particularly preferably 2.

Examples of —(CY$_2$)$_p$—OY, —(CY$_2$)$_p$—OZ, —(CY$_2$)$_p$—O-Het$^2$, —(CY$_2$)$_p$—O—(CY$_2$)$_t$-Het$^2$, —(CY$_2$)$_p$—O—(CY$_2$)$_t$—NYY, —(CY$_2$)$_p$—O—(CY$_2$)$_t$—OY, —(CY$_2$)$_p$—O—(CY$_2$)$_t$—POAA, —(CY$_2$)$_p$—NYY, —(CY$_2$)$_p$—COOY, —(CY$_2$)$_p$—CO—NYY, —(CY$_2$)$_p$—NY—COY, —(CY$_2$)$_p$—O—(CY$_2$)$_t$—SO$_2$-Y, —(CY$_2$)$_p$—NY—SO$_2$—Y, and —(CY$_2$)$_p$SO$_2$—Y are thus: —OY, —OH, —O-A, —O—CH$_3$, —O—CHF$_2$, —O—CH$_2$F, —O—CH$_2$CH$_3$, —(CH$_2$)$_p$—OY, —CH$_2$—O—CH$_3$, —CH$_2$—O—CH$_2$CH$_3$, —O—CH=CH$_2$, —CH$_2$—O—CH=CH$_2$, —O—CH$_2$—CH=CH$_2$, —CH$_2$—O—CH$_2$—CH=CH$_2$, —O-Het$^2$, —O—CH$_2$-Het$^2$, —O—CH$_2$CH$_2$-Het$^2$, —O—CH$_2$—NYY, —O—CH$_2$CH$_2$—NYY, —O—CH$_2$—NH$_2$, —O—CH$_2$CH$_2$—NH$_2$, —O—CH$_2$—NHCH$_3$, —O—CH$_2$CH$_2$—NHCH$_3$, —O—CH$_2$—OY, —O—CH$_2$CH$_2$—OY, —O—CH$_2$CH$_2$CH$_2$—OY, —O—CH$_2$—OH, —O—CH$_2$CH$_2$—OH, —O—CH$_2$CH$_2$CH$_2$—OH, —O—CH$_2$—OA, —O—CH$_2$CH$_2$—OA, —O—CH$_2$CH$_2$CH$_2$—OA, —O—CH$_2$—OCH$_3$, —O—CH$_2$CH$_2$—OCH$_3$, —O—CH$_2$CH$_2$CH$_2$—OCH$_3$, —O—CH$_2$—SO$_2$—Y, —O—CH$_2$—SO$_2$—CH$_3$, —NYY, —NH$_2$, —NHA, —NAA, —NHCH$_3$, —N(CH$_3$)$_2$, —CH$_2$—NYY, —CH$_2$—NH$_2$, —CH$_2$—NHA, —CH$_2$—NAA, —CH$_2$—NHCH$_3$, —CH$_2$—N(CH$_3$)$_2$, —COOY, —COOA, —CH$_2$—COOY, —CH$_2$—COOA, —CH$_2$—COOCH$_3$, —CO—NYY, —CON-AA, —CO—NHA, —CO—NH—CH$_3$, —CH$_2$—CO—NYY, —CH$_2$—CO—NAA, —(CH$_2$)$_p$—NY—COY, —(CH$_2$)$_p$NY—COA.

Correspondingly, the invention relates to the compounds of the formula (I) in which at least one of the said radicals has one of the meanings indicated above. Radicals not indicated in greater detail in the context of one of the formula (I), sub-formulae thereof or any residue thereon are intended to have the meaning indicated in the case of the formula (I), as disclosed herein, in order to achieve the object of the invention. This means that the said radicals can adopt all meanings ascribed to them as described above or below, including all preferred embodiments, without being restricted thereto and independently of their occurrence in another particular context. In particular, it goes without saying that each embodiment of a certain radical can be combined with each embodiment of one or more other radicals.

In an illustrative embodiment:

Het$^1$ denotes mono- or bicyclic heteroaryl having 2, 3, 4, 5, 6, 7, 8 or 9 C atoms and 1, 2, 3 or 4 N, O and/or S atoms, which may be unsubstituted or mono-, di- or trisubstituted, independently of one another, by Hal, A, CN, —(CY$_2$)$_p$—OY, —(CY$_2$)$_p$—NYY, —(CY$_2$)$_p$—COOY, —(CY$_2$)$_p$—CO—NYY, —(CY$_2$)$_p$—NY—COY and/or —SO$_2$-Het$^2$, HET denotes a 5- or 6-membered aromatic heterocycle having 1, 2 or 3 N atoms and optionally an O atom or S atom, where this heterocycle is linked to the N atom of the skeleton via a ring C atom and where this heterocycle may be unsubstituted or substituted by one, two or three substituents, which are selected, independently of one another, from the group consisting of: Hal, A, Het$^2$, CN, —(CY$_2$)$_p$—OY, —(CY$_2$)$_p$—O—(CY$_2$)$_t$—OY, —(CY$_2$)$_p$—O—(CY$_2$)$_t$—POAA, —(CY$_2$)$_p$—NYY, —(CY$_2$)$_p$—COOY, —(CY$_2$)$_p$—CO—NYY, —(CY$_2$)$_p$—NY—COY or —SO$_2$-Het$^2$; and may be part of a bicyclic 11- or 12-membered aromatic heterocycle, where this bicyclic aromatic heterocycle may overall be unsubstituted or substituted by one, two, three or more substituents, which are selected, independently of one another, from the group consisting of: Hal, A, Het$^2$, —CN, —(CY$_2$)$_p$—OY, —(CY$_2$)$_p$—O—(CY$_2$)$_t$—OY, —(CY$_2$)$_p$—O—(CY$_2$)$_t$—POAA, —(CY$_2$)$_p$—NYY, —(CY$_2$)$_p$—COOY, —(CY$_2$)$_p$—CO—NYY, —(CY$_2$)$_p$—NY—COY or —SO$_2$-Het$^2$, Hal denotes F, Cl, Br or I, P denotes, independently of one another, 0, 1, 2, 3, 4, 5 or 6 and t denotes 1, 2, 3, 4, 5 or 6.

Compounds of the formula (I) where R3=A can also be depicted as follows:

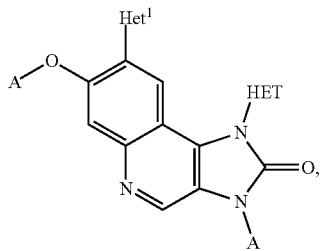

(IA)

where it is to be understood that the groups A can have the same or different meaning.

In preferred embodiments of the compounds of the formula (I) or (IA), R1 stands for unsubstituted or substituted $C_1$-$C_3$-alkyl, particularly preferably methyl. Correspondingly, the present invention provides preferred compounds of the following formulae (II):

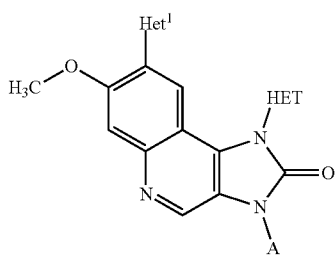

(II)

and the alternatives where R3=H.

In preferred embodiments of the compounds of the formulae (I) or (IA) and (II), R3 denotes H or, more preferably, unbranched or branched alkyl having 1, 2, or 3 C atoms, where 1, 2, 3, 4, or 5 H atoms may be replaced, independently of one another, by Hal. R3 particularly preferably denotes methyl. The present invention thus also provides compounds of the following formulae (III) and (IV):

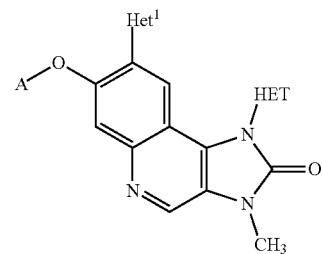

(III)

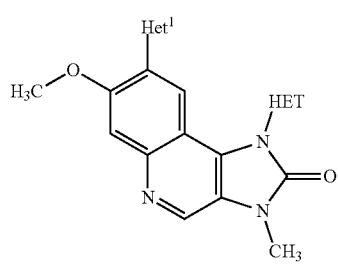

(IV)

In each of the formulae (I), (II), (III) and (IV), Het[1] is preferably a monocyclic heteroaryl having 2, 3, or 4 C atoms and 1, 2, or 3 N atoms, which may be unsubstituted or substituted as given defined in compound having formula (I). Het[1] (in each of the formulae shown) is furthermore particularly preferably selected from pyridinyl, pyrimidinyl, pyrazolyl, triazolyl and imidazolyl, which may be unsubstituted or substituted as defined above, where pyrazolyl and triazolyl, in particular 1,2,3-triazolyl, are particularly preferred.

Het[1] can be, for example, unsubstituted or substituted by one or two substituents, which are preferably selected, independently of one another, from: Hal, A, —(CY$_2$)$_p$—OY, —(CY$_2$)$_p$—NYY, and -Het[2], particularly preferably alkyl, which may be unsubstituted or mono- or polysubstituted by halogen, in particular F; —OY, —NYY, halogen, and -Het[2], particularly preferably methyl, ethyl, amino, methoxy, fluoromethyl, difluoromethyl, fluorine, azetidinyl, where methyl and ethyl are particularly preferred.

Het[1] (in each of the formulae shown) is particularly preferably selected from: 1H-pyrazol-4-yl, 2H-pyrazol-3-yl, 1H-pyrazol-3-yl, 1-methyl-1H-pyrazol-4-yl, 3-methyl-1H-pyrazol-4-yl, 5-methyl-1H-pyrazol-3-yl, 4-methyl-1H-pyrazol-3-yl, 1-fluoromethyl-1H-pyrazol-4-yl, 1-difluoromethyl-1H-pyrazol-4-yl, 1,3-dimethyl-1H-pyrazol-4-yl, 1-ethyl-1H-pyrazol-4-yl, 1-ethyl-3-methyl-1H-pyrazolyl, 3-fluoro-1-methyl-1H-pyrazol-4-yl, 3-amino-1H-pyrazol-5-yl, 2H-1,2,3-triazol-4-yl, 3H-1,2,3-triazol-4-yl-, 1-methyl-1H-1,2,3-triazol-4-yl, 2-methyl-2H-1,2,3-triazol-4-yl, 2-amino-1H-imidazol-4-yl, 6-methoxypyridin-3-yl, and 1-(azetidin-3-yl)-3-methyl-1H-pyrazol-4-yl. Het[1] is very preferably pyrazolyl, which may be unsubstituted or substituted as defined above, and can be selected, for example, from 1H-pyrazol-4-yl, 2H-pyrazol-3-yl, 1H-pyrazol-3-yl, 1-methyl-1H-pyrazol-4-yl, 3-methyl-1H-pyrazol-4-yl, 5-methyl-1H-pyrazol-3-yl, 4-methyl-1H-pyrazol-3-yl, 1-fluoromethyl-1H-pyrazol-4-yl, 1-diluormethyl-1H-pyrazol-4-yl, 1,3-dimethyl-1H-pyrazol-4-yl, 1-ethyl-1H-pyrazol-4-yl, 1-ethyl-3-methyl-1H-pyrazolyl, 3-fluoro-1-methyl-1H-pyrazol-4-yl, 3-amino-1H-pyrazol-5-yl, where 1H-pyrazol-4-yl, 2H-pyrazol-3-yl, 1H-pyrazol-3-yl, 1-methyl-1H-pyrazol-4-yl, 3-methyl-1H-pyrazol-4-yl, 5-methyl-1H-pyrazol-3-yl, 4-methyl-1H-pyrazol-3-yl, 1-fluoromethyl-1H-pyrazol-4-yl, 1,3-dimethyl-1H-pyrazol-4-yl, 1-ethyl-1H-pyrazol-4-yl and are particularly preferred. Alternatively, Het[1] is preferably triazolyl, which may be unsubstituted or substituted as defined above, and can be selected, for example, from 2H-1,2,3-triazol-4-yl, 3H-1,2,3-triazol-4-yl-, 1-methyl-1H-1,2,3-triazol-4-yl, 2-methyl-2H-1,2,3-triazol-4-yl, particularly preferably 2-methyl-2H-1,2,3-triazol-4-yl.

In other embodiments of the compounds of one of each of the of the formulae (I), (II), (III) and (IV), Het[1] can be a bicyclic heteroaryl having 6, 7 or 8 C atoms and 1, 2, or 3 N atoms sein, which may be unsubstituted or substituted as defined above. Preferred substituents are, analogously to the monocyclic heteroaryls, Hal, A, —(CY$_2$)$_p$—OY, —(CY$_2$)$_p$—NYY, and -Het[2], particularly preferably alkyl. For example, Het[1] can be selected from bezimidazolyl, imidazo[4,5-b]pyridinyl, benzodiazolyl, which may be unsubstituted or substituted as mentioned as preferred in relation to formula (I) and above, preferably, for example, 2-methyl-3H-benzimidazol-5-yl, 3H-benzimidazol-5-yl, 2-methyl-1H-imidazo[4,5-b]pyridin-6-yl.

In preferred embodiments of compounds of one of each of the of the formulae (I), (II), (III) and (IV), HET is selected from the following aromatic heterocycles, which may in each case be unsubstituted or substituted as defined above: HET denotes, irrespective of possible substitution, pyrrolyl, oxazolyl, isoxazolyl, thiazolyl, isothiazolyl, pyrazolyl, imidazolyl, 1-oxa-2,3-diazolyl, 1-oxa-2,4-diazolyl, 1-oxa-3,4-diazolyl, 1-oxa-2,5-diazolyl, 1-thia-2,3-diazolyl, 1-thia-2,4-diazolyl, 1-thia-3,4-diazolyl, 1-thia-2,5-diazolyl, 1,2,3-triazolyl, 1,3,4-triazolyl, and tetrazolyl; pyridinyl, pyrimidinyl, pyrazinyl and pyridazinyl; indolyl, isoindolyl, benzimidazolyl, indazolyl, benzoxazolyl, benzothiazolyl, benzotriazolyl, pyrrolo[2,3-b]pyridinyl, pyrrolo[2,3-c]pyridinyl, pyrrolo[3,2-b]pyridinyl, pyrrolo[3,2-c]pyridinyl, imidazo[4,5-b]pyridinyl, imidazo[4,5-c]pyridinyl, pyrazolo[4,3-d]pyridinyl, pyrazolo[4,3-c]pyridinyl, pyrazolo[3,4-c]pyridinyl, pyrazolo[3,4-b]pyridinyl, purinyl, indozilinyl, imidazo[1,2-a]pyridinyl, imidazo[1,5-a]pyridinyl, pyrazolo[1,5-a]pyridinyl, pyrrolo[1,2-b]-pyridazinyl, imidazo[1,2-c]pyrimidinyl, quinolinyl, isoquinolinyl, cinnolinyl, quinazolinyl, quinoxalinyl, phtalazinyl, 1,6-naphtyridinyl, 1,7-naphtyridinyl, 1,8-naphtyridinyl, 1,5-naphtyridinyl, 2,6-naphthyridinyl, 2,7-naphthyridinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-d]pyrazinyl, pyrido[3,4-b]-pyrazinyl, pyrazino[2,3-b]pyrazinyl, pyrimido[5,4-d]pyrimidinyl, pyrimido[4,5-d]pyrimidinyl, benzoxazolyl, benzothiazolyl, benzisoxazolyl, benzisothiazolyl, furopyridinyl, and thienopyridinyl.

HET is particularly preferably selected from the following 5- or 6-membered monocyclic aromatic heterocycles, which may in each case be unsubstituted or substituted as defined above: pyridinyl, pyrimidinyl, pyrazolyl, thiazolyl, imidazolyl.

These preferences for HET also apply, in particular, to compounds of the formulae (I), (II), (III), (IV), in combination with the preferred embodiments for $Het^1$, in particular the selection of $Het^1$ from pyridinyl, pyrimidinyl, pyrazolyl, triazolyl and imidazolyl, as well as bezimidazolyl, imidazo[4,5-b]pyridinyl, benzodiazolyl, which may in each case be unsubstituted or substituted as defined above, for example 1H-pyrazol-4-yl, 2H-pyrazol-3-yl, 1H-pyrazol-3-yl, 1-methyl-1H-pyrazol-4-yl, 3-methyl-1H-pyrazol-4-yl, 5-methyl-1H-pyrazol-3-yl, 4-methyl-1H-pyrazol-3-yl, 1-fluoromethyl-1H-pyrazol-4-yl, 1-diluormethyl-1H-pyrazol-4-yl, 1,3-dimethyl-1H-pyrazol-4-yl, 1-ethyl-1H-pyrazol-4-yl, 1-ethyl-3-methyl-1H-pyrazolyl, 3-fluoro-1-methyl-1H-pyrazol-4-yl, 3-amino-1H-pyrazol-5-yl, 2H-1,2,3-triazol-4-yl, 3H-1,2,3-triazol-4-yl-, 1-methyl-1H-1,2,3-triazol-4-yl, 2-methyl-2H-1,2,3-triazol-4-yl, 2-amino-1H-imidazol-4-yl, 6-methoxypyridin-3-yl, and 1-(azetidin-3-yl)-3-methyl-1H-pyrazol-4-yl, 2-methyl-3H-benzimidazol-5-yl, 3H-benzimidazol-5-yl, 2-methyl-1H-imidazo[4,5-b]pyridin-6-yl, and especially and in particular also to embodiments in which $Het^1$ stands for pyrazolyl, which may be unsubstituted or substituted as defined above and can be selected, for example, from 1H-pyrazol-4-yl, 2H-pyrazol-3-yl, 1H-pyrazol-3-yl, 1-methyl-1H-pyrazol-4-yl, 3-methyl-1H-pyrazol-4-yl, 5-methyl-1H-pyrazol-3-yl, 4-methyl-1H-pyrazol-3-yl, 1-fluoromethyl-1H-pyrazol-4-yl, 1,3-dimethyl-1H-pyrazol-4-yl, 1-ethyl-1H-pyrazol-4-yl.

Of the possible substituents on HET, preference is given to: Hal, in particular F, Cl; A, in particular methyl, ethyl, propyl; $Het^2$, in particular azetidinyl, tetrahydropyranyl, piperazinyl; CN; —$(CY_2)_p$—OY, —$(CY_2)_p$—OA, —$(CY_2)_p$—OH, preferably in each case where p=0, 1, 2, 3; —$(CY_2)_p$—OZ, —$(CY_2)_p$—O-$Het^2$, —O-$Het^2$, —$(CY_2)_p$—O—$(CY_2)_t$-$Het^2$, —O—$(CY_2)_t$-$Het^2$, —O—$(CH_2)_t$-$Het^2$, —$(CY_2)_p$—O—$(CY_2)_t$—NYY, —O—$(CY_2)_t$—NYY, —$(CY_2)_p$—O—$(CY_2)_t$—OY, —O—$(CY_2)_t$—OY, —O—$(CY_2)_t$—OA, —O—$(CY_2)_t$—OH, —O—$(CH_2)_t$—OA, —O—$(CH_2)_t$—OH, —$(CY_2)_p$—CO—NYY, —$(CY_2)_p$—CO—NHA, CyA, —$(CY_2)_p$—O—$(CY_2)_t$—SO_2-Y, —O—$(CY_2)_t$—SO_2-Y, —O—$(CY_2)_t$—SO_2-A, —$(CY_2)_p$—SO_2-Y, —$(CY_2)_p$—SO_2-A. For example, the aromatic heterocycles HET generally, and the preferred embodiments in particular, for example pyridinyl, pyrimidinyl, pyrazolyl, thiazolyl, imidazolyl, may in each case be substituted by one, two, three or more substituents, which are selected, independently of one another, from the group consisting of: F, Cl, methyl, ethyl, propyl, isopropyl, methoxy, ethoxy, propoxy, piperazinyl, tetrahydropyranyl, —CN, 2-methoxyethoxy, 2-hydroxyethoxy, fluoromethoxy, difluoromethoxy, N-methylcarbamoyl (—C(=O)—NH—$CH_3$), 2-methylamino-ethoxy, 1-methyl-azetidin-3-ylmethoxy, trideuteriomethoxy, trifluoromethoxy, methylsulfonylmethoxy, methylsulfonyl, cyclopropyl, allyloxy, piperazinyl, and azetidinyloxy. No, mono- or disubstitution are preferred.

A preferred embodiment of HET is unsubstituted or substituted pyridinyl, for example mono- or disubstituted pyridinyl. Monosubstituted pyridinyls are preferably substituted in position 3 of the pyridine ring and linked via positions 2 or 4, disubstituted pyridinyls are preferably substituted in positions 3 and 5 of the pyridine ring and linked via positions 2 or 4. This preferred embodiment can advantageously be combined with the preferred embodiments of $Het^1$, in particular the preferred embodiments in which $Het^1$ is unsubstituted or substituted pyrazolyl or alternatively unsubstituted or substituted triazolyl, and in particular with the above-mentioned particularly preferred embodiments.

In other preferred embodiments, HET is an unsubstituted, but preferably mono- or disubstituted pyrazole. This embodiment too can advantageously be combined with the preferred embodiments of $Het^1$, in particular the preferred embodiments in which $Het^1$ is unsubstituted or substituted pyrazolyl or alternatively unsubstituted or substituted triazolyl, and in particular with the above-mentioned particularly preferred embodiments.

In a further preferred embodiment, HET is an unsubstituted, but preferably monosubstituted pyrimidine, where the pyrimidine is preferably substituted in position 5 and linked via positions 2 or 4. This embodiment too can advantageously be combined with the preferred embodiments of $Het^1$, in particular the preferred embodiments in which $Het^1$ is unsubstituted or substituted pyrazolyl or alternatively unsubstituted or substituted triazolyl, and in particular with the above-mentioned particularly preferred embodiments.

In preferred embodiments of one of each of the formulae (I), (II), (III), (IV), HET can be selected, for example, from the following 5- or 6-membered monocyclic aromatic heterocycles: pyridin-2-yl, pyridin-4-yl, 5-allyloxy-3-fluoropyridin-2-yl, 5-(azetidin-3-yloxy)-3-fluoropyridin-2-yl, 5-chloro-3-fluoropyridin-2-yl, 3-cyclopropylpyridin-4-yl, 3-cyclopropyl-5-fluoropyridin-4-yl, 3,5-difluoropyridin-2-yl, 3,5-difluoropyridin-4-yl, 5-difluoromethoxy-3-fluoropyridin-2-yl, 3-difluoromethoxy-5-fluoropyridin-4-yl, 5-ethoxy-3-fluoropyridin-2-yl, 3-fluoro-5-(1-methylazetidin-3-ylmethoxy)pyridin-2-yl, 3-fluoro-5-methoxypyridin-4-yl, 3-fluoro-5-methoxypyridin-2-yl, 3-fluoro-5-fluoromethoxypyridin-2-yl, 3-fluoro-5-fluoromethoxypyridin-4-yl, 3-fluoropyridin-2-yl, 3-fluoro-5-methylsulfonylmethoxypyridin-2-yl, 3-fluoro-5-methylsulfonylpyridin-2-yl 3-fluoro-5-(2-methylaminoethoxy)pyridin-2-yl, 3-fluoro-5- methylpyridin-4-yl, 3-fluoro-5-methylpyridin-2-yl, 3-fluoropyridin-4-yl, 3-fluoropyridin-2-yl, 3-fluoro-5-piperazin-1-ylpyridin-2-yl, 3-chloropyridin-4-yl, 3-ethylpyridin-4-yl, 3-ethyl-5-fluoropyridin-4-yl, 3-ethyl-5-methylpyridin-4-yl, 5-fluoropyridin-2-yl, 3-methylpyridin-4-yl, 3-methoxypyridin-4-yl, 2-cyanopyridin-4-yl, 3-cyanopyridin-4-yl, 3-cyanopyridin-6-yl, 3-cyano-5-fluoropyridin-4-yl, 3-fluoro-5-(2-methoxyethoxy)pyridin-2-yl, 3-fluoro-5-(2-hydroxyethoxy)pyridin-2-yl, 3-fluoro-5-(trideuteriomethoxy)pyridin-4-yl, 3-fluoro-5-(trideuteriomethoxy)pyridin-2-yl, 5-fluoro-3-(N-methylcarbamoyl)pyridin-6-yl, 5-fluoropyrimidin-2-yl, 5-fluoropyrimidin-4-yl, pyrimidin-2-yl, pyrimidin-5-yl, 1H-pyrazol-4-yl, 1-ethyl-3-methyl-1H-pyrazol-4-yl, 1,2-dimethyl-1H-pyrazol-4-yl, 1,3-dimethyl-1H-pyrazol-4-yl, 1-methyl-1H-pyrazol-4-yl, 1-(tetrahydropyran-4-yl)-1H-pyrazol-4-yl, 2-methyl-2H-pyrazol-3-yl, 3-methyl-1H-pyrazol-4-yl, 3,5-dimethyl-1H-pyrazol-4-yl, 3-fluoro-1-methylpyrazol-4-yl, thiazol-2-yl, 2-methylthiazol-4-yl, and 1-methyl-1H-imidazolyl. Particular preference is given to: 5-chloro-3-fluoropyridin-2-yl, 3,5-difluoropyridin-2-yl, 3,5-difluoropyridin-4-yl, 5-difluoromethoxy-3-fluoropyridin-2-yl, 3-difluoromethoxy-5-fluoropyridin-4-yl, 5-ethoxy-3-fluoropyridin-2-yl, 3-fluoro-5-methoxypyridin-4-yl, 3-fluoro-5-methoxypyridin-2-yl, 3-fluoro-5-fluoromethoxypyridin-2-yl, 3-fluoro-5-fluoromethoxypyridin-4-yl, 3-fluoropyridin-2-yl, 3-fluoro-5-methylsulfonylmethoxypyridin-2-yl, 3-fluoro-5-methylpyridin-4-yl, 3-fluoro-5-methylpyridin-2-yl, 3-fluoropyridin-4-yl, 3-ethylpyridin-4-yl, 3-ethyl-5-fluoropyridin-4-yl, 3-methylpyridin-4-yl, 3-methoxypyridin-4-yl, 3-fluoro-5-(2-methoxyethoxy)pyridin-2-yl, 3-fluoro-5-(2-hydroxyethoxy)pyridin-2-yl, 3-fluoro-5-(trideuteriomethoxy)pyridin-4-yl, 3-fluoro-5-(trideuteriomethoxy)pyridin-2-yl, 5-fluoropyrimidin-2-yl, 5-fluoropyrimidin-4-yl, 1,3-dimethyl-1H-pyrazol-4-yl, 1-methyl-1H-pyrazol-4-yl, 1-(tetrahydropyran-4-yl)-1H-pyrazol-4-yl, and 2-methylthiazol-4-yl.

The preference for the above-mentioned 5- or 6-membered monocyclic aromatic or heterocycles also applies, in particular, to compounds of the formulae (I), (II), (III), (IV) in combination with the preferred embodiments for Het$^1$, in particular the selection of Het$^1$ from pyridinyl, pyrimidinyl, pyrazolyl, triazolyl and imidazolyl, which may be unsubstituted or substituted as defined above and especially and in particular also to the embodiments in which Het$^1$ stands for pyrazolyl, which may be unsubstituted or substituted as defined above and can be selected, for example, from the examples explicitly mentioned above. They also apply, in particular, to the embodiments in which Het$^1$ stands for triazolyl, and can be selected, for example, from the examples explicitly mentioned above.

In other illustrative embodiments of one of each of the formulae (I), (II), (III), (IV), HET can be selected from pyrrolo[3,2-c]pyridinyl, pyrrolo[2,3-b]pyridinyl and quinolinyl, which may in each case be unsubstituted or substituted as mentioned for compound (I) and in particular for the monocyclic preferred embodiments. Examples are 1H-pyrrolo[3,2-c]pyridin-6-yl, 1H-pyrrolo[2,3-b]pyridin-6-yl or 5-fluoro-1H-pyrrolo[2,3-b]pyridin-6-yl, in each case in particular also in each case in combination with one of the preferred embodiments of Het$^1$ mentioned above.

Very particular preference is given to the compounds shown in Table 1 below, and pharmaceutically usable derivatives, salts, solvates, tautomers and/or stereoisomers thereof, or free forms including mixtures thereof in all ratios.

TABLE 1

Particularly preferred compounds

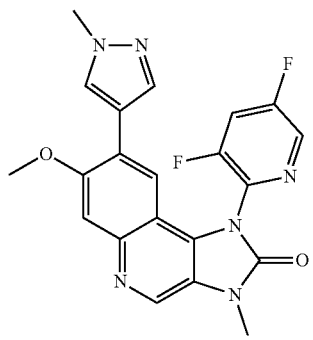 [SMILES: COc1cc2ncc3c(c2cc1-c1cnn(C)c1)n(-c1ncc(F)cc1F)c(=O)n3C]

1-(3,5-Difluoropyridin-2-yl)-7-methoxy-3-methyl-8-(1-methyl-1H-pyrazol-4-yl)-1,3-dihydroimidazo[4,5-c]quinolin-2-one

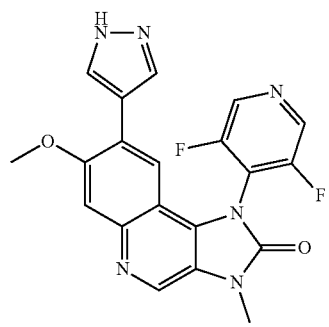 [SMILES: COc1cc2ncc3c(c2cc1-c1cn[nH]c1)n(-c1c(F)cncc1F)c(=O)n3C]

1-(3,5-Difluoropyridin-4-yl)-7-methoxy-3-methyl-8-(1H-pyrazol-4-yl)-1,3-dihydroimidazo[4,5-c]quinolin-2-one TABLE 1-continued Particularly preferred compounds

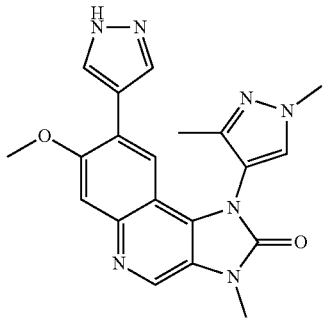

1-(1,3-Dimethyl-1H-pyrazol-4-yl)-7-methoxy-3-methyl-8-(1H-pyrazol-4-yl)-1,3-dihydroimidazo[4,5-c]quinolin-2-one

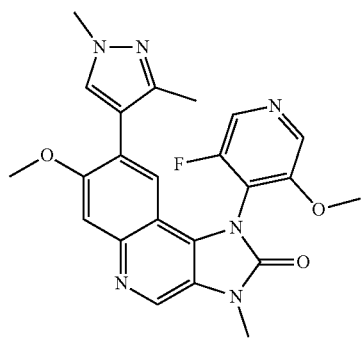

8-(1,3-Dimethyl-1H-pyrazol-4-yl)-1-(3-fluoro-5-methoxypyridin-4-yl)-7-methoxy-3-methyl-1,3-dihydro-imidazo[4,5-c]quinolin-2-one

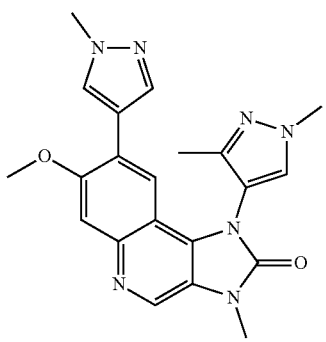

1-(1,3-Dimethyl-1H-pyrazol-4-yl)-7-methoxy-3-methyl-8-(1-methyl-1H-pyrazol-4-yl)-1,3-dihydroimidazo[4,5-c]quinolin-2-one

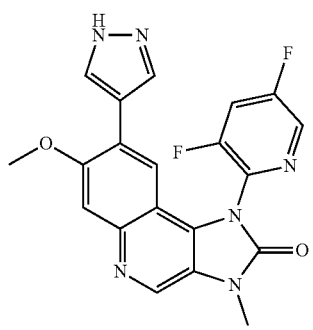 [SMILES: COc1cc2ncc3c(c2cc1-c1cn[nH]c1)n(-c1ncc(F)cc1F)c(=O)n3C]

1-(3,5-Difluoropyridin-2-yl)-7-methoxy-3-methyl-8-(1H-pyrazol-4-yl)-1,3-dihydroimidazo[4,5-c]quinolin-2-one TABLE 1-continued Particularly preferred compounds 1-(3-Fluoropyridin-2-yl)-7-methoxy-3-methyl-8-(1H-pyrazol-4-yl)-1,3-dihydroimidazo[4,5-c]quinolin-2-one 1-(3-Fluoro-5-methylpyridin-4-yl)-7-methoxy-3-methyl-8-(1H-pyrazol-4-yl)-1,3-dihydroimidazo[4,5-c]quinolin-2-one 1-(3-Fluoropyridin-4-yl)-7-methoxy-3-methyl-8-(1H-pyrazol-4-yl)-1,3-dihydroimidazo[4,5-c]quinolin-2-one 1,8-Bis(1,3-dimethyl-1H-pyrazol-4-yl)-7-methoxy-3-methyl-1,3-dihydroimidazo[4,5-c]quinolin-2-one TABLE 1-continued Particularly preferred compounds

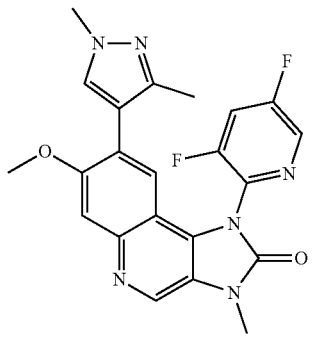 [SMILES: COc1cc2ncc3c(c2cc1-c1cn(C)nc1C)n(-c1ncc(F)cc1F)c(=O)n3C]
1-(3,5-Difluoropyridin-2-yl)-8-(1,3-dimethyl-1H-pyrazol-4-yl)-7-methoxy-3-methyl-1,3-dihydroimidazo[4,5-c]quinolin-2-one

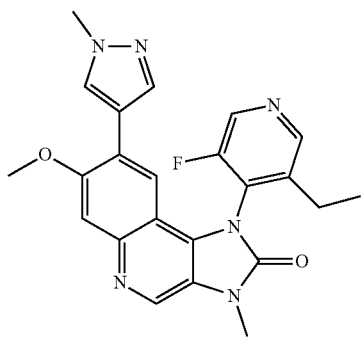 [SMILES: CCc1cncc(F)c1-n1c(=O)n(C)c2cnc3cc(OC)c(-c4cnn(C)c4)cc3c21]
1-(3-Ethyl-5-fluoropyridin-4-yl)-7-methoxy-3-methyl-8-(1-methyl-1H-pyrazol-4-yl)-1,3-dihydroimidazo[4,5-c]quinolin-2-one

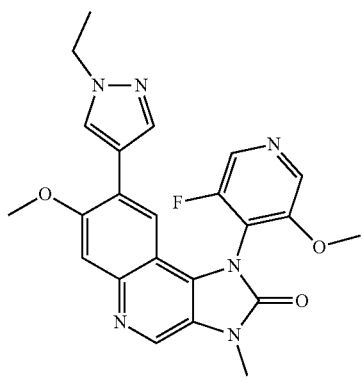
8-(1-Ethyl-1H-pyrazol-4-yl)-1-(3-fluoro-5-methoxypyridin-4-yl)-7-methoxy-3-methyl-1,3-dihydroimidazo[4,5-c]quinolin-2-one

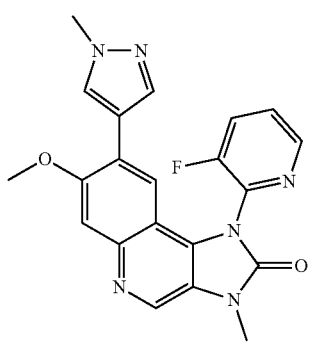 [SMILES: COc1cc2ncc3c(c2cc1-c1cnn(C)c1)n(-c1ncccc1F)c(=O)n3C]
1-(3-Fluoropyridin-2-yl)-7-methoxy-3-methyl-8-(1-methyl-1H-pyrazol-4-yl)-1,3-dihydroimidazo[4,5-c]quinolin-2-one TABLE 1-continued Particularly preferred compounds

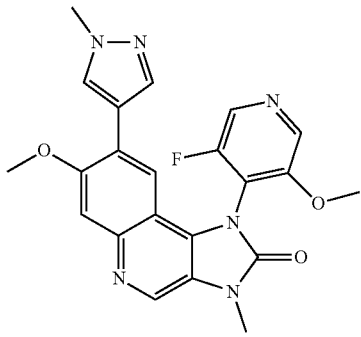

1-(3-Fluoro-5-methoxypyridin-4-yl)-7-methoxy-3-methyl-8-(1-methyl-1H-pyrazol-4-yl)-1,3-dihydroimidazo[4,5-c]quinolin-2-one

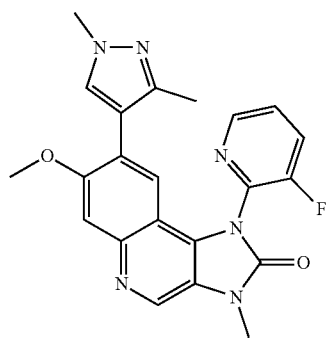 [SMILES: COc1cc2ncc3c(c2cc1-c1cn(C)nc1C)n(-c1ncccc1F)c(=O)n3C]

8-(1,3-Dimethyl-1H-pyrazol-4-yl)-1-(3-fluoropyridin-2-yl)-7-methoxy-3-methyl-1,3-dihydroimidazo[4,5-c]quinolin-2-one

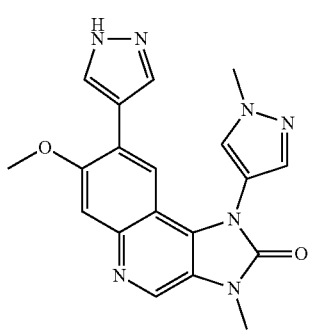 [SMILES: COc1cc2ncc3c(c2cc1-c1cn[nH]c1)n(-c1cnn(C)c1)c(=O)n3C]

7-Methoxy-3-methyl-1-(1-methyl-1H-pyrazol-4-yl)-8-(1H-pyrazol-4-yl)-1,3-dihydroimidazo[4,5-c]quinolin-2-one

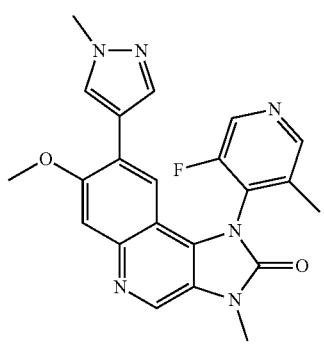

1-(3-Fluoro-5-methylpyridin-4-yl)-7-methoxy-3-methyl-8-(1-methyl-1H-pyrazol-4-yl)-1,3-dihydroimidazo[4,5-c]quinolin-2-one TABLE 1-continued Particularly preferred compounds

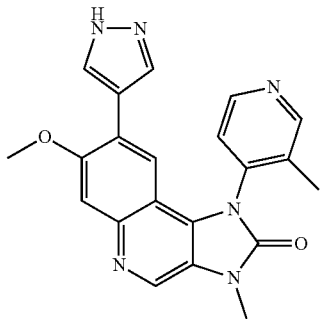
7-Methoxy-3-methyl-1-(3-methylpyridin-4-yl)-8-(1H-pyrazol-4-yl)-1,3-dihydroimidazo[4,5-c]quinolin-2-one

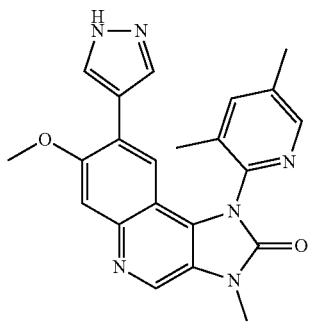 [SMILES: COc1cc2ncc3c(c2cc1-c1cn[nH]c1)n(-c1ncc(C)cc1C)c(=O)n3C]
1-(3-Fluoro-5-methylpyridin-2-yl)-7-methoxy-3-methyl-8-(1H-pyrazol-4-yl)-1,3-dihydroimidazo[4,5-c]quinolin-2-one

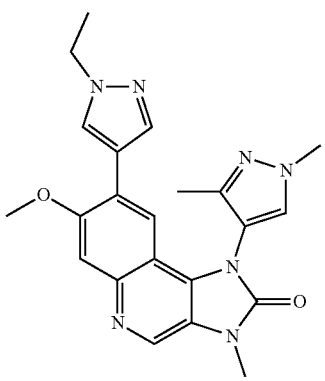
1-(1,3-Dimethyl-1H-pyrazol-4-yl)-8-(1-ethyl-1H-pyrazol-4-yl)-7-methoxy-3-methyl-1,3-dihydroimidazo[4,5-c]quinolin-2-one

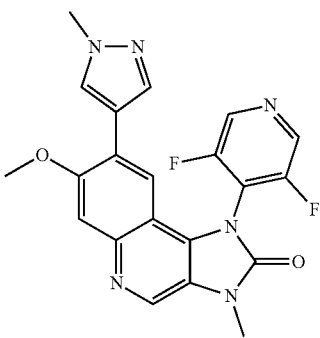 [SMILES: COc1cc2ncc3c(c2cc1-c1cnn(C)c1)n(-c1c(F)cncc1F)c(=O)n3C]
1-(3,5-Difluoropyridin-4-yl)-7-methoxy-3-methyl-8-(1-methyl-1H-pyrazol-4-yl)-1,3-dihydroimidazo[4,5-c]quinolin-2-one TABLE 1-continued Particularly preferred compounds

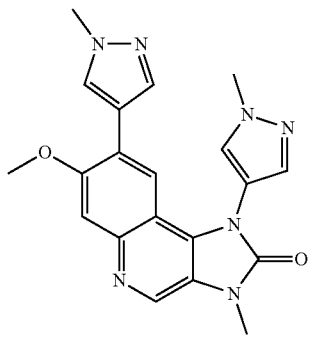 [SMILES: COc1cc2ncc3c(c2cc1-c1cnn(C)c1)n(-c1cnn(C)c1)c(=O)n3C]
7-Methoxy-3-methyl-1,8-bis(1-methyl-1H-pyrazol-4-yl)-1,3-dihydroimidazo[4,5-c]quinolin-2-one

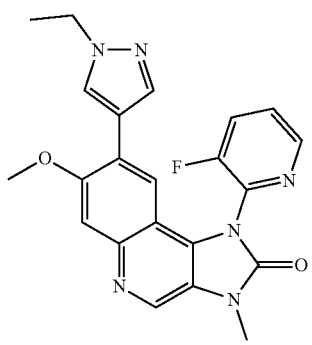 [SMILES: CCn1cc(-c2cc3c(cc2OC)ncc2c3n(-c3ncccc3F)c(=O)n2C)cn1]
8-(1-Ethyl-1H-pyrazol-4-yl)-1-(3-fluoropyridin-2-yl)-7-methoxy-3-methyl-1,3-dihydroimidazo[4,5-c]quinolin-2-one

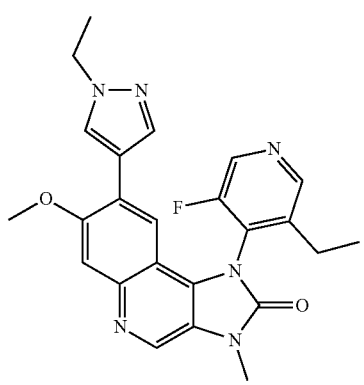 [SMILES: CCc1cncc(F)c1-n1c(=O)n(C)c2cnc3cc(OC)c(-c4cnn(CC)c4)cc3c21]
1-(3-Ethyl-5-fluoropyridin-4-yl)-8-(1-ethyl-1H-pyrazol-4-yl)-7-methoxy-3-methyl-1,3-dihydroimidazo[4,5-c]quinolin-2-one

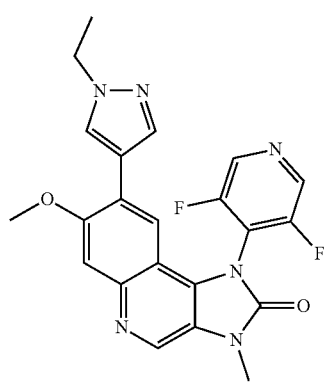 [SMILES: CCn1cc(-c2cc3c(cc2OC)ncc2c3n(-c3c(F)cncc3F)c(=O)n2C)cn1]
1-(3,5-Difluoropyridin-4-yl)-8-(1-ethyl-1H-pyrazol-4-yl)-7-methoxy-3-methyl-1,3-dihydroimidazo[4,5-c]quinolin-2-one TABLE 1-continued Particularly preferred compounds

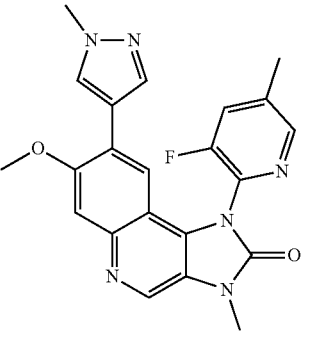 [SMILES: COc1cc2ncc3c(c2cc1-c1cnn(C)c1)n(-c1ncc(C)cc1F)c(=O)n3C]

1-(3-Fluoro-5-methylpyridin-2-yl)-7-methoxy-3-methyl-8-(1-methyl-1H-pyrazol-4-yl)-1,3-dihydroimidazo[4,5-c]quinolin-2-one

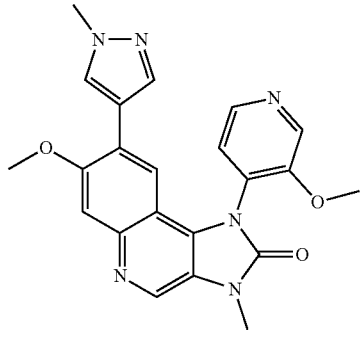

7-Methoxy-1-(3-methoxypyridin-4-yl)-3-methyl-8-(1-methyl-1H-pyrazol-4-yl)-1,3-dihydroimidazo[4,5-c]quinolin-2-one

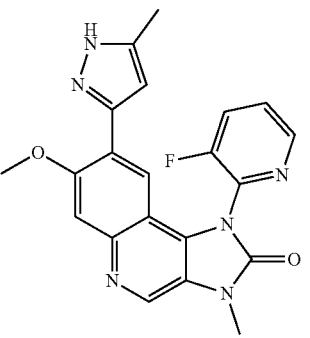 [SMILES: COc1cc2ncc3c(c2cc1-c1cc(C)[nH]n1)n(-c1ncccc1F)c(=O)n3C]

1-(3-Fluoropyridin-2-yl)-7-methoxy-3-methyl-8-(5-methyl-1H-pyrazol-3-yl)-1,3-dihydroimidazo[4,5-c]quinolin-2-one

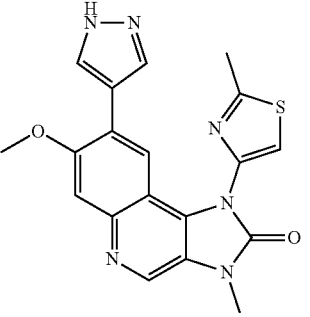 [SMILES: COc1cc2ncc3c(c2cc1-c1cn[nH]c1)n(-c1csc(C)n1)c(=O)n3C]

7-Methoxy-3-methyl-1-(2-methylthiazol-4-yl)-8-(1H-pyrazol-4-yl)-1,3-dihydroimidazo[4,5-c]quinolin-2-one TABLE 1-continued Particularly preferred compounds

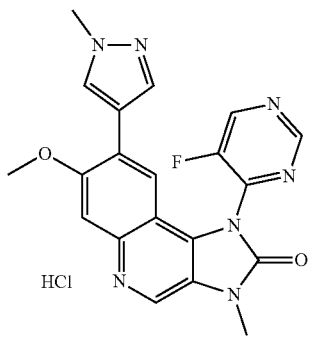 [SMILES: COc1cc2ncc3c(c2cc1-c1cnn(C)c1)n(-c1ncncc1F)c(=O)n3C ; Cl]
1-(5-Fluoropyrimidin-4-yl)-7-methoxy-3-methyl-8-(1-methyl-1H-pyrazol-4-yl)-1H,2H,3H-imidazo[4,5-c]quinolin-2-one hydrochloride

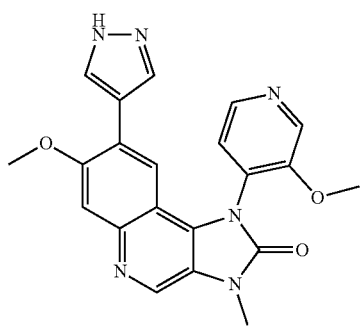
7-Methoxy-1-(3-methoxypyridin-4-yl)-3-methyl-8-(1H-pyrazol-4-yl)-1,3-dihydroimidazo[4,5-c]quinolin-2-one

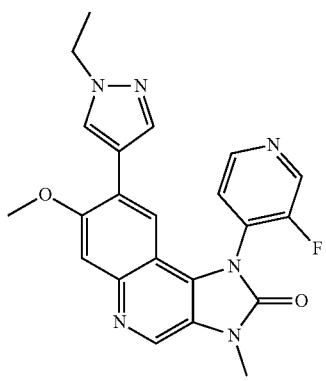 [SMILES: CCn1cc(-c2cc3c(cc2OC)ncc2c3n(-c3ccncc3F)c(=O)n2C)cn1]
8-(1-Ethyl-1H-pyrazol-4-yl)-1-(3-fluoropyridin-4-yl)-7-methoxy-3-methyl-1,3-dihydroimidazo[4,5-c]quinolin-2-one

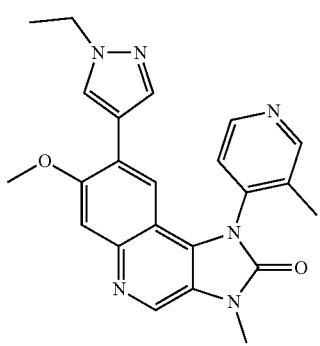
8-(1-Ethyl-1H-pyrazol-4-yl)-7-methoxy-3-methyl-1-(3-methylpyridin-4-yl)-1,3-dihydroimidazo[4,5-c]quinolin-2-one TABLE 1-continued Particularly preferred compounds

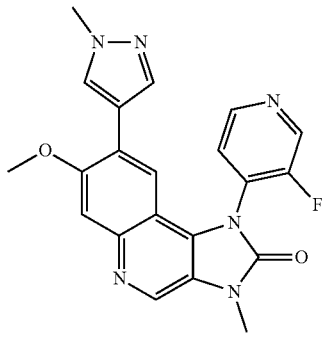 [SMILES: COc1cc2ncc3c(c2cc1-c1cnn(C)c1)n(-c1ccncc1F)c(=O)n3C]

1-(3-Fluoropyridin-4-yl)-7-methoxy-3-methyl-8-(1-methyl-1H-pyrazol-4-yl)-1,3-dihydroimidazo[4,5-c]quinolin-2-one

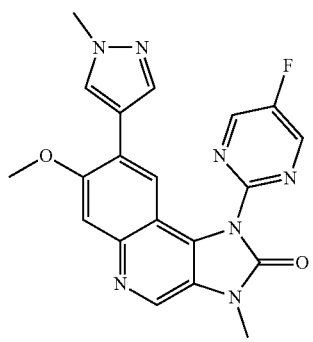 [SMILES: COc1cc2ncc3c(c2cc1-c1cnn(C)c1)n(-c1ncc(F)cn1)c(=O)n3C]

1-(5-Fluoropyrimidin-2-yl)-7-methoxy-3-methyl-8-(1-methyl-1H-pyrazol-4-yl)-1,3-dihydroimidazo[4,5-c]quinolin-2-one

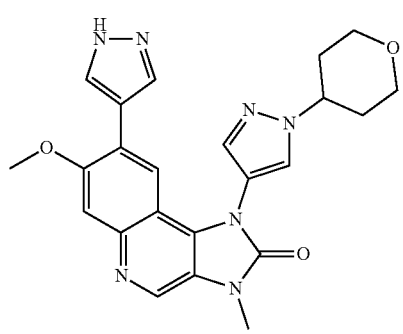 [SMILES: COc1cc2ncc3c(c2cc1-c1cn[nH]c1)n(-c1cnn(C2CCOCC2)c1)c(=O)n3C]

7-Methoxy-3-methyl-8-(1H-pyrazol-4-yl)-1-[1-(tetrahydropyran-4-yl)-1H-pyrazol-4-yl]-1,3-dihydroimidazo-[4,5-c]quinolin-2-one

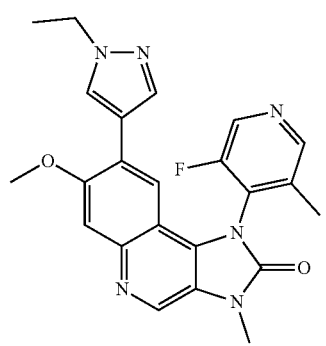

8-(1-Ethyl-1H-pyrazol-4-yl)-1-(3-fluoro-5-methylpyridin-4-yl)-7-methoxy-3-methyl-1,3-dihydroimidazo[4,5-c]quinolin-2-one TABLE 1-continued Particularly preferred compounds

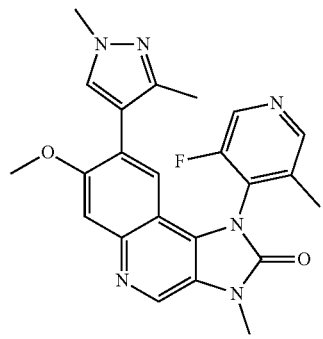

8-(1,3-Dimethyl-1H-pyrazol-4-yl)-1-(3-fluoro-5-methylpyridin-4-yl)-7-methoxy-3-methyl-1,3-dihydroimidazo[4,5-c]quinolin-2-one

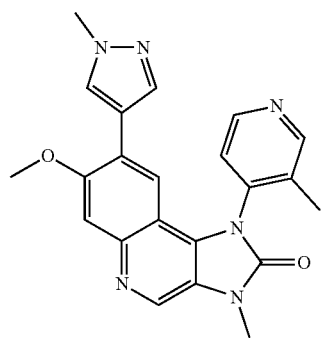

7-Methoxy-3-methyl-8-(1-methyl-1H-pyrazol-4-yl)-1-(3-methylpyridin-4-yl)-1,3-dihydroimidazo[4,5-c]quinolin-2-one

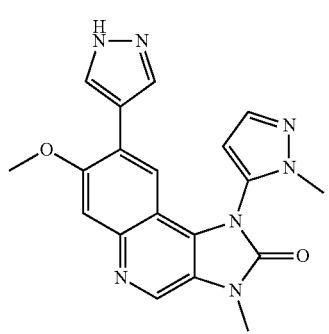

7-Methoxy-3-methyl-1-(2-methyl-2H-pyrazol-3-yl)-8-(1H-pyrazol-4-yl)-1,3-dihydroimidazo[4,5-c]quinolin-2-one

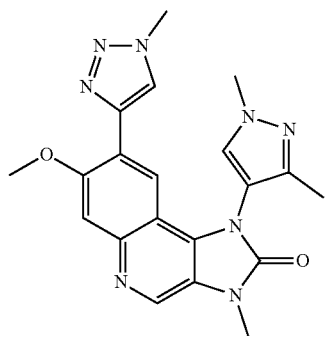

1-(1,3-Dimethyl-1H-pyrazol-4-yl)-7-methoxy-3-methyl-8-(1-methyl-1H-1,2,3-triazol-4-yl)-1,3-dihydroimidazo[4,5-c]-quinolin-2-one TABLE 1-continued Particularly preferred compounds

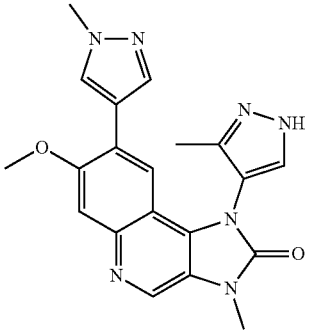 [SMILES: COc1cc2ncc3c(c2cc1-c1cnn(C)c1)n(-c1c[nH]nc1C)c(=O)n3C]
7-Methoxy-3-methyl-1-(3-methyl-1H-pyrazol-4-yl)-8-(1-methyl-1H-pyrazol-4-yl)-1,3-dihydroimidazo[4,5-c]quinolin-2-one

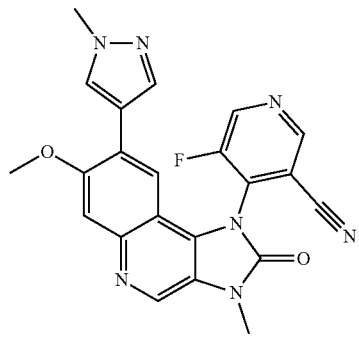
5-Fluoro-4-[7-methoxy-3-methyl-8-(1-methyl-1H-pyrazol-4-yl)-2-oxo-2,3-dihydroimidazo[4,5-c]quinolin-1-yl]nicotinonitrile

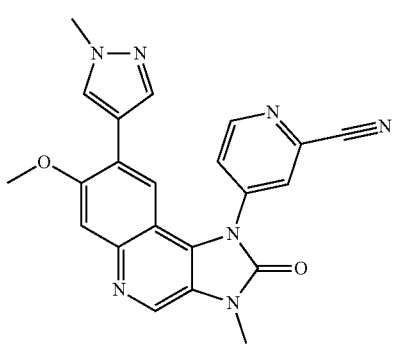 [SMILES: COc1cc2ncc3c(c2cc1-c1cnn(C)c1)n(-c1ccnc(C#N)c1)c(=O)n3C]
4-[7-Methoxy-3-methyl-8-(1-methyl-1H-pyrazol-4-yl)-2-oxo-2,3-dihydroimidazo[4,5-c]quinolin-1-yl]pyridine-2-carbonitrile

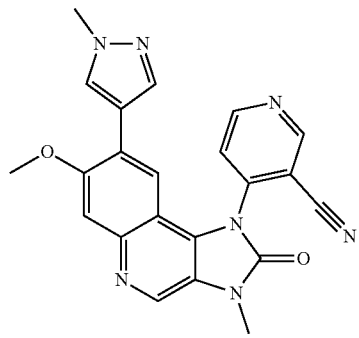
4-[7-Methoxy-3-methyl-8-(1-methyl-1H-pyrazol-4-yl)-2-oxo-2,3-dihydroimidazo[4,5-c]quinolin-1-yl]nicotinonitrile TABLE 1-continued Particularly preferred compounds

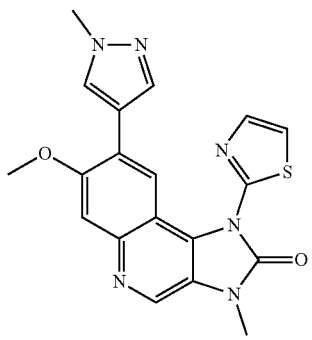 [SMILES: COc1cc2ncc3c(c2cc1-c1cnn(C)c1)n(-c1nccs1)c(=O)n3C]

7-Methoxy-3-methyl-8-(1-methyl-1H-pyrazol-4-yl)-1-thiazol-2-yl-1,3-dihydroimidazo[4,5-c]quinolin-2-one

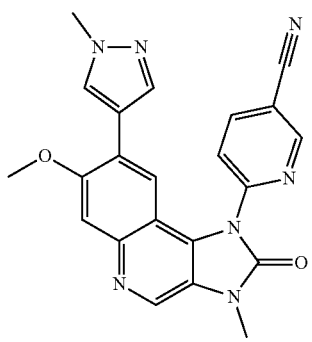 [SMILES: COc1cc2ncc3c(c2cc1-c1cnn(C)c1)n(-c1ccc(C#N)cn1)c(=O)n3C]

6-[7-Methoxy-3-methyl-8-(1-methyl-1H-pyrazol-4-yl)-2-oxo-2,3-dihydroimidazo[4,5-c]quinolin-1-yl]nicotinonitrile

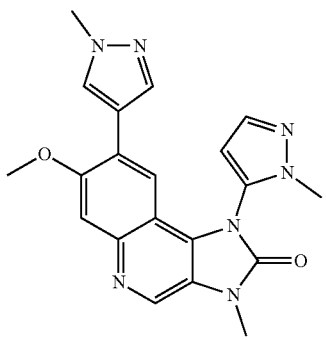

7-Methoxy-3-methyl-1-(2-methyl-2H-pyrazol-3-yl)-8-(1-methyl-1H-pyrazol-4-yl)-1,3-dihydroimidazo[4,5-c]quinolin-2-one

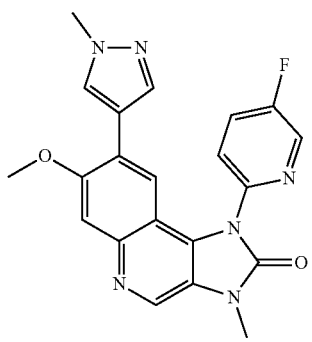 [SMILES: COc1cc2ncc3c(c2cc1-c1cnn(C)c1)n(-c1ccc(F)cn1)c(=O)n3C]

1-(5-Fluoropyridin-2-yl)-7-methoxy-3-methyl-8-(1-methyl-1H-pyrazol-4-yl)-1,3-dihydroimidazo[4,5-c]quinolin-2-one TABLE 1-continued Particularly preferred compounds

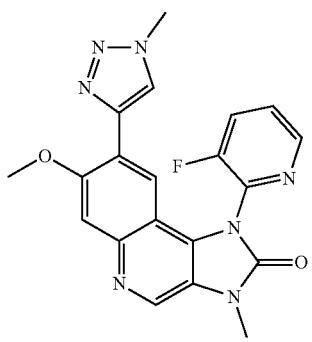 [SMILES: COc1cc2ncc3c(c2cc1-c1cn(C)nn1)n(-c1ncccc1F)c(=O)n3C]
1-(3-Fluoropyridin-2-yl)-7-methoxy-3-methyl-8-(1-methyl-1H-1,2,3-triazol-4-yl)-1,3-dihydroimidazo[4,5-c]quinolin-2-one

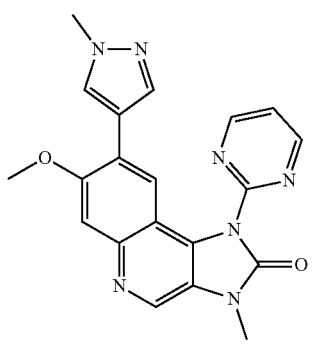
7-Methoxy-3-methyl-8-(1-methyl-1H-pyrazol-4-yl)-1-pyrimidin-2-yl-1,3-dihydroimidazo[4,5-c]quinolin-2-one

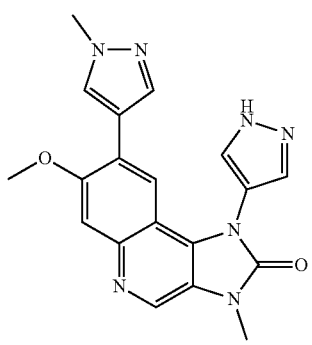 [SMILES: COc1cc2ncc3c(c2cc1-c1cnn(C)c1)n(-c1cn[nH]c1)c(=O)n3C]
7-Methoxy-3-methyl-8-(1-methyl-1H-pyrazol-4-yl)-1-(1H-pyrazol-4-yl)-1,3-dihydroimidazo[4,5-c]quinolin-2-one

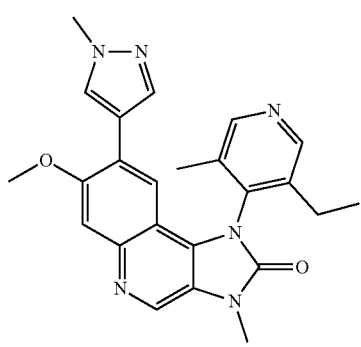 [SMILES: CCc1cncc(C)c1-n1c(=O)n(C)c2cnc3cc(OC)c(-c4cnn(C)c4)cc3c21]
1-(3-Ethyl-5-methylpyridin-4-yl)-7-methoxy-3-methyl-8-(1-methyl-1H-pyrazol-4-yl)-1,3-dihydroimidazo[4,5-c]quinolin-2-one TABLE 1-continued Particularly preferred compounds

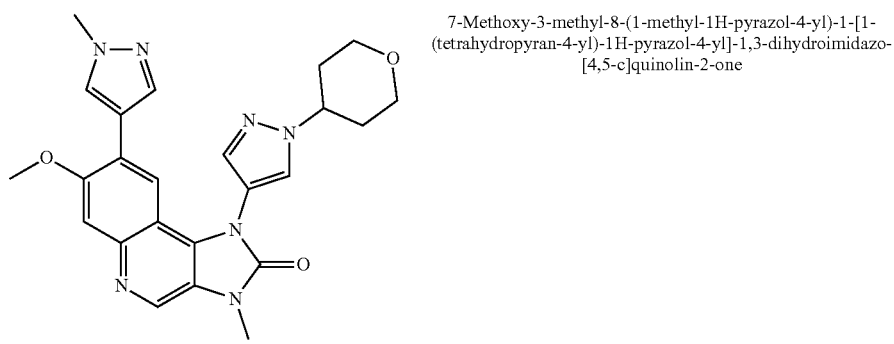
7-Methoxy-3-methyl-8-(1-methyl-1H-pyrazol-4-yl)-1-[1-(tetrahydropyran-4-yl)-1H-pyrazol-4-yl]-1,3-dihydroimidazo-[4,5-c]quinolin-2-one

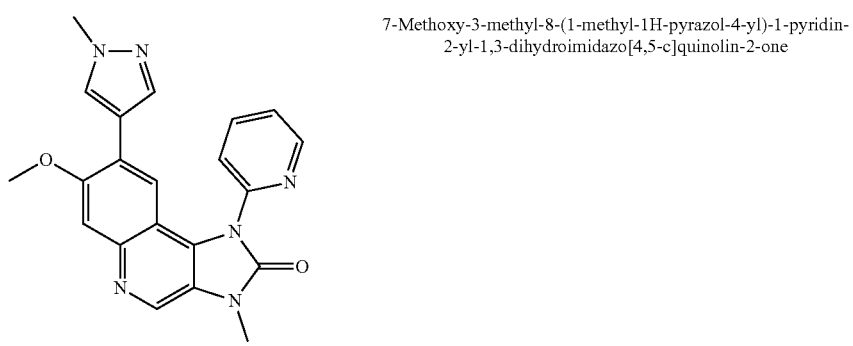
7-Methoxy-3-methyl-8-(1-methyl-1H-pyrazol-4-yl)-1-pyridin-2-yl-1,3-dihydroimidazo[4,5-c]quinolin-2-one

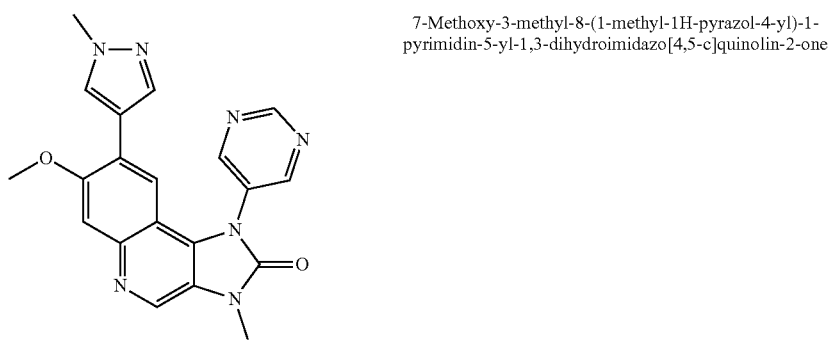
7-Methoxy-3-methyl-8-(1-methyl-1H-pyrazol-4-yl)-1-pyrimidin-5-yl-1,3-dihydroimidazo[4,5-c]quinolin-2-one

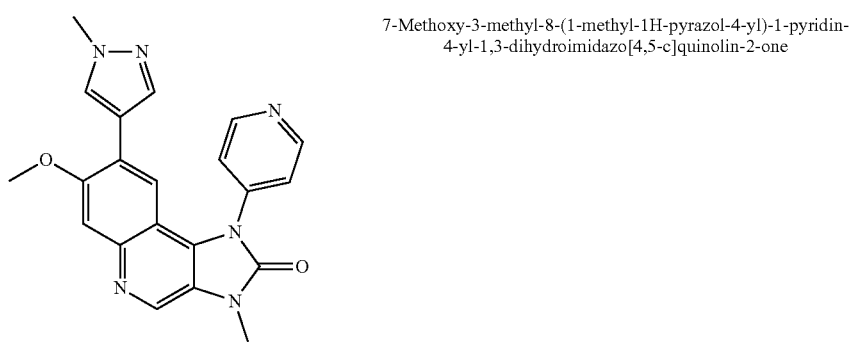
7-Methoxy-3-methyl-8-(1-methyl-1H-pyrazol-4-yl)-1-pyridin-4-yl-1,3-dihydroimidazo[4,5-c]quinolin-2-one TABLE 1-continued Particularly preferred compounds

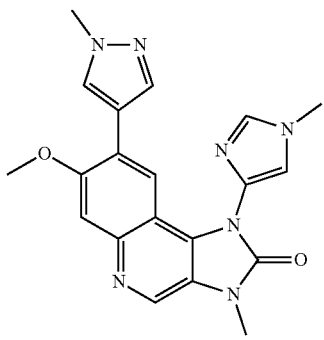
7-Methoxy-3-methyl-1-(1-methyl-1H-imidazol-4-yl)-8-(1-methyl-1H-pyrazol-4-yl)-1,3-dihydroimidazo[4,5-c]quinolin-2-one

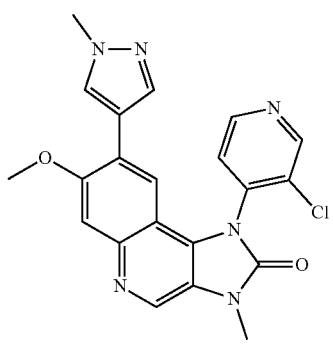 [SMILES: COc1cc2ncc3c(c2cc1-c1cnn(C)c1)n(-c1ccncc1Cl)c(=O)n3C]
1-(3-Chloropyridin-4-yl)-7-methoxy-3-methyl-8-(1-methyl-1H-pyrazol-4-yl)-1,3-dihydroimidazo[4,5-c]quinolin-2-one

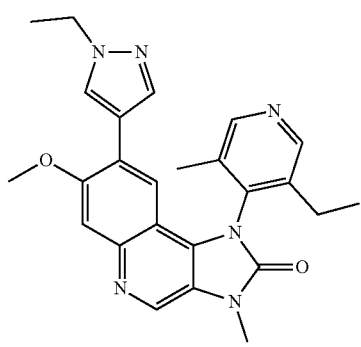 [SMILES: CCc1cncc(C)c1-n1c(=O)n(C)c2cnc3cc(OC)c(-c4cnn(CC)c4)cc3c21]
1-(3-Ethyl-5-methylpyridin-4-yl)-8-(1-ethyl-1H-pyrazol-4-yl)-7-methoxy-3-methyl-1,3-dihydroimidazo[4,5-c]quinolin-2-one

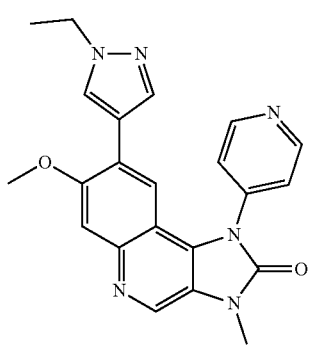 [SMILES: CCn1cc(-c2cc3c(cc2OC)ncc2c3n(-c3ccncc3)c(=O)n2C)cn1]
8-(1-Ethyl-1H-pyrazol-4-yl)-7-methoxy-3-methyl-1-pyridin-4-yl-1,3-dihydroimidazo[4,5-c]quinolin-2-one TABLE 1-continued Particularly preferred compounds

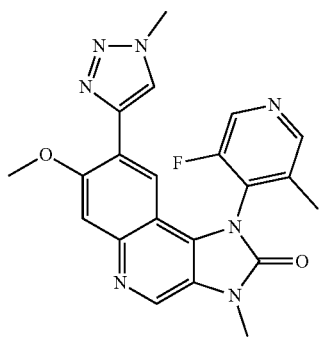

1-(3-Fluoro-5-methylpyridin-4-yl)-7-methoxy-3-methyl-8-(1-methyl-1H-1,2,3-triazol-4-yl)-1,3-dihydroimidazo[4,5-c]-quinolin-2-one

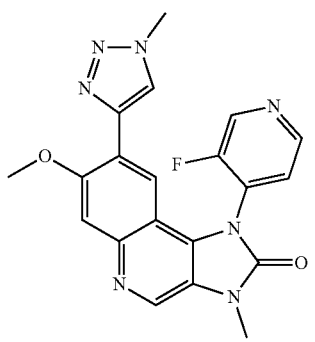 [SMILES: COc1cc2ncc3c(c2cc1-c1cn(C)nn1)n(-c1ccncc1F)c(=O)n3C]

1-(3-Fluoropyridin-4-yl)-7-methoxy-3-methyl-8-(1-methyl-1H-1,2,3-triazol-4-yl)-1,3-dihydroimidazo[4,5-c]quinolin-2-one

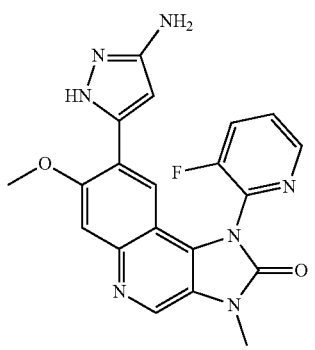 [SMILES: COc1cc2ncc3c(c2cc1-c1cc(N)n[nH]1)n(-c1ncccc1F)c(=O)n3C]

8-(3-Amino-1H-pyrazol-5-yl)-1-(3-fluoro-2-pyridyl)-7-methoxy-3-methylimidazo[4,5-c]quinolin-2-one

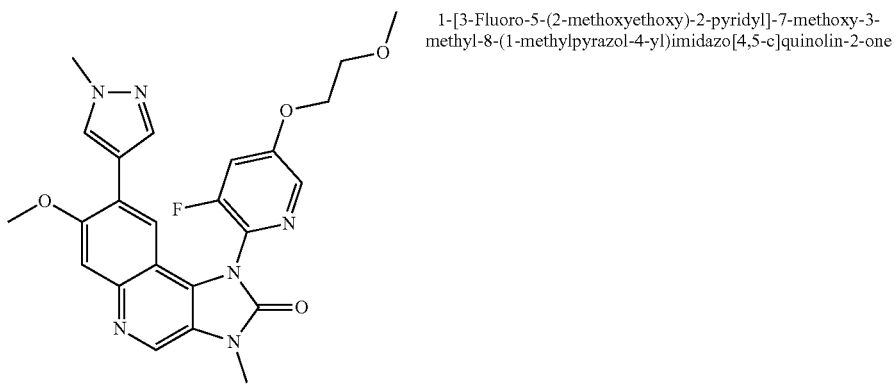

1-[3-Fluoro-5-(2-methoxyethoxy)-2-pyridyl]-7-methoxy-3-methyl-8-(1-methylpyrazol-4-yl)imidazo[4,5-c]quinolin-2-one TABLE 1-continued

*Particularly preferred compounds*

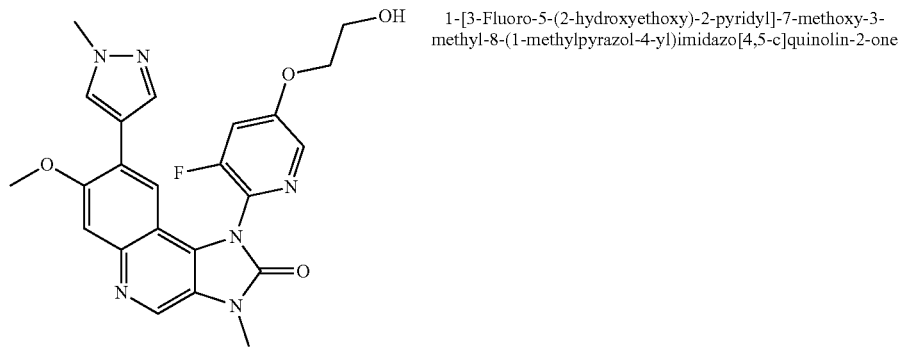 1-[3-Fluoro-5-(2-hydroxyethoxy)-2-pyridyl]-7-methoxy-3-methyl-8-(1-methylpyrazol-4-yl)imidazo[4,5-c]quinolin-2-one

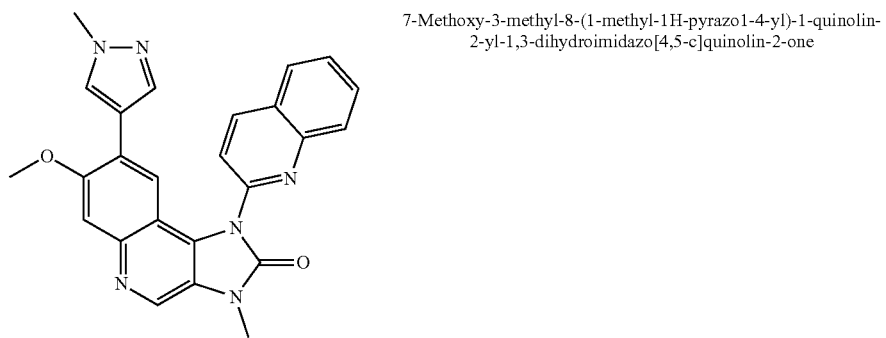 7-Methoxy-3-methyl-8-(1-methyl-1H-pyrazol-4-yl)-1-quinolin-2-yl-1,3-dihydroimidazo[4,5-c]quinolin-2-one

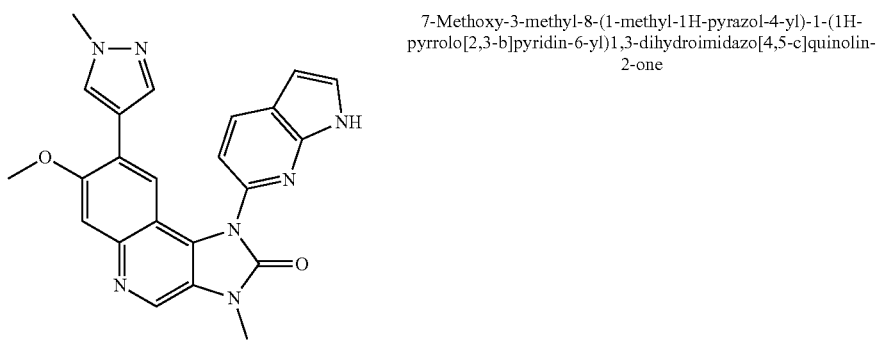 7-Methoxy-3-methyl-8-(1-methyl-1H-pyrazol-4-yl)-1-(1H-pyrrolo[2,3-b]pyridin-6-yl)1,3-dihydroimidazo[4,5-c]quinolin-2-one

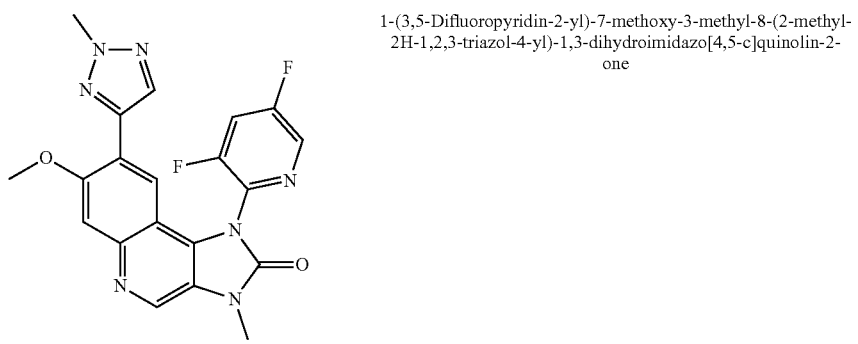 1-(3,5-Difluoropyridin-2-yl)-7-methoxy-3-methyl-8-(2-methyl-2H-1,2,3-triazol-4-yl)-1,3-dihydroimidazo[4,5-c]quinolin-2-one TABLE 1-continued Particularly preferred compounds

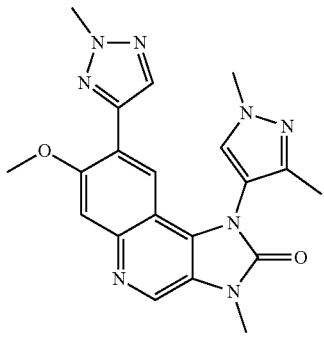

1-(1,3-Dimethyl-1H-pyrazol-4-yl)-7-methoxy-3-methyl-8-(2-methyl-2H-1,2,3-triazol-4-yl)-1,3-dihydroimidazo[4,5-c]-quinolin-2-one

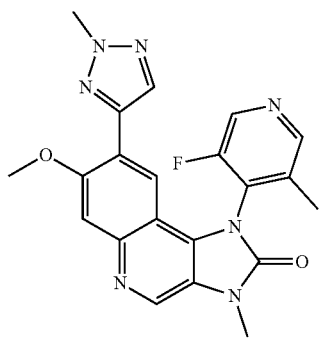

1-(3-Fluoro-5-methylpyridin-4-yl)-7-methoxy-3-methyl-8-(2-methyl-2H-1,2,3-triazol-4-yl)-1,3-dihydroimidazo[4,5-c]quinolin-2-one

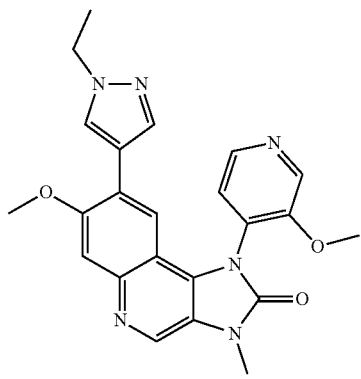

8-(1-Ethyl-1H-pyrazol-4-yl)-7-methoxy-1-(3-methoxypyridin-4-yl)-3-methyl-1,3-dihydroimidazo[4,5-c] quinolin-2-one

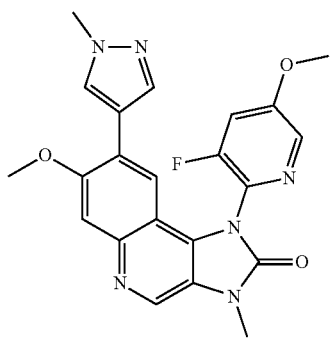

1-(3-Fluoro-5-methoxypyridin-2-yl)-7-methoxy-3-methyl-8-(1-methyl-1H-pyrazol-4-yl)-1,3-dihydroimidazo[4,5-c]quinolin-2-one TABLE 1-continued Particularly preferred compounds

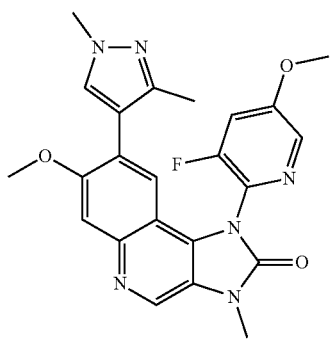

8-(1,3-Dimethyl-1H-pyrazol-4-yl)-1-(3-fluoro-5-methoxy-pyridin-2-yl)-7-methoxy-3-methyl-1,3-dihydroimidazo[4,5-c]-quinolin-2-one

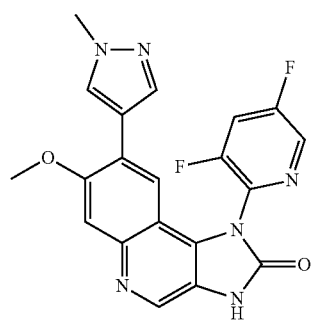 [SMILES: COc1cc2ncc3[nH]c(=O)n(-c4ncc(F)cc4F)c3c2cc1-c1cnn(C)c1]

1-(3,5-Difluoropyridin-2-yl)-7-methoxy-8-(1-methyl-1H-pyrazol-4-yl)-1,3-dihydroimidazo[4,5-c]quinolin-2-one

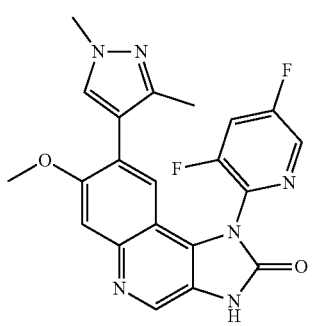 [SMILES: COc1cc2ncc3[nH]c(=O)n(-c4ncc(F)cc4F)c3c2cc1-c1cn(C)nc1C]

1-(3,5-Difluoropyridin-2-yl)-8-(1,3-dimethyl-1H-pyrazol-4-yl)-7-methoxy-1,3-dihydroimidazo[4,5-c]quinolin-2-one

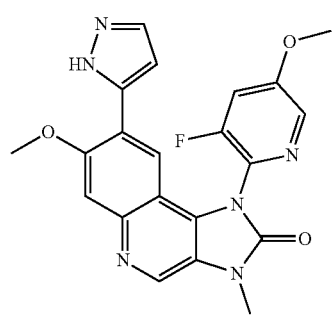

1-(3-Fluoro-5-methoxypyridin-2-yl)-7-methoxy-3-methyl-8-(2H-pyrazol-3-yl)-1,3-dihydroimidazo[4,5-c]quinolin-2-one

TABLE 1-continued

Particularly preferred compounds

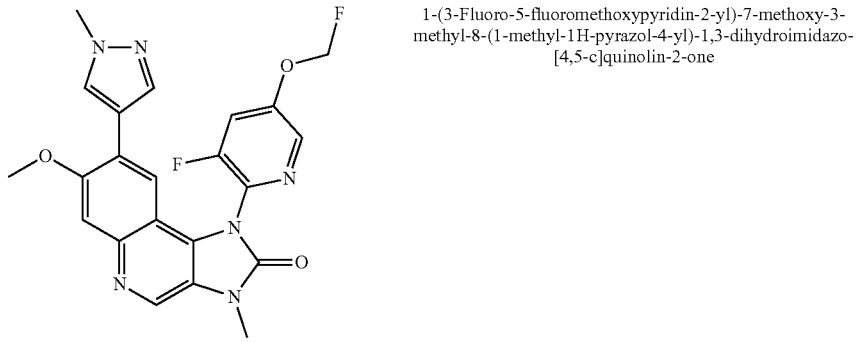

1-(3-Fluoro-5-fluoromethoxypyridin-2-yl)-7-methoxy-3-methyl-8-(1-methyl-1H-pyrazol-4-yl)-1,3-dihydroimidazo-[4,5-c]quinolin-2-one

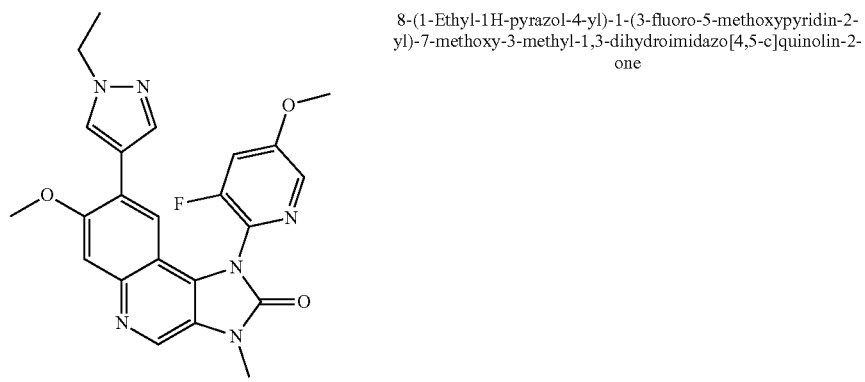

8-(1-Ethyl-1H-pyrazol-4-yl)-1-(3-fluoro-5-methoxypyridin-2-yl)-7-methoxy-3-methyl-1,3-dihydroimidazo[4,5-c]quinolin-2-one

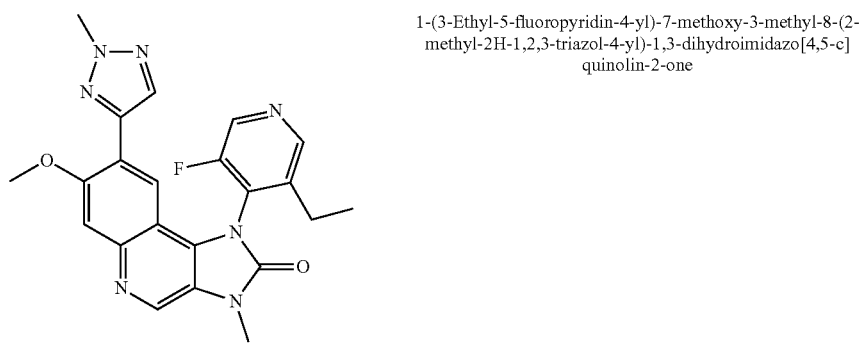

1-(3-Ethyl-5-fluoropyridin-4-yl)-7-methoxy-3-methyl-8-(2-methyl-2H-1,2,3-triazol-4-yl)-1,3-dihydroimidazo[4,5-c]quinolin-2-one

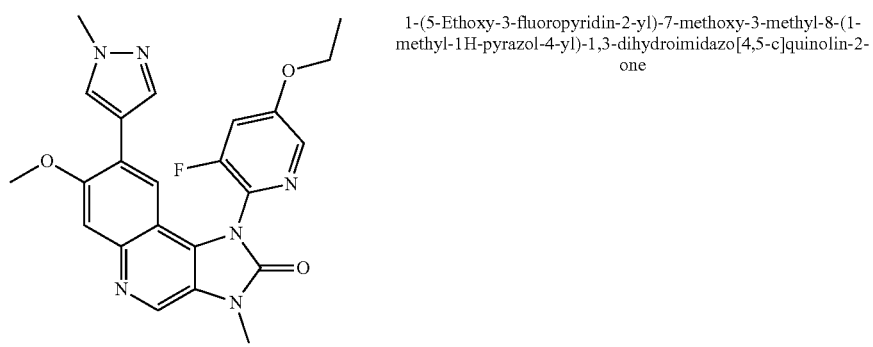

1-(5-Ethoxy-3-fluoropyridin-2-yl)-7-methoxy-3-methyl-8-(1-methyl-1H-pyrazol-4-yl)-1,3-dihydroimidazo[4,5-c]quinolin-2-one TABLE 1-continued Particularly preferred compounds

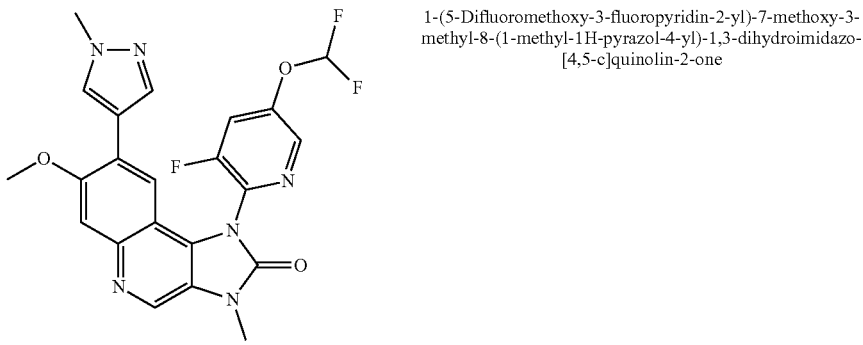

1-(5-Difluoromethoxy-3-fluoropyridin-2-yl)-7-methoxy-3-methyl-8-(1-methyl-1H-pyrazol-4-yl)-1,3-dihydroimidazo-[4,5-c]quinolin-2-one

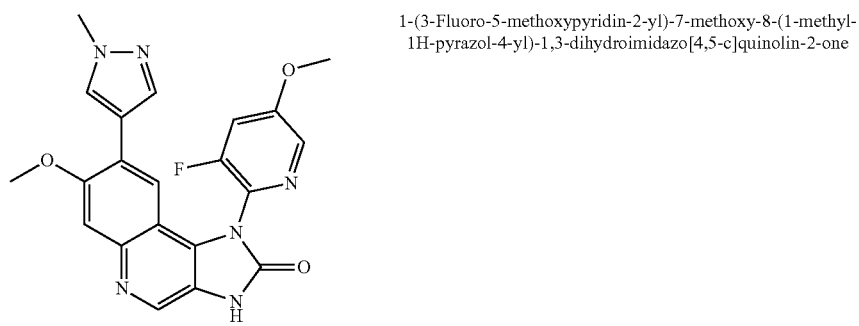

1-(3-Fluoro-5-methoxypyridin-2-yl)-7-methoxy-8-(1-methyl-1H-pyrazol-4-yl)-1,3-dihydroimidazo[4,5-c]quinolin-2-one

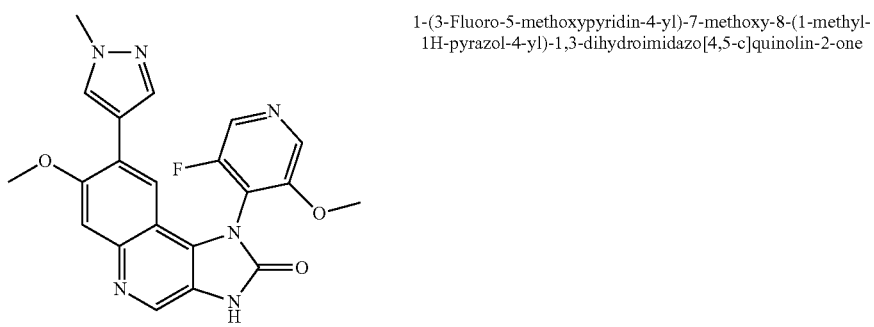

1-(3-Fluoro-5-methoxypyridin-4-yl)-7-methoxy-8-(1-methyl-1H-pyrazol-4-yl)-1,3-dihydroimidazo[4,5-c]quinolin-2-one

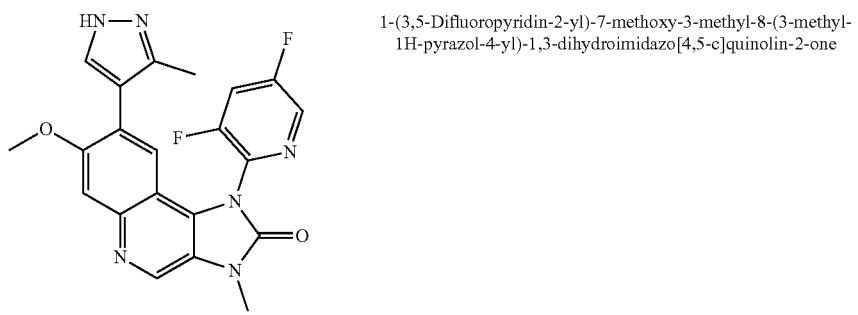

1-(3,5-Difluoropyridin-2-yl)-7-methoxy-3-methyl-8-(3-methyl-1H-pyrazol-4-yl)-1,3-dihydroimidazo[4,5-c]quinolin-2-one TABLE 1-continued Particularly preferred compounds

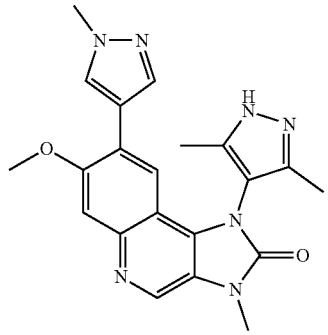

1-(3,5-Dimethyl-1H-pyrazol-4-yl)-7-methoxy-3-methyl-8-(1-methyl-1H-pyrazol-4-yl)-1,3-dihydroimidazo[4,5-c]quinolin-2-one

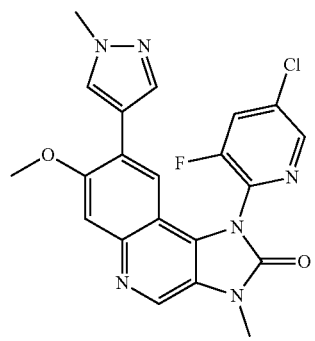 [SMILES: COc1cc2ncc3c(c2cc1-c1cnn(C)c1)n(-c1ncc(Cl)cc1F)c(=O)n3C]

1-(5-Chloro-3-fluoropyridin-2-yl)-7-methoxy-3-methyl-8-(1-methyl-1H-pyrazol-4-yl)-1,3-dihydroimidazo[4,5-c]quinolin-2-one

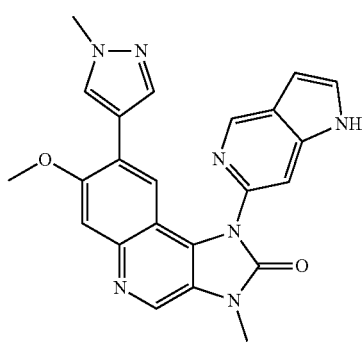 [SMILES: COc1cc2ncc3c(c2cc1-c1cnn(C)c1)n(-c1cc2[nH]ccc2cn1)c(=O)n3C]

7-Methoxy-3-methyl-8-(1-methyl-1H-pyrazol-4-yl)-1-(1H-pyrrolo[3,2-c]pyridin-6-yl)-1,3-dihydroimidazo[4,5-c]quinolin-2-one

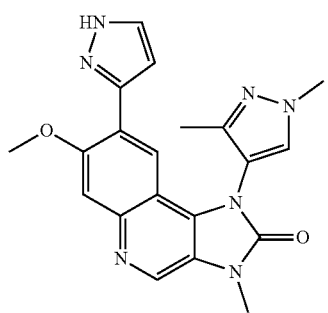

1-(1,3-Dimethyl-1H-pyrazol-4-yl)-7-methoxy-3-methyl-8-(1H-pyrazol-3-yl)-1,3-dihydroimidazo[4,5-c]quinolin-2-one TABLE 1-continued Particularly preferred compounds

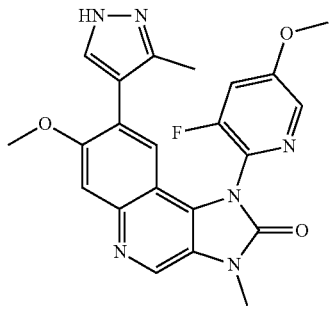
1-(3-Fluoro-5-methoxypyridin-2-yl)-7-methoxy-3-methyl-8-(3-methyl-1H-pyrazol-4-yl)-1,3-dihydroimidazo[4,5-c] quinolin-2-one

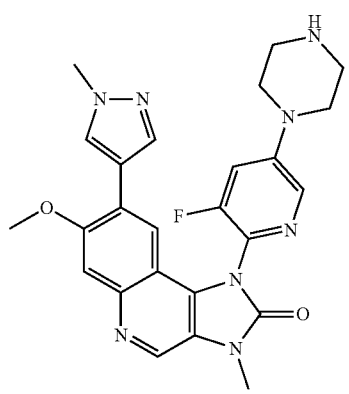 [SMILES: COc1cc2ncc3c(c2cc1-c1cnn(C)c1)n(-c1ncc(N2CCNCC2)cc1F)c(=O)n3C]
1-(3-Fluoro-5-piperazin-1-yl-pyridin-2-yl)-7-methoxy-3-methyl-8-(1-methyl-1H-pyrazol-4-yl)-1,3-dihydroimidazo-[4,5-c]quinolin-2-one

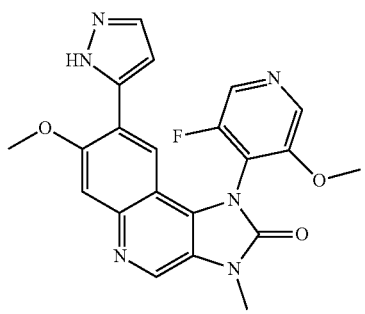
1-(3-Fluoro-5-methoxypyridin-4-yl)-7-methoxy-3-methyl-8-(2H-pyrazol-3-yl)-1,3-dihydroimidazo[4,5-c] quinolin-2-one

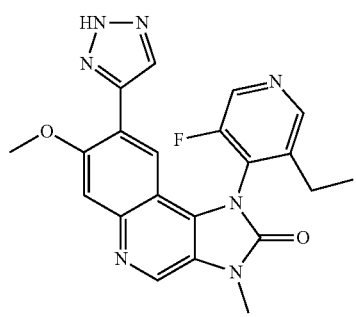 [SMILES: CCc1cncc(F)c1-n1c(=O)n(C)c2cnc3cc(OC)c(-c4cn[nH]n4)cc3c21]
1-(3-Ethyl-5-fluoropyridin-4-yl)-7-methoxy-3-methyl-8-(2H-1,2,3-triazol-4-yl)-1,3-dihydroimidazo[4,5-c] quinolin-2-one TABLE 1-continued Particularly preferred compounds

| | |
|---|---|
| 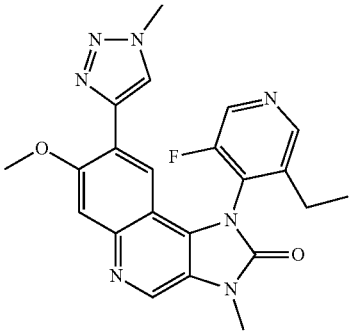 [SMILES: CCc1cncc(F)c1-n1c(=O)n(C)c2cnc3cc(OC)c(-c4cn(C)nn4)cc3c21] | 1-(3-Ethyl-5-fluoropyridin-4-yl)-7-methoxy-3-methyl-8-(1-methyl-1H-1,2,3-triazol-4-yl)-1,3-dihydroimidazo[4,5-c]quinolin-2-one |
| 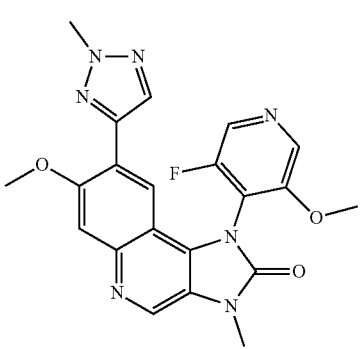 | 1-(3-Fluoro-5-methoxypyridin-4-yl)-7-methoxy-3-methyl-8-(2-methyl-2H-1,2,3-triazol-4-yl)-1,3-dihydroimidazo[4,5-c]quinolin-2-one |
| 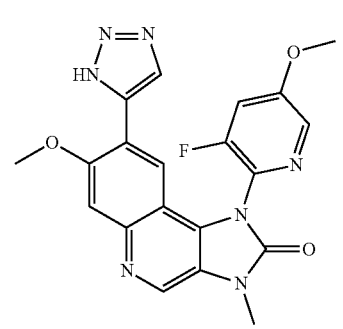 | 1-(3-Fluoro-5-methoxypyridin-2-yl)-7-methoxy-3-methyl-8-(3H-1,2,3-triazol-4-yl)-1,3-dihydroimidazo[4,5-c]quinolin-2-one |
| 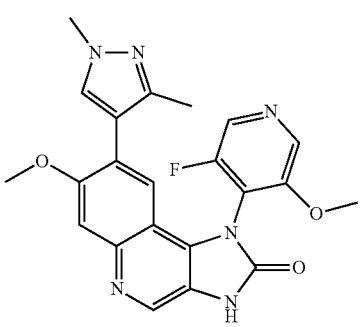 | 8-(1,3-Dimethyl-1H-pyrazol-4-yl)-1-(3-fluoro-5-methoxypyridin-4-yl)-7-methoxy-1,3-dihydroimidazo[4,5-c]quinolin-2-one |

TABLE 1-continued

Particularly preferred compounds

| Structure | Name |
|---|---|
| | 1-(1-Ethyl-3-methyl-1H-pyrazol-4-yl)-7-methoxy-3-methyl-8-(1-methyl-1H-pyrazol-4-yl)-1,3-dihydroimidazo[4,5-c]quinolin-2-one |
| | 1-(3-Fluoro-5-methoxypyridin-4-yl)-7-methoxy-3-methyl-8-(1-methyl-1H-1,2,3-triazol-4-yl)-1,3-dihydroimidazo[4,5-c]-quinolin-2-one |
| | 1-(1,3-Dimethyl-1H-pyrazol-4-yl)-7-methoxy-3-methyl-8-(2-methyl-3H-benzoimidazol-5-yl)-1,3-dihydroimidazo[4,5-c]-quinolin-2-one |
| | 1-(3-Fluoro-5-methoxypyridin-2-yl)-7-methoxy-3-methyl-8-(1-methyl-1H-1,2,3-triazol-4-yl)-1,3-dihydroimidazo[4,5-c]quinolin-2-one |

TABLE 1-continued

Particularly preferred compounds

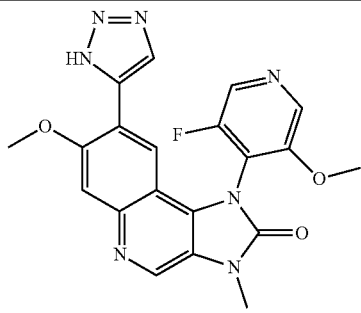

1-(3-Fluoro-5-methoxypyridin-4-yl)-7-methoxy-3-methyl-8-(3H-1,2,3-triazol-4-yl)-1,3-dihydroimidazo[4,5-c]quinolin-2-one

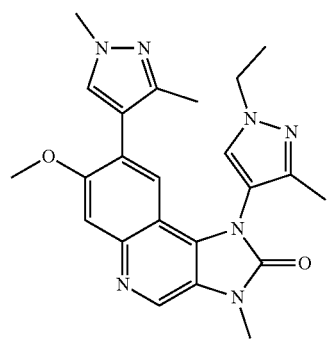

8-(1,3-Dimethyl-1H-pyrazol-4-yl)-1-(1-ethyl-3-methyl-1H-pyrazol-4-yl)-7-methoxy-3-methyl-1,3-dihydroimidazo[4,5-c]-quinolin-2-one

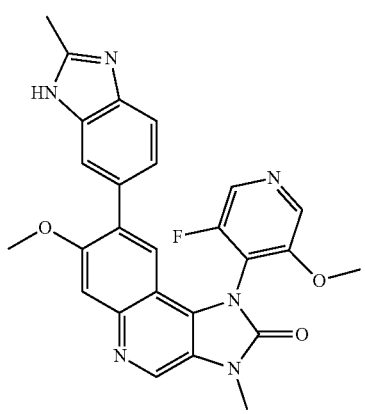

1-(3-Fluoro-5-methoxypyridin-4-yl)-7-methoxy-3-methyl-8-(2-methyl-3H-benzoimidazol-5-yl)-1,3-dihydroimidazo[4,5-c]-quinolin-2-one

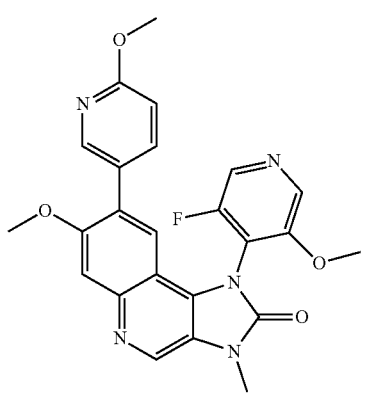

1-(3-Fluoro-5-methoxypyridin-4-yl)-7-methoxy-8-(6-methoxy-pyridin-3-yl)-3-methyl-1,3-dihydroimidazo[4,5-c]quinolin-2-one TABLE 1-continued Particularly preferred compounds

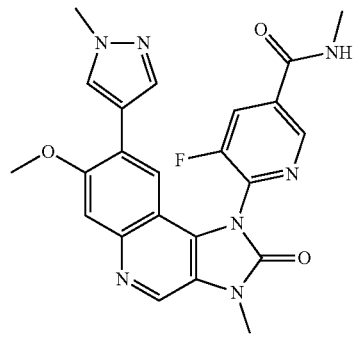

5-Fluoro-6-[7-methoxy-3-methyl-8-(1-methyl-1H-pyrazol-4-yl)-2-oxo-2,3-dihydroimidazo[4,5-c]quinolin-1-yl]-N-methyl-nicotinamide

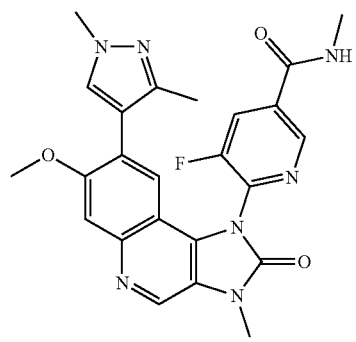

6-[8-(1,3-Dimethyl-1H-pyrazol-4-yl)-7-methoxy-3-methyl-2-oxo-2,3-dihydroimidazo[4,5-c]quinolin-1-yl]-5-fluoro-N-methylnicotinamide

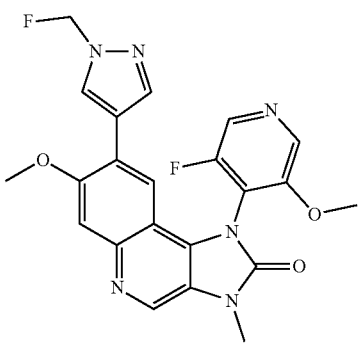

1-(3-Fluoro-5-methoxypyridin-4-yl)-8-(1-fluoromethyl-1H-pyrazol-4-yl)-7-methoxy-3-methyl-1,3-dihydroimidazo[4,5-c]-quinolin-2-one

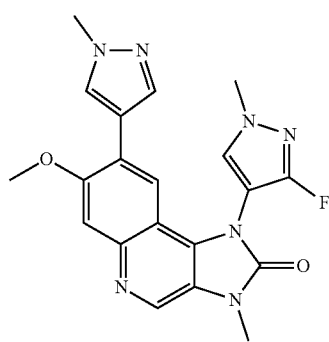 [SMILES: COc1cc2ncc3c(c2cc1-c1cnn(C)c1)n(-c1cn(C)nc1F)c(=O)n3C]

1-(3-Fluoro-1-methyl-1H-pyrazol-4-yl)-7-methoxy-3-methyl-8-(1-methyl-1H-pyrazol-4-yl)-1,3-dihydroimidazo[4,5-c]quinolin-2-one TABLE 1-continued Particularly preferred compounds

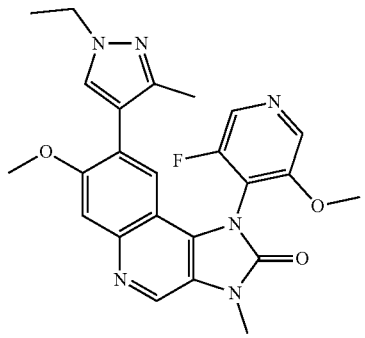
8-(1-Ethyl-3-methyl-1H-pyrazol-4-yl)-1-(3-fluoro-5-methoxy-pyridin-4-yl)-7-methoxy-3-methyl-1,3-dihydroimidazo[4,5-c]quinolin-2-one

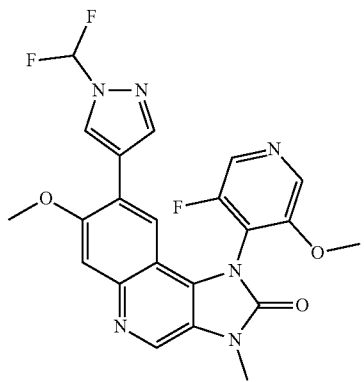
8-(1-Difluoromethyl-1H-pyrazol-4-yl)-1-(3-fluoro-5-methoxy-pyridin-4-yl)-7-methoxy-3-methyl-1,3-dihydroimidazo[4,5-c]quinolin-2-one

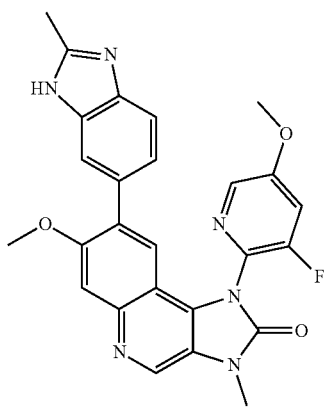 [SMILES: COc1cnc(-n2c(=O)n(C)c3cnc4cc(OC)c(-c5ccc6nc(C)[nH]c6c5)cc4c32)c(F)c1]
1-(3-Fluoro-5-methoxypyridin-2-yl)-7-methoxy-3-methyl-8-(2-methyl-3H-benzoimidazol-5-yl)-1,3-dihydroimidazo[4,5-c]-quinolin-2-one

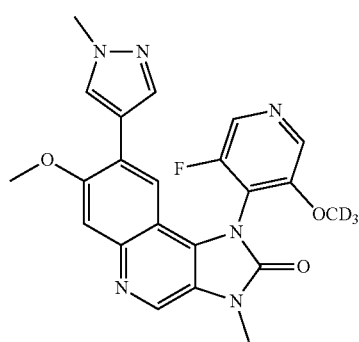
1-[3-Fluoro-5-(trideuteriomethoxy)-4-pyridyl]-7-methoxy-3-methyl-8-(1-methylpyrazol-4-yl)imidazo[4,5-c]quinolin-2-one TABLE 1-continued

*Particularly preferred compounds*

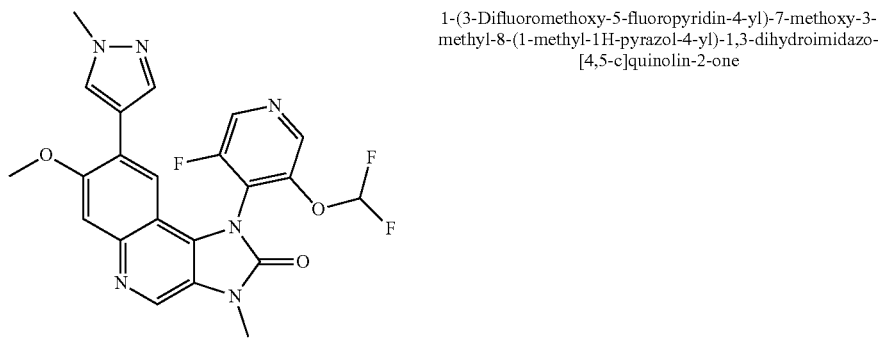

1-(3-Difluoromethoxy-5-fluoropyridin-4-yl)-7-methoxy-3-methyl-8-(1-methyl-1H-pyrazol-4-yl)-1,3-dihydroimidazo-[4,5-c]quinolin-2-one

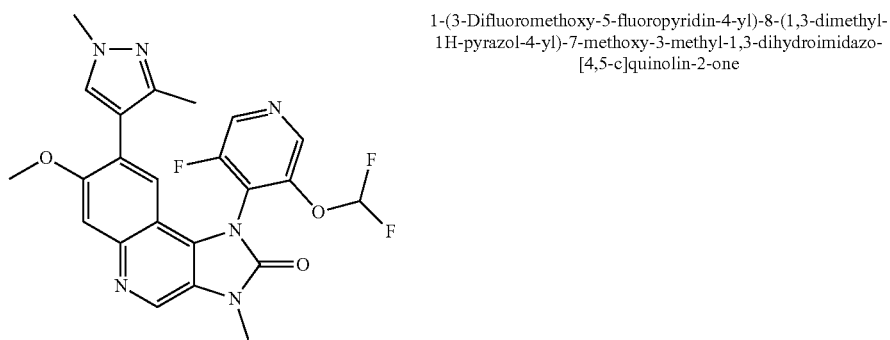

1-(3-Difluoromethoxy-5-fluoropyridin-4-yl)-8-(1,3-dimethyl-1H-pyrazol-4-yl)-7-methoxy-3-methyl-1,3-dihydroimidazo-[4,5-c]quinolin-2-one

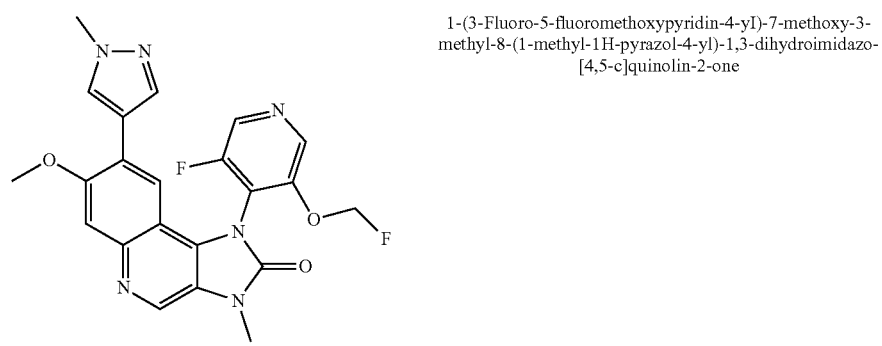

1-(3-Fluoro-5-fluoromethoxypyridin-4-yl)-7-methoxy-3-methyl-8-(1-methyl-1H-pyrazol-4-yl)-1,3-dihydroimidazo-[4,5-c]quinolin-2-one

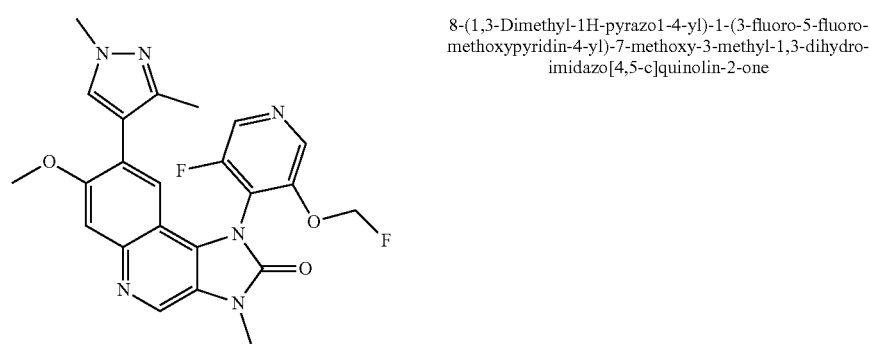

8-(1,3-Dimethyl-1H-pyrazol-4-yl)-1-(3-fluoro-5-fluoromethoxypyridin-4-yl)-7-methoxy-3-methyl-1,3-dihydro-imidazo[4,5-c]quinolin-2-one TABLE 1-continued Particularly preferred compounds

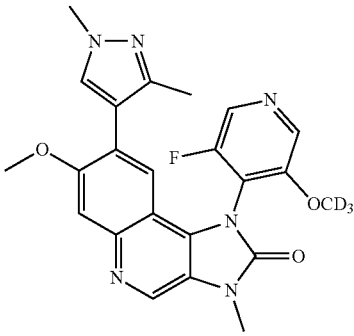
8-(1,3-Dimethylpyrazol-4-yl)-1-[3-fluoro-5-(trideuterio-methoxy)-4-pyridyl]-7-methoxy-3-methylimidazo[4,5-c]-quinolin-2-one

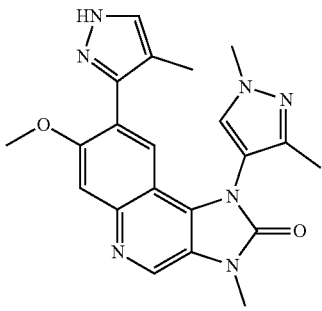
1-(1,3-Dimethyl-1H-pyrazol-4-yl)-7-methoxy-3-methyl-8-(4-methyl-1H-pyrazol-3-yl)-1,3-dihydroimidazo[4,5-c] quinolin-2-one

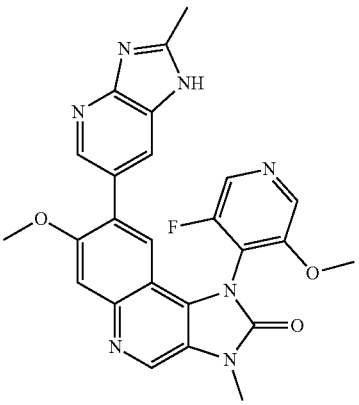
1-(3-Fluoro-5-methoxypyridin-4-yl)-7-methoxy-3-methyl-8-(2-methyl-1H-imidazo[4,5-b]pyridin-6-yl)-1,3-dihydroimidazo-[4,5-c]quinolin-2-one

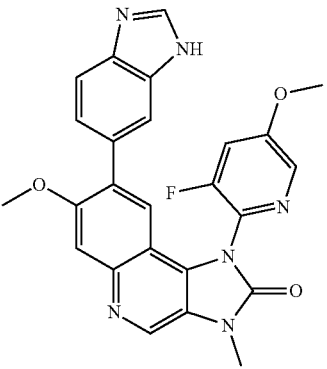
8-(3H-Benzimidazol-5-yl)-1-(3-fluoro-5-methoxypyridin-2-yl)-7-methoxy-3-methyl-1,3-dihydroimidazo[4,5-c]quinolin-2-one TABLE 1-continued Particularly preferred compounds

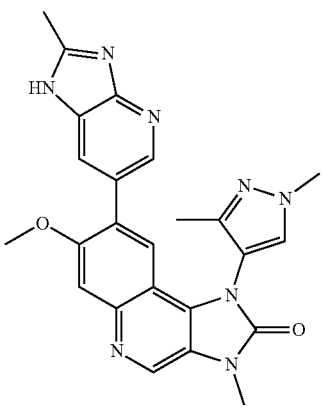

1-(1,3-Dimethyl-1H-pyrazol-4-yl)-7-methoxy-3-methyl-8-(2-methyl-1H-imidazo[4,5-b]pyridin-6-yl)-1,3-dihydroimidazo-[4,5-c]quinolin-2-one

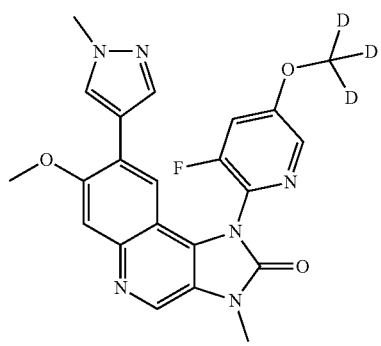 [SMILES: [2H]C([2H])([2H])Oc1cnc(-n2c(=O)n(C)c3cnc4cc(OC)c(-c5cnn(C)c5)cc4c32)c(F)c1]

1-[3-Fluoro-5-(trideuteriomethoxy)-2-pyridyl]-7-methoxy-3-methyl-8-(1-methylpyrazol-4-yl)imidazo[4,5-c]quinolin-2-one

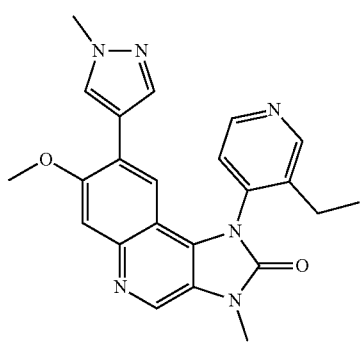 [SMILES: CCc1cnccc1-n1c(=O)n(C)c2cnc3cc(OC)c(-c4cnn(C)c4)cc3c21]

1-(3-Ethylpyridin-4-yl)-7-methoxy-3-methyl-8-(1-methyl-1H-pyrazol-4-yl)-1,3-dihydroimidazo[4,5-c] quinolin-2-one

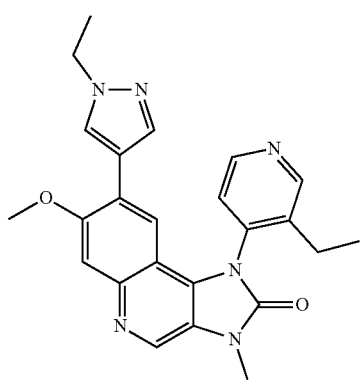 [SMILES: CCc1cnccc1-n1c(=O)n(C)c2cnc3cc(OC)c(-c4cnn(CC)c4)cc3c21]

8-(1-Ethyl-1H-pyrazol-4-yl)-1-(3-ethylpyridin-4-yl)-7-methoxy-3-methyl-1,3-dihydroimidazo[4,5-c] quinolin-2-one TABLE 1-continued Particularly preferred compounds

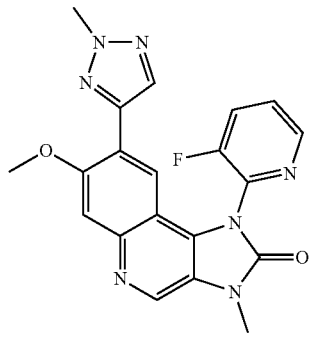 [SMILES: COc1cc2ncc3c(c2cc1-c1cnn(C)n1)n(-c1ncccc1F)c(=O)n3C]
1-(3-Fluoropyridin-2-yl)-7-methoxy-3-methyl-8-(2-methyl-2H-1,2,3-triazol-4-yl)-1,3-dihydroimidazo[4,5-c] quinolin-2-one

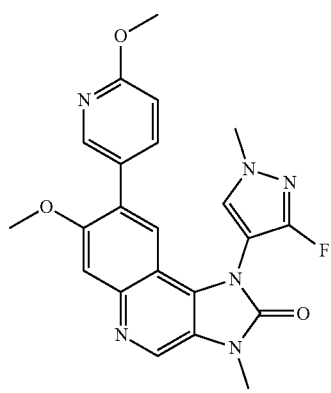 [SMILES: COc1ccc(-c2cc3c(cc2OC)ncc2c3n(-c3cn(C)nc3F)c(=O)n2C)cn1]
1-(3-Fluoro-1-methyl-1H-pyrazol-4-yl)-7-methoxy-8-(6-methoxypyridin-3-yl)-3-methyl-1,3-dihydroimidazo[4,5-c]-quinolin-2-one

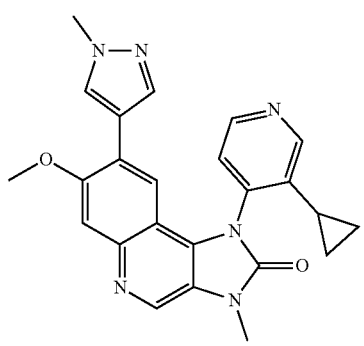 [SMILES: COc1cc2ncc3c(c2cc1-c1cnn(C)c1)n(-c1ccncc1C1CC1)c(=O)n3C]
1-(3-Cyclopropylpyridin-4-yl)-7-methoxy-3-methyl-8-(1-methyl-1H-pyrazol-4-yl)-1,3-dihydroimidazo[4,5-c]quinolin-2-one

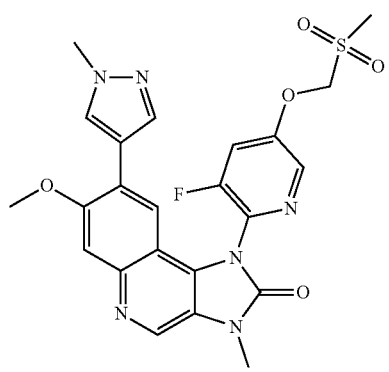 [SMILES: COc1cc2ncc3c(c2cc1-c1cnn(C)c1)n(-c1ncc(OCS(C)(=O)=O)cc1F)c(=O)n3C]
1-(3-Fluoro-5-methylsulfonylmethoxypyridin-2-yl)-7-methoxy-3-methyl-8-(1-methyl-1H-pyrazol-4-yl)-1,3-dihydroimidazo-[4,5-c]quinolin-2-one TABLE 1-continued Particularly preferred compounds

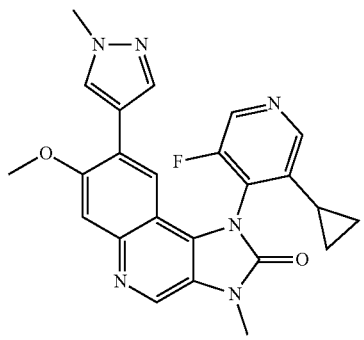 [SMILES: COc1cc2ncc3c(c2cc1-c1cnn(C)c1)n(-c1c(F)cncc1C1CC1)c(=O)n3C]

1-(3-Cyclopropyl-5-fluoropyridin-4-yl)-7-methoxy-3-methyl-8-(1-methyl-1H-pyrazol-4-yl)-1,3-dihydroimidazo[4,5-c]quinolin-2-one

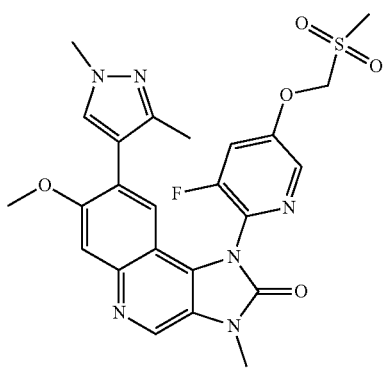 [SMILES: COc1cc2ncc3c(c2cc1-c1cn(C)nc1C)n(-c1ncc(OCS(C)(=O)=O)cc1F)c(=O)n3C]

8-(1,3-Dimethyl-1H-pyrazol-4-yl)-1-(3-fluoro-5-methylsulfonylmethoxypyridin-2-yl)-7-methoxy-3-methyl-1,3-dihydroimidazo[4,5-c]quinolin-2-one

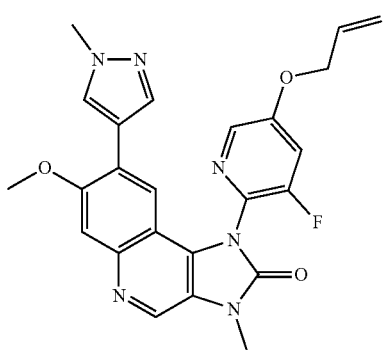 [SMILES: C=CCOc1cnc(-n2c(=O)n(C)c3cnc4cc(OC)c(-c5cnn(C)c5)cc4c32)c(F)c1]

1-(5-Allyloxy-3-fluoropyridin-2-yl)-7-methoxy-3-methyl-8-(1-methyl-1H-pyrazol-4-yl)-1,3-dihydroimidazo[4,5-c]quinolin-2-one

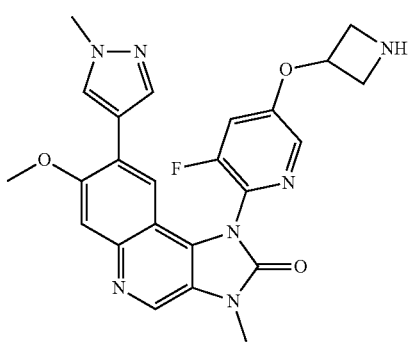 [SMILES: COc1cc2ncc3c(c2cc1-c1cnn(C)c1)n(-c1ncc(OC2CNC2)cc1F)c(=O)n3C]

1-[5-(Azetidin-3-yloxy)-3-fluoropyridin-2-yl]-7-methoxy-3-methyl-8-(1-methyl-1H-pyrazol-4-yl)-1,3-dihydroimidazo-[4,5-c]quinolin-2-one TABLE 1-continued

| Particularly preferred compounds |
|---|

1-[3-Fluoro-5-(2-methylaminoethoxy)-pyridin-2-yl]-7-methoxy-3-methyl-8-(1-methyl-1H-pyrazol-4-yl)-1,3-dihydro-imidazo[4,5-c]quinolin-2-one 1-[3-Fluoro-5-(1-methylazetidin-3-ylmethoxy)pyridin-2-yl]-7-methoxy-3-methyl-8-(1-methyl-1H-pyrazol-4-yl)-1,3-dihydro-imidazo[4,5-c]quinolin-2-one 8-[1-(Azetidin-3-yl)-1H-pyrazol-4-yl]-1-(3-fluoro-5-methoxy-pyridin-4-yl)-7-methoxy-3-methyl-1H,2H,3H-imidazo[4,5-c]-quinolin-2-one 1-(3-Fluoro-5-methoxypyridin-4-yl)-7-methoxy-3-methyl-8-(3-fluoro-1-methyl-1H-pyrazol-4-yl)-1,3-dihydroimidazo[4,5-c]-quinolin-2-one TABLE 1-continued Particularly preferred compounds

| Structure | Name |
|---|---|
| | 1-(1,3-Dimethyl-1H-pyrazol-4-yl)-7-methoxy-3-methyl-8-(3-fluoro-1-methyl-1H-pyrazol-4-yl)-1,3-dihydroimidazo[4,5-c]-quinolin-2-one |
| | 1-(5-Fluoro-1H-pyrrolo[2,3-b]pyridin-6-yl)-7-methoxy-3-methyl-8-(1-methyl-1H-pyrazol-4-yl)-1,3-dihydroimidazo-[4,5-c]quinolin-2-one |
| | 1-[3-Fluoro-5-(trifluoromethoxy)-4-pyridyl]-7-methoxy-3-methyl-8-(1-methyl-1H-pyrazol-4-yl)-1,3-dihydroimidazo-[4,5-c] quinolin-2-one |
| | 1-[3-Fluoro-5-(trifluoromethoxy)-4-pyridyl]-7-methoxy-3-methyl-8-(1,3-dimethylpyrazol-4-yl)-1,3-dihydroimidazo-[4,5-c]quinolin-2-one |

TABLE 1-continued

Particularly preferred compounds 1-(3-Fluoro-5-methylsulfonylpyridin-2-yl)-7-methoxy-3-methyl-8-(1-methyl-1H-pyrazol-4-yl)-1H,2H,3H-imidazo[4,5-c]quinolin-2-one 8-[1-(Azetidin-3-yl)-3-methyl-1H-pyrazol-4-yl]-1-(3-fluoro-5-methoxypyridin-4-yl)-7-methoxy-3-methyl-1H,2H,3H-imidazo[4,5-c]quinolin-2-one Each of the meanings for R1, R3, HET, and Het1 disclosed in the context of the above preferred compounds is also to be regarded as preferred meaning of the corresponding radical, irrespective of the other substitution of the molecule's basic structure, i.e. as possible meanings of R1, R3, HET, and Het1 in each case independently of one another.

Preparation

The compounds of the formula (I) and also the starting materials for their preparation are prepared by methods known per se, as described in the literature (for example in standard works, such as Houben-Weyl, Methoden der organischen Chemie [Methods of Organic Chemistry], Georg-Thieme-Verlag, Stuttgart) and/or are known to the person skilled in the art, and under reaction conditions which are known and suitable for the said reactions. Use can also be made of variants known per se which are not mentioned in greater detail here. The compounds according to the invention can be prepared by means of or analogously to the syntheses described in detail in EXAMPLES 1 to 13 through suitable choice or adaptation of the starting materials. For most compounds according to the invention, the synthesis described in EXAMPLE 1 can be suitably modified and thus employed analogously. Amine derivatives and boronic acid esters or analogues which can be employed in the corresponding syntheses are summarised below in Scheme 4. In addition, reference is also made to the disclosure WO 2010/139731, which is to be incorporated in its full scope into the present disclosure by way of reference.

The process and the subsequent work-up of the reaction mixture can basically be carried out as a batch reaction or in continuous reaction procedure. The continuous reaction procedure comprises, for example, the reaction in a continuous stirred-tank reactor, a stirred-tank cascade, a loop or cross-flow reactor, a flow tube or in a microreactor. The reaction mixtures are optionally worked up, if necessary, by filtration through solid phases, chromatography, separation between immiscible phases (for example extraction), adsorption onto solid supports, distilling off solvents and/or azeotropic mixtures, selective distillation, sublimation, crystallisation, co-crystallisation or by nanofiltration on membranes.

The starting compounds are generally known. If they are novel, they can be prepared by methods known per se. If desired, the starting materials can be formed in situ by not isolating them from the reaction mixture, but instead immediately converting them further into the compounds according to the invention. It is likewise possible to carry out the reaction stepwise.

Pharmaceutically Usable Forms

For the purposes of the invention, the compounds according to the invention are defined in such a way that they also include pharmaceutically usable derivatives, salts, solvates including hydrates, precursors of the compounds, tautomers and optically active forms (such as, for example, stereoisomers, diastereomers, enantiomers, racemates). The invention also relates to the use of mixtures of the compounds of the formula (I), for example mixtures of two diastereomers, for example in the ratio 1:1, 1:2, 1:3, 1:4, 1:5, 1:10, 1:100 or 1:1000. They are particularly preferably mixtures of stereoisomeric compounds.

Solvates of the compounds are taken to mean adductions of inert solvent molecules onto the compounds which form owing to their mutual attractive force. Solvates are, for example, mono- or dihydrates or alcoholates.

Pharmaceutically usable derivatives are taken to mean, for example, the salts of the compounds according to the invention and so-called precursors or prodrugs of the compounds. Prodrugs or precursors are taken to mean, for example, compounds of the formula (I) modified by means of alkyl or acyl groups, sugars or oligopeptides, which are rapidly cleaved in the organism to give the effective compounds according to the invention. These also include biodegradable polymer derivatives of the compounds according to the invention, as described, for example, in Int. J. Pharm. 115, 61-67 (1995). Any compound which can be converted in vivo into a bioactive agent, i.e. compounds of the formula (I), is a precursor in the sense of this invention. Any biologically active compound which results from the in vivo metabolisation of a compound according to the invention is a metabolite in the sense of the present invention.

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds according to the invention are for the most part prepared by conventional methods. If the compounds contain a carboxyl group, one of its suitable salts can be formed by reacting the compound with a suitable base to give the corresponding base-addition salt. Such bases are, for example, alkali metal hydroxides (for example potassium hydroxide, sodium hydroxide and lithium hydroxide), alkaline-earth metal hydroxides (for example barium hydroxide and calcium hydroxide), alkali metal alkoxides (for example potassium ethoxide and sodium propoxide) and various organic bases, such as piperidine, diethanolamine and N-methylglutamine. A base can be converted into the associated acid-addition salt using an acid, for example by reaction of equivalent amounts of the base and the acid in an inert solvent, such as, for example, ethanol, and subsequent evaporation. Suitable acids for this reaction are, in particular, those which give physiologically acceptable salts, such as, for example, hydrogen halides (for example hydrogen chloride, hydrogen bromide or hydrogen iodide), other mineral acids and corresponding salts thereof (for example sulfate, nitrate or phosphate and the like), alkyl- and monoarylsulfonates (for example ethanesulfonate, toluenesulfonate and benzenesulfonate) and other organic acids and corresponding salts thereof (for example acetate, trifluoroacetate, tartrate, maleate, succinate, citrate, benzoate, salicylate, ascorbate and the like. Salts with physiologically unacceptable acids, for example picrates, can be used for the isolation and/or purification of the compounds according to the invention.

With regard to that stated above, it can be seen that the expression "pharmaceutically usable salt", or also "pharmaceutically acceptable salt" in the present connection is to be taken to mean a compound according to the invention which is in the form of one of its salts, in particular if this salt form of the compound imparts improved pharmacokinetic properties compared with its free form. The pharmaceutically acceptable salt form of the compound may also provide this compound with a desired pharmacokinetic property for the first time and can even have a positive influence on the pharmacodynamics of the compound with respect to its therapeutic efficacy in the body.

Compounds according to the invention may be chiral owing to their molecular structure and accordingly occur in various enantiomeric forms. They can therefore exist in racemic or in optically active form. Since the pharmaceutical activity of the racemates or stereoisomers of the compounds of the formula I may differ, it may be desirable to use the enantiomers. In these cases, the end product or even the intermediate can be separated into enantiomeric compounds by chemical or physical measures known to the person skilled in the art or even employed as such in the synthesis.

It is generally known that atoms can have atomic masses or mass numbers which can differ from the usual naturally occurring atomic masses or mass numbers. Examples of isotopes which are commercially available and which can be incorporated into a compound according to the invention by known methods are isotopes of hydrogen, carbon, nitrogen, oxygen, phosphorus, fluorine and chlorine, for example $^2$H, $^3$H, $^{13}$C, $^{14}$C, $^{15}$N, $^{18}$O, $^{17}$O, $^{31}$P, $^{32}$P, $^{35}$S, $^{18}$F and $^{36}$Cl. The incorporation of heavier isotopes, in particular deuterium ($^2$H), into a compound according to the invention has therapeutic advantages which have their roots in the higher metabolic stability of this isotope-labelled compound. Higher metabolic stability directly results in an increased in vivo half life, which enables a lower dosage.

The definitions of the atoms H, C, N, etc., as used in the compounds according to the invention, therefore also relate to the heavier isotopes of these atoms.

Particular preference is given in accordance with the invention to the use of D (deuterium, $^2$H) instead of hydrogen ($^1$H). Deuterium can be incorporated into the compounds according to invention, for example, by means of a suitable substituent on HET for example trideuteriomethyl or trideuteriomethoxy.

Use

It has surprisingly been found that the compounds according to the invention effect specific inhibition of protein kinases, especially ATM kinase. Correspondingly, the present invention provides ATM inhibitors which are selected from the compounds according to the invention.

As part of the invention presented here, novel 2,3-dihydro-1H-imidazol[4,5-c]quinoline compounds were provided for the first time. The compounds according to the invention control serine/threonine protein kinases, in particular ATM kinase, affinitively and/or selectively. The compounds of the formula (I) and derivatives thereof are distinguished by high specificity and stability, low preparation costs and easy handling. Such properties form the basis for a reproducible mode of action and reliable and safe interaction with the corresponding target structures. The invention also includes the use of the present 2,3-dihydro-1H-imidazol[4,5-c]quinoline derivatives for the inhibition, regulation and/or modulation of the signalling cascade of serine/threonine protein kinases, in particular ATM kinase, and thus offers novel tools for research and/or diagnostics.

The invention therefore furthermore relates to the use of compounds according to the invention and/or physiologically acceptable solvates, salts, tautomers and/or stereoisomers thereof, including mixtures thereof in all ratios, for the inhibition of serine/threonine protein kinases, in particular ATM kinase. The term "inhibition" relates to any reduction in the activity which is based on the action of the specific compounds according to the invention in that the latter are capable of interacting with the target molecule in such a way that recognition, binding and blocking is made possible. The compounds are distinguished by high affinity to ATM kinase, ensuring reliable binding and preferably complete blocking of the kinase activity. The compounds are furthermore very selective and thus enable exclusive and direct recognition of ATM kinase. The term "recognition" relates here to any type of interaction between the compound and the said target molecules, in particular covalent or non-covalent bonds, such as, for example, a covalent bond, hydrophobic/hydrophilic interactions, van der Waals forces, ion attraction, hydrogen bonds, ligand/receptor interactions, base pairs of nucleotides or interactions between epitope and antibody binding site.

Compounds according to the invention and/or physiologically acceptable salts, tautomers and/or stereoisomers thereof, including mixtures thereof in all ratios, are suitable for use in the treatment of disease which are caused, mediated and/or propagated by the activity of serine/threonine protein kinases, in particular ATM.

The present invention relates to the compounds according to the invention and/or physiologically acceptable derivatives, solvates, salts, tautomers and/or stereoisomers thereof, including mixtures thereof in all ratios, for use as medicament.

The invention discloses the compounds according to the invention and/or physiologically acceptable salts, tautomers and/or stereoisomers thereof, including mixtures thereof in all ratios, for use in the treatment of diseases which are caused, mediated and/or propagated by the activity of serine/threonine protein kinases, in particular ATM kinase.

The present invention therefore also relates to the compounds according to the invention and/or physiologically acceptable derivatives, solvates, salts, tautomers and/or stereoisomers thereof, including mixtures thereof in all ratios, for use in the treatment of diseases which are caused, mediated and/or propagated by the activity of serine/threonine protein kinases, in particular ATM kinase. The present invention correspondingly also relates to the use of compounds according to the invention and/or physiologically acceptable derivatives, solvates, salts, tautomers and/or stereoisomers thereof, including mixtures thereof in all ratios, for the preparation of a medicament for the treatment of diseases which are caused, mediated and/or propagated by the activity of serine/threonine protein kinases, in particular ATM kinase. In other words, the present invention also discloses a compound according to the invention and/or a pharmaceutically usable derivative, salt, solvate, tautomer or stereoisomer thereof, for use in the treatment of diseases which are influenced by inhibition of ATM kinase.

For the identification of a corresponding signalling pathway and in order to detect interactions between various signalling pathways, suitable models or model systems have been developed, for example cell culture models (Khwaja et al. (1997) EMBO 16: 2783) and models of transgenic animals (White et al. (2001) Oncogene 20: 7064). In order to determine certain stages in the signalling cascade, interacting compounds can be used in order to modulate the signal (Stephens et al. (2000) Biochemical J 351: 95). In addition, the compounds according to the invention can also be used as reagents for testing kinase-dependent signalling pathways in animals and/or cell culture models or in the clinical diseases mentioned in this application. As discussed herein, these signalling pathways are relevant for various diseases. Accordingly, the compounds according to the invention are useful in the prophylaxis, therapy and/or progress control of diseases which are dependent on signalling pathways with participation by serine/threonine protein kinases, preferably ATM kinase.

The present invention also relates to the compounds according to the invention and/or physiologically acceptable derivatives, solvates, salts, tautomers and/or stereoisomers thereof, including mixtures thereof in all ratios, for use in the treatment of cancer, tumours and/or metastases and to the use thereof in the preparation of a medicament for precisely these uses.

The tumour is selected, in particular, from the group of diseases of the squamous epithelium, bladder, stomach, kidneys, head, neck, oesophagus, cervix, thyroid, intestine, liver, brain, prostate, urogenital tract, lymphatic system, larynx, lung, skin, blood and immune system, and/or the cancer is selected from the group of monocytic leukaemia, lung adenocarcinoma, small-cell lung carcinoma, pancreatic cancer, glioblastoma, bowel carcinoma, breast carcinoma, acute myeloid leukaemia, chronic myeloid leukaemia, acute lymphatic leukaemia, chronic lymphatic leukaemia, Hodgkin's lymphoma and non-Hodgkin's lymphoma.

The present invention additionally relates to a process for the preparation of a medicament, preferably for use in the treatment of cancer and/or tumours, preferably the types of cancer or tumour mentioned above, comprising:

i. determination that a concentration at which a compound according to the invention and/or a pharmaceutically usable derivative, salt, solvate, tautomer or stereoisomer thereof achieves 50% inhibition of the activity of ATM kinase is 500 nM or less, preferably 100 nM, 10 nM, 1 nM or less, and ii. preparation of a pharmaceutical composition which comprises the compound.

The determination of 50% inhibition of the activity of ATM kinase is preferably carried out here with the aid of the assay described herein (1050 ATM).

Compounds according to the invention and/or physiologically acceptable derivatives, solvates, salts, tautomers and/or stereoisomers thereof, including mixtures thereof in all ratios, may also be suitable for use in the slowing of ageing processes, where the slowing occurs with reference to the comparison of the life span of the treated host or cells, cell cultures, tissues or organs thereof with corresponding positive of negative controls and/or statistics.

The invention furthermore teaches a method for the treatment of cancer, tumours and/or metastases in which an effective amount of at least one compound according to the invention and/or physiologically acceptable derivatives, solvates, salts, tautomers and/or stereoisomers thereof, including mixtures thereof in all ratios, is administered to a subject to be treated. Preferred subjects in the sense of the invention are humans or animals, particularly preferably humans. It is known to the person skilled in the art here that he can administer the compounds according to the invention, which can of course also be used as the pharmaceutical composition according to the invention, in various doses to an organism, in particular a human patient. The effective amount and the type of administration can be determined by the person skilled in the art by routine experiments. The previous teaching of the invention and embodiments thereof are valid and can be applied without restrictions to the treatment method, if it appears appropriate.

The compounds according to the invention, salts, isomers, tautomers, enantiomers, diastereomers, racemates, derivatives, prodrugs and/or metabolites thereof are effective not only in the case of the said clinical pictures, but likewise in the diagnosis and therapy of all diseases in connection with the ATM signalling cascade, especially with a view to inhibition of cell proliferation and migration.

In addition, the inhibitors according to the invention can be used in the treatment of retroviral diseases by suppression of retroviral integration (R. Daniel (1999) Science 284: 644). Finally, the inhibitors according to the invention can be employed as immunomodulators and modulators of telomere maintenance.

The present invention furthermore relates to the use of a compound according to the invention and/or pharmaceutically usable derivative, salt, solvate, tautomer or stereoisomer thereof for the inhibition of a protein kinase, in particular ATM kinase in vitro.

The said use of compounds according to the invention and/or pharmaceutically usable derivatives, solvates, salts, tautomers and/or stereoisomers thereof, including mixtures thereof in all ratios, for the inhibition of serine/threonine protein kinases, in particular ATM kinase, can take place in in vitro or in vivo models. The susceptibility of a particular cell to treatment with the compounds according to the invention can be determined by testing in vitro. Typically, a culture of the cell is incubated with a compound according to the invention at various concentrations for a period of time which is sufficient to enable the active agents to induce cell death or to inhibit cell proliferation, cell vitality or migration, usually between about one hour and one week. For testing in vitro, cultivated cells from a biopsy sample can be used. The amount of cells remaining after the treatment is then determined. The use in vitro takes place, in particular, on samples of mammal species which are suffering from cancer, tumours, metastases, angiogenesis disorders, retroviral diseases, immune diseases and/or pathogenic ageing processes. The host or patient can belong to any mammal species, for example a primate species, in particular humans, but also rodents (including mice, rats and hamsters), rabbits, horses, cows, dogs, cats, etc. Animal models are of interest for experimental investigations, providing a model for the treatment of a human disease.

The testing of a plurality of specific compounds enables the selection of the compound or active compound which appears the most suitable for the treatment of the patient. The in vivo dose of the selected compound is advantageously matched to the susceptibility of the kinase and/or severity of the disease of the patient taking into account the in vitro data, as a result of which the therapeutic efficacy is noticeably increased. The dose varies depending on the specific compound used, the specific disease, the patient status, etc. A therapeutic dose is typically sufficient considerably to reduce the undesired cell population in the target tissue, while the viability of the patient is maintained.

The teaching of the invention disclosed herein and embodiments thereof relating to the use of compounds as or for the preparation of a medicament for the treatment is valid and can be applied without restrictions to the use of the compounds for the inhibition of kinase activity if it appears appropriate.

The treatment is generally continued until a considerable reduction has occurred, for example at least about 50% reduction of the cell load, and can be continued until essentially no more undesired cells are detected in the body. In tests of this type, the compounds according to the invention exhibit and cause an inhibiting effect, which is usually documented by $IC_{50}$ values in a suitable range, preferably in the micromolar range and more preferably in the nanomolar range. The kinase is, in particular, inhibited to the extent of 50% if the concentration of the compounds is less than 1 µM, preferably equal to or less than 0.5 µM, particularly preferably less than 0.1 µM, 0.05 µM or 0.001 µM. This concentration is called the $IC_{50}$ value and is preferably determined with the aid of the assay described herein (IC50 ATM). In accordance with the usual nomenclature, "µM" stands for micromoles per litre, "nM" stands for nanomoles per litre.

Assays

The compounds according to the invention exhibit an advantageous biological activity which can be demonstrated in the tests described herein, such as, for example, enzyme-based assays.

Measurement of the kinase activity is a technique which is well known to the person skilled in the art. Generic test systems for the determination of the kinase activity using substrates, for example histone (Alessi et al. (1996) FEBS Lett. 399(3): 333) or the basic myelin protein, are described in the literature (Campos-Gonzalez & Glenney (1992) JBC 267: 14535). Various assay systems are available for the identification of kinase inhibitors. In the scintillation proximity assay (Sorg et al. (2002) J Biomolecular Screening 7: 11) and the flashplate assay, the radioactive phosphorylation of a protein or peptide as substrate are measured using ATP. In the presence of an inhibitory compound, a decreased radioactive signal, or none at all, is detectable. Furthermore, homogeneous time-resolved fluorescence resonance energy transfer (HTR-FRET) and fluorescence polarisation (FP) technologies are useful as assay methods (Sills et al. (2002) J Biomolecular Screening 191). Other non-radioactive ELISA methods use specific phospho-antibodies (phospho-ABs). The phospho-AB binds only the phosphorylated substrate. This binding can be detected by chemiluminescence using a second peroxidase-conjugated anti-sheep antibody.

For the purposes of the present invention, the inhibition of the activity of ATM is preferably determined with the aid of the following assay:

ATM Kinase Assay—Determination of ATM Inhibition (IC50 ATM):

The $IC_{50}$ value was determined with the aid of a biochemical ATM kinase assay. The assay consists of two steps: the enzymatic reaction and the detection step. Firstly, ATM (ataxia telangiectasia mutated) protein and the test substance are incubated at different concentrations with addition of substrate protein p53 and ATP. ATM mediates the phosphorylation of p53 at several positions, including at amino acid S15. The amount of phosphorylated p53 is determined with the aid of specific antibodies and the TR-FRET technique. The enzymatic ATM assay is carried out as TR-FRET (HTRF™, Cisbio Bioassays) based 384-well assay. In the first step, purified human recombinant ATM (human ATM, full length, GenBank ID NM_000051, expressed in a mammal cell line) is incubated in assay buffer for 15 minutes with the ATM inhibitor in various concentrations and without test substance as negative or neutral control. The assay buffer comprises 25 mM HEPES pH 8.0, 10 mM $Mg(CH_3COO)_2$, 1 mM $MnCl_2$, 0.1% BSA and 0.01% Brij® 35, 5 mM dithiothreitol (DTT). The test-substance solutions were dispensed into the microtitre plates using an ECHO 555 (Labcyte). In the second step, purified human recombinant cmyc-labelled p53 (human p53, full length, GenBank ID BC003596, expressed in Sf21 insect cells) and ATP are added, and the reaction mixture is incubated at 22° C. for 30-35 minutes. The pharmacologically relevant assay volume is 5 µl. The final concentrations in the assay during incubation of the reaction mixture are 0.3-0.4 nM ATM, 50-75 nM p53 and 10 µM ATP. The enzymatic reaction is stopped by addition of EDTA. The formation of phosphorylated p53 as the result of the ATM-mediated reaction in the presence of ATP is detected via specific antibodies [labelled with the fluorophorene europium (Eu) as donor and d2 as acceptor (Cisbio Bioassays)] which enable FRET. 2 µl of antibody-containing stop solution (12.5 mM HEPES pH 8.0, 125 mM EDTA, 30 mM sodium chloride, 300 mM potassium fluoride, 0.1006% Tween-20, 0.005% Brij® 35, 0.21 nM anti-phospho-p53(ser15)-Eu antibody and 15 nM anti-cmyc-d2 antibody) are added to the reaction mixture. After incubation, usually for 2 hours (between 1.5 and 15 h), for signal development, the plates are analysed in a plate reader (EnVision, PerkinElmer) using TRF mode (and with laser excitation). After excitation of the donor europium at a wavelength of 340 nm, the emitted fluorescence light both of the acceptor d2 at 665 nm and also of the donor Eu at 615 nm is measured. The amount of phosphorylated p53 is directly proportional to the quotient of the amounts of light emitted, i.e. the relative fluorescence units (RFU) at 665 nm and 615 nm. The measurement data were processed by means of Genedata Screener software. $IC_{50}$ determinations are carried out, in particular, by fitting a dose/action curve to the data points by means of nonlinear regression analysis.
$IC_{50}$=half-maximum inhibitory concentration
ATP=adenosine triphosphate
TR-FRET=time-resolved fluorescence resonance energy transfer
HTRF®=homogeneous time resolved fluorescence
HEPES=2-(4-(2-hydroxyethyl)-1-piperazinyl)ethanesulfonic acid
$Mg(CH_3COO)_2$=magnesium acetate
$MnCl_2$=manganese(II) chloride
BSA=bovine serum albumin
EDTA=ethylenediamine tetraacetate
TRF=time resolved fluorescence The activity of the substances according to the invention in the cellular environment can be determined with the aid of the following assay:

Cellular pCHK2 Assay:

For the identification of substances which inhibit the phosphorylation of the protein kinase CHK2 at the amino acid threonine 68, an immunofluorescence-based "high content" analysis assay was used in HCT116 cells.

In vitro cell-based immunofluorescence assay for the identification of inhibitors of bleomycin-induced phosphorylation of CHK2 (phospho-Thr68) in the human colon carcinoma cell line HCT116:

HCT116 cells are sown out in a defined cell density in 384-well plates in culture medium (DMEM high glucose, 2 mM GlutaMax, 1 mM Na pyruvate, 10% FCS) and incubated overnight at 37° C. and 10% of $CO_2$. On the following day, the test substances are added in a defined concentration range (1 nM to 30 µM) in combination with 10 µM bleomycin, where the concentration of the solvent DMSO is kept constant at 0.5%. After incubation for four hours at 37° C. and 10% of $CO_2$, the cells are fixed (5 min, 4% formaldehyde in PBS), permeabilised (10 min, 0.2% Triton X-100 in PBS) and, after blocking of nonspecific binding sites (10% goat serum, 1% BSA in PBS), incubated overnight at 4° C. with a specific anti-pCHK2 antibody (cell signalling #2661). pCHK2 (Thr68) is determined using an Alexa488-labelled secondary anti-rabbit IgG antibody. Parallel staining of DNA with propidium iodide enables determination of the cell count. The pCHK2 signal is detected using a high-content imager (Molecular Devices IMX Ultra) and automatic image analysis using the MetaXpress software belonging to the instrument. The number of cell nuclei which have a pCHK2 signal above a defined background is determined.

Furthermore, the effect, in particular inhibition, of other kinases and thus the selectivity of the compounds according to the invention can be determined with the aid of the following assay:

mTor (Human)

mTOR (human) was incubated with 50 mM HEPES pH 7.5, 1 mM EGTA, 0.01% Tween 20, 2 mg/ml of the substrate, 3 mM $MnCl_2$ and [γ-$^{33}$P-ATP] (specific activity approximately 500 cpm/pmol, concentration as necessary). The reaction was initiated by addition of MgATP solution. After incubation at room temperature for 40 minutes, the reaction was stopped by addition of 3% phosphoric acid. 10 µl of the reaction solution were then transferred dropwise onto a P30 filtermat and washed three times for 5 min in 75 mM phosphoric acid and once in methanol, dried and evaluated by means of liquid scintillation counting.

PI3K p110α/p85α (Human), Non-Radioactive Assay

PI3K p110α/p85α (human) was incubated in an assay buffer comprising 10 µM phosphatidylinositol 4,5-bisphosphate and MgATP (concentration as necessary). The reaction was initiated by addition of MgATP solution. After incubation at room temperature for 40 minutes, the reaction was stopped by addition of a solution consisting of EDTA and biotinylated phosphatidylinositol 3,4,5-trisphosphate. Finally, the detection buffer, consisting of a europium-labelled anti-GST monoclonal antibody, a GST-labelled GRP1 PH domain and streptavidin allophycocyanin, was added. The plate was read out via homogeneous time-resolved fluorescence (HTRF) and the corresponding signals were evaluated via the formula HTRF=10000×(Em665 nm/Em620 nm).

PI3K p110β/p85α (Human), Non-Radioactive Assay

PI3K p110β/p85α (human) was incubated in an assay buffer comprising 10 µM phosphatidylinositol 4,5-bisphosphate and MgATP (concentration as necessary). The reaction was initiated by addition of MgATP solution. After an incubation time of 30 min at room temperature, the reaction was stopped by addition of a solution consisting of EDTA and biotinylated phosphatidylinositol 3,4,5-trisphosphate. Finally, the detection buffer, consisting of a europium-labelled anti-GST monoclonal antibody, a GST-labelled GRP1 PH domain and streptavidin allophycocyanin, was added. The plate was read out via homogeneous time-resolved fluorescence (HTRF) and the corresponding signals were evaluated via the formula HTRF=10000×(Em665 nm/Em620 nm).

PI3K p110δ/p85α (Human), Non-Radioactive Assay

PI3K p110δ/p85α (human) was incubated in an assay buffer comprising 10 µM phosphatidylinositol 4,5-bisphosphate and MgATP (concentration as necessary). The reaction was initiated by addition of MgATP solution. After an incubation time of 30 min at room temperature, the reaction was stopped by addition of a solution consisting of EDTA and biotinylated phosphatidylinositol 3,4,5-trisphosphate. Finally, the detection buffer, consisting of a europium-labelled anti-GST monoclonal antibody, a GST-labelled GRP1 PH domain and streptavidin allophycocyanin, was added. The plate was read out via homogeneous time-resolved fluorescence (HTRF) and the corresponding signals were evaluated via the formula HTRF=10000×(Em665 nm/Em620 nm).

PI3K (p120γ) (Human), Non-Radioactive Assay

PI3K (p120γ) (human) was incubated in an assay buffer comprising 10 µM phosphatidylinositol 4,5-bisphosphate and MgATP (concentration as necessary). The reaction was initiated by addition of MgATP solution. After an incubation time of 30 min at room temperature, the reaction was stopped by addition of a solution consisting of EDTA and biotinylated phosphatidylinositol 3,4,5-trisphosphate. Finally, the detection buffer, consisting of a europium-labelled anti-GST monoclonal antibody, a GST-labelled GRP1 PH domain and streptavidin allophycocyanin, was added. The plate was read out via homogeneous time-resolved fluorescence (HTRF) and the corresponding signals were evaluated via the formula HTRF=10000×(Em665 nm/Em620 nm).

MgATP=magnesium 5'-O-[hydroxy({[(hydroxyphosphinato)oxy]phosphinato}oxy)phosphoryl]adenosine $MgCl_2$=magnesium dichloride EGTA=ethylene glycol bis(aminoethyl ether) N,N,N',N'-tetraacetic acid Tween 20=polysorbate 20

Medicament/Pharmaceutical Composition

The invention also relates to a drug or medicament comprising at least one compound according to the invention and/or physiologically acceptable derivatives, solvates, salts, tautomers and/or stereoisomers thereof, including mixtures thereof in all ratios.

The invention furthermore relates to a pharmaceutical composition comprising an effective amount of at least one compound according to the invention and/or one of its physiologically acceptable derivatives, salts, solvates, tautomers and/or stereoisomers thereof, including mixtures thereof in all ratios, optionally together with at least one pharmaceutically tolerated adjuvant or optionally an excipient and/or adjuvant.

A "drug", "medicament" and a "pharmaceutical composition" or "pharmaceutical formulation" is to be taken to mean any composition which can be employed in the prophylaxis, therapy, progress control or aftertreatment of patients who, at least temporarily, exhibit a pathogenic modification of the overall condition or the condition of individual parts of the patient organism, preferably as a consequence of cancer, tumours and/or metastases.

In order to increase the protective or therapeutic action of the compounds according to the invention, pharmaceutically tolerated adjuvants can be added. For the purposes of the invention, any substance which facilitates, enhances or modifies an effect with the compounds in accordance with the invention is an "adjuvant". Known adjuvants are, for example, aluminium compounds, such as, for example, aluminium hydroxide or aluminium phosphate, saponins, such as, for example, QS 21, muramyl dipeptide or muramyl tripeptide, proteins, such as, for example, gamma-interferon or TNF, MF 59, phosphatdibylcholine, squalene or polyols. The co-application of egg albumin in complete Freund's adjuvant can likewise cause increased cell-mediated immunity and thus support the action of neutralising antibodies formed. Furthermore, DNA, which has an immunostimulatory property, or which encodes a protein with an adjuvant effect, such as, for example, a cytokine, can be applied in parallel or in a construct.

The introduction of the pharmaceutical composition into a cell or organism can be carried out in accordance with the invention in any manner which enables the kinases to be brought into contact with the compounds present in the composition, as a consequence of which a response is induced. The pharmaceutical composition of the present invention can be administered orally, transdermally, transmucosally, transurethrally, vaginally, rectally, pulmonarily, enterally and/or parenterally. The type of administration selected depends on the indication, the dose to be administered, individual-specific parameters, etc. In particular, the various types of administration facilitate site-specific therapy, which minimises side effects and reduces the active-compound dose. Very particularly preferred injections are intradermal, subcutaneous, intramuscular or intravenous injection. The administration can be carried out, for example, with the aid of so-called vaccination guns or by means of syringes. It is also possible to provide the substance as an aerosol, which is inhaled by the organism, preferably a human patient.

The administration forms of the pharmaceutical compositions are prepared using conventional solid or liquid excipients and/or diluents and the assistants usually employed corresponding to the desired type of administration in a suitable dosage and in a manner known per se. Thus, pharmaceutically acceptable excipients known to the person skilled in the art can basically form part of the pharmaceutical composition according to the invention, where the amount of the excipient material which is combined with the active compound in order to prepare a single dose varies depending on the individual to be treated and the type of administration. These pharmaceutically tolerated additions include salts, buffers, fillers, stabilisers, complexing agents, antioxidants, solvents, binders, lubricants, tablet coatings, flavours, dyes, preservatives, adjusters and the like. Examples of excipients of this type are water, vegetable oils, benzyl alcohols, alkylene glycol, polyethylene glycol, Kolliphor, glycerol triacetate, gelatine, carbohydrates, such as, for example, lactose or starch, hydroxypropylmethylcellulose (HPMC), magnesium stearate, talc and Vaseline. The pharmaceutical formulation can be in the form of a tablet, film tablet, dragee, lozenge, capsule, pill, powder, granules, syrup, juice, drops, solution, dispersion, suspension, suppository, emulsion, implant, cream, gel, ointment, paste, lotion, serum, oil, spray, aerosol, adhesive, plaster or bandage. Oral administration forms which are prepared are preferably tablets, film tablets, dragees, lozenges, capsules, pills, powders, granules, syrups, juices, drops, solutions, dispersions or suspensions—including as depot form. Furthermore, parenteral medicament forms, such as, for example, suppositories, suspensions, emulsions, implants or solutions, should be considered, preferably oily or aqueous solutions. For topical application, the medicament active compound is formulated in a conventional manner with at least one pharmaceutically acceptable vehicle, such as, for example, microcrystalline cellulose, and optionally further assistants, such as, for example, moisturisers, to give solid formulations which can be applied to the skin, such as, for example, creams, gels, ointments, pastes, powders or emulsions, or to give liquid formulations which can be applied to the skin, such as, for example, solutions, suspensions, lotions, sera, oils, sprays or aerosols. The pharmaceutical composition is preferably in the form of an injection solution. For the preparation of the injection solution, aqueous media, such as, for example, distilled water or physiological salt solutions, can be used, where the latter include acidic and basic addition salts. The pharmaceutical composition may also be in the form of a solid composition, for example in the lyophilised state, and is then prepared before use by addition of a dissolving agent, such as, for example, distilled water. The person skilled in the art is familiar with the basic principles of the preparation of lyophilisates.

The concentration of the active compound in the formulation can be 0.1 to 100 percent by weight. It is crucial that the pharmaceutical composition comprises, as active compound, an effective amount of the compound together with the pharmaceutically tolerated assistants. The terms "effective amount" or "effective dose" are used interchangeably herein and denote an amount of the pharmaceutical active compound which has a prophylactically or therapeutically relevant action on a disease or pathological change in cell, tissue, organ or mammal. A "prophylactic action" prevents the outbreak of a disease or even infection with a pathogen after ingress of individual representatives in such a way that subsequent propagation is greatly reduced or it is even completely deactivated. A "prophylactic action" also includes an increase in normal physiological function. Prophylaxis is advisable, in particular, if an individual has predispositions for the onset of the above-mentioned diseases, such as, for example, a family history, a gene defect or a recently survived disease. A "therapeutically relevant action" frees in part or full from one, more than one or all disease symptoms or results in the partial or complete reversal of one, more than one or all physiological or biochemical parameters which are associated with or causally involved in the disease or pathological change into the normal state. Progress control is also taken to be a type of therapeutic treatment if the compounds are administered at certain time intervals, for example in order completely to eliminate the symptoms of a disease. The respective dose or dose range for the administration of the compounds according to the invention is sufficiently large to achieve the desired prophylactic or therapeutic effect of induction of a biological or medical response. In general, the dose will vary with the age, constitution and gender of the patient, and the severity of the disease will be taken into account. It goes without saying that the specific dose, frequency and duration of administration are, in addition, dependent on a multiplicity of factors, such as, for example, the targeting and binding ability of the compounds, feeding habits of the individual to be treated, type of administration, excretion rate and combination with other drugs. The individual dose can be adjusted both with respect to the primary disease and also with respect to the occurrence of any complications. The precise dose can be established by a person skilled in the art using known means and methods. This teaching of the invention is valid and can be applied without restrictions to the pharmaceutical composition comprising the compounds according to invention, so long as it appears appropriate.

In an embodiment of the invention, the compounds are administered in a dose of 0.01 mg to 1 g per dosage unit, preferably between 1 to 700 mg, particularly preferably 5 to 100 mg. The daily dose is, in particular, between 0.02 and 100 mg/kg of body weight.

Owing to their surprisingly strong and/or selective kinase inhibition, in particular inhibition of ATM kinase, which regulates cellular processes via repair of double-strand DNA, the compounds of the invention can be administered in an advantageously low dose, while they achieve similar or even superior biological efficacy compared with less-potent or less-selective inhibitors. A reduced dose is typically associated with reduced medical side effects. In addition, highly selective inhibition is generally also reflected in a reduction in undesired side effects.

All said and further constituents or components of a medicament or pharmaceutical formulation are familiar to the person skilled in the art and may undergo special formulation for the teaching according to the invention in routine experiments.

Combination Therapy

Medicaments and pharmaceutical compositions which comprise the compounds according to the invention, and the use of these compounds for the treatment of kinase-mediated disorders are a highly promising approach for a broad range of therapies, enabling the achievement of direct and immediate amelioration of symptoms in humans and animals. This is particularly advantageous for effective combating of severe diseases, such as cancer, either as monotherapy, as outlined above, or in combination with other therapies, such as, for example, chemo- or radiotherapy. The key participation of ATM in DNA repair processes and the evidence that ATM kinase deficiency allows mammal cells to become more radiation sensitive enables therapeutic use of the ATM-specific inhibitors as part of the treatment of, for example, solid cancer tumours by irradiation therapy and/or chemotherapy, preferably aimed at DNA double-strand damage.

In order to support the medical action, the pharmaceutical composition may correspondingly, in an embodiment of the invention, also comprise one or more further active compounds, for example an anticancer agent, where simultaneous or successive administration is conceivable. The therapeutic action of the pharmaceutical composition according to the invention can consist, for example, in certain anticancer agents having a better action through the kinase inhibition or the number of side effects of these medicaments being reduced by the reduction in the dose. Correspondingly, the compounds according to the invention can be administered in combination with other active compounds, including anticancer agents.

In a preferred embodiment of the invention, the pharmaceutical composition according to the invention is combined with or comprises an anticancer agent. Correspondingly, the present invention also relates to a compound according to the invention and/or a pharmaceutically usable derivative, salt, solvate, tautomer or stereoisomer thereof for use in the treatment of cancer, tumours and/or metastases in combination with at least one anticancer agent.

As used here, the term "anticancer agent" relates to any agent which is administered to a patient with cancer, tumours and/or metastases for the purpose of treatment of the cancer.

The anticancer agent is particularly preferably selected from the group comprising cytokines, chemokines, pro-apoptotic agents, interferons, radioactive compounds, oestrogen receptor modulators, androgen receptor modulators, retinoid receptor modulators, cytotoxic agents, cytostatic agents, prenyl-protein transferase inhibitors and angiogenesis inhibitors or combinations thereof. It is preferred for the anticancer agent to modify, in particular reduce, nucleic acid and/or protein metabolism, cell division, DNA replication, purine, pyrimidine and/or amino acid biosynthesis, gene expression, mRNA processing, protein synthesis, apoptosis or combinations thereof.

Anticancer agents which are preferred in accordance with the invention are those which damage the DNA of tumour cells and thus engage in DNA replication, DNA transcription or gene expression. The following, in particular, are suitable for this purpose:

alkylating agents, such as altretamine, bendamustine, busulfan, carmustine, chloroambucil, chloromethine, cyclophosphamide, dacarbazine, ifosfamide, improsulfan tosylate, lomustine, melphalan, mitobronitol, mitolactol, nimustine, ranimustine, temozolomide, thiotepa, treosulfan, mechloroetamine, carboquone, apaziquone, fotemustine, glufosfamide, palifosfamide, pipobroman, trofosfamide, uramustine, platinum compounds, such as carboplatin, cisplatin, eptaplatin, miriplatin hydrate, oxaliplatin, lobaplatin, nedaplatin, picoplatin, satraplatin;

DDR (DNA damage response) inhibitors, such as topoisomerase inhibitors, for example etoposide, irinotecan, razoxane, sobuzoxane, topotecan, camptothecin, doxorubicin, amsacrine; poly-(ADP-ribose)-polymerase (PARP) inhibitors, for example talazoparib, olaparib, veliparib, rucaparib, CEP 9722, MK4827, BGB-290; ATR (ataxia telangiectasia and Rad3 related) inhibitors, for example VE-822, AZ20, AZD6738

DNA-modifying agents, such as amrubicin, bisantrene, decitabine, mitoxantrone, procarbazine, trabectedine, clofarabine, amsacrine, brostallicin, pixantrone, laromustine;

anticancer antibiotics, such as bleomycin, dactinomycin, doxorubicin, epirubicin, idarubicin, levamisol, miltefosine, mitomycin C, romidepsin, streptozocin, valrubicin, zinostatin, zorubicin, daunurobicin, plicamycin, aclarubicin, peplomycin, pirarubicin;

alpha emitters, such as alpharadin ($^{223}$Ra dichloride, Xofgio), $^{211}$At, $^{213}$Bi, $^{225}$Ac, $^{227}$Th;

Particular preference is given to bleomycin, alpharadin and DDR inhibitors, for example etoposide, irinotecan, razoxane, sobuzoxane, topotecan, camptothecin, doxorubicin, amsacrine, talazoparib, olaparib, veliparib, rucaparib, CEP 9722, MK4827, BGB-290; VE-822, AZ20, AZD6738.

The invention can also be practised as a kit which contains the compounds according to the invention. The kit consists of separate packs (a) of an effective amount of a compound according to the invention and/or a physiologically acceptable derivative, salt, tautomer and/or stereoisomer thereof, including mixtures thereof in all ratios, and (b) of an effective amount of a further active compound. The further active compound is preferably an anticancer agent.

The kit contains suitable containers, such as, for example, boxes or cartons, individual bottles, bags or ampoules. The kit may contain, for example, separate ampoules, each containing an effective amount of a compound according to the invention and/or pharmaceutically usable derivatives, solvates, salts, tautomers and/or stereoisomers thereof, including mixtures thereof in all ratios, or an effective amount of a further medicament active compound in dissolved or lyophilised form. The kit of the invention may also contain an article which contains written instructions or points the user towards written instructions which explain the handling of the compounds of the invention.

A further embodiment of the present invention relates to the compounds according to the invention in combination with radiotherapy and/or with at least one further active compound, preferably in combination with radiotherapy and/or an anticancer agent. In other words, a further embodiment of the present invention relates to the compounds according to the invention for use in the treatment of cancer, tumours and/or metastases in combination with radiotherapy. The present invention furthermore relates to a compound according to the invention or a pharmaceutically usable derivative, salt, solvate, tautomer and/or stereoisomer thereof for use in the sensitisation of cancer cells to an anticancer agent and/or ionising radiation.

Industrial irradiation methods which are used clinically preferably include photon irradiation (classical, electromagnetic X-ray/gamma radiation), proton irradiation, heavy-ion irradiation (ionised carbon) and neutron irradiation, without being restricted thereto. These radiotherapies and other suitable irradiation therapies in the sense of the invention are known to the person skilled in the art, such as, for example, from Herrmann et al. (2006) Klinische Strahlenbiologie [Clinical Radiation Biology], Elsevier Munich, 4th Edition, 67-68; Bhide & Nutting (2010) BMC Medicine 8: 25; Choi & Hung (2010) Current Urology Reports 11(3): 172. As the most frequent application, photon irradiation has been refined technically by the IMRT (intensity-modulated radiotherapy) method and by imaging methods (three-dimensional conformal radiotherapy) in irradiation planning and performance for the most precise focusing possible. The compounds according to the invention achieve synergistic effects in existing therapies and irradiations and/or restore the efficacy of existing therapies and irradiations. Still a further embodiment of the invention relates to the use of at least one compound and/or pharmaceutically usable derivatives, salts, solvates, tautomers and/or stereoisomers thereof, including mixtures thereof in all ratios, for the sensitisation of cancer cells to an anticancer agent and/or ionising radiation (radiotherapy), with the proviso that the sensitisation does not take place in vivo on the human or animal body.

The sensitisation is preferably carried out ex vivo or in vitro by administering the compounds to cells, cell cultures, tissues or organs which comprise serine/threonine protein kinases. The ex vivo use is used, in particular, in the case of animal cells which originate from an animal organism which is affected by a disease which is selected from the group of cancer, tumours, metastases and/or angiogenesis disorders. The cells treated ex vivo can either continue to be kept in culture for subsequent investigations or transferred into an animal, which can be the host animal or another animal. The ex vivo sensitisation according to the invention is particularly advantageous for testing the specific action of the compounds, so that the in vivo dose can be pre-adjusted correspondingly with evaluation of these ex vivo data. As a result thereof, the therapeutic effect is increased significantly. Alternatively, the invention is also designed for use in vivo and relates to at least one compound according to the invention and/or physiologically acceptable salts, tautomers and/or stereoisomers thereof, including mixtures thereof in all ratios, for use for the sensitisation of cancer cells to an anticancer agent and/or ionising radiation.

In summary, it should be noted that the compounds according to the invention can be used individually and/or in combination with other treatment measures, such as, for example, surgical interventions, immunotherapy, radiotherapy and/or chemotherapy. The latter relate to targeted therapy with any desired NME (i.e. NCE and/or NBE) as monotherapy and/or on-target/off-target combination therapy.

All documents cited in the description are hereby intended to be incorporated in their entirety into the disclosure of the present invention by way of reference.

It goes without saying that this invention is not restricted to the specific compounds, pharmaceutical compositions, uses and methods as described herein, since such things can vary. It furthermore goes without saying that the terminology used here serves exclusively the purpose of description of particular embodiments and is not intended to restrict the scope of protection of the invention. As used here in the specification, including the appended claims, word forms in the singular, such as, for example, "a" or "the", include the equivalent in the plural, so long as the context does not specifically indicate otherwise. For example, the reference to "a compound" includes a single compound or a plurality of compounds, which may in turn be identical or different, or the reference to "a method" includes equivalent steps and methods which are known to the person skilled in the art.

Further Compounds

Besides the above-mentioned compounds of the formula (I), the invention encompasses compounds of the following general formula (X):

(X)

[Chemical structure of formula (X): a tricyclic compound with R1-O and R2-X substituents on a benzene ring fused to a pyridine ring fused to an imidazolone ring bearing HET and R3 substituents]

in which
R1 denotes A or —(CY$_2$)$_n$—Ar,
R2 denotes Y, —(CY$_2$)$_p$—(C[YR4])$_s$—R5 or -Alk-R5,
R3 denotes Y, —(CY$_2$)$_p$—COOY or —(CY$_2$)$_p$—CO—NYY,
R4 denotes Y, Hal, —(CY$_2$)$_n$—NYY, —(CY$_2$)$_n$—NY—COO—(CY$_2$)$_n$—SiA$_3$, —(CY$_2$)$_n$—COOY, —CO—NYY, —CO—NY—(CY$_2$)$_n$—OY, —CO—NY—(CY$_2$)$_n$—NYY or —SO$_2$A,
R5 denotes —(CY$_2$)$_p$—Ar or —(CY$_2$)$_p$-Het$^1$,
X denotes CH$_2$, O, S or a single bond,
Y denotes H or A,
A denotes unbranched or branched alkyl having 1, 2, 3, 4, 5, 6, 7, 8, 9 or 10 C atoms, where 1, 2, 3, 4, 5, 6 or 7 H atoms may be replaced, independently of one another, by Hal,
Alk denotes alkenylene having 2, 3, 4, 5 or 6 C atoms, where 1, 2, 3 or 4 H atoms may be replaced, independently of one another, by Hal and/or OY,
CyA denotes cycloalkyl having 3, 4, 5, 6, 7 or 8 ring C atoms which is unsubstituted or mono- or polysubstituted, independently of one another, by Hal, A, CN, —(CY$_2$)$_p$—OY, —(CY$_2$)$_p$—NYY, —(CY$_2$)$_p$—COOY, —(CY$_2$)$_p$—CO—NYY and/or —(CY$_2$)$_p$—NY—COY,
Ar denotes phenyl which is unsubstituted or mono-, di- or trisubstituted, independently of one another, by Hal, A, CN, —NO$_2$, —(CY$_2$)$_p$—OY, —(CY$_2$)$_p$—NYY, —(CY$_2$)$_p$—COOY, —(CY$_2$)$_p$CO—NYY and/or —(CY$_2$)$_p$—NY—COY,
Het$^1$ denotes mono- or bicyclic heteroaryl having 2, 3, 4, 5, 6, 7, 8 or 9 C atoms and 1, 2, 3 or 4 N, O and/or S atoms, which may be unsubstituted or mono-, di- or trisubstituted, independently of one another, by Hal, A, CN, —(CY$_2$)$_p$—OY, —(CY$_2$)$_p$—NYY, —(CY$_2$)$_p$—COOY, —(CY$_2$)$_p$—CO—NYY, —(CY$_2$)$_p$—NY—COY and/or —SO$_2$-Het$^2$,
Het$^2$ denotes a monocyclic saturated heterocycle having 2, 3, 4, 5, 6 or 7 C atoms and 1, 2, 3 or 4 N, O and/or S atoms, which may be unsubstituted or monosubstituted by A,
HET denotes a 5- or 6-membered aromatic heterocycle having 1, 2 or 3 N atoms and optionally an O atom or S atom, where this heterocycle is linked to the N atom of the skeleton via a ring C atom and where this heterocycle may be unsubstituted or substituted by one, two or three substituents, which are selected, independently of one another, from the group consisting of: Hal, A, Het$^2$, —CN, —(CY$_2$)$_p$—OY, —(CY$_2$)$_p$—O—(CY$_2$)$_t$—OY, —(CY$_2$)$_p$—O—(CY$_2$)$_t$—POAA, —(CY$_2$)$_p$—NYY, —(CY$_2$)$_p$—COOY, —(CY$_2$)$_p$—CO—NYY, —(CY$_2$)$_p$—NY—COY or —SO$_2$-Het$^2$; and may be part of a bicyclic 11- or 12-membered aromatic heterocycle, where this bicyclic aromatic heterocycle may overall be unsubstituted or substituted by one, two, three or more substituents, which are selected, independently of one another, from the group consisting of: Hal, A, Het$^2$, CN, —(CY$_2$)$_p$OY, —(CY$_2$)$_p$—O—(CY$_2$)$_t$—OY, —(CY$_2$)$_p$—O—(CY$_2$)$_t$—POAA, —(CY$_2$)$_p$—NYY, —(CY$_2$)$_p$—COOY, —(CY$_2$)$_p$—CO—NYY, —(CY$_2$)$_p$—NY—COY or —SO$_2$-Het$^2$,
Hal denotes F, Cl, Br or I,
m denotes 0, 1, 2, 3 or 4,
n, p, s, independently of one another, denote 0, 1, 2, 3, 4, 5 or 6 and
t denotes 1, 2, 3, 4, 5 or 6,
and/or pharmaceutically usable salts, solvates, tautomers and stereoisomers thereof, including mixtures thereof in all ratios,
where, in addition to or in contrast to formula (I), it is not simultaneously possible for R1 and R3 to denote A and X to denote a single bond, R2 to denote —(CY$_2$)$_p$—(C[YR4])$_s$—R5 where p and s=0 and R5 to denote —(CY$_2$)$_p$-Het$^1$ where p=0.

The term "Alk" here denotes unbranched or branched alkenylene having 2, 3, 4, 5 or 6 C atoms, i.e. C$_{2-6}$-alkenyls, where, independently of one another, 1, 2, 3 or 4 H atoms may be replaced by Hal and/or OY. Alkenyls have at least one C—C double bond, may, in particular, also have two double bonds (dienes). Examples of suitable alkenylenes are divalent alkene radicals based on vinyl, allyl, propenyl (—CH$_2$CH=CH$_2$; —CH=CH—CH$_3$; —C(=CH$_2$)—CH$_3$), 1-, 2- or 3-butenyl, isobutenyl, 2-methyl-1- or 2-butenyl, 3-methyl-1-butenyl, 1,3-butadienyl, 2-methyl-1,3-butadienyl, 2,3-dimethyl-1,3-butadienyl, 1-, 2-, 3- or 4-pentenyl and hexenyl, i.e. —CH=CH—, —CH$_2$—CH=CH—, —CH=CH—CH$_2$—, —C(=CH$_2$)—CH$_2$—, —C(CH$_3$)=CH—, —CH=C(CH$_3$)—, —CH=CH—CH$_2$—CH$_2$—, —CH$_2$—CH=CH—CH$_2$—, —CH$_2$—CH$_2$—CH=CH—, —CH=C(CH$_3$)—CH$_2$—, —CH$_2$—C(CH$_3$)=CH—, —CH=CH—CH(CH$_3$)—, —C(CH$_3$)=CH—CH$_2$—, —CH=CH—CH=CH—, —CH=C(CH$_3$)—CH=CH—, —CH=C(CH$_3$)—C(CH$_3$)=CH—, —CH=CH—CH$_2$—CH$_2$—CH$_2$—, —CH$_2$—CH=CH—, —CH$_2$—CH$_2$—, —CH$_2$—CH$_2$—CH=CH—CH$_2$—, —CH$_2$—CH$_2$—CH$_2$—CH=CH—, —CH$_2$—CH=CH—CH$_2$—CH$_2$—, —CH$_2$—CH$_2$—CH$_2$—CH=CH—CH$_2$—CH$_2$—, —CH$_2$—CH$_2$—CH=CH—CH$_2$—CH$_2$—, —CH$_2$—CH$_2$—CH=CH—CH$_2$—, —CH$_2$—CH$_2$—CH$_2$—CH$_2$—CH=CH—. "Alk" particularly preferably denotes alkenylene having 2 or 3 C atoms, where 1 or 2 H atoms may be replaced by Hal and/or OH. Very particularly preferred examples thereof are ethenylene (—CH=CH—) and propenylene (propenediyl, —CH=CH—CH$_2$—). It goes without saying that the respective meanings of "Alk" are independent of one another in the radicals of a formula according to the invention.

"Ar" herein denotes phenyl which is unsubstituted or mono-, di- or trisubstituted, independently of one another, by Hal, A, CN, NO$_2$, —(CY$_2$)$_p$—OY, —(CY$_2$)$_p$—NYY, —(CY$_2$)$_p$—COOY, —(CY$_2$)$_p$CO—NYY or —(CY$_2$)$_p$—NY—COY. "Ar" particularly preferably denotes phenyl which is unsubstituted or mono- or disubstituted by Hal. It goes without saying that the respective meanings of "Ar" are independent of one another in the radicals of a formula according to the invention. Examples of suitable "Ar" are, in particular, (unsubstituted), phenyl, o-, m- or p-tolyl, o-, m- or p-ethylphenyl, o-, m- or p-proylphenyl, o-, m- or p-isoproylphenyl, o-, m- or p-tert-butylphenyl, o-, m- or p-trifluoromethylphenyl, o-, m- or p-fluorophenyl, o-, m- or p-bromophenyl, o-, m- or p-chlorophenyl, o-, m- or p-hydroxyphenyl, o-, m- or p-methoxyphenyl, o-, m- or p-nitrophenyl, o-, m- or p-aminophenyl, o-, m- or p-methylaminophenyl, o-, m- or p-dimethylaminophenyl, o-, m- or p-aminocarbonylphenyl, o-, m- or p-carboxyphenyl, o-, m- or p-methoxycarbonylphenyl, o-, m- or p-ethoxycarbonylphenyl, o-, m- or p-acetylphenyl, o-, m- or p-formylphenyl, o-, m- or p-cyanophenyl, 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3,4-, 2,3,5-, 2,3,6-, 2,4,6- or 3,4,5-trichlorophenyl, p-iodophenyl, 4-fluoro-3-chlorophenyl, 2-fluoro-4-bromophenyl, 2,5-difluoro-4-bromophenyl or 2,5-dimethyl-4-chlorophenyl.

The definitions and preferred meanings or embodiments mentioned in connection with the compounds of the formula (I) apply with respect to the other variables, radicals and substituents.

In compounds of the formula (X), R1 can stand for A, preferably unsubstituted or substituted $C_1$-$C_3$-alkyl, particularly preferably methyl. Correspondingly, the present invention provides compounds of the following formulae:

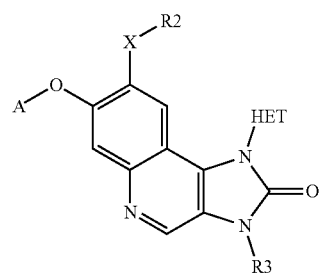

(Xa)

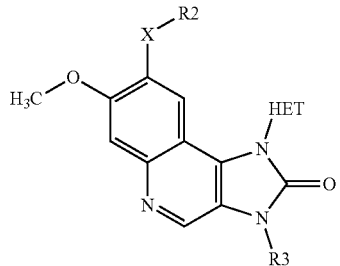

(Xb)

Further preferably, R3 stands for Y, i.e. H or A, or Hal. R3 particularly preferably stands for A, in particular unbranched or branched alkyl having 1, 2, or 3 C atoms, where 1, 2, 3, 4, or 5 H atoms may be replaced, independently of one another, by Hal. R3 particularly preferably denotes unsubstituted $C_{1-3}$ alkyl and particularly preferably methyl.

Correspondingly, the present invention provides compounds of the following formulae:

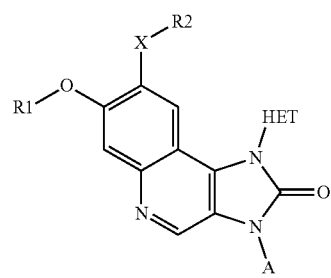

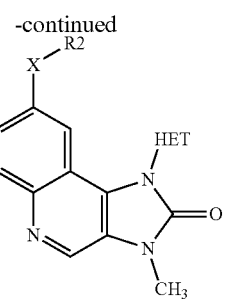

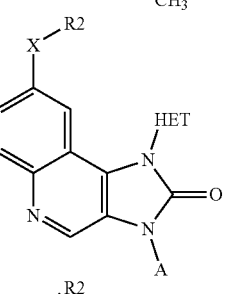

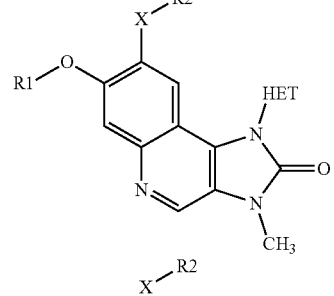

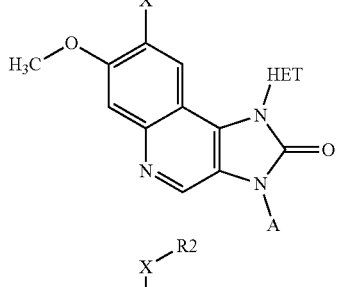

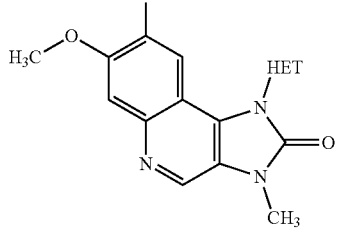

EXAMPLES

The invention is explained in greater detail below with reference to non-limiting examples of specific embodiments. The examples (in particular compound examples) should, in particular, be interpreted in such a way that they are not restricted to the feature combinations specifically illustrated, but instead the illustrative features can in turn be freely combined so long as the object of the invention is achieved.

Analytical Methods

NMR ($^1$H) was carried out with the following parameters.
Instruments: Bruker Avance DRX 500, Bruker Avance 400, Bruker DPX 300

Standard conditions (different in individual cases)
Reference: TMS
TD (time domain=number of data points or digital resolution): 65536
Solvent: DMSO-d6
NS(=number of scans): 32
SF (spectrometer frequency): see above
TE (temperature): 297 K
Coupling constants (J) are indicated in hertz (Hz)
HPLC-MS was carried out with the following parameters.

Instruments:
Shimadzu LCMS-2020,
Shimadzu SP-M20A 2010EV
Shimadzu UFLC-MS 2010EV
Columns used:
Shim-pack VP-ODS,
Shim-pack XR-ODS,
Kinetex XB-C18 100A,
Xbridge BEH C18,
Gemini-NX 3 u C18 110A
ACE UltraCore 2.5 SuperC18
Methods: solvent gradients with
A: water+0.1% of formic acid, B: acetonitrile+0.1% of formic acid;
A: water+0.05% of trifluoroacetic acid, B: acetonitrile+0.05% of trifluoroacetic acid A: water+5 mM ammonium carbonate, B: acetonitrile
Detection wavelength: 220 nm
MS type: API-ES Description of the Syntheses Example 1

Synthesis of 1-(3-fluoro-2-pyridyl)-7-methoxy-3-methyl-8-(1-methylpyrazol-4-yl)imidazo[4,5-c]quinolin-2-one (Compound Example 14)

Scheme 1: Synthesis of Compound Example 14

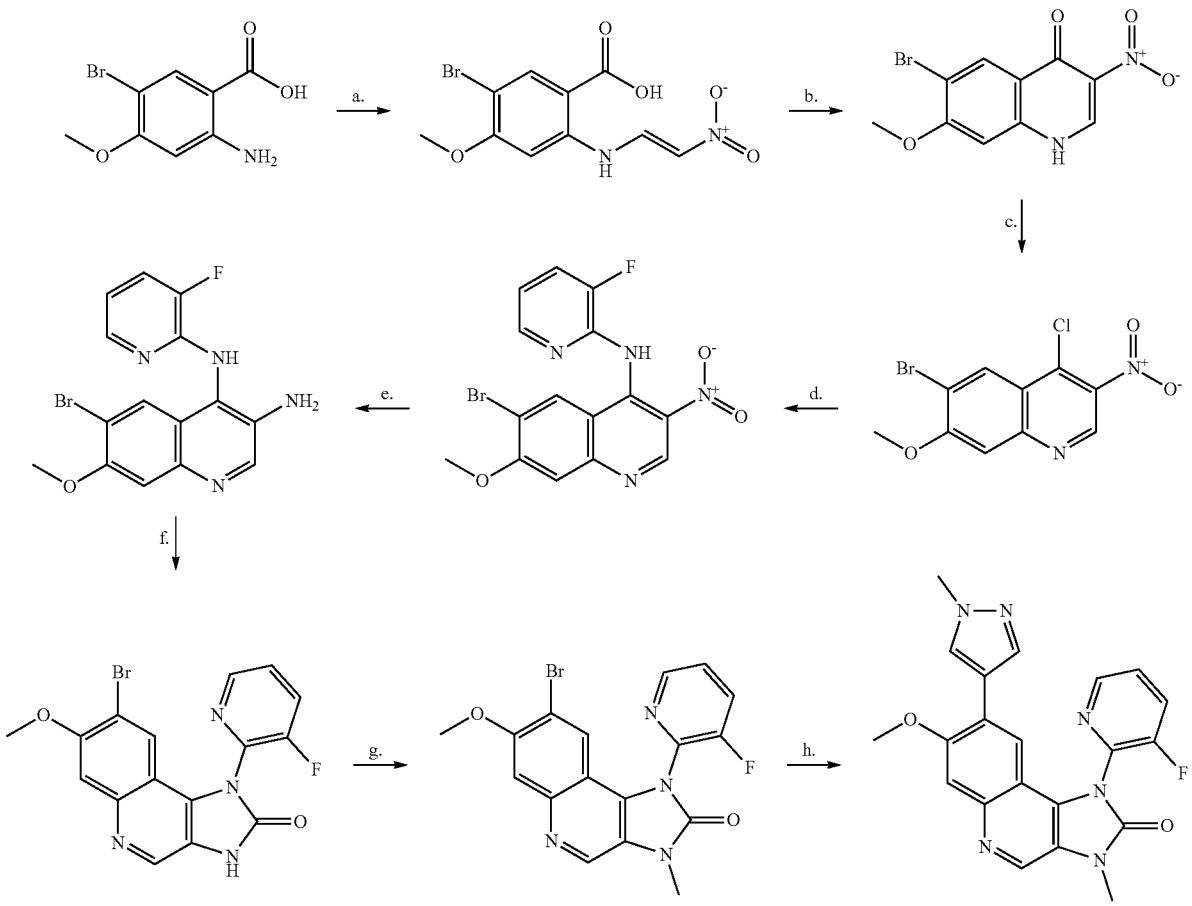

a. Synthesis of 5-bromo-4-methoxy-2-[[(E)-2-nitrovinyl]amino]benzoic Acid

Nitromethane (0.63 ml, 11.7 mmol) was added dropwise at room temperature to a solution of sodium hydroxide (14.7 g, 368 mmol) in water (33 ml) with stirring. The mixture was subsequently warmed slowly at 45° C. for 5 minutes with stirring. The reaction solution was then cooled to room temperature, and nitromethane (0.63 ml, 11.7 mmol) was again added dropwise. The reaction mixture was subsequently stirred for a further 10 minutes, during which a clear, reddish solution formed. After brief warming (5 minutes) at 50° C., the mixture was cooled to room temperature and decanted off onto ice (11 g). The aqueous solution was carefully acidified to pH<2 using conc. hydrochloric acid and subsequently immediately added to a solution of 2-amino-5-bromo-4-methoxybenzoic acid (8.00 g, 32.5 mmol) in water (259 ml), acidified using conc. hydrochloric acid (126 ml, 2.75 mol), with stirring. The suspension obtained was stirred overnight and subsequently filtered. The residue was dried at 50°, giving 9.60 g (93%) of 5-bromo-4-methoxy-2-[[(E)-2-nitrovinyl]amino]benzoic acid as colourless solid.

b. Synthesis of 6-bromo-7-methoxy-3-nitro-1H-quinolin-4-one

5-Bromo-4-methoxy-2-((E)-2-nitrovinylamino)benzoic acid (4.0 g, 12.6 mmol) was dissolved in N,N-dimethylformamide (150 ml). 1,1'-Carbonyldiimidazole (3.07 g, 18.9 mmol) was subsequently added at room temperature with stirring. The reaction solution was stirred overnight at room temperature. Acetonitrile (120 ml) was subsequently added. The suspension obtained was cooled and then filtered off. The yellow residue was washed with diethyl ether and dried overnight at 40° C., giving 3.0 g (80%) of 6-bromo-7-methoxy-3-nitro-1H-quinolin-4-one as colourless solid.

c. Synthesis of 6-bromo-4-chloro-7-methoxy-3-nitroquinoline

6-Bromo-7-methoxy-3-nitro-1H-quinolin-4-one (2.50 g, 8.36 mmol) was initially introduced under a dry nitrogen atmosphere. Phosphoryl chloride (20 ml, 215 mmol) and N,N-dimethylformamide (0.13 ml, 1.68 mmol) were subsequently added. The reaction solution was heated at 115° C. for 12 hours with stirring. The mixture was subsequently evaporated in vacuo, and the residue obtained was purified by chromatography on silica gel (petroleum ether/ethyl acetate=87:13, proportions by volume), giving 2.40 g (90%) of 6-bromo-4-chloro-7-methoxy-3-nitroquinoline as colourless solid.

d. Synthesis of 6-bromo-N-(3-fluoro-2-pyridyl)-7-methoxy-3-nitroquinolin-4-amine 3-Fluoropyridin-2-amine (390 mg, 3.48 mmol), dissolved in N,N-dimethylformamide (10 ml), was initially introduced under a dry nitrogen atmosphere. Sodium hydride (630 mg, 26.3 mmol) was subsequently added to the solution, and the mixture was stirred at room temperature for a further 5 minutes. 6-Bromo-4-chloro-7-methoxy-3-nitroquinoline (1.00 g, 3.15 mmol) was then added to the reaction mixture, the mixture was stirred at room temperature for 30 minutes, and the reaction was subsequently terminated by addition of ice-water (100 ml). The aqueous solution was extracted three times with 100 ml of ethyl acetate each time. The combined organic phases were dried over anhydrous sodium sulfate, filtered off and evaporated to dryness in vacuo, giving 1.0 g (81%) of 6-bromo-N-(3-fluoro-2-pyridyl)-7-methoxy-3-nitroquinolin-4-amine as yellow solid.

e. Synthesis of 6-bromo-N-4-(3-fluoro-2-pyridyl)-7-methoxyquinoline-3,4-diamine 6-Bromo-N-(3-fluoro-2-pyridyl)-7-methoxy-3-nitroquinolin-4-amine (1.0 g, 2.54 mmol) dissolved in methanol (50 ml) was initially introduced under a nitrogen protective-gas atmosphere. Raney Ni (100 mg, 1.17 mmol) was subsequently added to the solution, and the reaction mixture was stirred under a hydrogen atmosphere at atmospheric pressure for 30 minutes. After aeration with nitrogen, the suspension was filtered, and the filtrate was evaporated to dryness in vacuo, giving 0.8 g (87%) of 6-bromo-N-4-(3-fluoro-2-pyridyl)-7-methoxyquinoline-3,4-diamine as yellow solid.

f. Synthesis of 8-bromo-1-(3-fluoro-2-pyridyl)-7-methoxy-3H-imidazo[4,5-c]quinolin-2-one 6-Bromo-N-4-(3-fluoro-2-pyridyl)-7-methoxyquinoline-3,4-diamine (0.8 g, 2.20 mmol) dissolved in tetrahydrofuran were initially introduced. 1,1'-Carbonyldiimidazole (1.78 g, 11.0 mmol) and Hünig base (1.42 g, 11.0 mmol) were subsequently added. The reaction solution was warmed at 40° C. with stirring for 2 hours. The reaction was then terminated by addition of ice-water (200 ml). The aqueous phase was extracted three times with 50 ml of ethyl acetate each time. The combined organic phases were dried over anhydrous sodium sulfate, filtered off and evaporated to dryness in vacuo, giving 0.8 g (93%) of 8-bromo-1-(3-fluoro-2-pyridyl)-7-methoxy-3H-imidazo[4,5-c]quinolin-2-one as pale-yellow solid.

g. Synthesis of 8-bromo-1-(3-fluoro-2-pyridyl)-7-methoxy-3-methylimidazo[4,5-c]-quinolin-2-one 8-Bromo-1-(3-fluoro-2-pyridyl)-7-methoxy-3H-imidazo[4,5-c]quinolin-2-one (0.8 g, 2.06 mmol), dissolved in N,N-dimethylformamide (10 ml), was initially introduced under a dry nitrogen protective atmosphere. Sodium hydride (412 mg, 17.2 mmol) and methyl iodide (1.46 g, 10.3 mmol) were subsequently added. The reaction mixture was stirred at room temperature for one hour. The reaction was subsequently terminated by addition of ice-water (100 ml). The precipitate obtained was filtered off and dried in vacuo, giving 0.6 g (72%) of 8-bromo-1-(3-fluoro-2-pyridyl)-7-methoxy-3-methylimidazo[4,5-c]quinolin-2-one as pale-yellow solid.

h. Synthesis of 1-(3-fluoro-2-pyridyl)-7-methoxy-3-methyl-8-(1-methylpyrazol-4-yl)imidazo[4,5-c]quinolin-2-one (Compound Example 14)

8-Bromo-1-(3-fluoro-2-pyridyl)-7-methoxy-3-methyl-imidazo[4,5-c]quinolin-2-one (150 mg, 0.37 mmol), 1-methyl-4-(tetramethyl-1,3,2-dioxaborolan-2-yl)-1H-pyrazole (93 mg, 0.45 mmol), Pd(PPh$_3$)$_4$ (43 mg, 0.04 mmol) and potassium carbonate (103 mg, 0.75 mmol) in 1,4-dioxane (10 ml) and water (3 ml) were initially introduced under an argon inert-gas atmosphere in a sealed apparatus. The reaction mixture was heated at 80° C. for 2 hours with stirring. The mixture was subsequently cooled to room temperature, and the reaction mixture was evaporated to dryness in vacuo. The residue was pre-purified by chromatography on silica gel (ethyl acetate/methanol=10:1, proportions by volume). The eluate was evaporated to dryness, and the crude product obtained was subjected to final purification by means of preparative RP-HPLC (water/acetonitrile). Evaporation of the product fractions gave 1-(3-fluoro-2-pyridyl)-7-methoxy-3-methyl-8-(1-methylpyrazol-4-yl)imidazo[4,5-c]-quinolin-2-one (60 mg, 40%, Compound Example 14) as colourless solid.

Example 2

Synthesis of 7-methoxy-3-methyl-8-(1-methylpyrazol-4-yl)-1-thiazol-2-ylimidazo[4,5-c]quinolin-2-one (Compound Example 47)

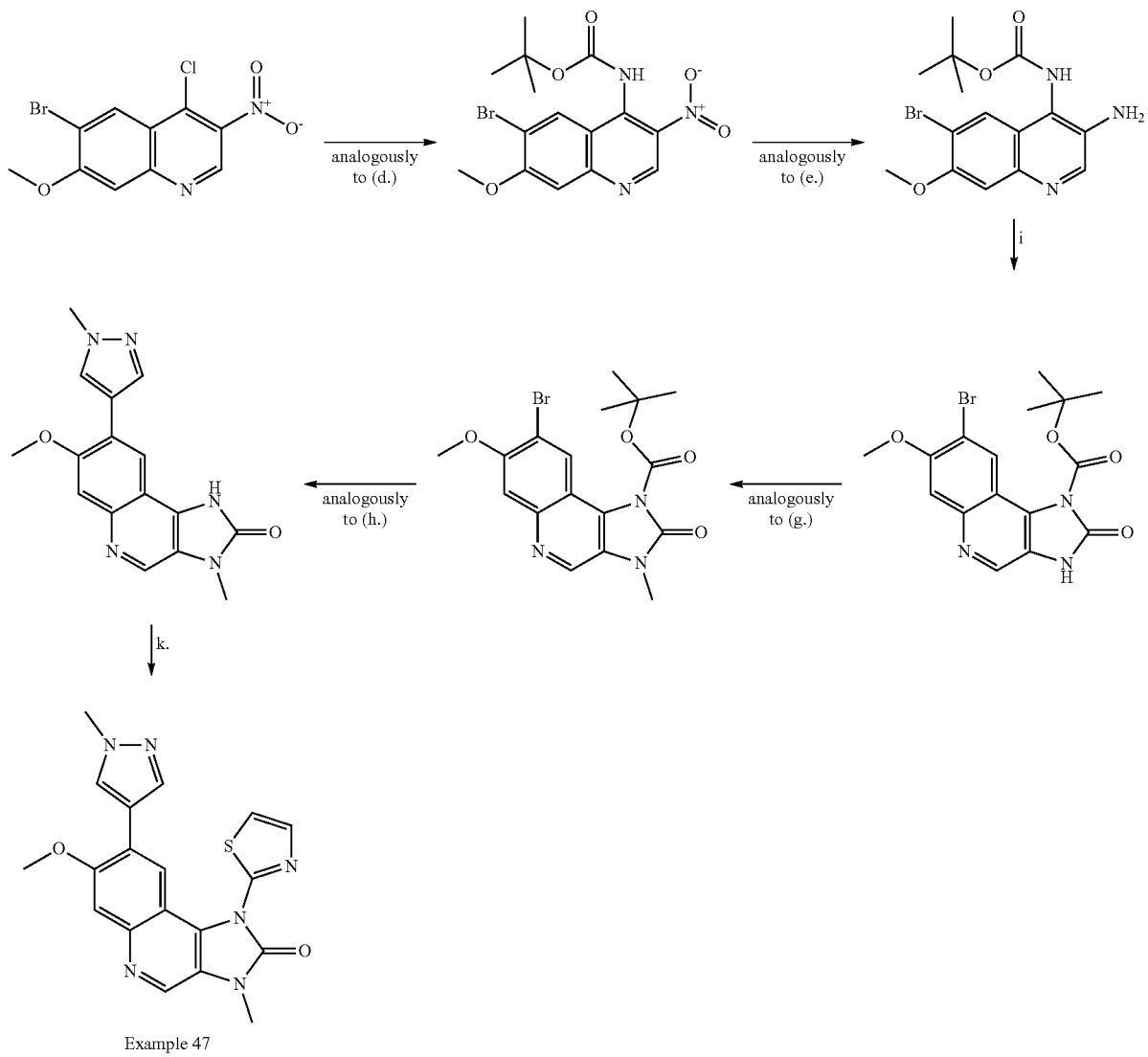

i. Synthesis of tert-butyl 8-bromo-7-methoxy-2-oxo-3H-imidazo[4,5-c]quinoline-1-carboxylate tert-Butyl N-(3-amino-6-bromo-7-methoxyquinolin-4-yl)carbamate (50.0 mg, 0.14 mmol), ditrichloromethyl carbonate (119 mg, 0.40 mmol) and triethylamine (0.18 ml, 1.29 mmol) were dissolved in dichloromethane (3 ml) and stirred at 25° C. for 2 hours. The mixture was evaporated to dryness in vacuo, and the residue was purified by chromatography on silica gel (ethyl acetate:methanol=10:1, proportions by volume), giving 50.0 mg (93%) of tert-butyl 8-bromo-7-methoxy-2-oxo-3H-imidazo[4,5-c]quinoline-1-carboxylate as colourless solid.

k. Synthesis of 7-methoxy-3-methyl-8-(1-methylpyrazol-4-yl)-1-thiazol-2-ylimidazo[4,5-c]-quinolin-2-one 7-Methoxy-3-methyl-8-(1-methylpyrazol-4-yl)-1H-imidazo[4,5-c]quinolin-2-one (20 mg, 0.06 mmol), 2-bromo-1,3-thiazole (20 mg, 0.12 mmol), CuI (20.00 mg, 0.11 mmol), $K_3PO_4$ (50 mg, 0.24 mmol) were taken up in toluene (4 ml) under argon in a sealable reaction vessel. (1S,2S)-1-N,2-N-Dimethylcyclohexane-1,2-diamine (30 mg, 0.21 mmol) was subsequently added at room temperature. The mixture was heated at 100° C. for 18 hours with stirring. The cooled solution was evaporated to dryness in vacuo, and the residue was purified by chromatography on silica gel (water/0.05% of $NH_4HCO_3$:acetonitrile=10:1), giving 10 mg (43%) of 7-methoxy-3-methyl-8-(1-methylpyrazol-4-yl)-1-thiazol-2-ylimidazo[4,5-c]quinolin-2-one as colourless solid.

Example 3

Synthesis of 1-[5-(azetidin-3-ylmethoxy)-3-fluoro-pyridin-2-yl]-7-methoxy-3-methyl-8-(1-methyl-1H-pyrazol-4-yl)-1,3-dihydroimidazo[4,5-c]quinolin-2-one

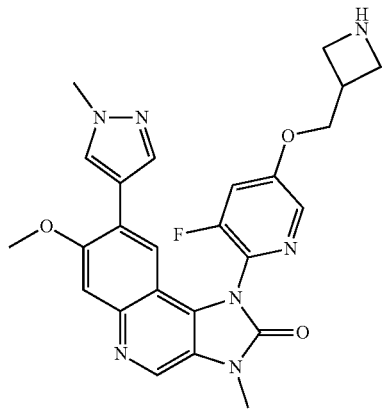 [SMILES: COc1cc2ncc3c(c2cc1-c1cnn(C)c1)n(-c1ncc(OCC2CNC2)cc1F)c(=O)n3C]

i. 1-(5-Benzyloxy-3-fluoro-2-pyridyl)-7-methoxy-3-methyl-8-(1-methylpyrazol-4-yl)imidazo[4,5-c]quinolin-2-one (1.1 g, 2.15 mmol), MeOH (200 ml), and Pd/C (229 mg, 2.15 mmol) were initially introduced in a 500 ml round-necked flask, the flask was flushed with H₂ and an H₂ atmosphere was maintained. The solution was stirred at room temperature for 8 hours. Solid was filtered off, and the mixture was evaporated in vacuo, giving 740 mg (80%) of 1-(3-fluoro-5-hydroxy-2-pyridyl)-7-methoxy-3-methyl-8-(1-methylpyrazol-4-yl)imidazo[4,5-c]quinolin-2-one as white solid.

ii. 1-(3-Fluoro-5-hydroxy-2-pyridyl)-7-methoxy-3-methyl-8-(1-methylpyrazol-4-yl)imidazo[4,5-c]quinolin-2-one (100 mg, 0.23 mmol, 98%), 3-(bromomethyl)azetidine 1-tert-butylcarbamate (80 mg, 0.32 mmol), potassium carbonate (66.2 mg, 0.48 mmol) and N,N-dimethylformamide (10 ml) were initially introduced in a 30 ml reaction vessel. The solution was stirred at 50° C. overnight. The reaction was then terminated by addition of 10 ml of water. The solution was then extracted three times with 10 ml of ethyl acetate each time, the combined organic phases were dried over anhydrous sodium sulfate, filtered off and evaporated in vacuo, giving 160 mg (>100%) of 3-[[5-fluoro-6-[7-methoxy-3-methyl-8-(1-methylpyrazol-4-yl)-2-oxoimidazo[4,5-c]quinolin-1-yl]-3-pyridyl]oxymethyl]azetidine 1-tert-butylcarbamate as yellow oil.

iii. 3-[[5-Fluoro-6-[7-methoxy-3-methyl-8-(1-methylpyrazol-4-yl)-2-oxoimidazo[4,5-c]quinolin-1-yl]-3-pyridyl]oxymethyl]azetidine 1-tert-butylcarbamate (160 mg, 0.27 mmol, 99%), dichloromethane (5 ml) and trifluoroacetic acid (1 ml) were initially introduced in a 50 ml round-bottomed flask. The solution was stirred at 25° C. overnight. The crude product obtained was purified by means of preparative HPLC, giving 30 mg (21%) of 1-[5-(azetidin-3-ylmethoxy)-3-fluoropyridin-2-yl]-7-methoxy-3-methyl-8-(1-methyl-1H-pyrazol-4-yl)-1,3-dihydroimidazo[4,5-c]quinolin-2-one as yellow solid.

Example 4

Synthesis of 1-(3-fluoro-5-fluoromethoxypyridin-2-yl)-7-methoxy-3-methyl-8-(1-methyl-1H-pyrazol-4-yl)-1,3-dihydroimidazo[4,5-c]quinolin-2-one (Compound Example 110)

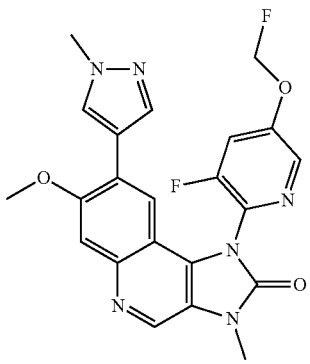 [SMILES: COc1cc2ncc3c(c2cc1-c1cnn(C)c1)n(-c1ncc(OCF)cc1F)c(=O)n3C]

1-(3-Fluoro-5-hydroxy-2-pyridyl)-7-methoxy-3-methyl-8-(1-methylpyrazol-4-yl)imidazo[4,5-c]quinolin-2-one (80 mg, 0.19 mmol, 98%), potassium carbonate (52.4 mg, 0.38 mmol), N,N-dimethylformamide (5 ml) and bromofluoromethane (43.0 mg, 0.36 mmol, 95%) were initially introduced in a sealed 30 ml reaction vessel. The solution was stirred at room temperature for 2 hours. The reaction was then terminated by addition of water. The solution was then extracted three times with 10 ml of ethyl acetate each time, and the organic phases were combined. The residue was pre-purified on silica gel with EtOAC/MeOH (97/3). The crude product was purified by means of preparative HPLC, giving 45 mg (53%) of 1-(3-fluoro-5-fluoromethoxypyridin-2-yl)-7-methoxy-3-methyl-8-(1-methyl-1H-pyrazol-4-yl)-1,3-dihydroimidazo[4,5-c]quinolin-2-one as white solid.

Example 5

Synthesis of 1-(5-difluoromethoxy-3-fluoropyridin-2-yl)-7-methoxy-3-methyl-8-(1-methyl-1H-pyrazol-4-yl)-1,3-dihydroimidazo[4,5-c]quinolin-2-one (Compound Example 114)

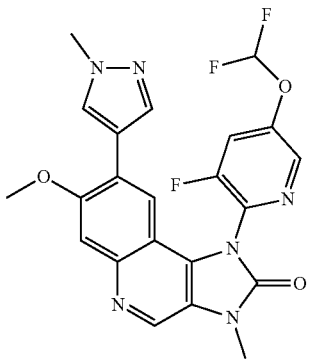 [SMILES: COc1cc2ncc3c(c2cc1-c1cnn(C)c1)n(-c1ncc(OC(F)F)cc1F)c(=O)n3C]

1-(3-Fluoro-5-hydroxy-2-pyridyl)-7-methoxy-3-methyl-8-(1-methylpyrazol-4-yl)imidazo[4,5-c]quinolin-2-one (80 mg, 0.18 mmol, 95%), potassium carbonate (52.5 mg, 0.36 mmol, 95%), N,N-dimethylformamide (5 ml) were initially introduced in a sealed 8 ml reaction vessel, the vessel was flushed with chlorodifluoromethane and a chlorodifluoromethane atmosphere was maintained at −30° C. The solution was stirred at 40° C. for 2 days. The reaction was then terminated by addition of 20 ml of ice-water. The solution was extracted three times with 50 ml of ethyl acetate each time, and the organic phases were combined. The mixture was washed once with 20 ml of salt solution, dried over anhydrous sodium sulfate and evaporated in vacuo. The crude product was purified by means of preparative HPLC, giving 27.7 mg (32%) of 1-(5-difluoromethoxy-3-fluoropyridin-2-yl)-7-methoxy-3-methyl-8-(1-methyl-1H-pyrazol-4-yl)-1,3-dihydroimidazo[4,5-c]quinolin-2-one as white solid.

Example 6

Synthesis of 1-[5-(dimethylphosphinoylmethoxy)-3-fluoropyridin-2-yl]-8-(1,3-dimethyl-1H-pyrazol-4-yl)-7-methoxy-3-methyl-1,3-dihydroimidazo[4,5-c]quinolin-2-one

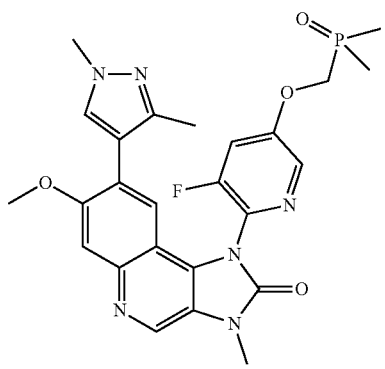

8-(1,3-Dimethylpyrazol-4-yl)-1-(3-fluoro-5-hydroxy-2-pyridyl)-7-methoxy-3-methylimidazo-[4,5-c]quinolin-2-one (80 mg, 0.18 mmol, 98%), chloro(dimethylphosphoryl)methane (76.3 mg, 0.54 mmol, 90%), potassium carbonate (50 mg, 0.36 mmol) and N,N-dimethylformamide (5 ml) were initially introduced in an 8 ml reaction vessel which had been flushed with argon and kept under argon inert-gas atmosphere. The reaction mixture was heated at 180° C. for 2 hours (microwave). The solids obtained were filtered off. The crude product was purified by means of preparative HPLC, giving 11.7 mg (12%) of 1-[5-(dimethylphosphinoylmethoxy)-3-fluoropyridin-2-yl]-8-(1,3-dimethyl-1H-pyrazol-4-yl)-7-methoxy-3-methyl-1,3-dihydroimidazo[4,5-c]quinolin-2-one as solid.

Example 7

Synthesis of 8-(1,3-dimethyl-1H-pyrazol-4-yl)-1-(3-fluoro-5-methylsulfonylmethoxypyridin-2-yl)-7-methoxy-3-methyl-1,3-dihydroimidazo[4,5-c]cquinolin-2-one (Compound Example 201)

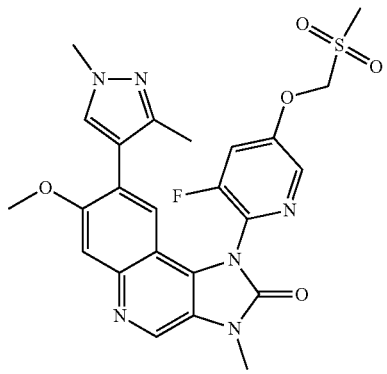 [SMILES: COc1cc2ncc3c(c2cc1-c1cn(C)nc1C)n(-c1ncc(OCS(C)(=O)=O)cc1F)c(=O)n3C]

i. 8-(1,3-Dimethylpyrazol-4-yl)-1-(3-fluoro-5-hydroxy-2-pyridyl)-7-methoxy-3-methylimidazo[4,5-c]quinolin-2-one (80 mg, 0.18 mmol, 98%), N,N-dimethylformamide (5 ml), potassium carbonate (50 mg, 0.36 mmol) and chloro(methylsulfanyl)methane (110 mg, 1.09 mmol, 95%) were initially introduced in a 25 ml round-bottomed flask. The solution was stirred overnight at 25° C. The reaction was then terminated by addition of 50 ml of water. The solution was extracted four times with 30 ml of ethyl acetate each time, and the organic phases were combined. The mixture was evaporated in vacuo. The residue was pre-purified on silica gel with MeOH:EtOAc (6:94), giving 80 mg (85%) of 8-(1,3-dimethylpyrazol-4-yl)-1-[3-fluoro-5-(methylsulfanylmethoxy)-2-pyridyl]-7-methoxy-3-methylimidazo[4,5-c]quinolin-2-one as yellow solid.

ii. 8-(1,3-Dimethylpyrazol-4-yl)-1-[3-fluoro-5-(methylsulfanylmethoxy)-2-pyridyl]-7-methoxyl-3-methylimidazo[4,5-c]quinolin-2-one (80 mg, 0.15 mmol, 95%), MeOH (5.00 ml) and a solution of potassium peroxodisulfate (220 mg, 0.77 mmol, 95%) in water (0.5 ml) was initially introduced in a 25 ml round-bottomed flask. The solution was stirred at 25° C. for 3 hours. The residue was pre-purified on silica gel with EtOAc:MeOH (70:30), and the crude product was purified by means of preparative HPLC, giving 15 mg (18%) of 8-(1,3-dimethyl-1H-pyrazol-4-yl)-1-(3-fluoro-5-methylsulfonylmethoxypyridin-2-yl)-7-methoxy-3-methyl-1,3-dihydroimidazo[4,5-c]quinolin-2-one as white solid.

Example 8

Synthesis of 1-[3-fluoro-5-(trideuteriomethoxy)-2-pyridyl]-7-methoxy-3-methyl-8-(1-methylpyrazol-4-yl)imidazo[4,5-c]quinolin-2-one (Compound Example 155)

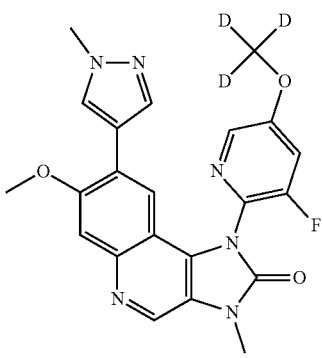 [SMILES: [2H]C([2H])([2H])Oc1cnc(-n2c(=O)n(C)c3cnc4cc(OC)c(-c5cnn(C)c5)cc4c32)c(F)c1]

1-(3-Fluoro-5-hydroxy-2-pyridyl)-7-methoxy-3-methyl-8-(1-methylpyrazol-4-yl)imidazo[4,5-c]quinolin-2-one (80 mg, 0.19 mmol, 98%), N,N-dimethylformamide (5.00 ml), potassium carbonate (51.7 mg, 0.37 mmol) and iodo(D3) methane (57.1 mg, 0.37 mmol, 95%) were initially introduced in a 25 ml round-bottomed flask. The solution was stirred at room temperature for 30 minutes. The progress of the reaction was followed by means of LCMS (dichloromethane/MeOH=10:1). The reaction was then terminated by addition of 50 ml of ice-water. The solution was extracted three times with 20 ml of ethyl acetate each time, and the organic phases were combined. The mixture was evaporated in vacuo, giving 38.5 mg (47%) of 1-[3-fluoro-5-(trideuteriomethoxy)-2-pyridyl]-7-methoxy-3-methyl-8-(1-methylpyrazol-4-yl)imidazo[4,5-c]quinolin-2-one as white solid.

Example 9

Synthesis of 1-(3-fluoro-5-piperazin-1-ylpyridin-2-yl)-7-methoxy-3-methyl-8-(1-methyl-1H-pyrazol-4-yl)-1,3-dihydroimidazo[4,5-c]quinolin-2-one (Compound Example 123)

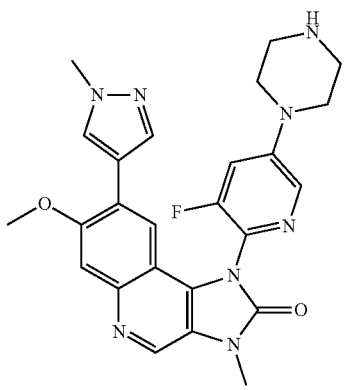 [SMILES: COc1cc2ncc3c(c2cc1-c1cnn(C)c1)n(-c1ncc(N2CCNCC2)cc1F)c(=O)n3C]

1-(5-Chloro-3-fluoro-2-pyridyl)-7-methoxy-3-methyl-8-(1-methylpyrazol-4-yl)imidazo[4,5-c]-quinolin-2-one (100 mg, 0.22 mmol, 95%), piperazine 1-tert-butylcarbamate (128 mg, 0.65 mmol, 95%), $Pd_2(dba)_3$ (21 mg, 0.02 mmol), Xantphos (27 mg, 0.05 mmol), $Cs_2CO_3$ (150 mg, 0.46 mmol) and toluene (10 ml) were initially introduced in a sealed 30 ml reaction vessel which had been flushed with argon and kept under argon inert-gas atmosphere. The mixture was stirred at 90° C. overnight and subsequently evaporated in vacuo. The residue was purified on silica gel with EtOAc/MeOH (95:5, volume units), giving 120 mg (94%) of 4-[5-fluoro-6-[7-methoxy-3-methyl-8-(1-methylpyrazol-4-yl)-2-oxoimidazo-[4,5-c]quinolin-1-yl]-3-pyridyl]piperazine 1-tert-butylcarbamate as yellow solid.

ii. 4-[5-Fluoro-6-[7-methoxy-3-methyl-8-(1-methylpyrazol-4-yl)-2-oxoimidazo[4,5-c]quinolin-1-yl]-3-pyridyl]piperazine 1-tert-butylcarbamate (115 mg, 0.18 mmol, 92%), dichloromethane (10 ml) and trifluoroacetic acid (4 ml) were initially introduced in a 25 ml round-bottomed flask. The mixture was stirred for 30 minutes at 0° C. in a water/ice bath and evaporated in vacuo. The crude product was purified by means of preparative HPLC, giving 50 mg (55%) of 1-(3-fluoro-5-piperazin-1-ylpyridin-2-yl)-7-methoxy-3-methyl-8-(1-methyl-1H-pyrazol-4-yl)-1,3-dihydroimidazo[4,5-c]quinolin-2-one as white solid.

Example 10

Synthesis of 5-fluoro-6-[7-methoxy-3-methyl-8-(1-methyl-1H-pyrazol-4-yl)-2-oxo-2,3-dihydroimidazo[4,5-c]quinolin-1-yl]-N-methylnicotinamide (Compound Example 138)

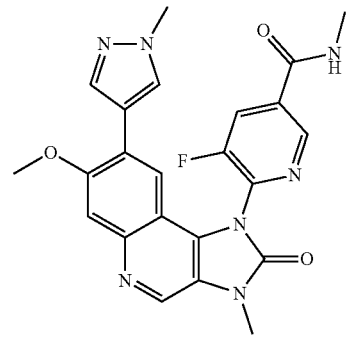

i. A solution of sulfuric acid (2 ml, 98%) in water (2 ml) and 5-fluoro-6-[7-methoxy-3-methyl-8-(1-methylpyrazol-4-yl)-2-oxoimidazo[4,5-c]quinolin-1-yl]pyridine-3-nitrile (110 mg, 0.26 mmol) were initially introduced in an 8 ml reaction vessel. The mixture was stirred at 80° C. overnight. Sodium hydroxide (4 mol/l) was used to adjust the pH to 8. The mixture was evaporated in vacuo, and the residue was purified on silica gel with a 0.5% aqueous $NH_4HCO_3$ solution and $CH_3CN$ (82/18), giving 70 mg (61%) of 5-fluoro-6-[7-methoxy-3-methyl-8-(1-methylpyrazol-4-yl)-2-oxoimidazo[4,5-c]quinolin-1-yl]pyridine-3-carboxylic acid as white solid.

ii. 5-Fluoro-6-[7-methoxy-3-methyl-8-(1-methylpyrazol-4-yl)-2-oxoimidazo[4,5-c]quinolin-1-yl]pyridine-3-carboxylic acid (65.0 mg, 0.14 mmol), a solution of methylamine (10 mg, 0.32 mmol) in tetrahydrofuran (0.5 ml), triethylamine (44 mg, 0.43 mmol), BOP (64.9 mg, 0.15 mmol), and tetrahydrofuran (5 ml) were initially introduced in a sealed 30 ml reaction vessel. The solution was stirred at room temperature for 18 hours and evaporated in vacuo, the

117 residue was diluted with 10 ml of EtOAc. The mixture was dried over anhydrous sodium sulfate and evaporated in vacuo. The crude product was purified by means of preparative HPLC, giving 20 mg (30%) of 5-fluoro-6-[7-methoxy-3-methyl-8-(1-methyl-1H-pyrazol-4-yl)-2-oxo-2,3-dihydro-imidazo[4,5-c]quinolin-1-yl]-N-methylnicotinamide as white solid.

Example 11

Synthesis of 1-[3-fluoro-5-(trideuteriomethoxy)-4-pyridyl]-7-methoxy-3-methyl-8-(1-methylpyrazol-4-yl)imidazo[4,5-c]quinolin-2-one (Compound Example 145)

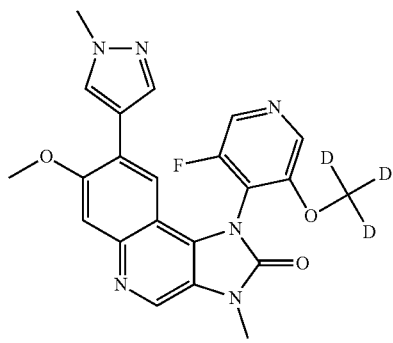 [SMILES: [2H]C([2H])([2H])Oc1cncc(F)c1-n1c(=O)n(C)c2cnc3cc(OC)c(-c4cnn(C)c4)cc3c21]

1-(3-Fluoro-5-hydroxy-4-pyridyl)-7-methoxy-3-methyl-8-(1-methylpyrazol-4-yl)imidazo[4,5-c]quinolin-2-one (145 mg, 0.33 mmol, 97%), CD$_3$OD (0.3 ml), potassium carbonate (143 mg, 1.03 mmol) and N,N-dimethylformamide (3 ml) were initially introduced in a sealed 8 ml reaction vessel. The mixture was stirred at 100° C. overnight. The reaction was then terminated by addition of 10 ml of water. The solution was extracted three times with 10 ml of ethyl acetate each time. The organic phases were combined, dried over anhydrous sodium sulfate and evaporated in vacuo. The crude product was purified by means of preparative HPLC, giving 20 mg (14%) of 1-[3-fluoro-5-(trideuteriomethoxy)-4-pyridyl]-7-methoxy-3-methyl-8-(1-methylpyrazol-4-yl) imidazo[4,5-c]quinolin-2-one as white solid.

118

Example 12

Synthesis of 1-(3-fluoro-5-methoxypyridin-4-yl)-8-(1-fluoromethyl-1H-pyrazol-4-yl)-7-methoxy-3-methyl-1,3-dihydroimidazo[4,5-c]quinolin-2-one (Compound Example 140)

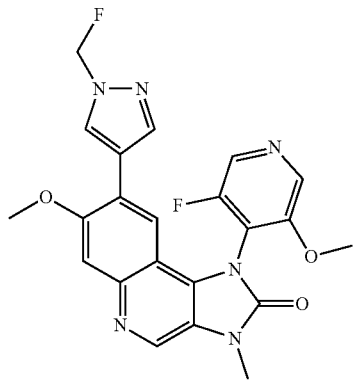

1-(3-Fluoro-5-methoxy-4-pyridyl)-7-methoxy-3-methyl-8-(1H-pyrazol-4-yl)imidazo[4,5-c]-quinolin-2-one (60 mg, 0.14 mmol, 97%), potassium carbonate (57.6 mg, 0.42 mmol) and N,N-dimethylformamide (5 ml) were initially introduced in a sealed 30 ml reaction vessel. The mixture was stirred at room temperature for 5 minutes and cooled to 0° C. Bromofluoromethane (165 mg, 1.39 mmol, 95%) was added, the mixture was warmed to room temperature and stirred for a further hour. The reaction was then terminated by addition of 50 mL of water. The solution was extracted three times with 30 mL of ethyl acetate each time, the organic phases were combined and evaporated in vacuo. The crude product was purified by means of preparative HPLC, giving 5 mg (8%) of 1-(3-fluoro-5-methoxypyridin-4-yl)-8-(1-fluoromethyl-1H-pyrazol-4-yl)-7-methoxy-3-methyl-1,3-dihydroimidazo[4,5-c]quinolin-2-one as white solid.

Example 13

Synthesis of 1-(3-fluoro-5-methoxy-4-pyridyl)-7-methoxy-3-methyl-8-(1-methylpyrazol-4-yl)imidazo[4,5-c]quinolin-2-one (Compound Example 4)

Scheme 3: Synthesis of Compound Example 4

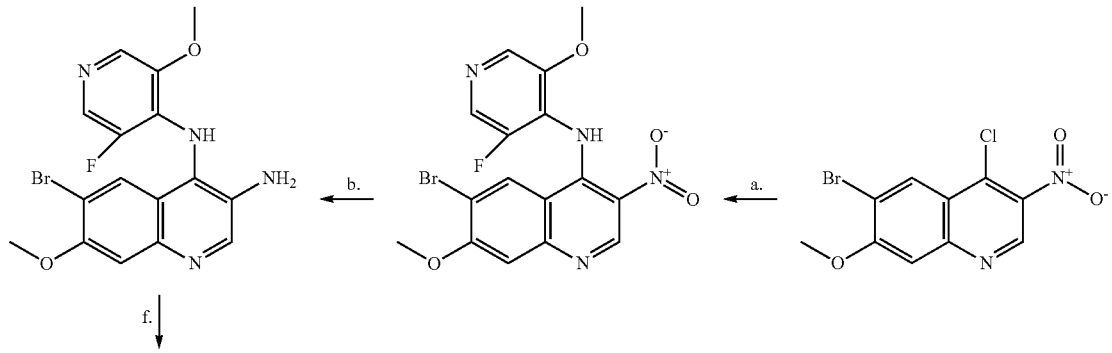

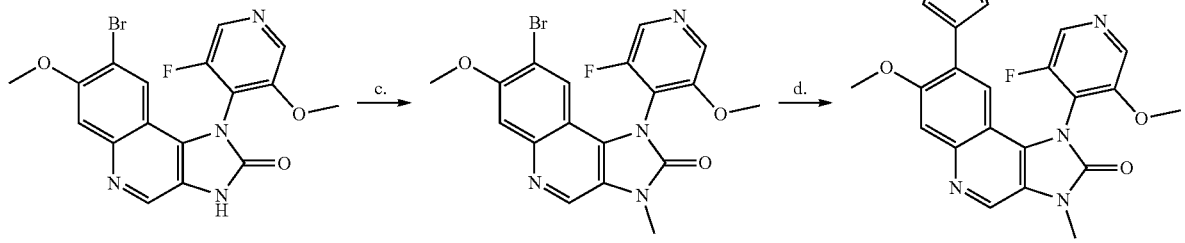

a. Synthesis of 6-bromo-N-(3-fluoro-5-methoxy-4-pyridyl)-7-methoxy-3-nitroquinolin-4-Amine 3-Fluoro-5-methoxypyridin-4-amine (447 mg, 3.02 mmol), dissolved in N,N-dimethylformamide (5 ml), were initially introduced under a dry nitrogen atmosphere. Sodium hydride (504 mg, 12.6 mmol, 60%) was subsequently added to the solution, and the mixture was stirred at room temperature for a further 5 minutes. 6-Bromo-4-chloro-7-methoxy-3-nitroquinoline (800 mg, 2.52 mmol) was then added to the reaction mixture, the mixture was stirred at room temperature for 15 minutes, and the reaction was subsequently terminated by addition of ice-water (100 ml). The deposited precipitate was filtered off, washed with ice-water and dried, giving 1.0 g (94%) of 6-bromo-N-(3-fluoro-5-methoxy-4-pyridyl)-7-methoxy-3-nitroquinolin-4-amine as yellow solid.

b. Synthesis of 6-bromo-N4-(3-fluoro-5-methoxy-4-pyridyl)-7-methoxyquinoline-3,4-diamine 6-Bromo-N-(3-fluoro-5-methoxy-4-pyridyl)-7-methoxy-3-nitroquinolin-4-amine (990 mg, 2.20 mmol), dissolved in methanol (100 ml), was initially introduced under a nitrogen protective-gas atmosphere. Raney Ni (100 mg, 1.17 mmol) was subsequently added, and the reaction mixture was stirred under a hydrogen atmosphere at atmospheric pressure for 30 minutes. After aeration with nitrogen, the suspension was filtered, and the filtrate was evaporated to dryness in vacuo. The residue was crystallised from ethyl acetate/petroleum ether, giving 0.86 g (99%) of 6-bromo-N4-(3-fluoro-5-methoxy-4-pyridyl)-7-methoxyquinoline-3,4-diamine as yellow solid.

c. Synthesis of 8-bromo-1-(3-fluoro-5-methoxy-4-pyridyl)-7-methoxy-3H-imidazo[4,5-c]-quinolin-2-one 6-Bromo-N4-(3-fluoro-5-methoxy-4-pyridyl)-7-methoxyquinoline-3,4-diamine (0.85 g, 2.20 mmol), dissolved in tetrahydrofuran (20 ml), were initially introduced. 1,1'-Carbonyldiimidazole (1.84 g, 11.3 mmol) and Hünig base (1.46 g, 11.3 mmol) were subsequently added. The reaction solution was warmed at 40° C. for 16 hours with stirring. The reaction was then terminated by addition of ice-water (200 mL). The deposited precipitate was filtered off, washed with ice-water and dried, giving 0.87 g (94%) of 8-bromo-1-(3-fluoro-5-methoxy-4-pyridyl)-7-methoxy-3H-imidazo[4,5-c]quinolin-2-one as pale-yellow solid.

d. Synthesis of 8-bromo-1-(3-fluoro-5-methoxy-4-pyridyl)-7-methoxy-3-methyl-imidazo-[4,5-c]quinolin-2-one 8-Bromo-1-(3-fluoro-5-methoxy-4-pyridyl)-7-methoxy-3H-imidazo[4,5-c]quinolin-2-one (0.86 g, 1.94 mmol), dissolved in N,N-dimethylformamide (5 ml), was initially introduced under a dry nitrogen protective atmosphere. Sodium hydride (388 mg, 9.71 mmol, 60%) and methyl iodide (2.76 g, 19.4 mmol) were subsequently added. The reaction mixture was stirred at room temperature for 10 minutes. The reaction was subsequently terminated by addition of ice-water (100 mL). The precipitate obtained was filtered off and dried in vacuo, giving 0.70 g (80%) of 8-bromo-1-(3-fluoro-5-methoxy-4-pyridyl)-7-methoxy-3-methylimidazo[4,5-c]quinolin-2-one as pale-yellow solid.

e. Synthesis of 1-(3-fluoro-5-methoxy-4-pyridyl)-7-methoxy-3-methyl-8-(1-methylpyrazol-4-yl)imidazo [4,5-c]quinolin-2-one (Compound Example 4)

8-Bromo-1-(3-fluoro-5-methoxy-4-pyridyl)-7-methoxy-3-methylimidazo[4,5-c]quinolin-2-one (150 mg, 0.33 mmol), 1-methyl-4-(tetramethyl-1,3,2-dioxaborolan-2-yl)-1H-pyrazole (88.4 mg, 0.44 mmol), Pd(PPh$_3$)$_4$ (76.6 mg, 0.07 mmol) and potassium carbonate (91.6 mg, 0.66 mmol) in 1,4-dioxane (15 ml) and water (5 ml) were initially introduced under an argon inert-gas atmosphere in a sealed apparatus. The reaction mixture was heated at 80° C. for 2 hours with stirring. The reaction mixture was subsequently cooled to room temperature and evaporated to dryness in vacuo. The residue was pre-purified by chromatography on silica gel (ethyl acetate/methanol=97:3, proportions by volume). The eluent was evaporated to dryness, and the crude product obtained was subjected to final purification by means of preparative RP-HPLC (water/acetonitrile). Evaporation of the product fractions gave 1-(3-fluoro-5-methoxy-4-pyridyl)-7-methoxy-3-methyl-8-(1-methylpyrazol-4-yl)imidazo[4,5-c]quinolin-2-one (70 mg, 47%, Compound Example 4) as colourless solid.

The abbreviations used above, which are usual in the specialist area, have the following meanings: MeOH: methanol; Pd(PPh$_3$)$_4$: tetrakis(triphenylphosphine)palladium; EtOAc: ethyl acetate; BOP: benzotriazolyloxytris(dimethylamino)phosphonium hexafluorophosphate; Pd$_2$(dba)$_3$: tris(dibenzylideneacetone)dipalladium

Example 14

Compound examples prepared correspondingly or analogously to EXAMPLES 1 to 13 are shown in Table 2 below. The amine derivatives, boronic acid esters or analogues used are summarised in Schema 4 below.

Schema 4: Amine derivatives, boronic acid esters or analogues
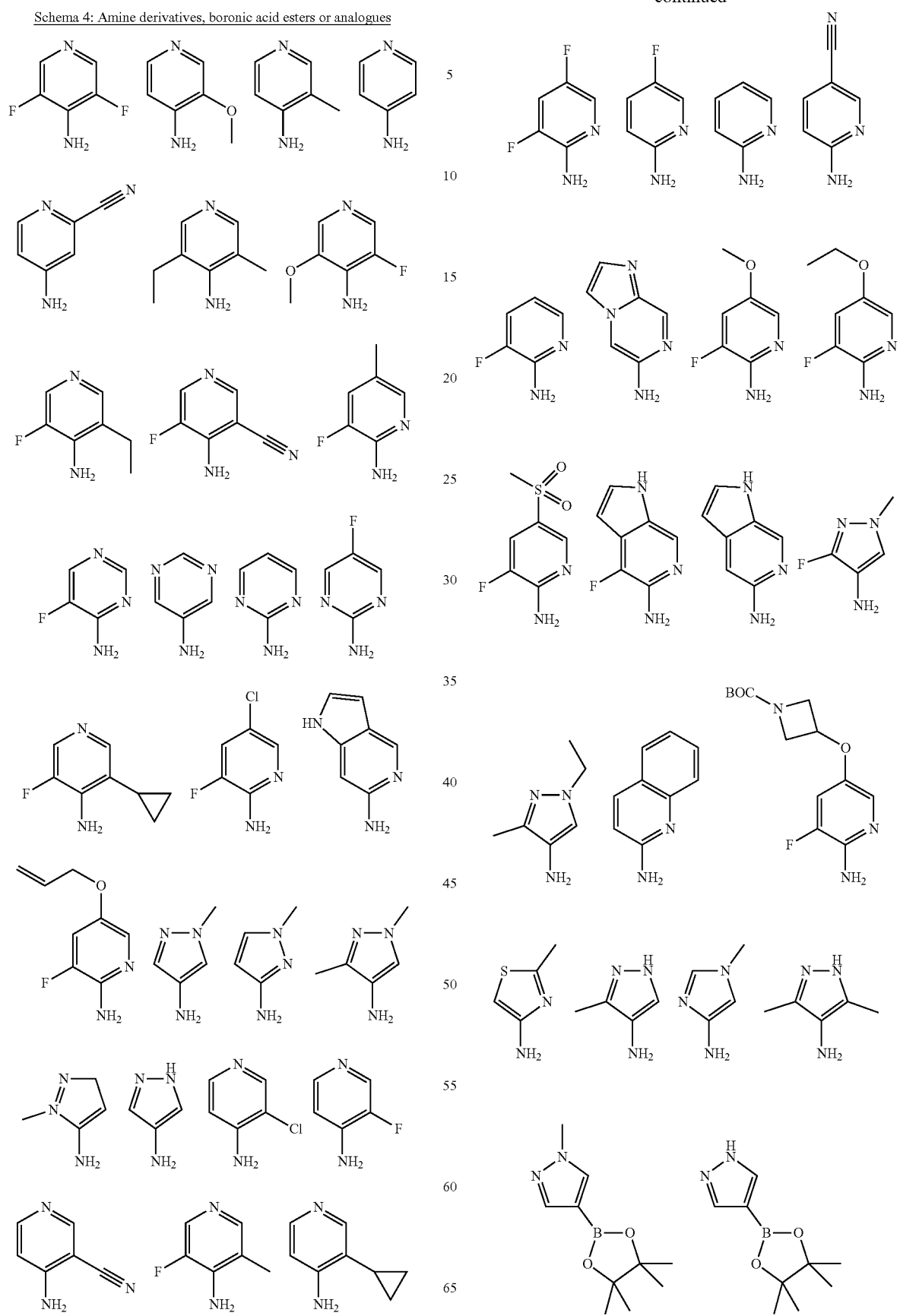

123
-continued
124
-continued
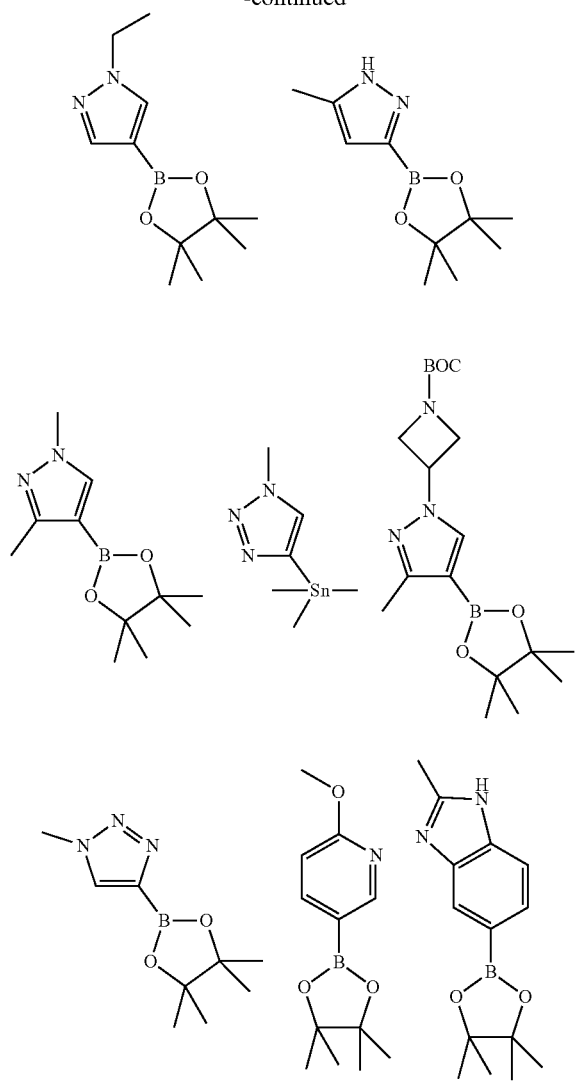
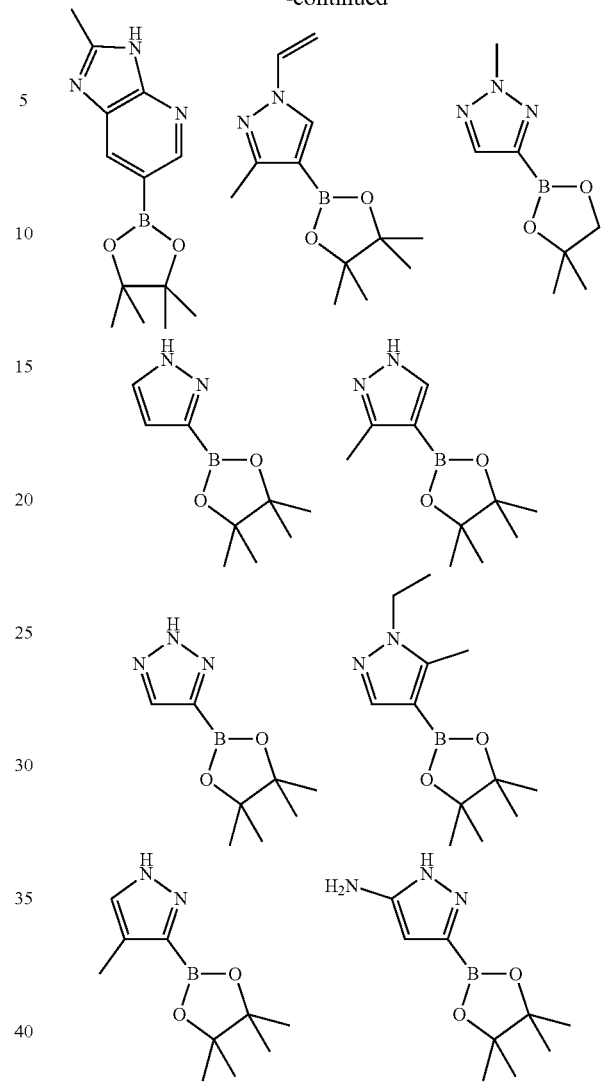
TABLE 2
| Ex. | Structural formula | Name | IC$_{50}$ (pCHK2) | IC$_{50}$ (ATM) [μM] |
|---|---|---|---|---|
| 1 | MS: 423 (M + H$^+$) | 1-(3,5-Difluoropyridin-2-yl)-7-methoxy-3-methyl-8-(1-methyl-1H-pyrazol-4-yl)-1,3-dihydroimidazo[4,5-c]quinolin-2-one | +++ | <0.01 |
1H NMR (400 MHz, DMSO-d6, ppm): 8.915 (s,1H), 8.855-8.849 (d, J = 2.4 Hz,1H), 8.544-8.495 (m,1H), 8.016 (s,1H), 7.538 (s,1H), 7.339 (s,1H), 6.944 (s,1H), 4.005 (s,3H), 3.864 (s,3H), 3.597 (s,3H)

TABLE 2-continued

| Ex. | Structural formula | Name | IC$_{50}$ (pCHK2) | IC$_{50}$ (ATM) [μM] |
|---|---|---|---|---|
| 2 | MS: 409 (M + H⁺) | 1-(3,5-Difluoropyridin-4-yl)-7-methoxy-3-methyl-8-(1H-pyrazol-4-yl)-1,3-dihydro-imidazo[4,5-c]quinolin-2-one | +++ | <0.001 |
| | 1H NMR (400 MHz, DMSO, ppm): 13.036 (s,1H), 9.050 (s,2H), 8.944 (s,1H), 7.992 (s,1H), 7.563 (s,1H), 7.440 (s,1H), 7.281(s,1H), 4.012 (s,3H), 3.613 (s,3H) | | | |
| 3 | MS: 390 (M + H⁺) | 1-(1,3-Dimethyl-1H-pyrazol-4-yl)-7-methoxy-3-methyl-8-(1H-pyrazol-4-yl)-1,3-dihydroimidazo[4,5-c]quinolin-2-one | +++ | <0.001 |
| | 1H NMR (400 MHz,DMSO,ppm): 13.03(s,1H), 8.80 (s,1H), 8.13 (s,1H), 7.96 (br,1H), 7.45 (d,3H), 3.97 (m,6H), 3.53 (s,3H), 1.94 (s,3H) | | | |
| 4 | MS: 449 (M + H⁺) | 8-(1,3-Dimethyl-1H-pyrazol-4-yl)-1-(3-fluoro-5-methoxy-pyridin-4-yl)-7-methoxy-3-methyl-1,3-dihydroimidazo-[4,5-c]quinolin-2-one | +++ | <0.001 |
| | 1H NMR (400 MHz,DMSO,ppm): 8.912 (s,1H),8.707-8.681 (m,2H),7.822 (s,1H),7.527 (s,1H), 6.985 (s,1H), 3.927 (s,3H), 3.861 (s,3H), 3.766(s,3H), 3.595 (s,3H), 1.744 (s,3H) | | | |

TABLE 2-continued

| Ex. | Structural formula | Name | IC$_{50}$ (pCHK2) | IC$_{50}$ (ATM) [μM] |
|---|---|---|---|---|
| 5 | | 1-(1,3-Dimethyl-1H-pyrazol-4-yl)-7-methoxy-3-methyl-8-(1-methyl-1H-pyrazol-4-yl)-1,3-dihydroimidazo[4,5-c]-quinolin-2-one | +++ | <0.001 |
| | MS: 404 (M + H$^+$) | 1H NMR (400 MHz,DMSO,ppm): 8.80 (s,1H), 8.13 (s,1H), 8.00 (s,1H), 7.41(m,3H), 3.97 (m,6H), 3.87 (d,3H), 3.54 (s,3H), 1.94 (s,3H) | | |
| 6 | | 1-(3,5-Difluoropyridin-2-yl)-7-methoxy-3-methyl-8-(1H-pyrazol-4-yl)-1,3-dihydro-imidazo[4,5-c]quinolin-2-one | +++ | <0.001 |
| | MS: 410 (M + H$^+$) | 1H NMR (400 MHz,DMSO,ppm): 12.95 (br,1H), 8.86 (d,2H), 8.51 (m,1H),7.71 (s,2H), 7.52 (s,1H), 6.96 (s,1 H), 3.99 (s,3H), 3.29 (s.3H) | | |
| 7 | | 1-(3-Fluoropyridin-2-yl)-7-methoxy-3-methyl-8-(1H-pyrazol-4-yl)-1,3-dihydro-imidazo[4,5-c]quinolin-2-one | +++ | <0.001 |
| | MS: 391 (M + H$^+$) | 1H NMR (300 MHz,DMSO,ppm): 13.007 (s,1H), 8.907 (s,1H), 8.727 (s,1H), 8.305-8.241 (m,1H), 7.981-7.939 (m,2H), 7.526 (s,1H), 7.321 (s,1H), 6.934 (s,1H), 3.997 (s,3H), 3.597 (s,3H) | | |

TABLE 2-continued

| Ex. | Structural formula | Name | IC$_{50}$ (pCHK2) | IC$_{50}$ (ATM) [μM] |
|---|---|---|---|---|
| 8 | MS: 405 (M + H⁺) | 1-(3-Fluoro-5-methylpyridin-4-yl)-7-methoxy-3-methyl-8-(1H-pyrazol-4-yl)-1,3-dihydroimidazo[4,5-c]quinolin-2-one | +++ | <0.001 |

1H NMR (400 MHz,DMSO,ppm): 13.035 (s,1H), 8.930 (s,1H), 8.901 (s,1H), 8.805 (s,1H), 7.920 (s,1H), 7.544 (s,1H), 7.271 (s,1H), 7.030 (s,1H), 3.999 (s,3H), 3.615 (s,3H), 2.220 (s,3H)

| Ex. | Structural formula | Name | IC$_{50}$ (pCHK2) | IC$_{50}$ (ATM) [μM] |
|---|---|---|---|---|
| 9 | MS: 391 (M + H⁺) | 1-(3-Fluoropyridin-4-yl)-7-methoxy-3-methyl-8-(1H-pyrazol-4-yl)-1,3-dihydroimidazo[4,5-c]quinolin-2-one | +++ | <0.001 |

1H NMR (400 MHz, DMSO, ppm): 13.023 (s,1H), 9.075 (s,1H), 8.908 (s,1H), 8.838-8.825 (d, J = 5.2 Hz, 1H), 7.997-7.940 (m,2H), 7.537 (s,1H), 7.337 (s,1H), 7.195 (s,1H), 4.000 (s,3H), 3.589 (s,3H)

| Ex. | Structural formula | Name | IC$_{50}$ (pCHK2) | IC$_{50}$ (ATM) [μM] |
|---|---|---|---|---|
| 10 | MS: 418 (M + H⁺) | 1,8-Bis-(1,3-dimethyl-1H-pyrazol-4-yl)-7-methoxy-3-methyl-1,3-dihydroimidazo-[4,5-c]quinolin-2-one | +++ | <0.001 |

1H NMR (400 MHz, DMSO, ppm): 8.82 (s,1H), 8.08 (s,1H), 7.86 (s,1H), 7.48 (s,1H), 7.35 (s,1H), 3.92 (d,3H), 3.87 (s,3H), 3.78 (s,3H), 3.54 (s,3H), 1.90 (d,6H)

TABLE 2-continued

| Ex. | Structural formula | Name | IC$_{50}$ (pCHK2) | IC$_{50}$ (ATM) [µM] |
|---|---|---|---|---|
| 11 | MS: 437 (M + H⁺) | 1-(3,5-Difluoropyridin-2-yl)-8-(1,3-dimethyl-1H-pyrazol-4-yl)-7-methoxy-3-methyl-1,3-dihydroimidazo[4,5-c]-quinolin-2-one | +++ | <0.001 |
|  |  | 1H NMR (400 MHz, DMSO, ppm): 8.829 (s,1H), 8.605-8.599 (d, J = 2.4 Hz,1H), 8.133-8.085 (m,1H), 7.700 (s,1H), 7.499 (s,1H), 6.874 (s,1H), 3.985 (s,3H), 3.852 (s,3H), 3.680 (s,3H), 1.948 (s,3H) |  |  |
| 12 | MS: 433 (M + H⁺) | 1-(3-Ethyl-5-fluoropyridin-4-yl)-7-methoxy-3-methyl-8-(1-methyl-1H-pyrazol-4-yl)-1,3-dihydroimidazo[4,5-c]-quinolin-2-one | +++ | <0.001 |
|  |  | 1H NMR (400 MHz,DMSO,ppm): 8.935 (s,2H), 8.853 (s,1H), 7.986 (s,1H), 7.545 (s,1H), 7.062 (s,1H), 6.960 (s,1H), 3.994 (s,3H), 3.844 (s,3H), 3.618 (s,3H), 2.672-2.600 (m,2H),1.069-1.002 (m,3H) |  |  |
| 13 | MS: 449 (M + H⁺) | 8-(1-Ethyl-1H-pyrazol-4-yl)-1-(3-fluoro-5-methoxypyridin-4-yl)-7-methoxy-3-methyl-1,3-dihydroimidazo[4,5-c]-quinolin-2-one | +++ | <0.001 |
|  |  | 1H NMR (400 MHz,DMSO,ppm): 8.896 (s,1H), 8.789 (s,1H), 8.744 (s,1H), 8.024 (s,1H), 7.527 (s,1H), 7.206 (s,1H), 7.158 (s,1H), 4.175-4.120 (m,2H), 4.002 (s,3H), 3.877 (s,3H), 3.333 (s,3H), 1.390-1.354 (m,3H) |  |  |

TABLE 2-continued

| Ex. | Structural formula | Name | IC$_{50}$ (pCHK2) | IC$_{50}$ (ATM) [μM] |
|---|---|---|---|---|
| 14 | MS: 405 (M + H⁺) | 1-(3-Fluoropyridin-2-yl)-7-methoxy-3-methyl-8-(1-methyl-1H-pyrazol-4-yl)-1,3-dihydroimidazo[4,5-c]-quinolin-2-one | +++ | <0.001 |
| | | 1H NMR (400 MHz,DMSO,ppm): 8.908 (s,1H), 8.719-8.708 (m,1H), 8.295-8.271 (m,1H), 7.977-7.930 (m, 2H), 7.525 (s,1H), 7.195-7.194 (s,1H), 6.896 (s,1H), 4.033 (s,3H), 3.994 (s,3H), 3.595 (s,3H) | | |
| 15 | MS: 435 (M + H⁺) | 1-(3-Fluoro-5-methoxypyridin-4-yl)-7-methoxy-3-methyl-8-(1-methyl-1H-pyrazol-4-yl)-1,3-dihydroimidazo[4,5-c]-quinolin-2-one | +++ | <0.001 |
| | | 1H NMR (400 MHz,DMSO,ppm): 8.896 (s,1H), 8.780 (s,1H), 8.739 (s,1H), 8.007 (s,1H), 7.528 (s,1H), 7.176-7.149 (m,2H), 3.998 (s,3H), 3.870 (s,6H), 3.596 (s,3H) | | |
| 16 | MS: 419 (M + H⁺) | 8-(1,3-Dimethyl-1H-pyrazol-4-yl)-1-(3-fluoropyridin-2-yl)-7-methoxy-3-methyl-1,3-dihydroimidazo[4,5-c]quinolin-2-one | +++ | <0.001 |
| | | 1H NMR (400 MHz, DMSO-d6) ppm = 8.93 (s,1H), 8.63-8.62 (d, J = 4.8 Hz, 1H), 8.25-8.20 (m, 1H), 7.89-7.85 (m, 1H), 7.77 (s, 1H), 7.53 (s, 1H), 6.77 (s, 1H), 3.92 (s, 3H), 3.76 (s, 3H), 3.59 (s, 3H), 1.75 (s, 3H) | | |

TABLE 2-continued

| Ex. | Structural formula | Name | IC$_{50}$ (pCHK2) | IC$_{50}$ (ATM) [μM] |
|---|---|---|---|---|
| 17 | | 7-Methoxy-3-methyl-1-(1-methyl-1H-pyrazol-4-yl)-8-(1H-pyrazol-4-yl)-1,3-dihydroimidazo[4,5-c]quinolin-2-one | +++ | <0.001 |
| | MS: 375 (M + H$^+$) | 1H NMR (300 MHz,DMSO,ppm): 13.009 (s,1H), 8.802 (s,1H), 8.239 (s,1H), 7.818 (s,1H), 7.729 (s,2H), 7.476 (m,2H), 4.034 (s,3H), 3.987 (s,3H), 3.532 (s,3H) | | |
| 18 | | 1-(3-Fluoro-5-methylpyridin-4-yl)-7-methoxy-3-methyl-8-(1-methyl-1H-pyrazol-4-yl)-1,3-dihydroimidazo[4,5-c]quinolin-2-one | +++ | <0.01 |
| | MS: 419 (M + H$^+$) | 1H NMR (400 MHz,DMSO,ppm): 8.930 (s,1H), 8.895 (s,1H), 8.800 (s,1H), 7.981 (s,1H), 7.544 (s,1H), 7.109 (s,1H), 6.999 (s,1H), 3.996 (s,3H), 3.844 (s,3H), 3.613 (s,3H), 2.215 (s,3H) | | |
| 19 | | 7-Methoxy-3-methyl-1-(3-methylpyridin-4-yl)-8-(1H-pyrazol-4-yl)-1,3-dihydro-imidazo[4,5-c]quinolin-2-one | +++ | <0.01 |
| | MS: 387 (M + H$^+$) | 1H NMR (400 Hz, DMSO,ppm): 2.141 (s, 3H), 3.596 (s, 3H), 3.991 (s, 3H), 6.970 (s, 1H), 7.202 (s, 1H), 7.517 (s, 1H), 7.682-7.695 (d, J = 5.2 Hz, 1H), 7.883 (s, 1H),8.777-8.789 (d, J = 4.8 Hz, 1H), 8.900 (s, 2H), 13.016 (s, 1H) | | |

TABLE 2-continued

| Ex. | Structural formula | Name | IC$_{50}$ (pCHK2) | IC$_{50}$ (ATM) [µM] |
|---|---|---|---|---|
| 20 | MS: 405 (M + H⁺) | 1-(3-Fluoro-5-methylpyridin-2-yl)-7-methoxy-3-methyl-8-(1H-pyrazol-4-yl)-1,3-dihydroimidazo[4,5-c]quinolin-2-one | +++ | <0.001 |
| | | 1H NMR (400 MHz,MeOD,ppm): 8.747 (s,1H), 8.514 (s,1 H), 7.941-7.914 (d,J = 10.8,2H), 7.422 (s,2H), 6.947 (s,1H), 4.019 (s,3H), 3.654 (s,3H), 2.618 (s,3H) | | |
| 21 | MS: 418 (M + H⁺) | 1-(1,3-Dimethyl-1H-pyrazol-4-yl)-8-(1-ethyl-1H-pyrazol-4-yl)-7-methoxy-3-methyl-1,3-dihydroimidazo[4,5-c]quinolin-2-one | +++ | <0.001 |
| | | 1H NMR (400 MHz,DMSO,ppm): 8.81 (s,1H), 8.14 (s,1H), 8.03 (s,1H), 7.78-7.38 (m,3H), 4.16 (m,2H), 3.99 (d,6H), 3.55 (s,3H), 1.95 (s,3H), 1.40 (m,3H) | | |
| 22 | MS: 423 (M + H⁺) | 1-(3,5-Difluoropyridin-4-yl)-7-methoxy-3-methyl-8-(1-methyl-1H-pyrazol-4-yl)-1,3-dihydroimidazo[4,5-c]quinolin-2-one | +++ | <0.001 |
| | | 1H NMR (400 MHz,DMSO,ppm): 9.050 (s,2H), 8.499 (s.,1H), 8.030 (s,1H), 7.562 (s,1H), 7.312-7.254 (d,J = 23.2,2H), 4.010 (s,3H), 3.854 (s,3H), 3.611 (s,3H). | | |

TABLE 2-continued

| Ex. | Structural formula | Name | IC$_{50}$ (pCHK2) | IC$_{50}$ (ATM) [μM] |
|---|---|---|---|---|
| 23 | MS: 390 (M + H⁺) | 7-Methoxy-3-methyl-1,8-bis-(1-methyl-1H-pyrazol-4-yl)-1,3-dihydroimidazo[4,5-c]quinolin-2-one | +++ | <0.01 |
| | | 1H NMR (300 MHz,DMSO,ppm): 8.798 (s,1H), 8.241 (s,1H), 8.005 (s,1H), 7.811 (s,1H), 7.471-7.462 (d, J = 2.7 Hz,2H), 7.348 (s,1H), 4.037 (s,3H), 3.984 (s,3H), 3.874 (s,3H), 3.525 (s,3H) | | |
| 24 | MS: 419 (M + H⁺) | 8-(1-Ethyl-1H-pyrazol-4-yl)-1-(3-fluoropyridin-2-yl)-7-methoxy-3-methyl-1,3-dihydroimidazo[4,5-c]quinolin-2-one | +++ | <0.001 |
| | | 1H NMR (400 MHz,DMSO,ppm): 8.907 (s,1H), 8.732-8.721 (m,1H), 8.300-8.252 (m,1H), 7.997-7.936 (m,2H), 7.524 (s,1H), 7.226 (s,1H), 6.907 (s,1H), 4.165-40125 (m,2H), 3.998 (s,3H), 3.596 (s,3H), 1.387-1.350 (m,3H) | | |
| 25 | MS: 447 (M + H⁺) | 1-(3-Ethyl-5-fluoropyridin-4-yl)-8-(1-ethyl-1H-pyrazol-4-yl)-7-methoxy-3-methyl-1,3-dihydroimidazo[4,5-c]quinolin-2-one | +++ | <0.001 |
| | | 1H NMR (400 MHz,DMSO,ppm): 8.934 (s,2H), 8.860 (s,1H), 8.001 (s,1H), 7.544 (s,1H), 7.098 (s,1H), 6.973 (s,1H), 4.165-4.111 (m,2H), 3.999 (s,3H), 3.619 (s,3H), 2.678-2.605 (m,2H), 1.384-1.348 (m,3H), 1.045-1.007 (m,3H) | | |

TABLE 2-continued

| Ex. | Structural formula | Name | IC$_{50}$ (pCHK2) | IC$_{50}$ (ATM) [μM] |
|---|---|---|---|---|
| 26 | MS: 437 (M + H⁺) | 1-(3,5-Difluoropyridin-4-yl)-8-(1-ethyl-1H-pyrazol-4-yl)-7-methoxy-3-methyl-1,3-dihydroimidazo[4,5-c]quinolin-2-one | +++ | <0.001 |

1H NMR (300 MHz,DMSO,ppm): 9.162 (s,1H), 9.078 (s,2H), 8.101 (s.,1H), 7.618 (s,1H), 7.380 (s,2H), 4.192-4.120 (m,2H), 4.062 (s,3H), 3.631 (s,3H), 1.398-1.351 (m,3H).

| 27 | MS: 419 (M + H⁺) | 1-(3-Fluoro-5-methylpyridin-2-yl)-7-methoxy-3-methyl-8-(1-methyl-1H-pyrazol-4-yl)-1,3-dihydroimidazo[4,5-c]quinolin-2-one | +++ | <0.001 |

1H NMR (400 MHz,DMSO,ppm): 8.896 (s,1H), 8.577 (s,1H), 8.144-8.118 (d, J = 10.4,1H), 7.948 (s,1H), 7.517 (s,1H), 7.218 (s,1H), 6.857 (s,1H), 3.992 (s,3H), 3.852 (s,3H), 3.588 (s,3H), 2.672 (s,3H)

| 28 | MS: 417 (M + H⁺) | 7-Methoxy-1-(3-methoxy-pyridin-4-yl)-3-methyl-8-(1-methyl-1H-pyrazol-4-yl)-1,3-dihydroimidazo[4,5-c]quinolin-2-one | +++ | <0.01 |

1H NMR (300 MHz,DMSO,ppm): 8.855 (m,2H), 8.581 (s,1H), 7.973 (s.,1H), 7.758 (s,1H), 7.492 (s,1H), 7.093 (s,2H), 4.021 (s,3H), 3.843 (m,3H), 3.570 (s,3H), 3.319 (s,3H)

TABLE 2-continued

| Ex. | Structural formula | Name | IC$_{50}$ (pCHK2) | IC$_{50}$ (ATM) [μM] |
|---|---|---|---|---|
| 29 | MS: 405 (M + H$^+$) | 1-(3-Fluoropyridin-2-yl)-7-methoxy-3-methyl-8-(5-methyl-1H-pyrazol-3-yl)-1,3-dihydroimidazo[4,5-c]quinolin-2-one | +++ | <0.01 |

1H NMR (400 MHz,DMSO,ppm): 8.936 (s,1H), 8.628 (s,1H), 8.263-8.239 (m,1H), 7.891-7.841 (m,2H), 7.541 (s,1H), 7.376 (s,1H), 6.319 (s,1H), 5.980 (s,1H), 4.016 (s,3H), 3.595 (s,3H), 2.220 (s,3H)

| Ex. | Structural formula | Name | IC$_{50}$ (pCHK2) | IC$_{50}$ (ATM) [μM] |
|---|---|---|---|---|
| 30 | MS: 393 (M + H$^+$) | 7-Methoxy-3-methyl-1-(2-methylthiazol-4-yl)-8-(1H-pyrazol-4-yl)-1,3-dihydro-imidazo[4,5-c]quinolin-2-one | +++ | <0.01 |

1H NMR (400 MHz,DMSO,ppm): 12.96 (br,1H), 8.84 (s,1H), 8.00 (s,1H), 7.73 (s,2H), 7.48 (s,1H), 7.15 (s,1H), 3.99 (s,3H), 3.55 (s,3H), 2.79 (s,3H)

| Ex. | Structural formula | Name | IC$_{50}$ (pCHK2) | IC$_{50}$ (ATM) [μM] |
|---|---|---|---|---|
| 31 | MS: 406 (M + H$^+$) | 1-(5-Fluoropyrimidin-4-yl)-7-methoxy-3-methyl-8-(1-methyl-1H-pyrazol-4-yl)-1H,2H,3H-imidazo[4,5-c]quinolin-2-one hydrochloride | +++ | <0.01 |

1H NMR (400 MHz,DMSO,ppm): 9.43-9.31 (m,3H), 8.14 (s,1H), 7.75 (s,1H), 7.56 (d,2H), 4.08 (s,3H), 3.88 (s,3H), 3.62 (s,3H)

TABLE 2-continued

| Ex. | Structural formula | Name | IC$_{50}$ (pCHK2) | IC$_{50}$ (ATM) [μM] |
|---|---|---|---|---|
| 32 | | 7-Methoxy-1-(3-methoxy-pyridin-4-yl)-3-methyl-8-(1H-pyrazol-4-yl)-1,3-dihydroimidazo[4,5-c]-quinolin-2-one | +++ | <0.01 |
| | MS: 403 (M + H⁺) | 1H NMR (300 MHz,DMSO,ppm): 13.016 (s,1H), 8.856 (s,2H), 8.584 (s.,1H), 7.908 (s,1H), 7.766 (s,1H), 7.492 (s,1H), 7.255 (s,1H), 7.119 (s,1H), 3.986 (s,3H), 3.801 (s,3H), 3.571 (s,3H) | | |
| 33 | | 8-(1-Ethyl-1H-pyrazol-4-yl)-1-(3-fluoropyridin-4-yl)-7-methoxy-3-methyl-1,3-dihydroimidazo[4,5-c]quinolin-2-one | +++ | <0.001 |
| | MS: 419 (M + H⁺) | 1H NMR (400 MHz,DMSO,ppm): 9.076 (s,1H), 8.908 (s,1H), 8.842-8.829 (d, J = 5.2 Hz,1H), 8.009 (s,1H), 7.997-7.969 (m,1H), 7.535 (s,1H), 7.217 (s,1H), 7.175 (s,1H), 4.166-4.112 (m,2H), 4.000 (s,3H), 3.587 (s,3H), 1.383-1.347 (m,3H) | | |
| 34 | | 8-(1-Ethyl-1H-pyrazol-4-yl)-7-methoxy-3-methyl-1-(3-methylpyridin-4-yl)-1,3-dihydroimidazo[4,5-c]quinolin-2-one | +++ | <0.01 |
| | MS: 415 (M + H⁺) | 1H NMR (400 MHz, DMSO,ppm): 1.349-1.386 (t, J = 7.4 Hz, 3H), 2.139 (s, 3H), 3.597 (s, 3H), 3.994 (s, 3H), 4.1-4.2 (m, 2H), 6.949 (s, 1H), 7.066 (s, 1H), 7.517 (s, 1H), 7.682-7.695 (d, J = 5.2 Hz, 1H), 7.968 (s, 1H), 8.780-8.793 (d, J = 5.2 Hz, 1H), 8.900 (s, 2H) | | |

TABLE 2-continued

| Ex. | Structural formula | Name | IC$_{50}$ (pCHK2) | IC$_{50}$ (ATM) [μM] |
|---|---|---|---|---|
| 35 | MS: 405 (M + H$^+$) | 1-(3-Fluoropyridin-4-yl)-7-methoxy-3-methyl-8-(1-methyl-1H-pyrazol-4-yl)-1,3-dihydroimidazo[4,5-c]quinolin-2-one | +++ | <0.01 |
| | 1H NMR (400 MHz,DMSO,ppm): 9.073-9.070 (d, J = 1.2 Hz,1H), 8.901 (s,1H), 8.838-8.825 (d, J = 5.2 Hz,1H), 7.993-7.964 (m,2H), 7.532 (s,1H), 7.185 (s,1H), 7.164 (s,1H), 3.995 (s,3H), 3.847 (s,3H), 3.583 (s,3H) | | | |
| 36 | MS: 406 (M + H$^+$) | 1-(5-Fluoropyrimidin-2-yl)-7-methoxy-3-methyl-8-(1-methyl-1H-pyrazol-4-yl)-1,3-dihydroimidazo[4,5-c]quinolin-2-one | +++ | <0.01 |
| | 1H NMR (400 MHz,DMSO,ppm): 9.33 (s,2H), 8.89 (s,1H), 8.08 (s,1H), 7.51 (s,1H), 7.42 (s,1H), 6.92 (s,1H), 4.11 (s,3H), 3.99 (s,3H), 3.57 (s,3H) | | | |
| 37 | MS: 446 (M + H$^+$) | 7-Methoxy-3-methyl-8-(1H-pyrazol-4-yl)-1-[1-(tetrahydropyran-4-yl)-1H-pyrazol-4-yl]-1,3-dihydro-imidazo[4,5-c]quinolin-2-one | +++ | <0.01 |
| | 1H NMR (400 MHz,DMSO,ppm): 12.98 (br,1H), 8.79 (s,1H), 8.35 (s,1H), 7.84 (s,1H), 7.69 (s,2H), 7.44 (d,2H), 4.58 (m,1H), 4.00 (m,5H), 3.52 (m,5H), 2.07 (m,4H) | | | |

TABLE 2-continued

| Ex. | Structural formula | Name | IC$_{50}$ (pCHK2) | IC$_{50}$ (ATM) [μM] |
|---|---|---|---|---|
| 38 | MS: 433 (M + H⁺) | 8-(1-Ethyl-1H-pyrazol-4-yl)-1-(3-fluoro-5-methylpyridin-4-yl)-7-methoxy-3-methyl-1,3-dihydroimidazo[4,5-c]quinolin-2-one | ++ | <0.001 |
| | | 1H NMR (400 MHz,DMSO,ppm): 8.929 (s,1H), 8.904 (s,1H), 8.806 (s,1H), 7.993 (s,1H), 7.543 (s,1H), 7.144 (s,1H), 7.010 (s,1H), 4.165-4.111 (m,2H), 4.000 (s,3H), 3.614 (s,3H), 2.218 (s,3H), 1.384-1.348 (m,3H) | | |
| 39 | MS: 433 (M + H⁺) | 8-(1,3-Dimethyl-1H-pyrazol-4-yl)-1-(3-fluoro-5-methyl-pyridin-4-yl)-7-methoxy-3-methyl-1,3-dihydroimidazo-[4,5-c]quinolin-2-one | ++ | <0.001 |
| | | 1H NMR (400 MHz,DMSO,ppm): 8.948 (s,1H), 8.833 (s,1H), 8.732 (s,1H), 7.824 (s,1H), 7.545 (s,1H), 6.874 (s,1H), 3.929 (s,3H), 3.759 (s,3H), 3.611 (s,3H), 2.189 (s,3H), 1.702 (s,3H) | | |
| 40 | MS: 401 (M + H⁺) | 7-Methoxy-3-methyl-8-(1-methyl-1H-pyrazol-4-yl)-1-(3-methylpyridin-4-yl)-1,3-dihydroimidazo[4,5-c]quinolin-2-one | ++ | <0.01 |
| | | 1H NMR (400 MHz, DMSO, ppm): 2.128 (s, 3H), 3.589 (s, 3H), 3.833 (s, 3H), 3.982 (s, 3H), 6.933 (s, 1H), 7.018 (s, 1H), 7.511 (s, 1H), 7.665-7.678 (d, J = 5.2 Hz, 1H), 7.953 (s, 1H), 8.764-8.777 (d, J = 5.2 Hz, 1H), 8.886-8.893 (d, J = 2.8 Hz, 2H). | | |

TABLE 2-continued

| Ex. | Structural formula | Name | IC$_{50}$ (pCHK2) | IC$_{50}$ (ATM) [μM] |
|---|---|---|---|---|
| 41 | | 7-Methoxy-3-methyl-1-(2-methyl-2H-pyrazol-3-yl)-8-(1H-pyrazol-4-yl)-1,3-dihydroimidazo[4,5-c]quinolin-2-one | ++ | <0.01 |
| | MS: 376 (M + H$^+$) | 1H NMR (400 MHz,DMSO,ppm): 8.77 (s,1H), 7.85 (s,1H), 7.73 (s,2H), 7.50 (s,1H), 6.92 (s,1H), 6.71 (s,1H), 6.04 (s,1H), 3.99 (s,3H), 3.73 (s,3H), 3.62 (s,3H) | | |
| 42 | | 1-(1,3-Dimethyl-1H-pyrazol-4-yl)-7-methoxy-3-methyl-8-(1-methyl-1H-1,2,3-triazol-4-yl)-1,3-dihydroimidazo-[4,5-c]quinolin-2-one | ++ | <0.01 |
| | MS: 405 (M + H$^+$) | 1H NMR (400 MHz,DMSO,ppm): 8.85 (s,1H), 8.40 (s,1H), 8.28 (s,1H), 8.08 (s,1H), 7.52 (s,1H), 4.07 (s,3H), 4.01 (s,3H), 3.91 (s,3H), 3.54 (s,3H), 1.93 (s,3H) | | |
| 43 | | 7-Methoxy-3-methyl-1-(3-methyl-1H-pyrazol-4-yl)-8-(1-methyl-1H-pyrazol-4-yl)-1,3-dihydroimidazo[4,5-c]-quinolin-2-one | ++ | <0.001 |
| | MS: 390 (M + H$^+$) | 1H NMR 1H NMR (400 MHz, DMSO): 13.21 (s, 1H), 8.80 (s, 1H), 7.98 (d, J = 25.3 Hz, 2H), 7.47 (s, 1H), 7.36 (s, 1H), 7.31 (s, 1H), 3.98 (s, 3H), 3.87 (s, 3H), 3.54 (s, 3H), 2.05 (s, 3H). | | |

TABLE 2-continued

| Ex. | Structural formula | Name | IC$_{50}$ (pCHK2) | IC$_{50}$ (ATM) [μM] |
|---|---|---|---|---|
| 44 | MS: 430 (M + H$^+$) | 5-Fluoro-4-[7-methoxy-3-methyl-8-(1-methyl-1H-pyrazol-4-yl)-2-oxo-2,3-dihydroimidazo[4,5-c]-quinolin-1-yl]nicotinonitrile | ++ | <0.01 |
| | | 1H NMR (400 MHz,DMSO,ppm): 9.399 (s,1H), 9.346 (s,1H), 8.968 (s,1H), 8.036 (s,1H), 7.578 (s,1H), 7.404 (s,1H), 7.215 (s,1H), 4.020 (s,3H), 3.851 (s,3H), 3.636 (s,3H) | | |
| 45 | MS: 412 (M + H$^+$) | 4-[7-Methoxy-3-methyl-8-(1-methyl-1H-pyrazol-4-yl)-2-oxo-2,3-dihydroimidazo-[4,5-c]quinolin-1-yl]pyridine-2-carbonitrile | ++ | <0.05 |
| | | 1H NMR (400 MHz,DMSO,ppm): 9.099 (s,1H), 8.913 (s,1H), 8.497 (s,1H), 8.106 (s,1H), 8.097 (s,1H), 7.549 (s,1 H), 7.332 (s,1H), 7.269 (s,1H), 4.007 (s,3H), 3.857 (s,3H), 3.574 (s,3H) | | |
| 46 | MS: 412 (M + H$^+$) | 4-[7-Methoxy-3-methyl-8-(1-methyl-1H-pyrazol-4-yl)-2-oxo-2,3-dihydroimidazo-[4,5-c]quinolin-1-yl]-nicotinonitrile | ++ | <0.05 |
| | | 1H NMR (400 MHz,CDCl3,ppm): 9.219 (s,1H), 9.122 (s,1H), 8.718 (s,1H), 7.767 (s,1H), 7.689 (s,2H), 7.300 (s,1H), 7.140 (s,1H), 4.071 (s,3H), 3.924 (s,3H), 3.686 (s,3H) | | |

TABLE 2-continued

| Ex. | Structural formula | Name | IC$_{50}$ (pCHK2) | IC$_{50}$ (ATM) [μM] |
|---|---|---|---|---|
| 47 | MS: 393 (M + H⁺) | 7-Methoxy-3-methyl-8-(1-methyl-1H-pyrazol-4-yl)-1-thiazol-2-yl-1,3-dihydro-imidazo[4,5-c]quinolin-2-one | ++ | <0.01 |
| | | 1H NMR (400 HMz,DMSO,ppm): 8.82 (s,1H), 8.04 (s,2H), 7.98 (s,1 H), 7.60 (s,1 H), 7.40 (d,2H), 3.94 (s,3H), 3.81 (s,3H), 3.50 (s,3H) | | |
| 48 | MS: 412 (M + H⁺) | 6-[7-Methoxy-3-methyl-8-(1-methyl-1H-pyrazol-4-yl)-2-oxo-2,3-dihydroimidazo-[4,5-c]quinolin-1-yl]-nicotinonitrile | ++ | <0.01 |
| | | 1H NMR (300 MHz,DMSO,ppm): 9.308 (s,1H), 8.909 (s,1H), 8.744 (m,1H), 8.090 (m,1H), 8.009 (s,1H), 7.524 (s,1H), 7.402 (s,1H), 7.242 (s,1H), 4.003 (s,3H), 3.865 (s,3H), 3.576 (s,3H) | | |
| 49 | MS: 390 (M + H⁺) | 7-Methoxy-3-methyl-1-(2-methyl-2H-pyrazol-3-yl)-8-(1-methyl-1H-pyrazol-4-yl)-1,3-dihydroimidazo[4,5-c]-quinolin-2-one | ++ | <0.01 |
| | | 1H NMR (300 MHz,MeOD,ppm): 8.79 (s,1H), 7.90 (m,2H), 7.51 (s,2H), 7.04 (s,1H), 6.72 (s,1H), 4.06 (s,3H), 3.92 (s,3H), 3.73 (s,3H), 3.66 (s,3H) | | |

TABLE 2-continued

| Ex. | Structural formula | Name | IC$_{50}$ (pCHK2) | IC$_{50}$ (ATM) [μM] |
|---|---|---|---|---|
| 50 | MS: 405 (M + H$^+$) | 1-(5-Fluoropyridin-2-yl)-7-methoxy-3-methyl-8-(1-methyl-1H-pyrazol-4-yl)-1,3-dihydroimidazo[4,5-c]-quinolin-2-one | ++ | <0.01 |

1H NMR (400 MHz,DMSO,ppm): 8.916 (m,2H), 8.240 (m,1H), 7.963 (m,2H), 7.515 (s,1H), 7.258 (m,1H), 6.993 (s,1H), 4.174 (s,3H), 3.854 (s,3H), 3.523 (s,3H)

| Ex. | Structural formula | Name | IC$_{50}$ (pCHK2) | IC$_{50}$ (ATM) [μM] |
|---|---|---|---|---|
| 51 | MS: 406 (M + H$^+$) | 1-(3-Fluoropyridin-2-yl)-7-methoxy-3-methyl-8-(1-methyl-1H-1,2,3-triazol-4-yl)-1,3-dihydroimidazo-[4,5-c]quinolin-2-one | ++ | <0.01 |

1H NMR (400 MHz,DMSO,ppm): 8.964 (s,1H), 8.643 (s,1H), 8.424 (s,1H), 8.287-8.239 (m,1H), 7.939-7.907 (m,1H), 7.769 (s,1H), 7.593 (s,1H), 4.057 (s,6H), 3.606 (s,3H)

| Ex. | Structural formula | Name | IC$_{50}$ (pCHK2) | IC$_{50}$ (ATM) [μM] |
|---|---|---|---|---|
| 52 | MS: 388 (M + H$^+$) | 7-Methoxy-3-methyl-8-(1-methyl-1H-pyrazol-4-yl)-1-pyrimidin-2-yl-1,3-dihydro-imidazo[4,5-c]quinolin-2-one | ++ | <0.01 |

1H NMR (300 MHz,DMSO): 3.57 (s,3H), 3.85 (s,3H), 3.99 (s,3H), 6.83 (s,1H), 7.26 (s,1H), 7.51 (s,1H), 7.93 (t, J = 4.8,1 H), 7.98 (s,1H), 8.89 (s,1H), 9.23 (d, J = 4.8,2H).

TABLE 2-continued

| Ex. | Structural formula | Name | IC$_{50}$ (pCHK2) | IC$_{50}$ (ATM) [μM] |
|---|---|---|---|---|
| 53 | | 7-Methoxy-3-methyl-8-(1-methyl-1H-pyrazol-4-yl)-1-(1H-pyrazol-4-yl)-1,3-dihydroimidazo[4,5-c]-quinolin-2-one | ++ | <0.01 |
| | MS: 376 (M + H$^+$) | 1H NMR (400 MHz, DMSO): 8.80 (s,1H), 8.03 (d, J = 20.4 Hz, 2H), 7.46 (s,1H), 7.39 (s,1H), 7.29 (s,1H), 3.97 (s,3H), 3.85 (s,3H), 3.53 (s,3H). | | |
| 54 | | 1-(3-Ethyl-5-methylpyridin-4-yl)-7-methoxy-3-methyl-8-(1-methyl-1H-pyrazol-4-yl)-1,3-dihydroimidazo[4,5-c]-quinolin-2-one | ++ | <0.01 |
| | MS: 429 (M + H$^+$) | 1H NMR (400 MHz,DMSO,ppm): 8.918 (s,1H), 8.751 (s,1H), 8.714 (s,1H), 7.952 (s,1H), 7.514 (s,1H), 6.963 (s,1H), 6.831 (s,1H), 3.982 (s,3H), 3.833 (s,3H), 3.681 (s,3H), 2.469-2.329 (m,3H), 1.977 (s,3H), 0.966-0.928 (m,3H) | | |
| 55 | | 7-Methoxy-3-methyl-8-(1-methyl-1H-pyrazol-4-yl)-1-[1-(tetrahydropyran-4-yl)-1H-pyrazol-4-yl]-1,3-dihydroimidazo[4,5-c]-quinolin-2-one | ++ | <0.01 |
| | MS: 460 (M + H$^+$) | 1H NMR (300 MHz,DMSO,ppm): 8.80 (s,1H), 8.35 (s,1H), 7.96 (s,1H), 7.83 (s,1H), 7.40 (m,3H), 4.60 (m,1H), 3.97 (m,5H), 3.84 (s,3H), 3.53 (m,5H), 2.07 (m,4H) | | |

TABLE 2-continued

| Ex. | Structural formula | Name | IC$_{50}$ (pCHK2) | IC$_{50}$ (ATM) [μM] |
|---|---|---|---|---|
| 56 | | 7-Methoxy-3-methyl-8-(1-methyl-1H-pyrazol-4-yl)-1-pyridin-2-yl-1,3-dihydro-imidazo[4,5-c]quinolin-2-one | ++ | <0.01 |
| | MS: 387 (M + H$^+$) | 1H NMR (DMSO, 400 MHz, ppm): 8.874 (s,1H), 8.816-8.832 (m,1H), 8.2-8.3 (t,1H), 7.964 (s,1H), 7.822-7.842 (d, J = 8.0 Hz,1H), 7.758-7.789 (m,1H), 7.494 (s,1H), 7.160 (s,1H), 6.984 (s,1H), 3.986 (s,3H), 3.842 (s,3H), 3.575 (s,3H) | | |
| 57 | | 7-Methoxy-3-methyl-8-(1-methyl-1H-pyrazol-4-yl)-1-pyrimidin-5-yl-1,3-dihydro-imidazo[4,5-c]quinolin-2-one | ++ | <0.05 |
| | MS: 388 (M + H$^+$) | 1H NMR (400 MHz,DMSO,ppm): 9.512 (s,1H), 9.241 (s,2H), 8.906 (s,1H), 7.991 (s,1H), 7.541 (s,1H), 7.247 (s,1H), 7.134 (s,1H), 4.035-4.004 (s,3H), 3.884-3.857 (s,3H), 3.590 (s,3H) | | |
| 58 | | 7-Methoxy-3-methyl-8-(1-methyl-1H-pyrazol-4-yl)-1-pyridin-4-yl-1,3-dihydro-imidazo[4,5-c]quinolin-2-one | ++ | <0.01 |
| | MS: 387 (M + H$^+$) | 1H NMR (300 MHZ,DMSO): 3.57 (s,3H), 3.84 (s,3H), 3.99 (s,3H), 7.11 (s,1H), 7.20 (s,1H), 7.50 (s,1 H),7.75 (d, J = 6.0 Hz,2H), 8.00 (s,1H), 8.90 (s,1H), 8.99 (d, J = 6.0 Hz,2H) | | |

TABLE 2-continued

| Ex. | Structural formula | Name | IC$_{50}$ (pCHK2) | IC$_{50}$ (ATM) [μM] |
|---|---|---|---|---|
| 59 | MS: 390 (M + H⁺) | 7-Methoxy-3-methyl-1-(1-methyl-1H-imidazol-4-yl)-8-(1-methyl-1H-pyrazol-4-yl)-1,3-dihydroimidazo[4,5-c]quinolin-2-one | + | <0.01 |
| | | 1H NMR (400 MHz,DMSO,ppm): 8.79 (s,1H), 7.96 (1d,2H), 7.58 (s,1H), 7.45 (s,1H), 7.39 (d,2H), 4.00 (s,3H), 3.88 (m,6H), 3.53 (s,3H) | | |
| 60 | MS: 421 (M + H⁺) | 1-(3-Chloropyridin-4-yl)-7-methoxy-3-methyl-8-(1-methyl-1H-pyrazol-4-yl)-1,3-dihydroimidazo[4,5-c]quinolin-2-one | + | <0.01 |
| | | 1H NMR (300 MHz, DMSO,ppm): 9.43 (s,1H), 9.24 (s,1H), 9.03 (d, J = 5.1 Hz, 1H), 8.10 (d, J = 5.1 Hz, 2H), 7.98 (s,1H), 7.13 (s,1H), 7.06 (s,1H), 4.07 (s,3H), 3.87 (s,3H), 3.67 (s,3H) | | |
| 61 | MS: 443 (M + H⁺) | 1-(3-Ethyl-5-methylpyridin-4-yl)-8-(1-ethyl-1H-pyrazol-4-yl)-7-methoxy-3-methyl-1,3-dihydroimidazo[4,5-c]quinolin-2-one | + | <0.01 |
| | | 1H NMR (400 MHz,DMSO,ppm): 8.918 (s,1H), 8.760 (s,1H), 8.723 (s,1H), 7.963 (s,1H), 7.516 (s,1H), 7.009 (s,1H), 6.847 (s,1H), 4.156-4.102 (m,2H), 3.989 (s,3H), 3.622 (s,3H), 2.514-2.458 (m,2H), 2.004 (s,3H), 1.382-1.345 (m,3H), 0.973-0.936 (m,3H) | | |

TABLE 2-continued

| Ex. | Structural formula | Name | IC$_{50}$ (pCHK2) | IC$_{50}$ (ATM) [μM] |
|---|---|---|---|---|
| 62 | MS: 401 (M + H⁺) | 8-(1-Ethyl-1H-pyrazol-4-yl)-7-methoxy-3-methyl-1-pyridin-4-yl-1,3-dihydro-imidazo[4,5-c]quinolin-2-one | + | <0.01 |

1H NMR (400 MHZ, DMSO, ppm): 1.35 (t, J = 7.6 Hz, 3H), 3.56 (s,3H), 3.98 (s,3H), 4.12 (q, J = 7.6,2H), 7.17 (d, J = 8.8 Hz,2H), 7.51 (s,1H), 7.74 (d, J = 6 Hz,2H), 7.98 (s,1H), 8.87 (s,1H), 8.95 (br,2H)

| Ex. | Structural formula | Name | IC$_{50}$ (pCHK2) | IC$_{50}$ (ATM) [μM] |
|---|---|---|---|---|
| 63 | MS: 420 (M + H⁺) | 1-(3-Fluoro-5-methylpyridin-4-yl)-7-methoxy-3-methyl-8-(1-methyl-1H-1,2,3-triazol-4-yl)-1,3-dihydroimidazo-[4,5-c]quinolin-2-one | ++ | <0.01 |

1H NMR (400 MHz, DMSO-d6) ppm = 8.97 (s,1H), 8.83 (s,1H), 8.74 (s,1H), 8.42 (s,1H) 7.91 (s,1H), 7.60 (s,1H), 4.10 (s,6H), 3.61 (s,3H), 2.19 (s,3H)

| Ex. | Structural formula | Name | IC$_{50}$ (pCHK2) | IC$_{50}$ (ATM) [μM] |
|---|---|---|---|---|
| 64 | MS: 406 (M + H⁺) | 1-(3-Fluoropyridin-4-yl)-7-methoxy-3-methyl-8-(1-methyl-1H-1,2,3-triazol-4-yl)-1,3-dihydroimidazo-[4,5-c]quinolin-2-one | ++ | <0.01 |

1H NMR (400 MHz, DMSO-d6) ppm = 9.01 (s,1H), 8.94 (s,1H), 8.78-8.77 (m,1H), 8.42 (s,1H), 8.04 (s,1H), 7.94-7.92 (m,1H), 7.58 (s,1H), 4.05 (s,6H), 3.58 (s,3H)

TABLE 2-continued

| Ex. | Structural formula | Name | IC$_{50}$ (pCHK2) | IC$_{50}$ (ATM) [μM] |
|---|---|---|---|---|
| 65 | MS: 406 (M + H⁺) | 8-(3-Amino-1H-pyrazol-5-yl)-1-(3-fluoro-2-pyridyl)-7-methoxy-3-methyl-imidazo-[4,5-c]quinolin-2-one | ++ | <0.001 |

1H NMR (400 MHz, DMSO) ppm = 11.3 (s, 1H), 8.87 (s, 1H), 8.60-8.59 (m,1H), 8.17-8.10 (m,1H), 7.86-7.80 (m,1H), 7.52 (s,1H), 7.16 (s,1H), 5.50 (s,1H), 4.40 (s,2H), 3.97 (s,3H), 3.58 (s,3H).

| Ex. | Structural formula | Name | IC$_{50}$ (pCHK2) | IC$_{50}$ (ATM) [μM] |
|---|---|---|---|---|
| 66 | MS: 479 (M + H⁺) | 1-[3-Fluoro-5-(2-methoxy-ethoxy)-2-pyridyl]-7-methoxy-3-methyl-8-(1-methylpyrazol-4-yl)imidazo-[4,5-c]quinolin-2-one | +++ | <0.001 |

1H NMR (400 MHz, DMSO) ppm = 8.90 (s,1H), 8.48 (s,1H), 8.02-7.97 (m,2H), 7.52 (s,1H), 7.29 (s,1H), 6.92 (s,1H), 4.43 (d, J = 4,2H), 4.00 (s,3H), 3.86 (s,3H), 3.79-3.77 (m,2H), 3.59 (s,3H), 3.37 (s,3H)

| Ex. | Structural formula | Name | IC$_{50}$ (pCHK2) | IC$_{50}$ (ATM) [μM] |
|---|---|---|---|---|
| 67 | MS: 465 (M + H⁺) | 1-[3-Fluoro-5-(2-hydroxy-ethoxy)-2-pyridyl]-7-methoxy-3-methyl-8-(1-methylpyrazol-4-yl)imidazo-[4,5-c]quinolin-2-one | +++ | <0.001 |

1H NMR (400 MHz, DMSO) ppm = 8.89 (s,1H), 8.46 (s,1H), 7.95 (m,2H), 7.51 (s,1H), 7.29 (s,1H), 6.92 (s,1H), 5.07 (m,1H), 4.30 (m,2H), 3.99 (s,3H), 3.85-3.82 (m,5H), 3.58 (s,3H)

TABLE 2-continued

| Ex. | Structural formula | Name | IC$_{50}$ (pCHK2) | IC$_{50}$ (ATM) [μM] |
|---|---|---|---|---|
| 68 | MS. 437 (M + H$^+$) | 7-Methoxy-3-methyl-8-(1-methyl-1H-pyrazol-4-yl)-1-quinolin-2-yl-1,3-dihydro-imidazo[4,5-c]quinolin-2-one<br><br>1H NMR (400 MHz, DMSO-d6) ppm = 8.905 (s,1H), 8.801-8.780 (m,1H), 8.254-8.235 (m,1H), 8.0-032 (m,1H), 7.949-7.928 (s,2H), 7.850-7.829 (m,1H), 7.829 (s,1H), 7.700 (s,1H), 7.113 (s,1H), 6.674 (s,1H), 3.965 (s,3H), 3.671 (s,3H), 3.596 (s,3H) | + | <0.01 |
| 69 | MS. 426 (M + H$^+$) | 7-Methoxy-3-methyl-8-(1-methyl-1H-pyrazol-4-yl)-1-(1H-pyrrolo[2,3-b]pyridin-6-yl)1,3-dihydroimidazo-[4,5-c]quinolin-2-one<br><br>1H NMR (400 MHz, DMSO-d6) ppm = 8.85 (s,1H), 8.36 (d, J = 8,1H), 7.76-7.71 (m,2H), 7.46-7.41 (m,2H), 6.75-6.67 (m,3H), 3.96 (s,3H), 3.74 (s,3H), 3.52 (s,3H) | ++ | <0.001 |
| 101 | MS: 424 (M + H$^+$) | 1-(3,5-Difluoropyridin-2-yl)-7-methoxy-3-methyl-8-(2-methyl-2H-1,2,3-triazol-4-yl)-1,3-dihydroimidazo-[4,5-c]quinolin-2-one<br><br>1H NMR (300 MHz, DMSO-d6) ppm = 8.97 (s,1H), 8.84 (s,1H), 8.57-8.51 (m,1H), 7.59 (s,1H), 7.45 (s, 1H), 4.13 (s,3H), 4.04 (s,3H), 3.61 (s,3H) | +++ | <0.05 |

TABLE 2-continued

| Ex. | Structural formula | Name | IC$_{50}$ (pCHK2) | IC$_{50}$ (ATM) [μM] |
|---|---|---|---|---|
| 102 | | 1-(1,3-Dimethyl-1H-pyrazol-4-yl)-7-methoxy-3-methyl-8-(2-methyl-2H-1,2,3-triazol-4-yl)-1,3-dihydroimidazo-[4,5-c]quinolin-2-one | +++ | <0.05 |
| | MS: 405 (M + H$^+$) | 1H NMR (400 MHz, DMSO-d6) ppm = 8.88 (s, 1H), 8.14-8.11 (s,2H), 8.04 (s,1 H), 7.54 (s,1 H), 4.19 (s,3H), 4.03-3.99 (d,6H), 3.56 (s,3H), 1.56 (s,3H) | | |
| 103 | | 1-(3-Fluoro-5-methylpyridin-4-yl)-7-methoxy-3-methyl-8-(2-methyl-2H-1,2,3-triazol-4-yl)-1,3-dihydroimidazo-[4,5-c]quinolin-2-one | ++ | <0.05 |
| | MS: 420 (M + H$^+$) | 1H NMR (300 MHz, DMSO-d6) ppm = 9.04 (s,1H), 8.87 (s,1H), 8.77 (s,1H), 8.09 (s,1H), 7.68 (s,1H), 7.61 (s,1H), 4.40 (s,3H), 4.04 (s,3H), 3.62 (s,3H), 2.20 (s,3H) | | |
| 104 | | 8-(1-Ethyl-1H-pyrazol-4-yl)-7-methoxy-1-(3-methoxy-pyridin-4-yl)-3-methyl-1,3-dihydroimidazo[4,5-c]quinolin-2-one | ++ | <0.01 |
| | MS: 431 (M + H$^+$) | 1H NMR (300 MHz,DMSO) ppm = 8.85-8.84 (d, J = 4.5, 2H), 8.58-8.57 (d,J = 4.8, 1H), 7.98 (s,1 H), 7.76-7.74 (d, J = 5.1, 1H), 7.49 (s,1H), 7.12-7.10 (d, J = 6.6, 2H), 4.17 (m,2H), 3.98 (s,3H), 3.57 (s,3H), 3.36 (s,3H), 1.39 (m,3H) | | |

TABLE 2-continued

| Ex. | Structural formula | Name | IC$_{50}$ (pCHK2) | IC$_{50}$ (ATM) [μM] |
|---|---|---|---|---|
| 105 | MS: 435 (M + H⁺) | 1-(3-Fluoro-5-methoxy-pyridin-2-yl)-7-methoxy-3-methyl-8-(1-methyl-1H-pyrazol-4-yl)-1,3-dihydro-imidazo[4,5-c]quinolin-2-one | ++ | <0.001 |
| | | 1H NMR (400 MHz,DMSO) ppm = 8.89 (s,1H), 8.45 (s,1H), 7.98 (m,2H), 7.51 (s,1H), 7.25 (s,1H), 6.88 (s,1H), 4.04 (s,3H), 3.99 (s,3H), 3.85 (s,3H), 3.58 (s,3H) | | |
| 106 | MS: 449 (M + H⁺) | 8-(1,3-Dimethyl-1H-pyrazol-4-yl)-1-(3-fluoro-5-methoxypyridin-2-yl)-7-methoxy-3-methyl-1,3-dihydroimidazo[4,5-c]-quinolin-2-one | ++ | <0.001 |
| | | 1H NMR (400 MHz,DMSO) ppm = 8.89 (s,1 H), 8.35 (s,1 H), 7.94 (s,1 H), 7.78 (s,1 H), 7.50 (s,1 H), 6.78 (s,1 H), 3.98 (m,3H), 3.90 (s,3H), 3.75 (s,3H), 3.63 (s,3H), 1.78 (s,3H) | | |
| 107 | MS: 409 (M + H⁺) | 1-(3,5-Difluoropyridin-2-yl)-7-methoxy-8-(1-methyl-1H-pyrazol-4-yl)-1,3-dihydro-imidazo[4,5-c]quinolin-2-one | ++ | <0.001 |
| | | 1H NMR (400 MHz,DMSO) ppm = 11.81 (s,1H), 8.84 (d ,J = 2.6 Hz, 1H), 8.68 (s,1H), 8.00 (s,1H), 7.49 (s,1H), 7.33 (d, J = 0.8 Hz, 1H), 6.93 (s,1H), 3.99 (s,3H), 3.85 (s,3H). | | |

TABLE 2-continued

| Ex. | Structural formula | Name | IC$_{50}$ (pCHK2) | IC$_{50}$ (ATM) [μM] |
|---|---|---|---|---|
| 108 | MS: 423 (M + H$^+$) | 1-(3,5-Difluoropyridin-2-yl)-8-(1,3-dimethyl-1H-pyrazol-4-yl)-7-methoxy-1,3-dihydroimidazo[4,5-c]-quinolin-2-one | ++ | <0.001 |
| | 1H NMR (400 MHz,DMSO) ppm = 11.84 (s,1H), 8.77 (d,J = 2.5 Hz, 1H), 8.70 (s,1H), 8.48 (m,1H), 7.79 (s,1H), 7.50 (s,1H), 6.76 (s,1H), 3.91 (s,3H), 3.77 (s,3H), 1.82 (s,3H). | | | |
| 109 | MS: 421 (M + H$^+$) | 1-(3-Fluoro-5-methoxy-pyridin-2-yl)-7-methoxy-3-methyl-8-(2H-pyrazol-3-yl)-1,3-dihydroimidazo[4,5-c]quinolin-2-one | +++ | <0.01 |
| | 1H NMR (400 MHz, DMSO) ppm = 8.91 (s,1H), 8.36 (d, J = 2.6 Hz, 1H), 7.93 (m,1H), 7.64 (s,1H), 7.53 (s,1H), 7.40 (s,1H), 6.54 (s,1H), 4.01 (s,3H), 3.97 (s,3H), 3.57 (s,3H). | | | |
| 110 | MS: 453 (M + H$^+$) | 1-(3-Fluoro-5-fluoro-methoxypyridin-2-yl)-7-methoxy-3-methyl-8-(1-methyl-1H-pyrazol-4-yl)-1,3-dihydroimidazo[4,5-c]-quinolin-2-one | +++ | <0.001 |
| | 1H NMR (400 MHz,DMSO) ppm = 8.90 (s,1H), 8.65-8.62 (s,1H), 8.23-8.20 (m,1H), 7.95 (s,1H), 7.52 (s,1H), 7.30 (s,1H), 6.90 (s,1H), 6.23-6.20 (m,1H), 6.10-6.01 (s,1H), 3.99 (s,3H), 3.84 (s,3H), 3.59 (s,3H) | | | |

TABLE 2-continued

| Ex. | Structural formula | Name | IC$_{50}$ (pCHK2) | IC$_{50}$ (ATM) [μM] |
|---|---|---|---|---|
| 111 | MS: 449 (M + H⁺) | 8-(1-Ethyl-1H-pyrazol-4-yl)-1-(3-fluoro-5-methoxy-pyridin-2-yl)-7-methoxy-3-methyl-1,3-dihydroimidazo-[4,5-c] quinolin-2-one | ++ | <0.01 |
| | | 1H NMR (400 MHz,DMSO) ppm = 8.87 (s,1H), 8.47 (s,1H), 7.96 (m,2H), 7.50 (s,1H), 7.29 (s,1H), 6.88 (s,1H), 4.16 (m,2H), 4.03 (s,3H), 3.98 (s,3H), 3.57 (s,3H), 1.36 (m,3H) | | |
| 112 | MS: 434 (M + H⁺) | 1-(3-Ethyl-5-fluoropyridin-4-yl)-7-methoxy-3-methyl-8-(2-methyl-2H-1,2,3-triazol-4-yl)-1,3-dihydroimidazo-[4,5-c] quinolin-2-one | ++ | <0.01 |
| | | 1H NMR (400 MHz,DMSO) ppm = 9.00 (s,1H), 8.88 (s,1H), 8.82 (s,1H), 8.08 (s,1H), 7.64-7.06 (d, J = 16, 2H), 4.08 (s,3H), 4.03 (s,3H), 3.62 (s,3H), 2.57-2.55 (m,2H), 1.03-1.00 (m,3H) | | |
| 113 | MS: 449 (M + H⁺) | 1-(5-Ethoxy-3-fluoropyridin-2-yl)-7-methoxy-3-methyl-8-(1-methyl-1H-pyrazol-4-yl)-1,3-dihydroimidazo[4,5-c]-quinolin-2-one | +++ | <0.001 |
| | | 1H NMR (400 MHz,DMSO) ppm = 8.87 (s,1H), 8.43 (s,1H), 7.94 (m,2H), 7.50 (s,1H), 7.24 (s,1H), 6.87 (s,1H), 4.32 (m,2 H), 3.98 (s,3H), 3.84 (s,3H), 3.57 (s,3H), 1.44 (m,3H) | | |

TABLE 2-continued

| Ex. | Structural formula | Name | IC$_{50}$ (pCHK2) | IC$_{50}$ (ATM) [μM] |
|---|---|---|---|---|
| 114 | MS: 471 (M + H⁺) | 1-(5-Difluoromethoxy-3-fluoropyridin-2-yl)-7-methoxy-3-methyl-8-(1-methyl-1H-pyrazol-4-yl)-1,3-dihydroimidazo[4,5-c]-quinolin-2-one<br><br>1H NMR (400 MHz,DMSO) ppm = 8.92 (s,1H), 8.71 (s,1H), 8.35 (m,1H), 7.96 (s,1H), 7.78 (s,2H), 7.34 (s,1H), 6.94 (s,1H), 4.00 (s,3H), 3.84 (s,3H), 3.32 (s,3H) | +++ | <0.001 |
| 115 | MS: 421 (M + H⁺) | 1-(3-Fluoro-5-methoxy-pyridin-2-yl)-7-methoxy-8-(1-methyl-1H-pyrazol-4-yl)-1,3-dihydroimidazo[4,5-c]-quinolin-2-one<br><br>1H NMR (400 MHz,DMSO) ppm = 11.71 (s,1H), 8.65 (s,1H), 8.46 (s,1H), 7.98 (m,2H), 7.47 (s,1H), 7.24 (s,1H), 6.87 (s,1H), 4.04 (s,3H), 3.98 (s,3H), 3.85 (s,3H) | ++ | <0.01 |
| 116 | MS: 421 (M + H⁺) | 1-(3-Fluoro-5-methoxy-pyridin-4-yl)-7-methoxy-8-(1-methyl-1H-pyrazol-4-yl)-1,3-dihydroimidazo[4,5-c]-quinolin-2-one<br><br>1H NMR (400 MHz, DMSO-d6) ppm = 11.77 (s,1H), 8.72 (d,J = 16.7 Hz, 2H), 8.64 (s,1H), 7.98 (s,1H), 7.47 (s,1H), 7.13 (d, J = 14.7 Hz, 2H), 3.97 (s,3H), 3.84 (d, J = 8.0 Hz, 6H). | + | <0.01 |

| Ex. | Structural formula | Name | IC$_{50}$ (pCHK2) | IC$_{50}$ (ATM) [μM] |
|---|---|---|---|---|
| 117 | | 1-(3,5-Difluoropyridin-2-yl)-7-methoxy-3-methyl-8-(3-methyl-1H-pyrazol-4-yl)-1,3-dihydroimidazo[4,5-c]-quinolin-2-one | ++ | <0.01 |
| | MS: 423 (M + H$^+$) | 1H NMR (300 MHz, DMSO) ppm = 12.34-12.31 (s,1H), 8.64-8.41 (s,1H), 8.78 (s,1H), 8.67-8.59 (m,1H), 7.52-7.44 (s,2H), 6.74 (s,1H), 3.91-3.82 (s,3H), 3.57-3.49 (s,3H), 2.02-1.87 (m,3H) | | |
| 118 | | 1-(3,5-Dimethyl-1H-pyrazol-4-yl)-7-methoxy-3-methyl-8-(1-methyl-1H-pyrazol-4-yl)-1,3-dihydroimidazo[4,5-c]-quinolin-2-one | ++ | <0.01 |
| | MS: 404 (M + H$^+$) | 1H NMR (400 MHz,DMSO) ppm = 12.9 (s,1H), 8.80 (s,1H), 8.00 (s,1H), 7.47 (s,1H), 7.33 (s,1H), 7.30 (d, J = 0.8 Hz, 1H), 3.97 (s,3H), 3.86 (s,3H), 3.55 (s,3H), 1.98 (s,6H). | | |
| 119 | | 1-(5-Chloro-3-fluoropyridin-2-yl)-7-methoxy-3-methyl-8-(1-methyl-1H-pyrazol-4-yl)-1,3-dihydroimidazo[4,5-c]-quinolin-2-one | +++ | <0.001 |
| | MS: 440 (M + H$^+$) | 1H NMR (400 MHz, DMSO) ppm = 8.91 (s,1H), 8.85 (s,1H), 8.66 (m,1H), 8.00 (s,1H), 7.53 (s,1H), 7.33 (s,1H), 6.96 (s,1H), 4.00 (s,3H), 3.86 (s,3H), 3.59 (s,3H) | | |

TABLE 2-continued

| Ex. | Structural formula | Name | IC$_{50}$ (pCHK2) | IC$_{50}$ (ATM) [μM] |
|---|---|---|---|---|
| 120 | MS: 426 (M + H$^+$) | 7-Methoxy-3-methyl-8-(1-methyl-1H-pyrazol-4-yl)-1-(1H-pyrrolo[3,2-c]pyridin-6-yl)-1,3-dihydroimidazo-[4,5-c]quinolin-2-one<br><br>1H NMR (400 MHz, DMSO) ppm = 11.97 (s,1 H), 9.00 (s,1H), 8.84 (s,1H), 7.78 (s,2H), 7.71 (d, J = 2.2 Hz, 1H), 7.44 (s,1H), 6.84 (d, J = 2.9 Hz, 1H), 6.80 (d,1H), 6.73 (s,1H), 3.95 (s,3H), 3.74 (s,3H), 3.57 (s,3H) | ++ | <0.001 |
| 121 | MS: 390 (M + H$^+$) | 1-(1,3-Dimethyl-1H-pyrazol-4-yl)-7-methoxy-3-methyl-8-(1H-pyrazol-3-yl)-1,3-dihydroimidazo[4,5-c]-quinolin-2-one<br><br>1H NMR (400 MHz, DMSO) ppm = 12.97 (s,1H), 8.84 (d, J = 40, 1H), 8.07-7.72 (m,2H), 7.54-6.72 (m,2H), 6.15 (s,1H), 4.00-3.92 (m,6H), 3.55 (s,3H), 1.95 (s,3H) | +++ | <0.01 |
| 122 | MS: 435 (M + H$^+$) | 1-(3-Fluoro-5-methoxy-pyridin-2-yl)-7-methoxy-3-methyl-8-(3-methyl-1H-pyrazol-4-yl)-1,3-dihydro-imidazo[4,5-c]quinolin-2-one<br><br>1H NMR (300 MHz,DMSO) ppm = 8.84 (s, 1H), 8.31-8.30 (s,1H), 7.81-7.77 (d, J = 12, 1H), 7.50 (s,2H), 6.76 (s,1 H), 3.99 (s,3H), 3.90 (s,3H), 3.56 (s,3H), 1.93 (s,3H) | +++ | <0.001 |

TABLE 2-continued

| Ex. | Structural formula | Name | IC$_{50}$ (pCHK2) | IC$_{50}$ (ATM) [μM] |
|---|---|---|---|---|
| 123 | 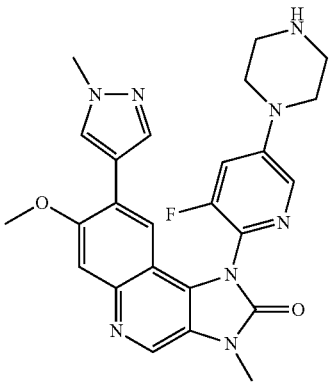 [SMILES: COc1cc2ncc3c(c2cc1-c1cnn(C)c1)n(-c1ncc(N2CCNCC2)cc1F)c(=O)n3C]<br>MS: 490(M + H⁺) | 1-(3-Fluoro-5-piperazin-1-yl-pyridin-2-yl)-7-methoxy-3-methyl-8-(1-methyl-1H-pyrazol-4-yl)-1,3-dihydro-imidazo[4,5-c]quinolin-2-one | ++ | <0.01 |
| | | 1H NMR (400 MHz, DMSO) ppm = 8.85 (s,1H), 8.36 (d, J = 2.5 Hz, 1H), 7.95 (s,1H), 7.64 (dd, J = 12.7, 2.6 Hz, 1H), 7.48 (s,1H), 7.28 (s,1H), 6.89 (s,1H), 3.97 (s,3H), 3.84 (s,3H), 3.56 (s,3H), 3.36 (dd, J = 6.1,3.8 Hz, 4H), 2.88 (t, J = 5.0 Hz, 4H) | | |
| 124 | 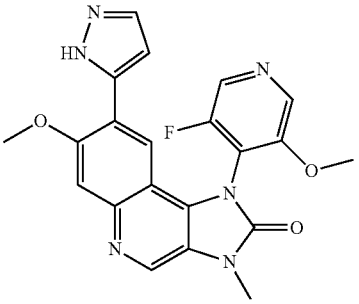<br>MS: 421 (M + H⁺) | 1-(3-Fluoro-5-methoxy-pyridin-4-yl)-7-methoxy-3-methyl-8-(2H-pyrazol-3-yl)-1,3-dihydroimidazo[4,5-c]quinolin-2-one | ++ | <0.05 |
| | | 1H NMR (400 MHz,DMSO) ppm = 13.0 (d, J = 22.4 Hz, 1H), 8.92 (d, J = 16.3 Hz, 1H), 8.68 (dd, J = 15.0, 10.1 Hz, 2H), 7.82 (s,1H), 7.70 (t, J = 1.9 Hz, 1H), 7.61-7.45 (m,1H), 6.73 (t, J = 2.1 Hz, 1H), 3.98 (d, J = 7.6 Hz, 3H), 3.84 (d, J = 12.8 Hz, 3H), 3.58 (s,3H). | | |
| 125 | 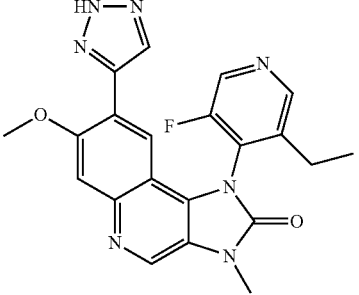 [SMILES: CCc1cncc(F)c1-n1c(=O)n(C)c2cnc3cc(OC)c(-c4cn[nH]n4)cc3c21]<br>MS: 420 (M + H⁺) | 1-(3-Ethyl-5-fluoropyridin-4-yl)-7-methoxy-3-methyl-8-(2H-1,2,3-triazol-4-yl)-1,3-dihydroimidazo[4,5-c]quinolin-2-one | ++ | <0.001 |
| | | 1H NMR (400 MHz, DMSO) ppm = 15.25 (s,1H), 9.00 (s,1H), 8.88 (s,1H), 8.82 (s,1H), 8.26 (s,1H), 7.83 (s,1H), 7.62 (s,1H), 4.05 (s,3H), 3.64 (s,3H), 2.67-2.51 (m,2H), 1.03 (m,3H). | | |

TABLE 2-continued

| Ex. | Structural formula | Name | IC$_{50}$ (pCHK2) | IC$_{50}$ (ATM) [µM] |
|---|---|---|---|---|
| 126 | MS: 434 (M + H⁺) | 1-(3-Ethyl-5-fluoropyridin-4-yl)-7-methoxy-3-methyl-8-(1-methyl-1H-1,2,3-triazol-4-yl)-1,3-dihydroimidazo-[4,5-c] quinolin-2-one | ++ | <0.01 |
|  |  | 1H NMR (400 MHz, DMSO) ppm = 9.00 (s,1H), 8.87 (s,1H), 8.82 (s,1H), 8.44 (s,1H), 7.92 (s,1H), 7.62 (s,1H), 4.06 (d, J = 6.0 Hz, 6H), 3.64 (s,3H), 2.59 (m,2H), 1.03 (t, J = 7.6 Hz, 3H) |  |  |
| 127 | MS: 436 (M + H⁺) | 1-(3-Fluoro-5-methoxy-pyridin-4-yl)-7-methoxy-3-methyl-8-(2-methyl-2H-1,2,3-triazol-4-yl)-1,3-dihydroimidazo[4,5-c] quinolin-2-one | ++ | <0.01 |
|  |  | 1H NMR (400 MHz, DMSO-d6) ppm = 8.94 (s, 1H), 8.76 (s, 1H), 8.68 (s,1H), 8.08 (s,1H), 7.81 (s,1H), 7.57 (s,1H), 4.11 (s,3H), 4.02 (s,3H), 3.86 (s,3H), 3.59 (s,3H). |  |  |
| 128 | MS: 422 (M + H⁺) | 1-(3-Fluoro-5-methoxy-pyridin-2-yl)-7-methoxy-3-methyl-8-(3H-1,2,3-triazol-4-yl)-1,3-dihydroimidazo-[4,5-c]quinolin-2-one | ++ | <0.01 |
|  |  | 1H NMR (400 MHz, DMSO-d6) ppm = 15.16 (s,1H), 8.93 (s,1H), 8.38 (d, J = 2.6 Hz, 1H), 8.23 (s,1H), 7.96 (dd, J = 11.0, 2.6 Hz, 1H), 7.66 (s,1H), 7.57 (s,1H), 4.02 (s,6H), 3.58 (s,3H). |  |  |

TABLE 2-continued

| Ex. | Structural formula | Name | IC$_{50}$ (pCHK2) | IC$_{50}$ (ATM) [μM] |
|---|---|---|---|---|
| 129 | MS: 435 (M + H$^+$) | 8-(1,3-Dimethyl-1H-pyrazol-4-yl)-1-(3-fluoro-5-methoxy-pyridin-4-yl)-7-methoxy-1,3-dihydroimidazo[4,5-c]-quinolin-2-one<br><br>1H NMR (400 MHz, DMSO-d6) ppm = 11.8 (s,1H), 8.69-8.62 (m,3H), 7.79 (s,1H), 7.46 (s,1H), 6.95 (s,1H), 3.90 (s,3H), 3.84 (s,3H), 3.75 (s,3H), 1.72 (s,3H). | + | <0.001 |
| 130 | MS: 418 (M + H$^+$) | 1-(1-Ethyl-3-methyl-1H-pyrazol-4-yl)-7-methoxy-3-methyl-8-(1-methyl-1H-pyrazol-4-yl)-1,3-dihydro-imidazo[4,5-c]quinolin-2-one<br><br>1H NMR (400 MHz,DMSO) ppm = 8.83 (s,1H), 8.19 (s,1H), 8.01 (s,1H), 7.49 (s,1H), 7.43 (s,1H), 7.36 (s,1H), 4.30-4.20 (m,2H), 4.00 (s,3H), 3.88 (s,3H), 3.56 (s,3H), 1.96 (s,3H), 1.50 (m,3H) | ++ | <0.001 |
| 131 | MS: 436 (M + H$^+$) | 1-(3-Fluoro-5-methoxy-pyridin-4-yl)-7-methoxy-3-methyl-8-(1-methyl-1H-1,2,3-triazol-4-yl)-1,3-dihydroimidazo[4,5-c]-quinolin-2-one<br><br>1H NMR (400 MHz, DMSO-d6) ppm = 8.93 (s,1H), 8.72 (s,1H), 8.67 (s,1H), 8.42 (s,1H), 8.05 (s,1H), 7.57 (s,1H), 4.04 (d, J = 9.80 Hz, 6H), 3.84 (s,3H), 3.59 (s,3H). | ++ | <0.01 |

TABLE 2-continued

| Ex. | Structural formula | Name | IC$_{50}$ (pCHK2) | IC$_{50}$ (ATM) [µM] |
|---|---|---|---|---|
| 132 | MS: 455 (M + H$^+$) | 1-(1,3-Dimethyl-1H-pyrazol-4-yl)-7-methoxy-3-methyl-8-(2-methyl-3H-benzo-imidazol-5-yl)-1,3-dihydro-imidazo[4,5-c]quinolin-2-one | ++ | <0.001 |
| | | 1H NMR (400 MHz, DMSO) ppm = 12.24 (d, J = 6.5 Hz, 1H), 8.85 (d, J = 2.1 Hz, 1H), 8.13 (d, J = 4.9 Hz, 1H), 7.55-7.47 (m,2H), 7.45-7.36 (m,1H), 7.26 (d, J = 2.2 Hz, 1H), 7.10 (m,1H), 3.94-3.77 (m,6H), 3.55 (s,3H), 2.49 (s,3H), 1.94 (s,3H). | | |
| 133 | MS: 436 (M + H$^+$) | 1-(3-Fluoro-5-methoxy-pyridin-2-yl)-7-methoxy-3-methyl-8-(1-methyl-1H-1,2,3-triazol-4-yl)-1,3-dihydroimidazo[4,5-c]quinolin-2-one | ++ | <0.01 |
| | | 1H NMR (400 MHz, DMSO-d6) ppm = 8.92 (s,1H), 8.43-8.34 (m,2H), 7.96 (dd, J = 11.0, 2.6 Hz, 1H), 7.73 (s,1H), 7.56 (s,1H), 4.04 (d, J = 13.4 Hz, 9H), 3.58 (s,3H) | | |
| 134 | MS: 422 (M + H$^+$) | 1-(3-Fluoro-5-methoxy-pyridin-4-yl)-7-methoxy-3-methyl-8-(3H-1,2,3-triazol-4-yl)-1,3-dihydroimidazo-[4,5-c]quinolin-2-one | ++ | <0.001 |
| | | 1H NMR (400 MHz, DMSO-d6) ppm = 15.11 (s,1H), 8.94 (s,1H), 8.70 (d, J = 16.3 Hz, 2H), 8.25 (s,1H), 7.96 (s,1H), 7.58 (s,1H), 4.03 (s,3H), 3.85 (s,3H), 3.59 (s,3H), 2.06 (s,1H). | | |

TABLE 2-continued

| Ex. | Structural formula | Name | IC$_{50}$ (pCHK2) | IC$_{50}$ (ATM) [μM] |
|---|---|---|---|---|
| 135 | MS: 432 (M + H$^+$) | 8-(1,3-Dimethyl-1H-pyrazol-4-yl)-1-(1-ethyl-3-methyl-1H-pyrazol-4-yl)-7-methoxy-3-methyl-1,3-dihydro-imidazo[4,5-c]quinolin-2-one | ++ | <0.001 |
| | | 1H NMR (400 MHz, DMSO) ppm = 8.84 (s,1H), 8.13 (s,1H), 7.82 (s,1H), 7.49 (s,1H), 7.32 (s,1H), 4.15 (q, J = 7.2 Hz, 2H), 3.92 (s,3H), 3.78 (s,3H), 3.55 (s,3H), 1.91 (d, J = 15.3 Hz, 6H), 1.40 (t, J = 7.2 Hz, 3H). | | |
| 136 | MS: 485 (M + H$^+$) | 1-(3-Fluoro-5-methoxy-pyridin-4-yl)-7-methoxy-3-methyl-8-(2-methyl-3H-benzoimidazol-5-yl)-1,3-dihydroimidazo[4,5-c]-quinolin-2-one | +++ | <0.001 |
| | | 1H NMR (400 MHz, DMSO) ppm = 12.23 (s,1H), 8.93 (s,1H), 8.65 (d, J = 1.9 Hz, 1H), 8.60 (s,1H), 7.56 (s,1H), 7.50-7.28 (m,2H), 7.07-6.94 (m,2H), 3.89 (d, J = 2.0 Hz, 6H), 3.59 (s,3H), 2.49 (s,3H). | | |
| 137 | MS: 462 (M + H$^+$) | 1-(3-Fluoro-5-methoxy-pyridin-4-yl)-7-methoxy-8-(6-methoxypyridin-3-yl)-3-methyl-1,3-dihydroimidazo-[4,5-c]quinolin-2-one | ++ | <0.01 |
| | | 1H NMR (400 MHz, DMSO) ppm = 8.95 (s,1H), 8.65 (d, J = 15.8 Hz, 2H), 8.00 (d, J = 2.4 Hz, 1H), 7.65 (dd, J = 8.6, 2.5 Hz, 1H), 7.57 (s,1H), 6.93 (s,1H), 6.83 (d, J = 8.6 Hz, 1H), 3.87 (d, J = 15.0 Hz, 9H), 3.59 (s,3H) | | |

TABLE 2-continued

| Ex. | Structural formula | Name | IC$_{50}$ (pCHK2) | IC$_{50}$ (ATM) [μM] |
|---|---|---|---|---|
| 138 | MS: 462 (M + H⁺) | 5-Fluoro-6-[7-methoxy-3-methyl-8-(1-methyl-1H-pyrazol-4-yl)-2-oxo-2,3-dihydroimidazo[4,5-c]quinolin-1-yl]-N-methyl-nicotinamid | ++ | <0.01 |

1H NMR (400 MHz, DMSO) ppm = 9.08-8.96 (m,2H), 8.93 (s,1H), 8.55 (dd, J = 9.6, 1.9 Hz, 1H), 7.94 (s,1H), 7.54 (s,1H), 7.30 (s,1H), 6.95 (s,1H), 4.01 (s,3H), 3.84 (s,3H), 3.61 (s,3H), 2.92 (d, J = 4.5 Hz, 3H)

| Ex. | Structural formula | Name | IC$_{50}$ (pCHK2) | IC$_{50}$ (ATM) [μM] |
|---|---|---|---|---|
| 139 | MS: 476 (M + H⁺) | 6-[8-(1,3-Dimethyl-1H-pyrazol-4-yl)-7-methoxy-3-methyl-2-oxo-2,3-dihydro-imidazo[4,5-c]quinolin-1-yl]-5-fluoro-N-methyl-nicotinamid | ++ | <0.001 |

1H NMR (400 MHz, DMSO) ppm = 9.02-8.93 (m,3H), 8.52 (dd, J = 9.5, 1.9 Hz, 1H), 7.80 (s,1H), 7.55 (s,1H), 6.81 (s,1H), 3.94 (s,3H), 3.76 (s,3H), 3.61 (s,3H), 2.90 (d, J = 4.5 Hz, 3H), 1.76 (s,3H)

| Ex. | Structural formula | Name | IC$_{50}$ (pCHK2) | IC$_{50}$ (ATM) [μM] |
|---|---|---|---|---|
| 140 | MS: 453 (M + H⁺) | 1-(3-Fluoro-5-methoxy-pyridin-4-yl)-8-(1-fluoro-methyl-1H-pyrazol-4-yl)-7-methoxy-3-methyl-1,3-dihydroimidazo[4,5-c]quinolin-2-one | +++ | <0.001 |

1H NMR (400 MHz, DMSO-d6) 8.91 (s,1H), 8.74 (d, J = 16.3 Hz, 2H), 8.40 (s,1H), 7.55 (s,1H), 7.40-7.35 (m,1H), 7.19 (s,1H), 6.22 (s,1H), 6.09 (s,1H), 4.00 (s,3H), 3.85 (s,3H), 3.59 (s,3H).

TABLE 2-continued

| Ex. | Structural formula | Name | IC$_{50}$ (pCHK2) | IC$_{50}$ (ATM) [μM] |
|---|---|---|---|---|
| 141 | MS: 408 (M + H⁺) | 1-(3-Fluoro-1-methyl-1H-pyrazol-4-yl)-7-methoxy-3-methyl-8-(1-methyl-1H-pyrazol-4-yl)-1,3-dihydro-imidazo[4,5-c]quinolin-2-one | ++ | <0.01 |
| | | 1H NMR (400 MHz, DMSO)ppm = 8.82 (s,1H), 8.03 (s,1H), 7.89 (d, J = 2.4 Hz, 1H), 7.60 (s,1H), 7.49 (s,1H), 7.46 (s,1H), 3.98 (s,3H), 3.91 (s,3H), 3.86 (s,3H), 3.53 (s,3H). | | |
| 142 | MS: 463 (M + H⁺) | 8-(1-Ethyl-3-methyl-1H-pyrazol-4-yl)-1-(3-fluoro-5-methoxypyridin-4-yl)-7-methoxy-3-methyl-1,3-dihydroimidazo[4,5-c]quinolin-2-one | ++ | <0.001 |
| | | 1H NMR (400 MHz, DMSO) ppm = 8.92 (s,1H), 8.71 (d, J = 11.5 Hz, 2H), 7.86 (s,1H), 7.54 (s,1H), 7.01 (s,1H), 4.07 (m,2H), 3.94 (s,3H), 3.88 (s,3H), 3.61 (s,3H), 1.78 (s,3H), 1.36 (t, J = 7.2 Hz, 3H). | | |
| 143 | MS: 471 (M + H⁺) | 8-(1-Difluoromethyl-1H-pyrazol-4-yl)-1-(3-fluoro-5-methoxypyridin-4-yl)-7-methoxy-3-methyl-1,3-dihydroimidazo[4,5-c]quinolin-2-one | ++ | <0.001 |
| | | 1H NMR (400 MHz, DMSO-d6) ppm = 8.93 (s,1H), 8.72 (d, J = 14.3 Hz, 2H), 8.47 (s,1H), 7.83 (t, J = 58.9 Hz, 1H), 7.57 (s,1H), 7.52 (s,1H), 7.21 (s,1H), 4.01 (s,3H), 3.85 (s,3H), 3.59 (s,3H). | | |

TABLE 2-continued

| Ex. | Structural formula | Name | IC$_{50}$ (pCHK2) | IC$_{50}$ (ATM) [μM] |
|---|---|---|---|---|
| 144 | MS: 485 (M + H⁺) | 1-(3-Fluoro-5-methoxy-pyridin-2-yl)-7-methoxy-3-methyl-8-(2-methyl-3H-benzoimidazol-5-yl)-1,3-dihydroimidazo[4,5-c]-quinolin-2-one | ++ | <0.001 |
| | | 1H NMR (400 MHz, DMSO-d6) ppm = 12.21 (s,1H), 8.93 (s,1H), 8.35 (d, J = 2.6 Hz, 1H), 7.95-7.81 (m,1 H), 7.55 (s,1H), 7.38 (d, J = 21.1 Hz, 2H), 7.01 (d, J = 32.5 Hz, 1H), 6.72 (s,1H), 3.93 (d,J = 27.1 Hz, 6H), 3.58 (s,3H), 2.48 (d, J = 1.9 Hz, 3H). | | |
| 145 | MS: 438 (M + H⁺) | 1-[3-Fluoro-5-(trideuterio-methoxy)-4-pyridyl]-7-methoxy-3-methyl-8-(1-methylpyrazol-4-yl)imidazo-[4,5-c]quinolin-2-one | ++ | <0.001 |
| | | 1H NMR (300 MHz, DMSO-d6) ppm = 8.89 (s,1H), 8.75 (d, J = 12.1 Hz, 2H), 7.99 (s,1H), 7.52 (s,1H), 7.20-7.11 (m,2H), 3.99 (s,3H), 3.85 (s,3H), 3.31 (s,3H). | | |
| 146 | MS: 471 (M + H⁺) | 1-(3-Difluoromethoxy-5-fluoropyridin-4-yl)-7-methoxy-3-methyl-8-(1-methyl-1H-pyrazol-4-yl)-1,3-dihydroimidazo[4,5-c]-quinolin-2-one | +++ | <0.001 |
| | | 1H NMR (400 MHz, DMSO-d6) ppm = 9.06 (s,1H), 8.93 (d, J = 3.7 Hz, 2H), 8.02 (s,1H), 7.58 (s,0H), 7.54 (s,1H), 7.42 (d, J = 1.6 Hz, 0H), 7.27-7.20 (m,1H), 7.16 (s,1H), 4.01 (s,3H), 3.86 (s,3H), 3.62 (s,3H) | | |

TABLE 2-continued

| Ex. | Structural formula | Name | IC$_{50}$ (pCHK2) | IC$_{50}$ (ATM) [µM] |
|---|---|---|---|---|
| 147 | | 1-(3-Difluoromethoxy-5-fluoropyridin-4-yl)-8-(1,3-dimethyl-1H-pyrazol-4-yl)-7-methoxy-3-methyl-1,3-dihydroimidazo[4,5-c]-quinolin-2-one | +++ | <0.001 |
| | MS: 485 (M + H⁺) | 1H NMR (400 MHz, DMSO-d6) ppm = 9.03 (s,1H), 8.96 (s,1H), 8.88 (s,1H), 7.84 (s,1H), 7.56 (d, J = 3.5 Hz, 1H), 7.39 (d, J = 1.7 Hz, 1H), 7.21 (s,0H), 7.00 (s,1H), 3.95 (s,3H), 3.78 (s,3H), 3.62 (s,3H), 1.75 (s,3H) | | |
| 148 | | 1-(3-Fluoro-5-fluoro-methoxypyridin-4-yl)-7-methoxy-3-methyl-8-(1-methyl-1H-pyrazol-4-yl)-1,3-dihydroimidazo[4,5-c]-quinolin-2-one | +++ | <0.001 |
| | MS: 453 (M + H⁺) | 1H NMR (400 MHz, DMSO-d6) ppm = 9.04-8.79 (m,3H), 8.00 (s,1H), 7.54 (s,1H), 7.18 (d, J = 21.6 Hz, 2H), 5.95 (m,2H), 4.01 (s,3H), 3.86 (s,3H), 3.61 (s,3H). | | |
| 149 | | 8-(1,3-Dimethyl-1H-pyrazol-4-yl)-1-(3-fluoro-5-fluoro-methoxypyridin-4-yl)-7-methoxy-3-methyl-1,3-dihydroimidazo[4,5-c]-quinolin-2-one | +++ | <0.001 |
| | MS: 467 (M + H⁺) | 1H NMR (400 MHz, DMSO-d6) ppm = 9.00-8.75 (m,3H), 7.83 (s,1H), 7.55 (s,1H), 6.99 (s,1H), 5.93 (m,2H), 3.94 (s,3H), 3.77 (s,3H), 3.61 (s,3H), 1.74 (s,3H) | | |

TABLE 2-continued

| Ex. | Structural formula | Name | IC$_{50}$ (pCHK2) | IC$_{50}$ (ATM) [μM] |
|---|---|---|---|---|
| 150 | MS: 452 (M + H$^+$) | 8-(1,3-Dimethylpyrazol-4-yl)-1-[3-fluoro-5-(trideuteriomethoxy)-4-pyridyl]-7-methoxy-3-methyl-imidazo-[4,5-c]quinolin-2-one | +++ | <0.001 |
| | | 1H NMR (400 MHz, DMSO-d6) ppm = 8.92 (s,1H), 8.70 (d, J = 9.5 Hz, 2H), 7.83 (s,1H), 7.54 (s,1H), 7.00 (s,1H), 3.94 (s,3H), 3.78 (s,3H), 3.60 (s,3H), 1.75 (s, 3H). | | |
| 151 | MS: 404 (M + H$^+$) | 1-(1,3-Dimethyl-1H-pyrazol-4-yl)-7-methoxy-3-methyl-8-(4-methyl-1H-pyrazol-3-yl)-1,3-dihydroimidazo[4,5-c]quinolin-2-one | +++ | <0.05 |
| 152 | MS: 486 (M + H$^+$) | 1-(3-Fluoro-5-methoxy-pyridin-4-yl)-7-methoxy-3-methyl-8-(2-methyl-1H-imidazo[4,5-b]pyridin-6-yl)-1,3-dihydroimidazo[4,5-c]-quinolin-2-one | +++ | <0.001 |
| | | 1H NMR (400 MHz, DMSO-d6) ppm = 12.87-12.50 (m,1H), 8.99 (s,1H), 8.65 (d, J = 14.3 Hz, 2H), 8.11 (d, J = 23.8 Hz, 1H), 7.78 (d, J = 12.4 Hz, 1H), 7.62 (d, J = 2.4 Hz, 1H), 7.06-6.98 (d, J = 20 Hz, 1H), 3.93 (s,3H), 3.89 (d, J = 6.8 Hz, 3H), 3.63 (s,3H), 2.55 (d, J = 14.3 Hz, 3H). | | |

TABLE 2-continued

| Ex. | Structural formula | Name | IC$_{50}$ (pCHK2) | IC$_{50}$ (ATM) [µM] |
|---|---|---|---|---|
| 153 | MS: 471 (M + H$^+$) | 8-(3H-Benzimidazol-5-yl)-1-(3-fluoro-5-methoxypyridin-2-yl)-7-methoxy-3-methyl-1,3-dihydroimidazo[4,5-c]-quinolin-2-one | ++ | <0.01 |
| | | 1H NMR (400 MHz, DMSO-d6) ppm = 12.47 (s,1H), 8.93 (s,1H), 8.36 (d, J = 2.6 Hz, 1H), 8.24 (s,1H), 7.88 (d, J = 10.9 Hz, 1H), 7.56 (s,3H), 7.19-7.00 (m,1H), 6.75 (s,1H), 3.90 (s,3H), 3.59 (s,3H), 3.31 (s,3H). | | |
| 154 | MS: 455 (M + H$^+$) | 1-(1,3-Dimethyl-1H-pyrazol-4-yl)-7-methoxy-3-methyl-8-(2-methyl-1H-imidazo[4,5-b]pyridin-6-yl)-1,3-dihydro-imidazo[4,5-c]quinolin-2-one | + | <0.001 |
| | | 1H NMR (400 MHz, DMSO-d6) ppm = 8.91 (s,1H), 8.21 (s,1H), 8.15 (s,1H), 7.87 (s,1H), 7.59 (s,1H), 7.29 (s,1H), 3.93 (s,3H), 3.87 (s,3H), 3.58 (s,3H), 2.56 (s,3H), 1.97 (s,3H). | | |
| 155 | MS: 438 (M + H$^+$) | 1-[3-Fluoro-5-(trideuterio-methoxy)-2-pyridyl]-7-methoxy-3-methyl-8-(1-methylpyrazol-4-yl) imidazo-[4,5-c]quinolin-2-one | +++ | <0.001 |
| | | 1H NMR (400 MHz,DMSO) ppm = 8.89 (s,1H), 8.47 (s,1H), 7.98 (m,2H), 7.52 (s,1H), 7.25 (s,1H), 6.88(s,1 H), 3.99 (s,3H), 3.85 (s,3H), 3.59 (s,3H) | | |

TABLE 2-continued

| Ex. | Structural formula | Name | IC$_{50}$ (pCHK2) | IC$_{50}$ (ATM) [μM] |
|---|---|---|---|---|
| 156 | MS: 415 (M + H$^+$) | 1-(3-Ethylpyridin-4-yl)-7-methoxy-3-methyl-8-(1-methyl-1H-pyrazol-4-yl)-1,3-dihydroimidazo[4,5-c]quinolin-2-one<br><br>1H NMR (400 MHz, DMSO-d6) ppm = 8.93 (s,1H), 8.89 (s,1H), 8.78 (d,1 H), 7.95 (s,1H), 7.65 (d,1H), 7.50 (s,1H), 6.97 (s,1H), 6.89 (s,1H), 3.98 (s,3H), 3.83 (s,3H), 3.59 (s,3H), 2.50 (m,2H), 0.99-0.95 (m,3H) | ++ | <0.001 |
| 157 | MS:429 (M + H$^+$) | 8-(1-Ethyl-1H-pyrazol-4-yl)-1-(3-ethylpyridin-4-yl)-7-methoxy-3-methyl-1,3-dihydroimidazo[4,5-c]quinolin-2-one<br><br>1H NMR (400 MHz, DMSO-d6) ppm = 8.88 (s,1H), 8.14-8.11 (s,2H), 8.04 (s,1H), 7.54 (s,1H), 4.19 (s,3H), 4.03-3.99 (d,6H), 3.56 (s,3H), 1.56 (s,3H) | +++ | <0.01 |
| 158 | MS: 406 (M + H$^+$) | 1-(3-Fluoropyridin-2-yl)-7-methoxy-3-methyl-8-(2-methyl-2H-1,2,3-triazol-4-yl)-1,3-dihydroimidazo-[4,5-c]quinolin-2-one<br><br>1H NMR (400 MHz, DMSO-d6) ppm = 8.96 (s,1H), 8.68 (s,1H), 8.27-8.23 (m,1 H), 8.07 (s,1H), 7.96-7.92 (m,1H), 7.57 (s,1H), 7.51 (s,1H), 4.10 (s,3H), 4.02 (s,3H), 3.59 (s,3H) | ++ | <0.5 |

TABLE 2-continued

| Ex. | Structural formula | Name | IC$_{50}$ (pCHK2) | IC$_{50}$ (ATM) [μM] |
|---|---|---|---|---|
| 159 | | 1-(3-Fluoro-1-methyl-1H-pyrazol-4-yl)-7-methoxy-8-(6-methoxypyridin-3-yl)-3-methyl-1,3-dihydroimidazo-[4,5-c]quinolin-2-one | + | <0.01 |
| | MS: 435 (M + H⁺) | 1H NMR (400 MHz, DMSO-d6) ppm = 8.90 (s,1H), 8.19 (dd, J = 2.4, 0.8 Hz, 1H), 7.89 (d, J = 2.4 Hz, 1H), 7.76 (dd, J = 8.6, 2.5 Hz, 1H), 7.56 (s,1H), 7.42 (s,1H), 6.92-6.84 (m,1H), 3.89 (d, J = 8.2 Hz, 6H), 3.82 (d, J = 1.1Hz, 3H), 3.55 (s,3H). | | |
| 200 | | 1-(3-Cyclopropylpyridin-4-yl)-7-methoxy-3-methyl-8-(1-methyl-1H-pyrazol-4-yl)-1,3-dihydroimidazo[4,5-c]quinolin-2-one | ++ | <0.05 |
| | MS: 427 (M + H⁺) | 1H NMR (400 MHz,DMSO) ppm = 8.87 (s,1 H), 8.73 (d, J = 5.1, 1H), 8.61 (s,1H), 7.95 (s,1H), 7.64 (d, J = 5.1Hz, 1H), 7.49 (s,1H), 6.98-6.92 (m,2H), 3.97 (s,3H), 3.82 (s,3H), 3.58 (s,3H), 1.59 (m,1H), 0.91 (m,1H), 0.82-0.73 (m,1H), 0.62-0.49 (m,2H). | | |
| 201 | | 1-(3-Fluoro-5-methyl-sulfonylmethoxypyridin-2-yl)-7-methoxy-3-methyl-8-(1-methyl-1H-pyrazol-4-yl)-1,3-dihydroimidazo[4,5-c]-quinolin-2-one | +++ | <0.001 |
| | MS: 514 (M + H⁺) | 1H NMR (400 MHz,DMSO) ppm = 8.91 (s,1H), 8.66 (s,1H), 8.28 (m,1H), 7.89 (s,1H), 7.53 (s,1H), 7.41 (s,1H), 6.95 (s,1H), 5.70 (s,2H), 4.02 (s,3H), 4.00 (s,3H), 3.59 (s,3H), 3.21 (s,3H) | | |

TABLE 2-continued

| Ex. | Structural formula | Name | IC$_{50}$ (pCHK2) | IC$_{50}$ (ATM) [μM] |
|---|---|---|---|---|
| 202 | MS: 445 (M + H⁺) | 1-(3-Cyclopropyl-5-fluoropyridin-4-yl)-7-methoxy-3-methyl-8-(1-methyl-1H-pyrazol-4-yl)-1,3-dihydroimidazo[4,5-c]quinolin-2-one | ++ | <0.001 |

1H NMR (400 MHz,DMSO) ppm = 8.91 (s,1H), 8.83 (s,1H), 8.50 (s,1H), 7.98 (s,1H), 7.52 (s,1H), 7.08-6.99 (m,2H), 3.98 (s,3H), 3.83 (s,3H), 3.60 (s,3H), 1.71-1.61 (m,1H), 1.04-0.95 (m,1H), 0.87 (m,1H), 0.37-0.62 (m,2H).

| Ex. | Structural formula | Name | IC$_{50}$ (pCHK2) | IC$_{50}$ (ATM) [μM] |
|---|---|---|---|---|
| 203 | MS: 528 (M + H⁺) | 8-(1,3-Dimethyl-1H-pyrazol-4-yl)-1-(3-fluoro-5-methylsulfonylmethoxypyridin-2-yl)-7-methoxy-3-methyl-1,3-dihydroimidazo[4,5-c]-quinolin-2-one | ++ | <0.001 |

1H NMR (400 MHz,DMSO) ppm = 8.92 (s,1H), 8.56 (s,1H), 8.22 (m,1H), 7.75 (s,1H), 7.53 (s,1H), 6.83 (s,1H), 5.64 (s,2H), 3.92 (s,3H), 3.76 (s,3H), 3.58 (s,3H), 3.17 (s,3H), 1.826(s,3H)

| Ex. | Structural formula | Name | IC$_{50}$ (pCHK2) | IC$_{50}$ (ATM) [μM] |
|---|---|---|---|---|
| 204 | MS: 461 (M + H⁺) | 1-(5-Allyloxy-3-fluoropyridin-2-yl)-7-methoxy-3-methyl-8-(1-methyl-1H-pyrazol-4-yl)-1,3-dihydroimidazo[4,5-c]-quinolin-2-one | ++ | <0.001 |

1H NMR (400 MHz,DMSO) ppm = 8.87 (s,1H), 8.46 (d, J = 2.6 Hz, 1H), 8.01-7.93 (m,2H), 7.50 (s,1H), 7.24 (d, J = 0.8 Hz, 1H), 6.87 (s,1H), 6.11 (ddt, J = 17.2, 10.6, 5.3 Hz, 1H), 5.51 (dq, J = 17.3, 1.6 Hz, 1H), 5.38 (dq, J = 10.5, 1.4 Hz, 1H), 4.88

TABLE 2-continued

| Ex. | Structural formula | Name | IC$_{50}$ (pCHK2) | IC$_{50}$ (ATM) [μM] |
|---|---|---|---|---|
| 205 | | 1-[5-(Azetidin-3-yloxy)-3-fluoropyridin-2-yl]-7-methoxy-3-methyl-8-(1-methyl-1H-pyrazol-4-yl)-1,3-dihydroimidazo[4,5-c]-quinolin-2-one | ++ | <0.001 |
| | MS: 476 (M + H⁺) | 1H NMR (400 MHz,DMSO) ppm = 8.87 (s,1H), 8.40 (s,1H), 7.98 (s,1H), 7.84 (m,1H), 7.50 (s,1H), 7.27 (s,1H), 6.89 (s,1H), 5.28 (m,1H), 3.98 (s,3H), 3.85 (s,2H), 3.84 (s,3H), 3.62 (s,2H), 3.57 (s,3H) | | |
| 206 | | 1-[3-Fluoro-5-(2-methyl-amino-ethoxy)-pyridin-2-yl]-7-methoxy-3-methyl-8-(1-methyl-1H-pyrazol-4-yl)-1,3-dihydroimidazo[4,5-c]quinolin-2-one | ++ | <0.01 |
| | MS: 478 (M + H⁺) | 1H NMR (400 MHz, DMSO-d6) ppm = 8.87 (s,1H), 8.44 (d, J = 2.6 Hz, 1H), 7.97 (d, J = 13.0 Hz, 2H), 7.50 (s,1 H), 7.26 (d, J = 0.8 Hz, 1H), 6.89 (s,1 H), 4.36-4.27 (m,2H), 3.97 (s,3H), 3.84 (s,3H), 3.57 (s,3H), 2.97-2.89 (m,2H), 2.37 (s,3H). | | |
| 207 | | 1-[3-Fluoro-5-(1-methyl-azetidin-3-ylmethoxy)-pyridin-2-yl]-7-methoxy-3-methyl-8-(1-methyl-1H-pyrazol-4-yl)-1,3-dihydro-imidazo[4,5-c]quinolin-2-one | ++ | <0.01 |
| | MS: 505 (M + H⁺) | 1H NMR (400 MHz, DMSO) ppm = 8.87 (s,1H), 8.45 (d, J = 2.5 Hz, 1H), 7.98 (d, J = 12.0 Hz, 2H), 7.50 (s,1H), 7.25 (s,1H), 6.86 (s,1H), 4.42-4.35 (m,2H), 3.97 (s,3H), 3.84 (s,3H), 3.57 (s,3H), 3.35 (s,2H), 3.02 (t, J = 6.20 Hz, 2H), 2.84 (m,1H), 2.22 (s,3H). | | |

TABLE 2-continued

| Ex. | Structural formula | Name | IC$_{50}$ (pCHK2) | IC$_{50}$ (ATM) [µM] |
|---|---|---|---|---|
| 208 | MS: 476 (M + H⁺) | 8-[1-(Azetidin-3-yl)-1H-pyrazol-4-yl]-1-(3-fluoro-5-methoxypyridin-4-yl)-7-methoxy-3-methyl-1H,2H,3H-imidazo[4,5-c]-quinolin-2-one<br><br>H NMR (400 MHz, DMSO-d6) ppm = 8.90 (s,1H), 8.78 (s,1H), 8.74 (s,1H), 8.11 (s,1H), 7.53 (s,1H), 7.28 (s,1H), 7.17 (s,1H), 5.21 (m,1H), 4.00 (s,3H), 3.96-3.84 (m,5H), 3.71 (t, J = 7.9 Hz, 2H), 3.59 (s,3H) | + | <0.01 |

+++: 0.2 µM or less
++: >0.2 µM to 1 µM
+: >1 µM to 2 µM

Compounds according to the invention not only have very good inhibition of ATM kinase, they are also in addition very selective towards other kinases, such as, for example, mTOR, PIK3 alpha, PI3K beta, PI3K delta and PI3K gamma, which is confirmed with reference to the experimental data shown in Table 3 below:

TABLE 3

| Ex. | IC$_{50}$ (ATM) [µM] | IC50 (PI3Kalpha) [µM] | IC50 (PI3Kbeta) [µM] | IC50 (PI3Kdelta) [µM] | IC50 (PI3Kgamma) [µM] | IC50 (mTOR) [µM] |
|---|---|---|---|---|---|---|
| 1 | <0.01 | >30 | >30 | >30 | >30 | >30 |
| 2 | <0.001 | >30 | >30 | >30 | >30 | >5 |
| 3 | <0.001 | >30 | >30 | >30 | >30 | >5 |
| 4 | <0.001 | >5 | >30 | >10 | >30 | >30 |
| 5 | <0.001 | >30 | >30 | >30 | >30 | >30 |
| 6 | <0.001 | >30 | >30 | >30 | >30 | >30 |
| 7 | <0.001 | >30 | >30 | >30 | >30 | >30 |
| 8 | <0.001 | >30 | >30 | >30 | >30 | >5 |
| 9 | <0.001 | >30 | >30 | >30 | >30 | >10 |
| 10 | <0.001 | >30 | >30 | >30 | >30 | >30 |
| 11 | <0.001 | >30 | >30 | >30 | >30 | >30 |
| 12 | <0.001 | >30 | >30 | >30 | >30 | >30 |
| 13 | <0.001 | >5 | >30 | >10 | >30 | >10 |
| 14 | <0.001 | >30 | >30 | >30 | >30 | >30 |
| 15 | <0.001 | >30 | >30 | >30 | >30 | >30 |
| 16 | <0.001 | >30 | >30 | >30 | >30 | >30 |
| 17 | <0.01 | >30 | >30 | >30 | >30 | >10 |
| 18 | <0.001 | >10 | >30 | >30 | >5 | >5 |
| 19 | <0.01 | >30 |  | >30 | >30 | >5 |
| 20 | <0.001 | >30 | >30 | >30 | >30 | >30 |
| 21 | <0.001 | >20 | >30 | >30 | >300 | >5 |
| 22 | <0.001 | >30 |  | >30 | >30 | >30 |
| 23 | <0.01 | >20 | >30 | >30 | >30 | >20 |
| 24 | <0.001 | >30 | >30 | >30 | >30 | >30 |
| 25 | <0.001 | >30 | >30 | >30 | >30 | >30 |
| 26 | <0.001 | >30 |  | >30 | >30 | >30 |
| 27 | <0.001 | >30 | >30 | >30 | >30 | >30 |
| 28 | <0.01 | >30 | >30 | >30 | >30 | >30 |
| 29 | <0.01 | >30 | >30 | >30 | >30 | >30 |
| 30 | <0.01 | >30 | >30 | >30 | >30 | >30 |

TABLE 3-continued

| Ex. | IC$_{50}$ (ATM) [μM] | IC50 (PI3Kalpha) [μM] | IC50 (PI3Kbeta) [μM] | IC50 (PI3Kdelta) [μM] | IC50 (PI3Kgamma) [μM] | IC50 (mTOR) [μM] |
|---|---|---|---|---|---|---|
| 31 | <0.01 | >30 | >30 | >30 | >30 | >30 |
| 32 | <0.01 | >30 |  | >30 | >30 | >10 |
| 33 | <0.001 | >30 | >30 | >30 | >30 | >30 |
| 34 | <0.01 | >30 | >30 | >30 | >30 | >30 |
| 35 | <0.01 | >30 | >30 | >30 | >30 | >30 |
| 36 | <0.001 | >30 | >30 | >30 | >30 | >30 |
| 37 | <0.01 | >30 | >30 | >30 | >30 | >10 |
| 38 | <0.001 | >30 | >30 | >30 | >30 | >30 |
| 39 | <0.001 | >30 |  | >30 | >30 | >30 |
| 40 | <0.01 | >30 | >30 | >30 | >30 | >30 |
| 41 | <0.01 | >30 | >30 | >30 | >30 | >10 |
| 43 | <0.001 | >30 | >30 | >30 | >30 | >30 |
| 44 | <0.01 | >30 | >30 | >30 | >30 | >30 |
| 45 | <0.05 | >30 | >30 | >30 | >30 | >30 |
| 46 | <0.05 | >30 | >30 | >30 | >30 | >30 |
| 47 | <0.01 | >30 | >30 | >30 | >30 | >30 |
| 49 | <0.01 | >30 | >30 | >30 | >30 | >30 |
| 51 | <0.01 | >30 | >30 | >30 | >30 | >30 |
| 53 | <0.01 | >30 | >30 | >30 | >30 | >30 |
| 54 | <0.01 | >30 |  | >30 | >30 | >30 |
| 55 | <0.01 | >30 | >30 | >30 | >30 | >30 |
| 57 | <0.05 | >30 | >30 | >30 | >30 | >30 |
| 58 | <0.01 | >30 | >30 | >30 | >30 | >30 |
| 59 | <0.01 | >30 | >30 | >30 | >30 | >30 |
| 60 | <0.01 | >30 | >30 | >30 | >30 | >30 |
| 61 | <0.01 | >30 |  | >30 |  | >30 |
| 62 | <0.01 | >30 | >30 | >30 | >30 | >30 |

For the other compound examples, the following advantageous values have already been determined:

With respect to mTOR, the following compound examples have an IC50 (ATM) which is at least 2000 times higher (compared with IC50 (mTOR)), where the ratio IC50 (ATM):IC50 (mTOR) even exceeds 100,000 in the case of some compound examples: 114, 118, 120, 121, 122, 125, 126, 136, 138, 140, 141, 145, 147, 149, 157, 159, 201.

With respect to PI3Kalpha, the following compound examples have an IC50 (ATM) which is at least 2000 times higher: 66, 67, 105, 108, 110, 114, 117, 120, 122, 123, 125, 126, 155, 201, 205.

With respect to PI3Kbeta, the following compound examples have an IC50 (ATM) which is at least 2000 times higher (compared with 1050 (PI3Kbeta)), where the ratio 1050 (ATM):IC50 (PI3Kbeta) exceeds 10,000 in the case of some compound examples: 108, 118, 125, 136, 137, 140, 145, 149, 159, 201.

With respect to PI3Kdelta, the following compound examples have an 1050 (ATM) which is at least 2000 times higher: 66, 67, 105, 108, 110, 114, 117, 120, 122, 123, 125, 126, 145, 155, 201, 205.

With respect to PI3Kgamma, the following compound examples have an 1050 (ATM) which is at least 2000 times higher: 66, 67, 105, 108, 110, 114, 117, 120, 122, 123, 125, 126, 136, 145, 149, 155, 201, 205.

Example 15

Further compounds which can be prepared correspondingly or analogously to EXAMPLES 1 to 12 are shown in Table 4 below.

TABLE 4

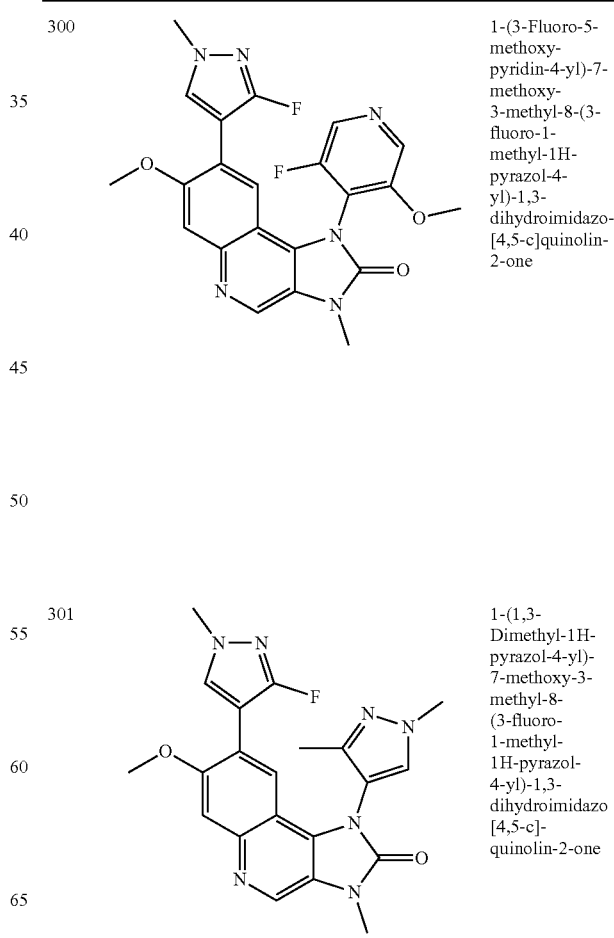

300 — 1-(3-Fluoro-5-methoxy-pyridin-4-yl)-7-methoxy-3-methyl-8-(3-fluoro-1-methyl-1H-pyrazol-4-yl)-1,3-dihydroimidazo-[4,5-c]quinolin-2-one 301 — 1-(1,3-Dimethyl-1H-pyrazol-4-yl)-7-methoxy-3-methyl-8-(3-fluoro-1-methyl-1H-pyrazol-4-yl)-1,3-dihydroimidazo[4,5-c]-quinolin-2-one

TABLE 4-continued

| | | |
|---|---|---|
| 302 | 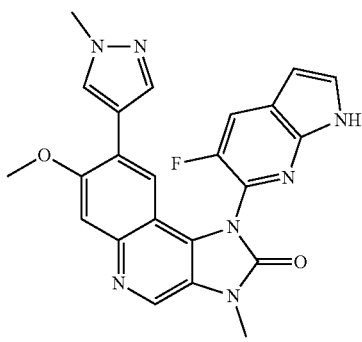 [SMILES: COc1cc2ncc3c(c2cc1-c1cnn(C)c1)n(-c1nc2[nH]ccc2cc1F)c(=O)n3C] | 1-(5-Fluoro-1H-pyrrolo[2,3-b]pyridin-6-yl)-7-methoxy-3-methyl-8-(1-methyl-1H-pyrazol-4-yl)-1,3-dihydroimidazo[4,5-c]quinolin-2-one |
| 303 | 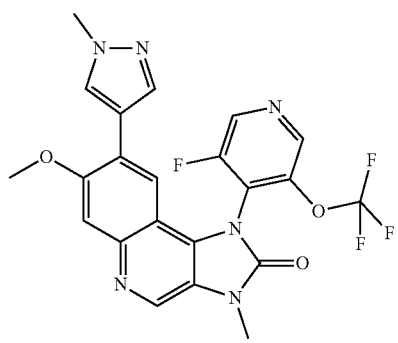 [SMILES: COc1cc2ncc3c(c2cc1-c1cnn(C)c1)n(-c1c(F)cncc1OC(F)(F)F)c(=O)n3C] | 1-[3-Fluoro-5-(trifluoromethoxy)-4-pyridyl]-7-methoxy-3-methyl-8-(1-methyl-1H-pyrazol-4-yl)-1,3-dihydroimidazo[4,5-c]quinolin-2-one |
| 304 | 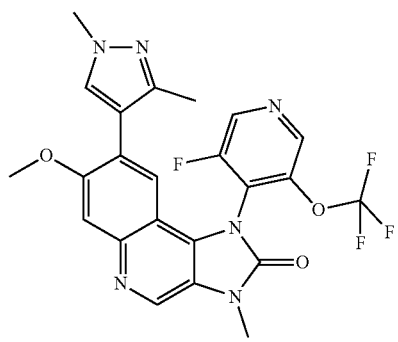 [SMILES: COc1cc2ncc3c(c2cc1-c1cn(C)nc1C)n(-c1c(F)cncc1OC(F)(F)F)c(=O)n3C] | 1-[3-Fluoro-5-(trifluoromethoxy)-4-pyridyl]-7-methoxy-3-methyl-8-(1,3-dimethylpyrazol-4-yl)-1,3-dihydroimidazol[4,5-c]quinolin-2-one |
| 400 | | 1-(3-Fluoro-5-methylsulfonyl-pyridin-2-yl)-7-methoxy-3-methyl-8-(1-methyl-1H-pyrazol-4-yl)-1H,2H,3H-imidazo[4,5-c]quinolin-2-one |
| 401 | 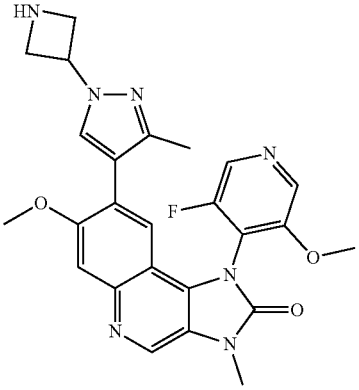 | 8-[1(Azetidin-3-yl)-3-methyl-1H-pyrazol-4-yl]-1-(3-fluoro-5-methoxypyridin-4-yl)-7-methoxy-3-methyl-1H,2H,3H-imidazo[4,5-c]quinolin-2-one |

Example 16

Pharmaceutical Compositions

Example A: Injection Vials

A solution of 100 g of active compound according to the invention and 5 g of disodium hydrogenphosphate in 3 l of bidistilled water is adjusted to pH 6.8 using 2 N hydrochloric acid, sterile-filtered, transferred into injection vials, lyophilised under sterile conditions and sealed under sterile conditions. Each injection vial contains 5 mg of active compound according to the invention.

Example B: Suppositories

A mixture of 20 g of active compound according to the invention with 100 g of soya lecithin and 1400 g of cocoa butter is melted, poured into moulds and allowed to cool. Each suppository contains 20 mg of active compound according to the invention.

Example C: Solution

A solution is prepared from 1 g of active compound according to the invention, 9.38 g of $NaH_2PO_4*2\ H_2O$, 28.48 g of $Na_2HPO_4*12\ H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

Example D: Ointment 500 mg of active compound according to the invention are mixed with 99.5 g of Vaseline under aseptic conditions.

Example E: Tablets

A mixture of 1 kg of active compound according to the invention, 4 kg of lactose, 1.2 kg of potato starch, 0.2 kg of talc and 0.1 kg of magnesium stearate is pressed in a conventional manner to give tablets in such a way that each tablet contains 10 mg of active compound according to the invention.

Example F: Dragees

Tablets are pressed analogously to Example E and then coated in a conventional manner with a coating of sucrose, potato starch, talc, tragacanth and dye.

Example G: Capsules 2 kg of active compound according to the invention are introduced into hard gelatine capsules in a conventional manner in such a way that each capsule contains 20 mg of active compound according to the invention.

Example H: Ampoules

A solution of 1 kg of active compound according to the invention in 60 l of bidistilled water is sterile-filtered, transferred into ampoules, lyophilised under sterile conditions and sealed under sterile conditions. Each ampoule contains 10 mg of active compound according to the invention.

Example I: Inhalation Spray 14 g of active compound according to the invention are dissolved in 10 l of isotonic NaCl solution, and the solution is transferred into standard commercial spray vessels with pump mechanism. The solution can be sprayed into the mouth or nose. One spray shot (approx. 0.1 ml) corresponds to a dose of approx. 0.14 mg.

The invention claimed is:
1. A compound, which is one of the following compounds:

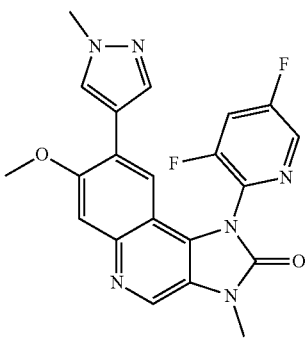 [SMILES: COc1cc2ncc3c(c2cc1-c1cnn(C)c1)n(-c1ncc(F)cc1F)c(=O)n3C]

1-(3,5-Difluoropyridin-2-yl)-7-methoxy-3-methyl-8-(1-methyl-1H-pyrazol-4-yl)-1,3-dihydroimidazo[4,5-c]quinolin-2-one

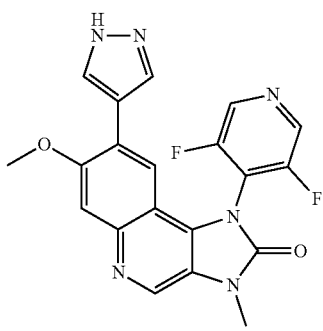

1-(3,5-Difluoropyridin-4-yl)-7-methoxy-3-methyl-8-(1H-pyrazol-4-yl)-1,3-dihydroimidazo[4,5-c]quinolin-2-one

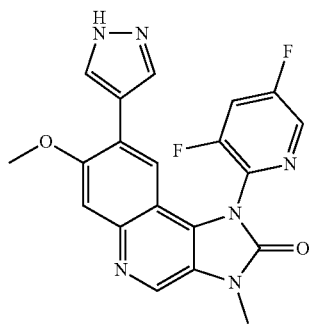

1-(3,5-Difluoropyridin-2-yl)-7-methoxy-3-methyl-8-(1H-pyrazol-4-yl)-1,3-dihydroimidazo[4,5-c]quinolin-2-one

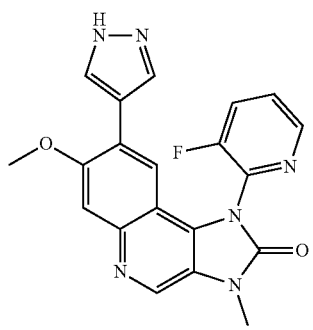
1-(3-Fluoropyridin-2-yl)-7-methoxy-3-methyl-8-(1H-pyrazol-4-yl)-1,3-dihydroimidazo[4,5-c]quinolin-2-one
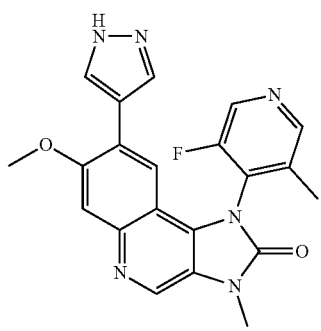
1-(3-Fluoro-5-methylpyridin-4-yl)-7-methoxy-3-methyl-8-(1H-pyrazol-4-yl)-1,3-dihydroimidazo[4,5-c]quinolin-2-one
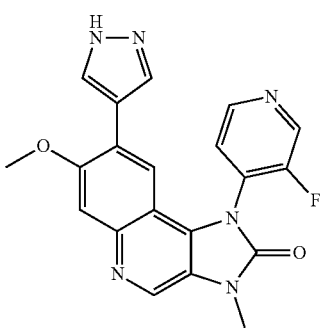
1-(3-Fluoropyridin-4-yl)-7-methoxy-3-methyl-8-(1H-pyrazol-4-yl)-1,3-dihydroimidazo[4,5-c]quinolin-2-one
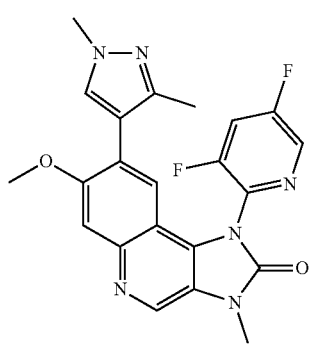 [SMILES: COc1cc2ncc3c(c2cc1-c1cn(C)nc1C)n(-c1ncc(F)cc1F)c(=O)n3C]
1-(3,5-Difluoropyridin-2-yl)-8-(1,3-dimethyl-1H-pyrazol-4-yl)-7-methoxy-3-methyl-1,3-dihydroimidazo[4,5-c]quinolin-2-one

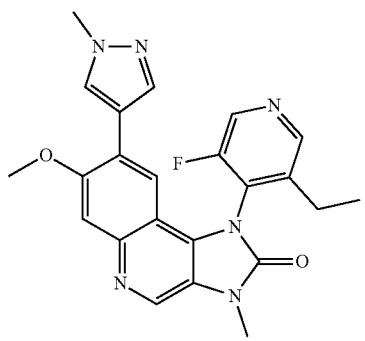 [SMILES: CCc1cncc(F)c1-n1c(=O)n(C)c2cnc3cc(OC)c(-c4cnn(C)c4)cc3c21]
1-(3-Ethyl-5-fluoropyridin-4-yl)-7-methoxy-3-methyl-8-(1-methyl-1H-pyrazol-4-yl)-1,3-dihydroimidazo[4,5-c]quinolin-2-one
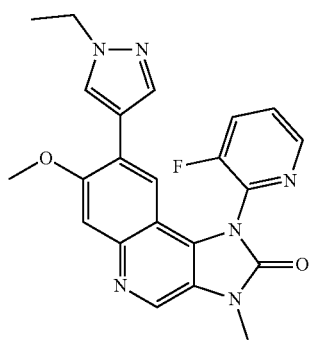 [SMILES: CCn1cc(-c2cc3c(cc2OC)ncc2c3n(-c3ncccc3F)c(=O)n2C)cn1]
1-(3-Fluoropyridin-2-yl)-7-methoxy-3-methyl-8-(1-methyl-1H-pyrazol-4-yl)-1,3-dihydroimidazo[4,5-c]quinolin-2-one
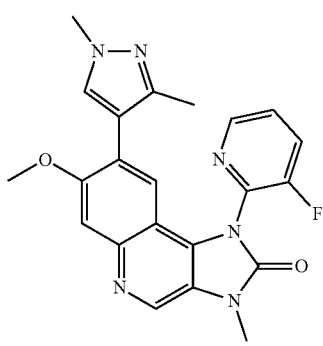 [SMILES: COc1cc2ncc3c(c2cc1-c1cn(C)nc1C)n(-c1ncccc1F)c(=O)n3C]
8-(1,3-Dimethyl-1H-pyrazol-4-yl)-1-(3-fluoropyridin-2-yl)-7-methoxy-3-methyl-1,3-dihydroimidazo[4,5-c]quinolin-2-one
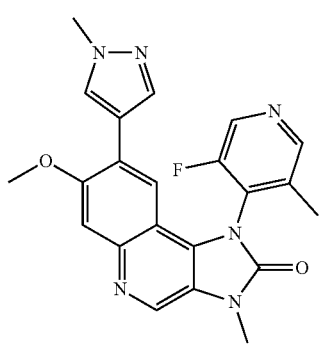
1-(3-Fluoro-5-methylpyridin-4-yl)-7-methoxy-3-methyl-8-(1-methyl-1H-pyrazol-4-yl)-1,3-dihydroimidazo[4,5-c]quinolin-2-one

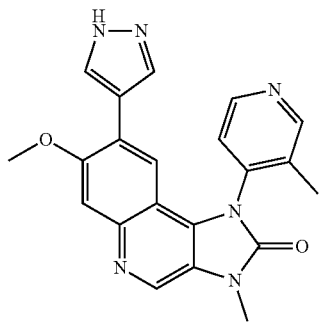
7-Methoxy-3-methyl-1-(3-methylpyridin-4-yl)-8-(1H-pyrazol-4-yl)-1,3-dihydroimidazo[4,5-c]quinolin-2-one
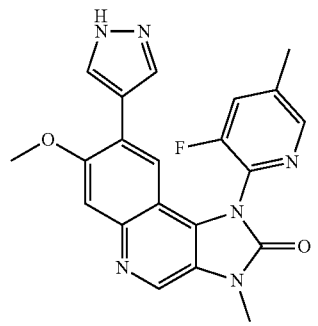
1-(3-Fluoro-5-methylpyridin-2-yl)-7-methoxy-3-methyl-8-(1H-pyrazol-4-yl)-1,3-dihydroimidazo[4,5-c]quinolin-2-one
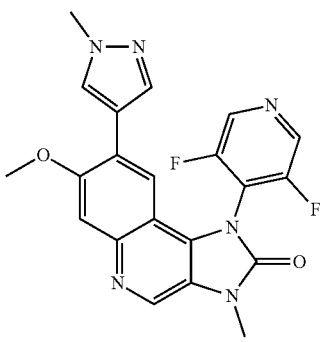
1-(3,5-Difluoropyridin-4-yl)-7-methoxy-3-methyl-8-(1-methyl-1H-pyrazol-4-yl)-1,3-dihydroimidazo[4,5-c]quinolin-2-one
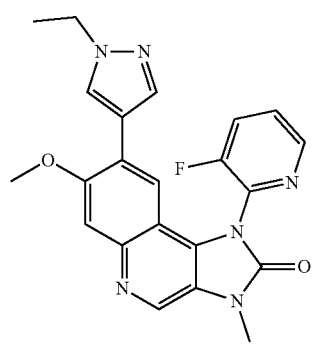 [SMILES: CCn1cc(-c2cc3c(cc2OC)ncc2c3n(-c3ncccc3F)c(=O)n2C)cn1]
8-(1-Ethyl-1H-pyrazol-4-yl)-1-(3-fluoropyridin-2-yl)-7-methoxy-3-methyl-1,3-dihydroimidazo[4,5-c]quinolin-2-one

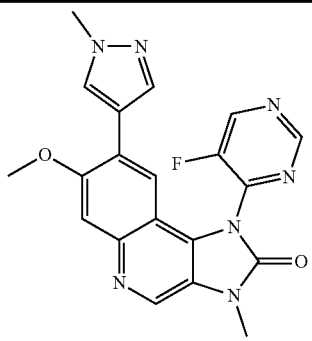
1-(3-Ethyl-5-fluoropyridin-4-yl)-8-(1-ethyl-1H-pyrazol-4-yl)-7-methoxy-3-methyl-1,3-dihydroimidazo[4,5-c]quinolin-2-one
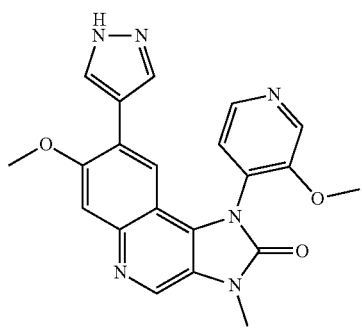
1-(3,5-Difluoropyridin-4-yl)-8-(1-ethyl-1H-pyrazol-4-yl)-7-methoxy-3-methyl-1,3-dihydroimidazo[4,5-c]quinolin-2-one
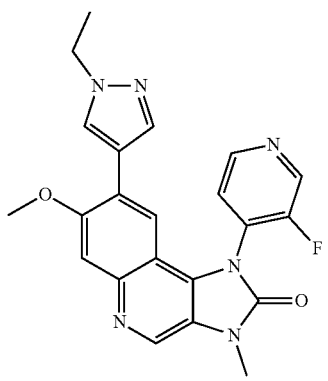 [SMILES: CCn1cc(-c2cc3c(cc2OC)ncc2c3n(-c3ccncc3F)c(=O)n2C)cn1]
1-(3-Fluoro-5-methylpyridin-2-yl)-7-methoxy-3-methyl-8-(1-methyl-1H-pyrazol-4-yl)-1,3-dihydroimidazo[4,5-c]quinolin-2-one
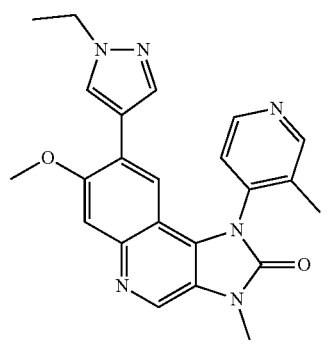
7-Methoxy-1-(3-methoxypyridin-4-yl)-3-methyl-8-(1-methyl-1H-pyrazol-4-yl)-1,3-dihydroimidazo[4,5-c]quinolin-2-one

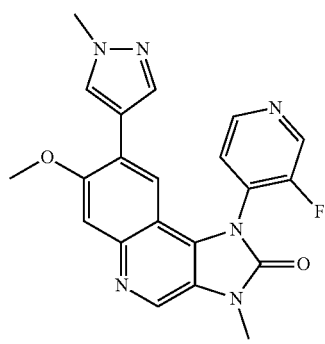 [SMILES: COc1cc2ncc3c(c2cc1-c1cnn(C)c1)n(-c1ccncc1F)c(=O)n3C]
1-(3-Fluoropyridin-2-yl)-7-methoxy-3-methyl-8-(5-methyl-1H-pyrazol-3-yl)-1,3-dihydroimidazo[4,5-c]quinolin-2-one
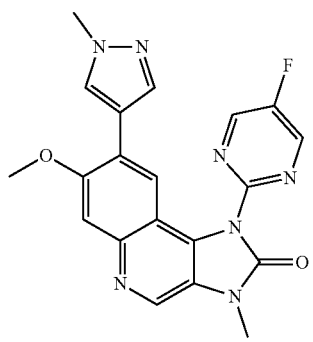 [SMILES: COc1cc2ncc3c(c2cc1-c1cnn(C)c1)n(-c1ncc(F)cn1)c(=O)n3C]
1-(5-Fluoropyrimidin-4-yl)-7-methoxy-3-methyl-8-(1-methyl-1H-pyrazol-4-yl)-1H,2H,3H-imidazo[4,5-c]quinolin-2-one
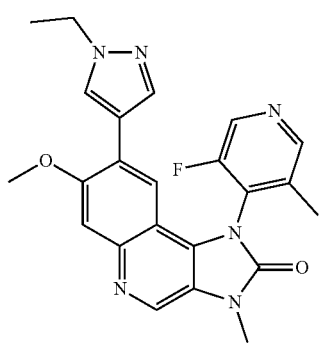
8-(1-Ethyl-1H-pyrazol-4-yl)-1-(3-fluoro-5-methylpyridin-4-yl)-7-methoxy-3-methyl-1,3-dihydroimidazo[4,5-c]quinolin-2-one
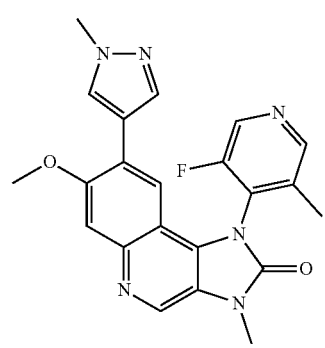
8-(1,3-Dimethyl-1H-pyrazol-4-yl)-1-(3-fluoro-5-methylpyridin-4-yl)-7-methoxy-3-methyl-1,3-dihydroimidazo[4,5-c]quinolin-2-one

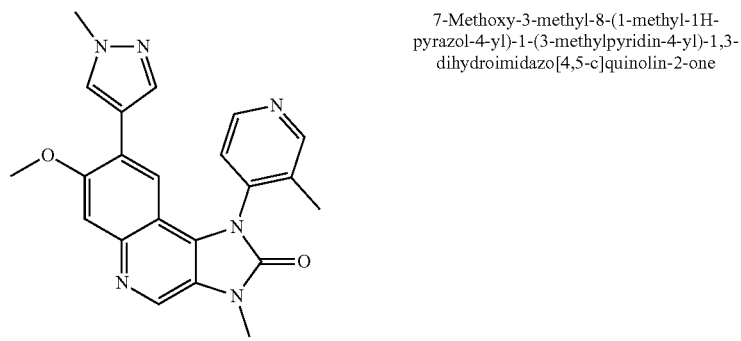
7-Methoxy-3-methyl-8-(1-methyl-1H-pyrazol-4-yl)-1-(3-methylpyridin-4-yl)-1,3-dihydroimidazo[4,5-c]quinolin-2-one
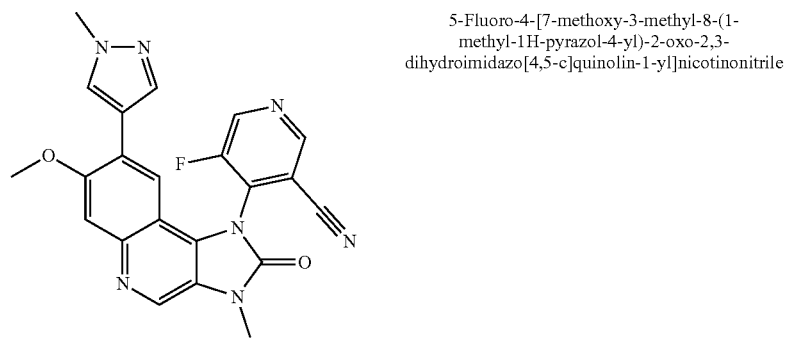
5-Fluoro-4-[7-methoxy-3-methyl-8-(1-methyl-1H-pyrazol-4-yl)-2-oxo-2,3-dihydroimidazo[4,5-c]quinolin-1-yl]nicotinonitrile
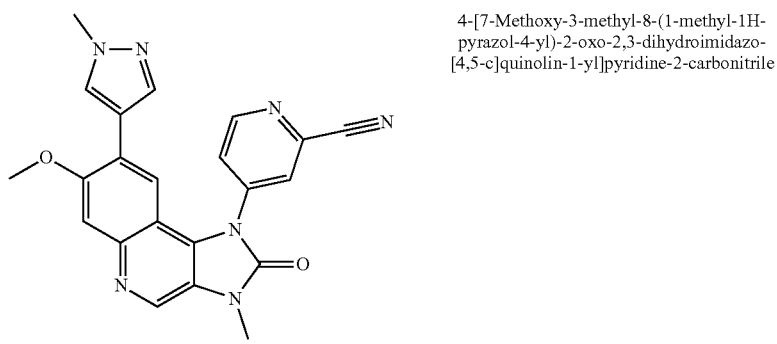
4-[7-Methoxy-3-methyl-8-(1-methyl-1H-pyrazol-4-yl)-2-oxo-2,3-dihydroimidazo-[4,5-c]quinolin-1-yl]pyridine-2-carbonitrile
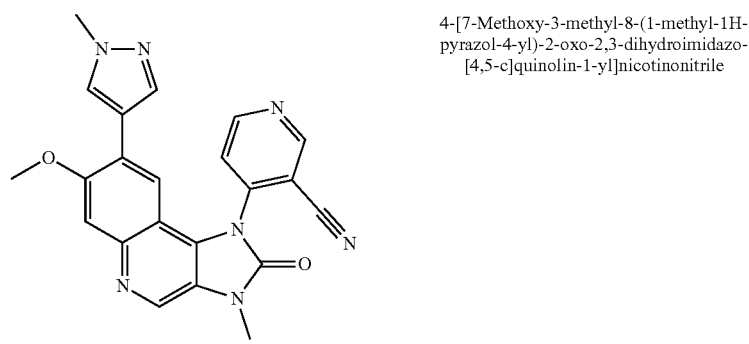
4-[7-Methoxy-3-methyl-8-(1-methyl-1H-pyrazol-4-yl)-2-oxo-2,3-dihydroimidazo-[4,5-c]quinolin-1-yl]nicotinonitrile

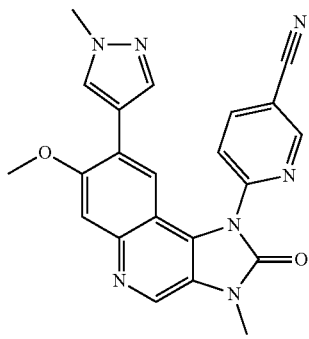 [SMILES: COc1cc2ncc3c(c2cc1-c1cnn(C)c1)n(-c1ccc(C#N)cn1)c(=O)n3C]
6-[7-Methoxy-3-methyl-8-(1-methyl-1H-pyrazol-4-yl)-2-oxo-2,3-dihydroimidazo-[4,5-c]quinolin-1-yl]nicotinonitrile
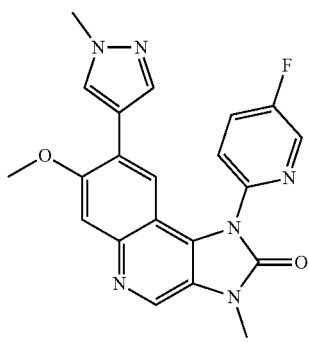 [SMILES: COc1cc2ncc3c(c2cc1-c1cnn(C)c1)n(-c1ccc(F)cn1)c(=O)n3C]
1-(5-Fluoropyridin-2-yl)-7-methoxy-3-methyl-8-(1-methyl-1H-pyrazol-4-yl)-1,3-dihydroimidazo[4,5-c]quinolin-2-one
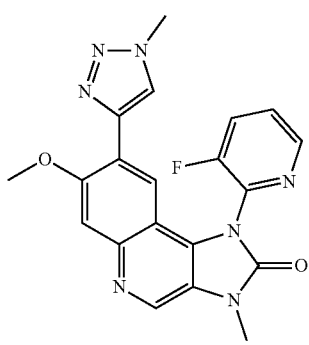 [SMILES: COc1cc2ncc3c(c2cc1-c1cn(C)nn1)n(-c1ncccc1F)c(=O)n3C]
1-(3-Fluoropyridin-2-yl)-7-methoxy-3-methyl-8-(1-methyl-1H-1,2,3-triazol-4-yl)-1,3-dihydroimidazo[4,5-c]quinolin-2-one
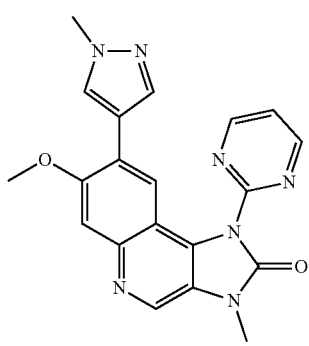 [SMILES: COc1cc2ncc3c(c2cc1-c1cnn(C)c1)n(-c1ncccn1)c(=O)n3C]
7-Methoxy-3-methyl-8-(1-methyl-1H-pyrazol-4-yl)-1-pyrimidin-2-yl-1,3-dihydroimidazo[4,5-c]quinolin-2-one

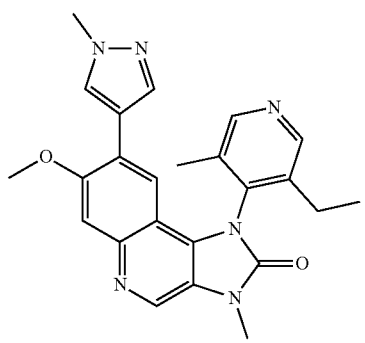 [SMILES: CCc1cncc(C)c1-n1c(=O)n(C)c2cnc3cc(OC)c(-c4cnn(C)c4)cc3c21]
1-(3-Ethyl-5-methylpyridin-4-yl)-7-methoxy-3-methyl-8-(1-methyl-1H-pyrazol-4-yl)-1,3-dihydroimidazo[4,5-c]quinolin-2-one
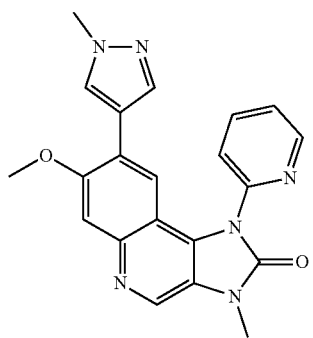 [SMILES: COc1cc2ncc3c(c2cc1-c1cnn(C)c1)n(-c1ccccn1)c(=O)n3C]
7-Methoxy-3-methyl-8-(1-methyl-1H-pyrazol-4-yl)-1-pyridin-2-yl-1,3-dihydroimidazo[4,5-c]quinolin-2-one
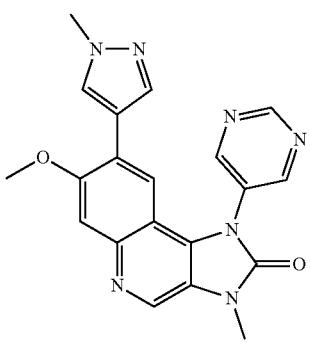 [SMILES: COc1cc2ncc3c(c2cc1-c1cnn(C)c1)n(-c1cncnc1)c(=O)n3C]
7-Methoxy-3-methyl-8-(1-methyl-1H-pyrazol-4-yl)-1-pyrimidin-5-yl-1,3-dihydroimidazo[4,5-c]quinolin-2-one
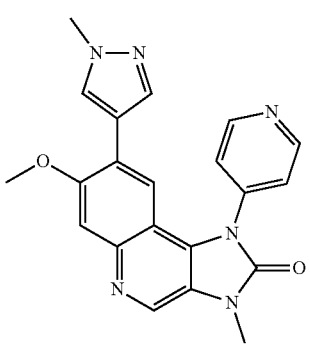 [SMILES: COc1cc2ncc3c(c2cc1-c1cnn(C)c1)n(-c1ccncc1)c(=O)n3C]
7-Methoxy-3-methyl-8-(1-methyl-1H-pyrazol-4-yl)-1-pyridin-4-yl-1,3-dihydroimidazo[4,5-c]quinolin-2-one

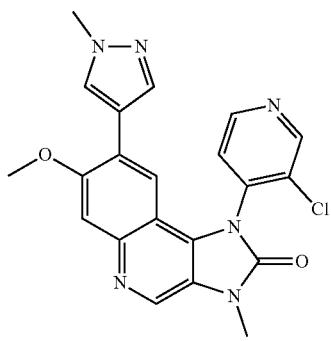 [SMILES: COc1cc2ncc3c(c2cc1-c1cnn(C)c1)n(-c1ccncc1Cl)c(=O)n3C]
1-(3-Chloropyridin-4-yl)-7-methoxy-3-methyl-8-(1-methyl-1H-pyrazol-4-yl)-1,3-dihydroimidazo[4,5-c]quinolin-2-one
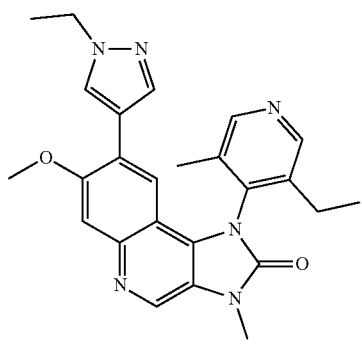 [SMILES: CCc1cncc(C)c1-n1c(=O)n(C)c2cnc3cc(OC)c(-c4cnn(CC)c4)cc3c21]
1-(3-Ethyl-5-methylpyridin-4-yl)-8-(1-ethyl-1H-pyrazol-4-yl)-7-methoxy-3-methyl-1,3-dihydroimidazo[4,5-c]quinolin-2-one
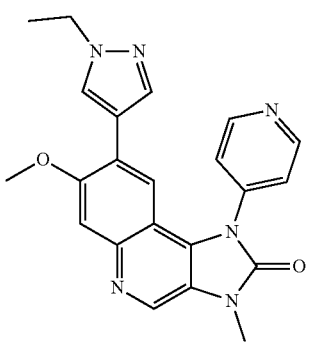 [SMILES: CCn1cc(-c2cc3c(cc2OC)ncc2c3n(-c3ccncc3)c(=O)n2C)cn1]
8-(1-Ethyl-1H-pyrazol-4-yl)-7-methoxy-3-methyl-1-pyridin-4-yl-1,3-dihydroimidazo[4,5-c]quinolin-2-one
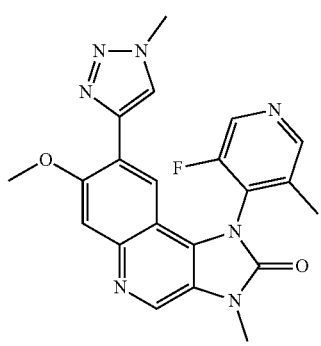
1-(3-Fluoro-5-methylpyridin-4-yl)-7-methoxy-3-methyl-8-(1-methyl-1H-1,2,3-triazol-4-yl)-1,3-dihydroimidazo[4,5-c]-quinolin-2-one -continued
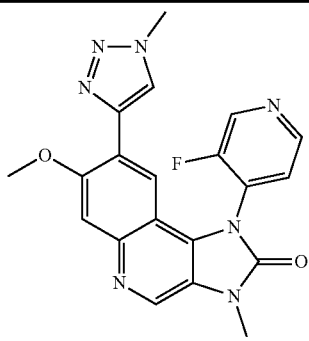
1-(3-Fluoropyridin-4-yl)-7-methoxy-3-methyl-8-(1-methyl-1H-1,2,3-triazol-4-yl)-1,3-dihydroimidazo[4,5-c]quinolin-2-one
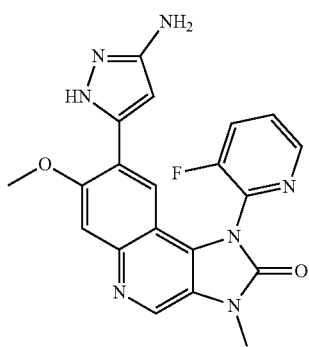 [SMILES: COc1cc2ncc3c(c2cc1-c1cc(N)n[nH]1)n(-c1ncccc1F)c(=O)n3C]
8-(3-Amino-1H-pyrazol-5-yl)-1-(3-fluoro-2-pyridyl)-7-methoxy-3-methylimidazo[4,5-c]-quinolin-2-one
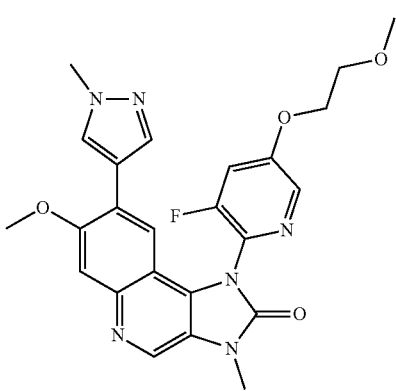
1-[3-Fluoro-5-(2-methoxyethoxy)-2-pyridyl]-7-methoxy-3-methyl-8-(1-methylpyrazol-4-yl)imidazo[4,5-c]quinolin-2-one
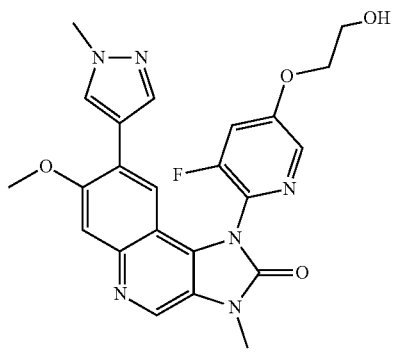 [SMILES: COc1cc2ncc3c(c2cc1-c1cnn(C)c1)n(-c1ncc(OCCO)cc1F)c(=O)n3C]
1-[3-Fluoro-5-(2-hydroxyethoxy)-2-pyridyl]-7-methoxy-3-methyl-8-(1-methylpyrazol-4-yl)imidazo[4,5-c]quinolin-2-one

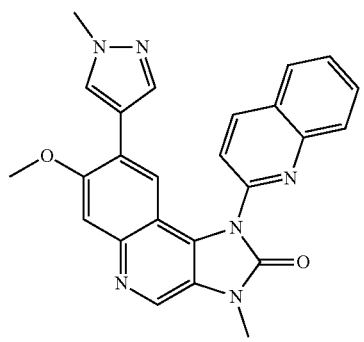 [SMILES: COc1cc2ncc3c(c2cc1-c1cnn(C)c1)n(-c1ccc2ccccc2n1)c(=O)n3C]
7-Methoxy-3-methyl-8-(1-methyl-1H-pyrazol-4-yl)-1-quinolin-2-yl-1,3-dihydroimidazo[4,5-c]quinolin-2-one
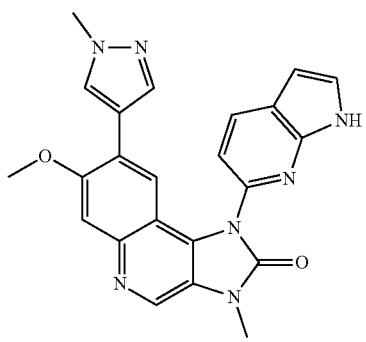 [SMILES: COc1cc2ncc3c(c2cc1-c1cnn(C)c1)n(-c1ccc2cc[nH]c2n1)c(=O)n3C]
7-Methoxy-3-methyl-8-(1-methyl-1H-pyrazol-4-yl)-1-(1H-pyrrolo[2,3-b]pyridin-6-yl)1,3-dihydroimidazo[4,5-c]quinolin-2-one
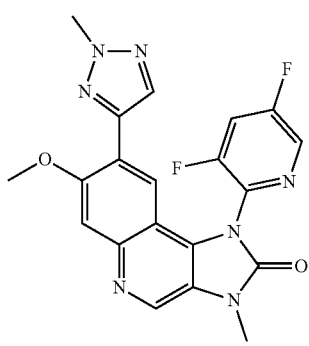 [SMILES: COc1cc2ncc3c(c2cc1-c1cnn(C)n1)n(-c1ncc(F)cc1F)c(=O)n3C]
1-(3,5-Difluoropyridin-2-yl)-7-methoxy-3-methyl-8-(2-methyl-2H-1,2,3-triazol-4-yl)-1,3-dihydroimidazo[4,5-c]quinolin-2-one
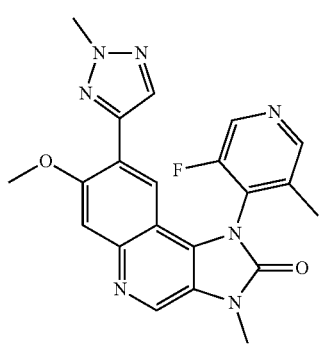
1-(3-Fluoro-5-methylpyridin-4-yl)-7-methoxy-3-methyl-8-(2-methyl-2H-1,2,3-triazol-4-yl)-1,3-dihydroimidazo[4,5-c]quinolin-2-one

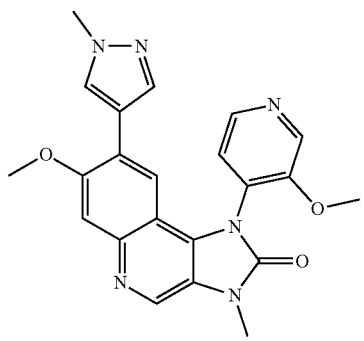
8-(1-Ethyl-1H-pyrazol-4-yl)-7-methoxy-1-(3-methoxypyridin-4-yl)-3-methyl-1,3-dihydroimidazo[4,5-c] quinolin-2-one
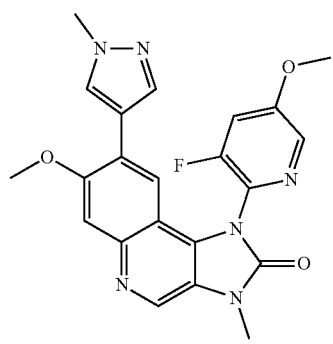
1-(3-Fluoro-5-methoxypyridin-2-yl)-7-methoxy-3-methyl-8-(1-methyl-1H-pyrazol-4-yl)-1,3-dihydroimidazo[4,5-c]quinolin-2-one
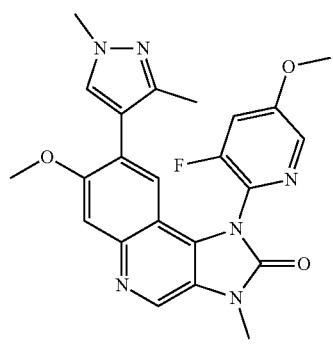
8-(1,3-Dimethyl-1H-pyrazol-4-yl)-1-(3-fluoro-5-methoxypyridin-2-yl)-7-methoxy-3-methyl-1,3-dihydroimidazo[4,5-c]-quinolin-2-one
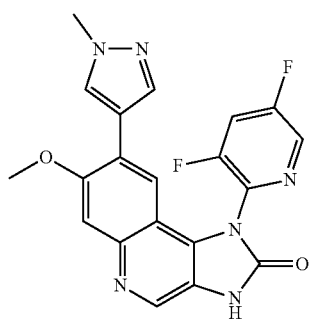 [SMILES: COc1cc2ncc3[nH]c(=O)n(-c4ncc(F)cc4F)c3c2cc1-c1cnn(C)c1]
1-(3,5-Difluoropyridin-2-yl)-7-methoxy-8-(1-methyl-1H-pyrazol-4-yl)-1,3-dihydroimidazo[4,5-c]quinolin-2-one

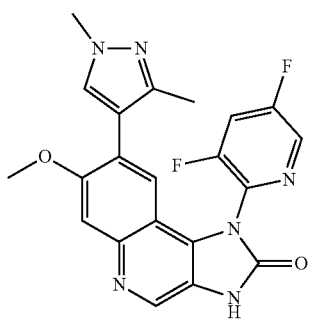 [SMILES: COc1cc2ncc3[nH]c(=O)n(-c4ncc(F)cc4F)c3c2cc1-c1cn(C)nc1C]
1-(3,5-Difluoropyridin-2-yl)-8-(1,3-dimethyl-1H-pyrazol-4-yl)-7-methoxy-1,3-dihydroimidazo[4,5-c]quinolin-2-one
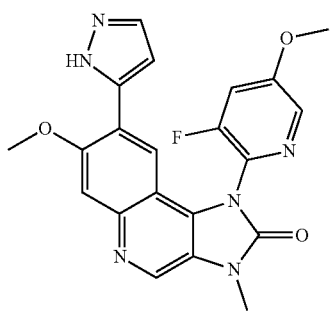
1-(3-Fluoro-5-methoxypyridin-2-yl)-7-methoxy-3-methyl-8-(2H-pyrazol-3-yl)-1,3-dihydroimidazo[4,5-c]quinolin-2-one
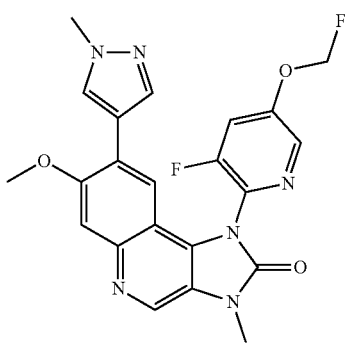 [SMILES: COc1cc2ncc3c(c2cc1-c1cnn(C)c1)n(-c1ncc(OCF)cc1F)c(=O)n3C]
1-(3-Fluoro-5-fluoromethoxypyridin-2-yl)-7-methoxy-3-methyl-8-(1-methyl-1H-pyrazol-4-yl)-1,3-dihydroimidazo[4,5-c]quinolin-2-one
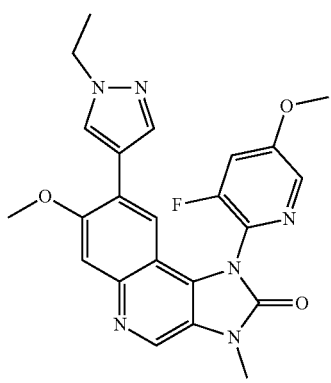
8-(1-Ethyl-1H-pyrazol-4-yl)-1-(3-fluoro-5-methoxypyridin-2-yl)-7-methoxy-3-methyl-1,3-dihydroimidazo[4,5-c]quinolin-2-one

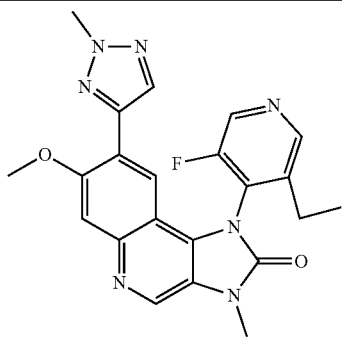

1-(3-Ethyl-5-fluoropyridin-4-yl)-7-methoxy-3-methyl-8-(2-methyl-2H-1,2,3-triazol-4-yl)-1,3-dihydroimidazo[4,5-c]quinolin-2-one

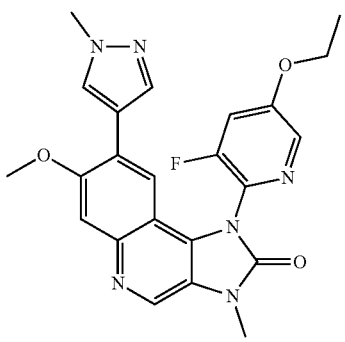 [SMILES: CCOc1cnc(-n2c(=O)n(C)c3cnc4cc(OC)c(-c5cnn(C)c5)cc4c32)c(F)c1]

1-(5-Ethoxy-3-fluoropyridin-2-yl)-7-methoxy-3-methyl-8-(1-methyl-1H-pyrazol-4-yl)-1,3-dihydroimidazo[4,5-c]quinolin-2-one

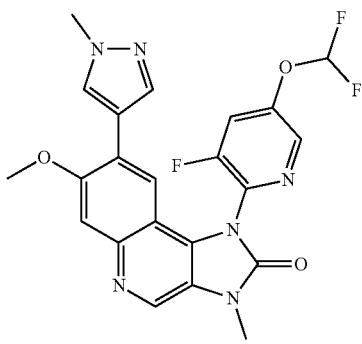 [SMILES: COc1cc2ncc3c(c2cc1-c1cnn(C)c1)n(-c1ncc(OC(F)F)cc1F)c(=O)n3C]

1-(5-Difluoromethoxy-3-fluoropyridin-2-yl)-7-methoxy-3-methyl-8-(1-methyl-1H-pyrazol-4-yl)-1,3-dihydroimidazo[4,5-c]quinolin-2-one

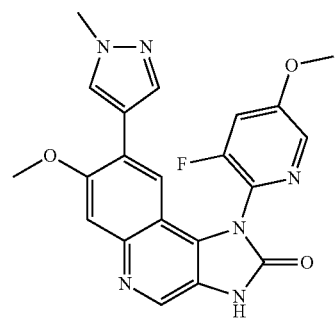

1-(3-Fluoro-5-methoxypyridin-2-yl)-7-methoxy-8-(1-methyl-1H-pyrazol-4-yl)-1,3-dihydroimidazo[4,5-c]quinolin-2-one

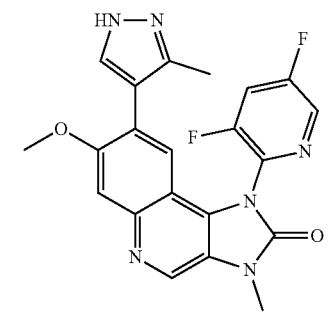 [SMILES: COc1cc2ncc3c(c2cc1-c1c[nH]nc1C)n(-c1ncc(F)cc1F)c(=O)n3C]

1-(3,5-Difluoropyridin-2-yl)-7-methoxy-3-methyl-8-(3-methyl-1H-pyrazol-4-yl)-1,3-dihydroimidazo[4,5-c]quinolin-2-one

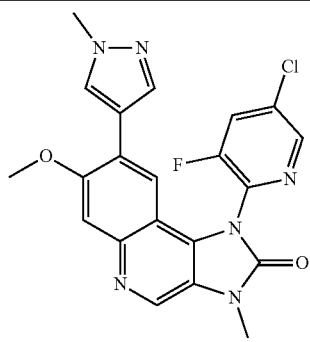

1-(5-Chloro-3-fluoropyridin-2-yl)-7-methoxy-3-methyl-8-(1-methyl-1H-pyrazol-4-yl)-1,3-dihydroimidazo[4,5-c]quinolin-2-one

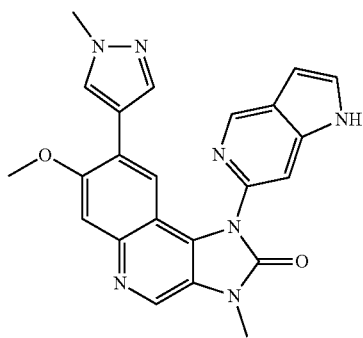 [SMILES: COc1cc2ncc3c(c2cc1-c1cnn(C)c1)n(-c1cc2[nH]ccc2cn1)c(=O)n3C]

7-Methoxy-3-methyl-8-(1-methyl-1H-pyrazol-4-yl)-1-(1H-pyrrolo[3,2-c]pyridin-6-yl)-1,3-dihydroimidazo[4,5-c]quinolin-2-one

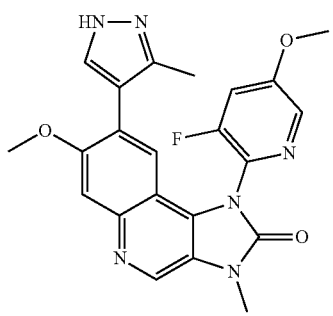

1-(3-Fluoro-5-methoxypyridin-2-yl)-7-methoxy-3-methyl-8-(3-methyl-1H-pyrazol-4-yl)-1,3-dihydroimidazo[4,5-c] quinolin-2-one

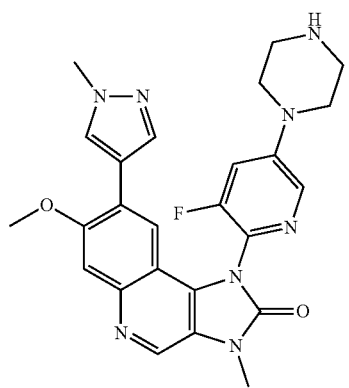 [SMILES: COc1cc2ncc3c(c2cc1-c1cnn(C)c1)n(-c1ncc(N2CCNCC2)cc1F)c(=O)n3C]

1-(3-Fluoro-5-piperazin-1-yl-pyridin-2-yl)-7-methoxy-3-methyl-8-(1-methyl-1H-pyrazol-4-yl)-1,3-dihydroimidazo[4,5-c]quinolin-2-one

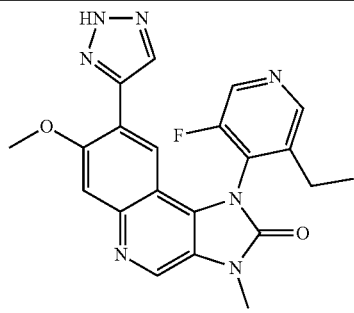
1-(3-Ethyl-5-fluoropyridin-4-yl)-7-methoxy-3-methyl-8-(2H-1,2,3-triazol-4-yl)-1,3-dihydroimidazo[4,5-c] quinolin-2-one

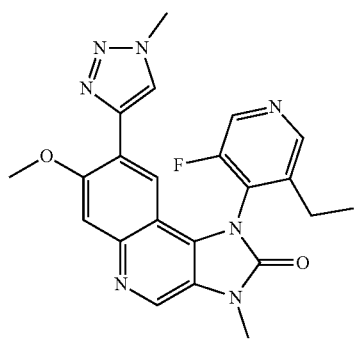 [SMILES: CCc1cncc(F)c1-n1c(=O)n(C)c2cnc3cc(OC)c(-c4cn(C)nn4)cc3c21]
1-(3-Ethyl-5-fluoropyridin-4-yl)-7-methoxy-3-methyl-8-(1-methyl-1H-1,2,3-triazol-4-yl)-1,3-dihydroimidazo[4,5-c] quinolin-2-one

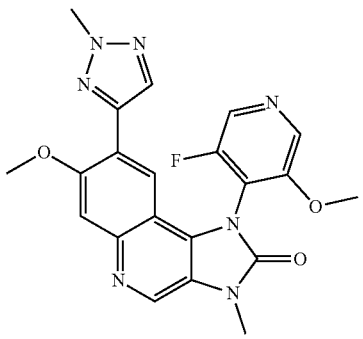
1-(3-Fluoro-5-methoxypyridin-4-yl)-7-methoxy-3-methyl-8-(2-methyl-2H-1,2,3-triazol-4-yl)-1,3-dihydroimidazo[4,5-c] quinolin-2-one

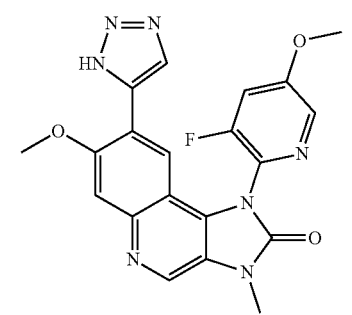
1-(3-Fluoro-5-methoxypyridin-2-yl)-7-methoxy-3-methyl-8-(3H-1,2,3-triazol-4-yl)-1,3-dihydroimidazo[4,5-c] quinolin-2-one

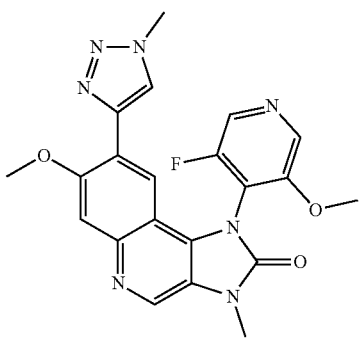
1-(3-Fluoro-5-methoxypyridin-4-yl)-7-methoxy-3-methyl-8-(1-methyl-1H-1,2,3-triazol-4-yl)-1,3-dihydroimidazo[4,5-c]-quinolin-2-one

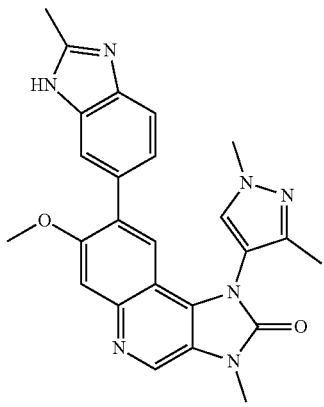

1-(1,3-Dimethyl-1H-pyrazol-4-yl)-7-methoxy-3-methyl-8-(2-methyl-3H-benzoimidazol-5-yl)-1,3-dihydroimidazo[4,5-c]quinolin-2-one

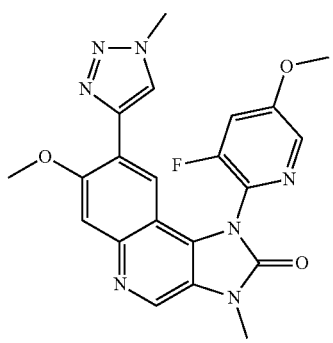

1-(3-Fluoro-5-methoxypyridin-2-yl)-7-methoxy-3-methyl-8-(1-methyl-1H-1,2,3-triazol-4-yl)-1,3-dihydroimidazo[4,5-c]quinolin-2-one

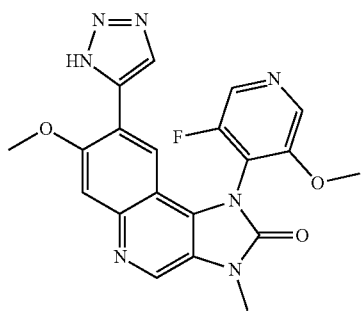

1-(3-Fluoro-5-methoxypyridin-4-yl)-7-methoxy-3-methyl-8-(3H-1,2,3-triazol-4-yl)-1,3-dihydroimidazo[4,5-c] quinolin-2-one

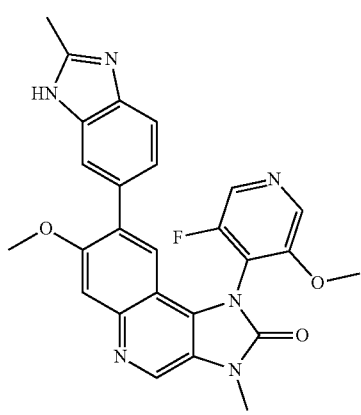

1-(3-Fluoro-5-methoxypyridin-4-yl)-7-methoxy-3-methyl-8-(2-methyl-3H-benzoimidazol-5-yl)-1,3-dihydroimidazo[4,5-c]-quinolin-2-one

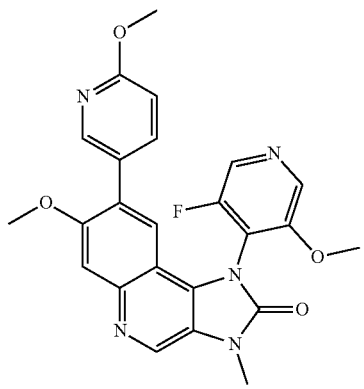

1-(3-Fluoro-5-methoxypyridin-4-yl)-7-methoxy-8-(6-methoxy-pyridin-3-yl)-3-methyl-1,3-dihydroimidazo[4,5-c]quinolin-2-one

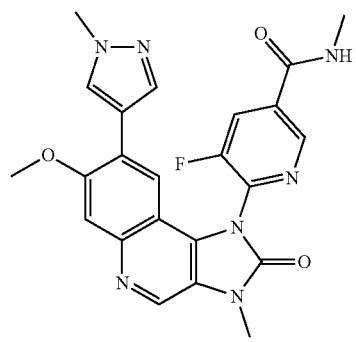

5-Fluoro-6-[7-methoxy-3-methyl-8-(1-methyl-1H-pyrazol-4-yl)-2-oxo-2,3-dihydroimidazo[4,5-c]quinolin-1-yl]-N-methyl-nicotinamide

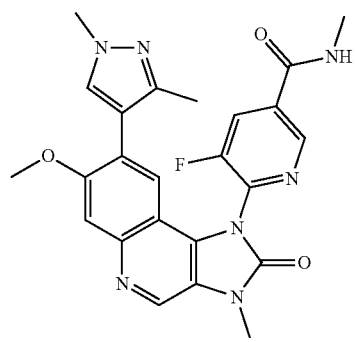

6-[8-(1,3-Dimethyl-1H-pyrazol-4-yl)-7-methoxy-3-methyl-2-oxo-2,3-dihydroimidazo[4,5-c]quinolin-1-yl]-5-fluoro-N-methylnicotinamide

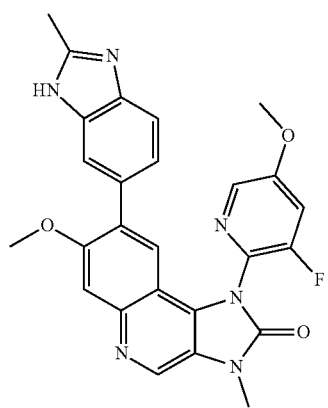 [SMILES: COc1cnc(-n2c(=O)n(C)c3cnc4cc(OC)c(-c5ccc6nc(C)[nH]c6c5)cc4c32)c(F)c1]

1-(3-Fluoro-5-fluoromethoxypyridin-4-yl)-7-methoxy-3-methyl-8-(2-methyl-3H-benzoimidazol-5-yl)-1,3-dihydroimidazo-[4,5-c]quinolin-2-one

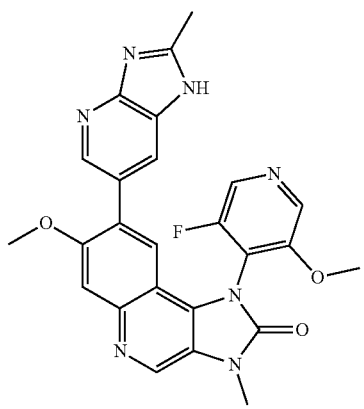

1-(3-Fluoro-5-methoxypyridin-4-yl)-7-methoxy-3-methyl-8-(2-methyl-1H-imidazo[4,5-b]pyridin-6-yl)-1,3-dihydroimidazo[4,5-c]quinolin-2-one

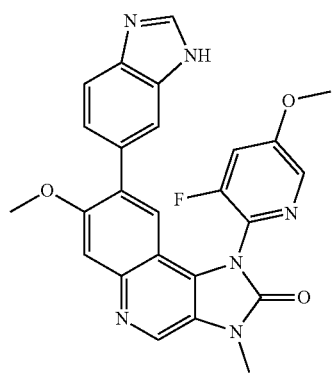

8-(3H-Benzimidazol-5-yl)-1-(3-fluoro-5-methoxypyridin-2-yl)-7-methoxy-3-methyl-1,3-dihydroimidazo[4,5-c]quinolin-2-one

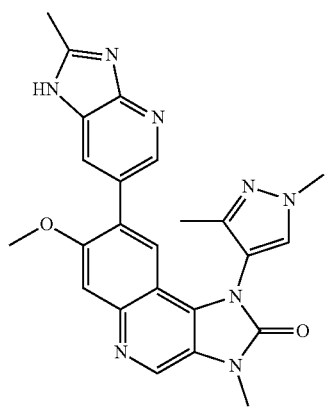

1-(1,3-Dimethyl-1H-pyrazol-4-yl)-7-methoxy-3-methyl-8-(2-methyl-1H-imidazo[4,5-b]-pyridin-6-yl)-1,3-dihydroimidazo[4,5-c]-quinolin-2-one

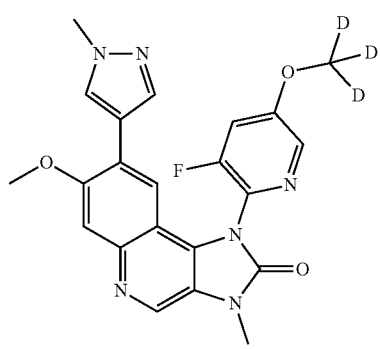 [SMILES: [2H]C([2H])([2H])Oc1cnc(-n2c(=O)n(C)c3cnc4cc(OC)c(-c5cnn(C)c5)cc4c32)c(F)c1]

1-[3-Fluoro-5-(trideuteriomethoxy)-2-pyridyl]-7-methoxy-3-methyl-8-(1-methyl-pyrazol-4-yl) imidazo[4,5-c]quinolin-2-one

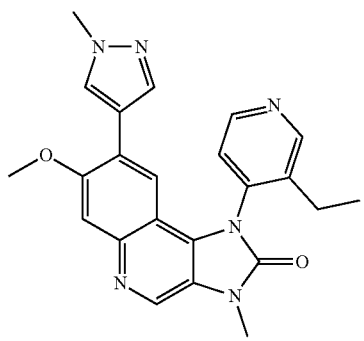 [SMILES: CCc1cnccc1-n1c(=O)n(C)c2cnc3cc(OC)c(-c4cnn(C)c4)cc3c21]
1-(3-Ethyl-pyridin-4-yl)-7-methoxy-3-methyl-8-(1-methyl-1H-pyrazol-4-yl)-1,3-dihydro-imidazo[4,5-c] quinolin-2-one
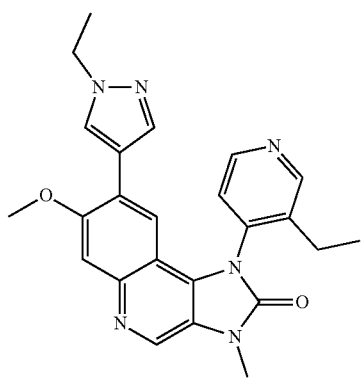 [SMILES: CCc1cnccc1-n1c(=O)n(C)c2cnc3cc(OC)c(-c4cnn(CC)c4)cc3c21]
8-(1-Ethyl-1H-pyrazol-4-yl)-1-(3-ethyl-pyridin-4-yl)-7-methoxy-3-methyl-1,3-dihydroimidazo[4,5-c] quinolin-2-one
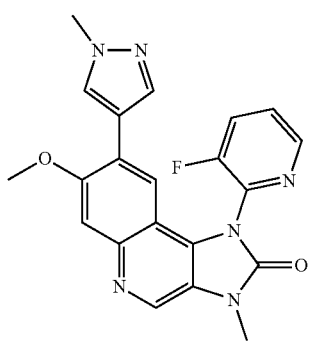 [SMILES: COc1cc2ncc3c(c2cc1-c1cnn(C)c1)n(-c1ncccc1F)c(=O)n3C]
1-(3-Fluoropyridin-2-yl)-7-methoxy-3-methyl-8-(2-methyl-2H-1,2,3-triazol-4-yl)-1,3-dihydroimidazo[4,5-c] quinolin-2-one
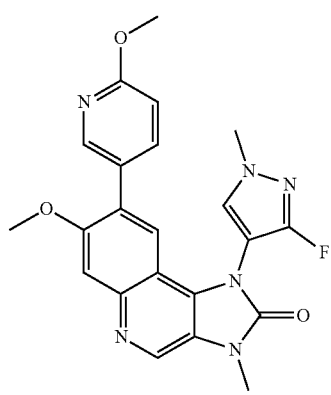 [SMILES: COc1ccc(-c2cc3c(cc2OC)ncc2c3n(-c3cn(C)nc3F)c(=O)n2C)cn1]
1-(3-Fluoro-1-methyl-1H-pyrazol-4-yl)-7-methoxy-8-(6-methoxypyridin-3-yl)-3-methyl-1,3-dihydroimidazo[4,5-c]-quinolin-2-one

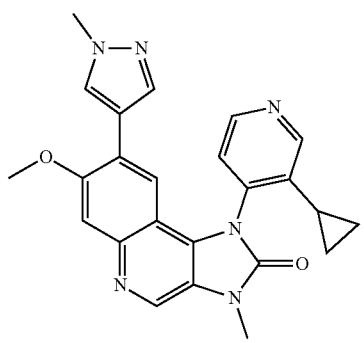 [SMILES: COc1cc2ncc3c(c2cc1-c1cnn(C)c1)n(-c1ccncc1C1CC1)c(=O)n3C]

1-(3-Cyclopropylpyridin-4-yl)-7-methoxy-3-methyl-8-(1-methyl-1H-pyrazol-4-yl)-1,3-dihydroimidazo[4,5-c]quinolin-2-one

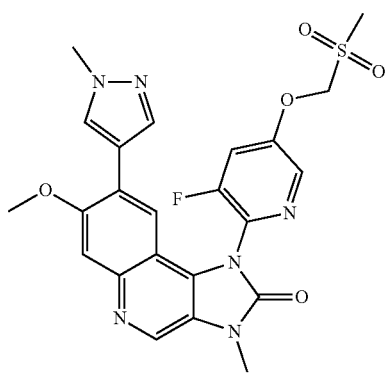 [SMILES: COc1cc2ncc3c(c2cc1-c1cnn(C)c1)n(-c1ncc(OCS(C)(=O)=O)cc1F)c(=O)n3C]

1-(3-Fluoro-5-methylsulfonylmethoxypyridin-2-yl)-7-methoxy-3-methyl-8-(1-methyl-1H-pyrazol-4-yl)-1,3-dihydroimidazo[4,5-c]-quinolin-2-one

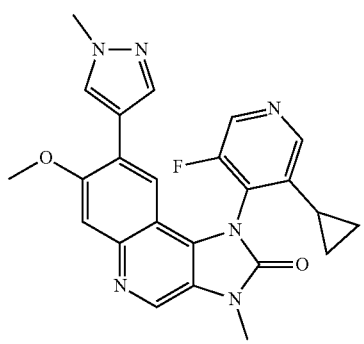 [SMILES: COc1cc2ncc3c(c2cc1-c1cnn(C)c1)n(-c1c(F)cncc1C1CC1)c(=O)n3C]

1-(3-Cyclopropyl-5-fluoropyridin-4-yl)-7-methoxy-3-methyl-8-(1-methyl-1H-pyrazol-4-yl)-1,3-dihydroimidazo[4,5-c]quinolin-2-one

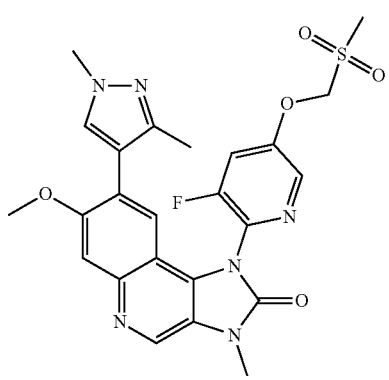 [SMILES: COc1cc2ncc3c(c2cc1-c1cn(C)nc1C)n(-c1ncc(OCS(C)(=O)=O)cc1F)c(=O)n3C]

8-(1,3-Dimethyl-1H-pyrazol-4-yl)-1-(3-fluoro-5-methyl-sulfonylmethoxypyridin-2-yl)-7-methoxy-3-methyl-1,3-dihydroimidazo-[4,5-c]quinolin-2-one -continued

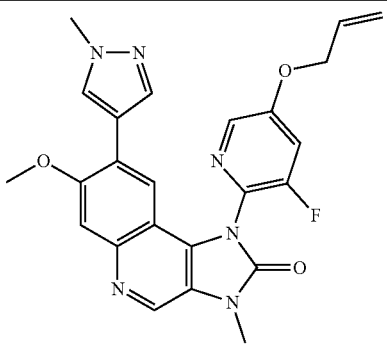

1-(5-Allyloxy-3-fluoropyridin-2-yl)-7-methoxy-3-methyl-8-(1-methyl-1H-pyrazol-4-yl)-1,3-dihydroimidazo[4,5-c]quinolin-2-one

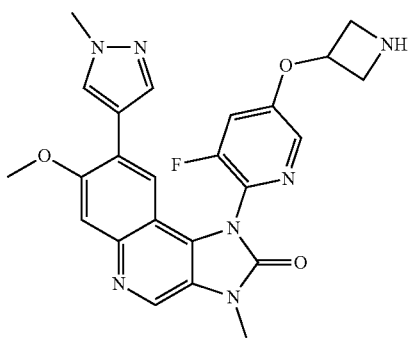 [SMILES: COc1cc2ncc3c(c2cc1-c1cnn(C)c1)n(-c1ncc(OC2CNC2)cc1F)c(=O)n3C]

1-[5-(Azetidin-3-yloxy)-3-fluoropyridin-2-yl]-7-methoxy-3-methyl-8-(1-methyl-1H-pyrazol-4-yl)-1,3-dihydroimidazo[4,5-c]quinolin-2-one

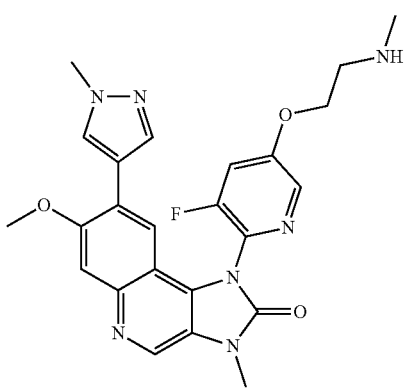

1-[3-Fluoro-5-(2-methylamino-ethoxy)-pyridin-2-yl]-7-methoxy-3-methyl-8-(1-methyl-1H-pyrazol-4-yl)-1,3-dihydroimidazo-[4,5-c] quinolin-2-one

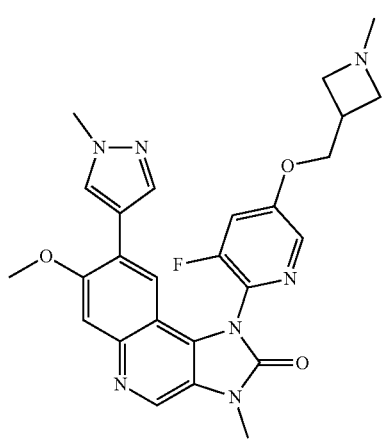 [SMILES: COc1cc2ncc3c(c2cc1-c1cnn(C)c1)n(-c1ncc(OCC2CN(C)C2)cc1F)c(=O)n3C]

1-[3-Fluoro-5-(1-methylazetidin-3-yl-methoxy)pyridin-2-yl]-7-methoxy-3-methyl-8-(1-methyl-1H-pyrazol-4-yl)-1,3-dihydro-imidazo[4,5-c]quinolin-2-one or pharmaceutically usable salt, solvate or tautomer thereof.

2. A pharmaceutical composition for cancer treatment comprising an effective amount of at least one compound according to claim 1 or a pharmaceutically usable salt, solvate or tautomer, thereof, together with at least one pharmaceutically tolerated excipient.

3. The pharmaceutical composition according to claim 2, further comprising at least one further anticancer agent.

4. A kit comprising separate packs of
   (a) a compound according to claim 1 or pharmaceutically usable salt, solvate or tautomer thereof, and
   (b) a further anticancer agent.

5. The compound according to claim 1 or a pharmaceutically usable salt thereof.

6. The compound according to claim 1, which is in the form of a pharmaceutically usable salt thereof.

7. A pharmaceutical composition comprising at least one compound according to claim 1 or a pharmaceutically usable salt, solvate or tautomer, thereof, together with at least one pharmaceutically tolerated excipient.

8. A kit comprising separate packs of
   (a) a compound according to claim 1 or pharmaceutically usable salt thereof, and
   (b) a further anticancer agent.

* * * * *